(12) United States Patent
Josephs et al.

(10) Patent No.: US 11,427,817 B2
(45) Date of Patent: Aug. 30, 2022

(54) COMPOSITIONS AND METHODS OF IMPROVING SPECIFICITY IN GENOMIC ENGINEERING USING RNA-GUIDED ENDONUCLEASES

(71) Applicant: Duke University, Durham, NC (US)

(72) Inventors: Eric Josephs, Durham, NC (US);
Dewran Kocak, Durham, NC (US);
Piotr Marszalek, Durham, NC (US);
Charles A. Gersbach, Durham, NC (US)

(73) Assignee: Duke University, Durham, NC (US)

( * ) Notice: Subject to any disclaimer, the term of this patent is extended or adjusted under 35 U.S.C. 154(b) by 605 days.

(21) Appl. No.: 15/754,861

(22) PCT Filed: Aug. 25, 2016

(86) PCT No.: PCT/US2016/048798
§ 371 (c)(1),
(2) Date: Feb. 23, 2018

(87) PCT Pub. No.: WO2017/035416
PCT Pub. Date: Mar. 2, 2017

(65) Prior Publication Data
US 2019/0136229 A1    May 9, 2019

Related U.S. Application Data

(60) Provisional application No. 62/209,466, filed on Aug. 25, 2015.

(51) Int. Cl.
| | |
|---|---|
| *C12N 15/11* | (2006.01) |
| *G16B 25/00* | (2019.01) |
| *G16B 15/10* | (2019.01) |
| *G16B 30/10* | (2019.01) |
| *G16B 15/30* | (2019.01) |
| *C12N 15/90* | (2006.01) |

(52) U.S. Cl.
CPC ............ *C12N 15/11* (2013.01); *C12N 15/111* (2013.01); *C12N 15/907* (2013.01); *G16B 15/10* (2019.02); *G16B 15/30* (2019.02); *G16B 25/00* (2019.02); *G16B 30/10* (2019.02); *C12N 2310/20* (2017.05)

(58) Field of Classification Search
CPC combination set(s) only.
See application file for complete search history.

(56) References Cited

U.S. PATENT DOCUMENTS

| | | |
|---|---|---|
| 5,139,941 A | 8/1992 | Muzyczka et al. |
| 5,593,972 A | 1/1997 | Weiner et al. |
| 5,658,784 A | 8/1997 | Eckner et al. |
| 5,741,683 A | 4/1998 | Zhou et al. |
| 5,773,700 A | 6/1998 | Van Grinsven et al. |
| 5,962,428 A | 10/1999 | Carrano et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,790,449 B2 | 9/2010 | Gao et al. |
| 7,906,111 B2 | 3/2011 | Wilson et al. |
| 8,697,359 B1 | 4/2014 | Zhang et al. |
| 8,889,356 B2 | 11/2014 | Zhang |
| 8,993,233 B2 | 3/2015 | Zhang et al. |
| 9,738,879 B2 | 8/2017 | Gersbach et al. |
| 9,828,582 B2 | 11/2017 | Perez-Pinera et al. |
| 9,834,791 B2 | 12/2017 | Zhang et al. |
| 10,011,850 B2 | 7/2018 | Joung et al. |
| 10,190,106 B2 | 1/2019 | Wolfe et al. |
| 10,676,726 B2 | 6/2020 | Gersbach et al. |
| 10,676,735 B2 | 6/2020 | Gersbach et al. |
| 10,704,060 B2 | 7/2020 | Gersbach et al. |
| 10,711,256 B2 | 7/2020 | Gersbach et al. |

(Continued)

FOREIGN PATENT DOCUMENTS

| | | |
|---|---|---|
| CA | 2749305 A1 | 7/2010 |
| EP | 2620161 A1 | 7/2013 |

(Continued)

OTHER PUBLICATIONS

Cho et al. Analysis of off-target effects of CRISPR/Cas-derived RNA-guided endonucleases and nickases. Genome Research 24: 132-141, (Year: 2014).*
Fu, Yanfang, et al. "Improving CRISPR-Cas nuclease specificity using truncated guide RNAs." Nature biotechnology 32.3 (2014): 279-284. (Year: 2014).*
Chinese Patent Office Action for Application No. 201680061639.8 dated Dec. 27, 2019 (19 pages, English translation included).
European Patent Office Action for Application No. 16840171.9 dated Jan. 24, 2020 (4 pages).
European Patent Office Extended Search Report for Application No. 16840171.9 dated May 29, 2019 (16 pages).
Farasat et al., "A Biophysical Model of CRISPR/Cas9 Activity for Rational Design of Genome Editing and Gene Regulation," PLOS Computational Biology, 2016, 12(1):e1004724.

(Continued)

*Primary Examiner* — G Steven Vanni
(74) *Attorney, Agent, or Firm* — Michael Best & Friedrich LLP

(57) ABSTRACT

Disclosed herein are optimized guide RNAs (gRNAs) that have increased target binding specificity and reduced off-target binding. Further disclosed herein are methods of designing and using the optimized gRNAs.

11 Claims, 63 Drawing Sheets

Specification includes a Sequence Listing.

(56) References Cited

U.S. PATENT DOCUMENTS

| | | | |
|---|---|---|---|
| 10,745,714 | B2 | 8/2020 | Gersbach et al. |
| 11,155,796 | B2 | 10/2021 | Gersbach et al. |
| 2004/0175727 | A1 | 9/2004 | Draghia-Akli et al. |
| 2008/0200409 | A1 | 8/2008 | Wilson et al. |
| 2011/0197290 | A1 | 8/2011 | Fahrenkrug et al. |
| 2011/0236353 | A1 | 9/2011 | Wilson et al. |
| 2011/0263682 | A1 | 10/2011 | De Kimpe et al. |
| 2011/0286957 | A1 | 11/2011 | Prieve et al. |
| 2011/0301073 | A1 | 12/2011 | Gregory et al. |
| 2011/0301218 | A1 | 12/2011 | Bozzoni et al. |
| 2012/0195917 | A1 | 8/2012 | Sahin et al. |
| 2013/0274129 | A1 | 10/2013 | Katzen et al. |
| 2013/0323001 | A1 | 12/2013 | Ueki et al. |
| 2014/0068797 | A1 | 3/2014 | Doudna et al. |
| 2014/0140969 | A1 | 5/2014 | Beausejour et al. |
| 2014/0170753 | A1 | 6/2014 | Zhang |
| 2014/0179006 | A1 | 6/2014 | Zhang |
| 2014/0186958 | A1 | 7/2014 | Zhang et al. |
| 2014/0234975 | A1 | 8/2014 | Silva et al. |
| 2014/0295557 | A1 | 10/2014 | Joung et al. |
| 2014/0309177 | A1 | 10/2014 | Perez-Pinera et al. |
| 2014/0356956 | A1 | 12/2014 | Church et al. |
| 2014/0357530 | A1 | 12/2014 | Zhang et al. |
| 2014/0377868 | A1 | 12/2014 | Joung et al. |
| 2015/0031089 | A1 | 1/2015 | Lindstrom |
| 2015/0045413 | A1 | 2/2015 | De Visser et al. |
| 2015/0056705 | A1 | 2/2015 | Conway et al. |
| 2015/0079064 | A1 | 3/2015 | Gersbach et al. |
| 2015/0159178 | A1 | 6/2015 | Green et al. |
| 2015/0166980 | A1 | 6/2015 | Liu et al. |
| 2016/0040189 | A1 | 2/2016 | Kennedy et al. |
| 2016/0201089 | A1 | 7/2016 | Gersbach et al. |
| 2017/0283831 | A1 | 10/2017 | Zhang et al. |
| 2017/0298331 | A1 | 10/2017 | Gersbach et al. |
| 2017/0327806 | A1 | 11/2017 | Joung et al. |
| 2018/0023064 | A1 | 1/2018 | Gersbach et al. |
| 2018/0094238 | A1 | 4/2018 | Perez-Pinera et al. |
| 2018/0291370 | A1 | 10/2018 | Gersbach et al. |
| 2018/0320197 | A1 | 11/2018 | Gersbach et al. |
| 2018/0334688 | A1 | 11/2018 | Gersbach et al. |
| 2018/0353615 | A1 | 12/2018 | Gersbach et al. |
| 2019/0127713 | A1 | 5/2019 | Gersbach et al. |
| 2019/0134221 | A1 | 5/2019 | Bumcrot et al. |
| 2019/0151476 | A1 | 5/2019 | Gersbach et al. |
| 2019/0194633 | A1 | 6/2019 | Gersbach et al. |
| 2019/0351074 | A1 | 11/2019 | Ahituv et al. |
| 2019/0359959 | A1 | 11/2019 | Jaenisch et al. |
| 2020/0109406 | A1 | 4/2020 | Miller et al. |
| 2020/0318139 | A1 | 10/2020 | Gersbach et al. |
| 2020/0332307 | A1 | 10/2020 | Hummel et al. |
| 2020/0347105 | A1 | 11/2020 | Gersbach et al. |
| 2020/0385695 | A1 | 12/2020 | Gersbach et al. |
| 2021/0002665 | A1 | 1/2021 | Gersbach et al. |
| 2021/0032654 | A1 | 2/2021 | Gersbach et al. |
| 2021/0040460 | A1 | 2/2021 | Gersbach et al. |

FOREIGN PATENT DOCUMENTS

| | | |
|---|---|---|
| JP | 2015-534817 A | 12/2015 |
| JP | 2016-521452 A | 7/2016 |
| JP | 2016-521975 A | 7/2016 |
| WO | WO 1993/024640 A2 | 12/1993 |
| WO | WO 1994/016737 A1 | 8/1994 |
| WO | WO 2001/083783 A2 | 11/2001 |
| WO | WO2003/042397 A2 | 5/2003 |
| WO | WO2005/033321 A2 | 4/2005 |
| WO | WO2006/110689 A2 | 10/2006 |
| WO | WO 2008/006028 A2 | 1/2008 |
| WO | WO2010/053572 A2 | 5/2010 |
| WO | WO 2011/036640 A2 | 3/2011 |
| WO | WO2011/126808 A2 | 10/2011 |
| WO | 2011/141820 A1 | 11/2011 |
| WO | WO 2011/154427 A1 | 12/2011 |
| WO | WO2012/170930 A1 | 12/2012 |
| WO | WO2013/049493 A1 | 4/2013 |
| WO | WO2013/143555 A1 | 10/2013 |
| WO | WO 2013/163628 A2 | 10/2013 |
| WO | WO2013/176772 A1 | 11/2013 |
| WO | WO2013/182683 A1 | 12/2013 |
| WO | 2014/018423 A2 | 1/2014 |
| WO | 2014/081855 A1 | 5/2014 |
| WO | WO 2014/065596 A1 | 5/2014 |
| WO | 2014/093595 A1 | 6/2014 |
| WO | 2014/093709 A1 | 6/2014 |
| WO | WO2014/089290 A1 | 6/2014 |
| WO | WO2014/093655 A2 | 6/2014 |
| WO | WO2014/093661 A2 | 6/2014 |
| WO | WO2014/144288 A1 | 9/2014 |
| WO | WO2014/152432 A2 | 9/2014 |
| WO | WO2014/172470 A2 | 10/2014 |
| WO | 2014/204728 A1 | 12/2014 |
| WO | WO2014/191128 A1 | 12/2014 |
| WO | WO 2014/197748 A2 | 12/2014 |
| WO | WO2015/017519 A1 | 2/2015 |
| WO | 2015/048690 A1 | 4/2015 |
| WO | WO2015/089419 A2 | 6/2015 |
| WO | WO2015/089465 A1 | 6/2015 |
| WO | WO2015/089486 A2 | 6/2015 |
| WO | WO2015/126927 A2 | 8/2015 |
| WO | WO2016/094880 A1 | 6/2016 |
| WO | WO2016/130600 A2 | 8/2016 |
| WO | WO2017/015637 A1 | 1/2017 |
| WO | WO2017/066497 A2 | 4/2017 |
| WO | WO2017/095967 A2 | 6/2017 |
| WO | WO2017/193029 A2 | 9/2017 |
| WO | WO2017/180915 A2 | 10/2017 |
| WO | WO2018/017754 A1 | 1/2018 |
| WO | WO2018/031762 A1 | 2/2018 |
| WO | WO2019/144061 A1 | 7/2019 |
| WO | WO2020/210776 A1 | 10/2020 |
| WO | WO2020/214609 A1 | 10/2020 |
| WO | WO2020/214613 A1 | 10/2020 |
| WO | WO2021/026516 A1 | 2/2021 |
| WO | WO2021/034984 A2 | 2/2021 |
| WO | WO2021/034987 A1 | 2/2021 |
| WO | WO2021/067878 A1 | 4/2021 |
| WO | WO2021/113536 A1 | 6/2021 |
| WO | WO2021/222268 A1 | 11/2021 |
| WO | WO2021/222314 A1 | 11/2021 |
| WO | WO2021/222327 A1 | 11/2021 |
| WO | WO2021/222328 A1 | 11/2021 |
| WO | WO2021/226555 A2 | 11/2021 |

OTHER PUBLICATIONS

Aartsma-Rus et al., "Antisense-mediated exon skipping: a versatile tool with therapeutic and research applications," RNA, 2007, 13: 1609-1624.

Aartsma-Rus et al., "Exploring the frontiers of therapeutic exon skipping for Duchenne muscular dystrophy by double targeting within one or multiple exons," Mol Ther, 2006, 14: 401-407.

Aartsma-Rus et al., "Theoretic applicability of antisense-mediated exon skipping for Duchenne muscular dystrophy mutations," Hum Mutat, 2009, 30: 293-299.

Adler et al., "Nonviral direct conversion of primary mouse embryonic fibroblasts to neuronal cells," Molecular therapy, 2012, Nucleic acids 1, e32.

Aiuti et al., "Lentiviral hematopoietic stem cell gene therapy inpatients with Wiskott-Aldrich syndrome," Science, 2013, 341(6148): 1233151.

Anders et al., "Differential expression analysis for sequence count data," Genome biology 11, 2010, R106.

Anders et al., "Structural basis of PAM-dependent target DNA recognition by the Cas9 endonuclease," Nature, 2014, 513, 569-573.

Anguela et al., "Robust ZFN-mediated genome editing in adult hemophilic mice," Blood, 2013, 122: 3283-3287.

Aoki et al., "Bodywide skipping of exons 45-55 in dystrophic mdx52 mice by systemic antisense delivery," Proc Natl Acad Sci USA, 2012, 109: 13763-13768.

(56) References Cited

OTHER PUBLICATIONS

Barrangou et al., "CRISPR provides acquired resistance against viruses in prokaryotes," Science, 2007, 315(5819): 1709-1712.
Bartsevich et al., "Engineered zinc finger proteins for controlling stem cell fate," StemCells, 2003, 21: 632-637.
Beerli et al., "Chemically regulated zinc finger transcription factors," J Biol Chem, 2000, 275(42): 32617-27.
Beerli et al., "Engineering polydactyl zinc-finger transcription factors," Nat Biotechnol, 2002, 20: 135-141.
Beerli et al., "Positive and negative regulation of endogenous genes by designed transcription factors," Proc Natl Acad Sci USA, 2000, 97: 1495-1500.
Beerli et al., "Toward controlling gene expression at will: specific regulation of the erbB-2/HER-2 promoter by using polydactyl zinc finger proteins constructed from modular building blocks," Proc Natl Acad Sci USA, 1998, 95: 14628-14633.
Beltran et al., "Re-activation of a dormant tumor suppressor gene maspinby designed transcription factors," Oncogene, 2007, 26: 2791-2798.
Benedetti et al., "Repair or Replace? Exploiting Novel Gene and Cell Therapy Strategies for Muscular Dystrophies," FEBS Journal, 2013, 280: 4263-4280.
Berghella et al., "Reversible immortalization of human myogenic cells by site-specific excision of a retrovirally transferred onco-gene," Human gene therapy, 1999, 10: 1607-1617.
Bhakta et al., "Highly active zinc-finger nucleases by extended modular assembly," Genome Res, 2013, 530-538.
Bidou et al., "Sense from nonsense: therapies for premature stop codon diseases," Trends in Molecular Medicine, 2012, 18: 679-688.
Blancafort et al., "Scanning the human genome with combinatorial transcription factor libraries," Nat Biotechnol, 2003, 21: 269-274.
Boch et al., "Breaking the code of DNA binding specificity of TAL-type III effectors," Science, 2009, 326: 1509.
Bowles et al., "Phase 1 Gene Therapy for Duchenne Muscular Dystrophy Using a Translation Optimized AAV Vector," Molecular Therapy, 2012, 20: 443-455.
Briner et al., "Guide RNA Functional Modules Direct Cas9 Activity and Orthogonality," Molecular Cell, 2014, 56(2): 333-339.
Brunet et al., "Chromosomal translocations induced at specific loci in human stem cells," Proc Natl Acad Sci USA, 2009, 106: 10620-10625.
Buler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, 2012, 287(3): 1847-1860.
Bultmann et al., "Targeted transcriptional activation of silent oct4 pluripotency gene by combining designer TALEs and inhibition of epigenetic modifiers," Nucleic Acids Res, 2012, 40: 5368-5377.
Cencic et al., "Protospacer adjacent motif (PAM)-distal sequences engage CRISPR Cas9 DNA target cleavage," PLoS one, 2014, 9, e109213, 13 pages.
Cerletti et al., "Highly efficient, functional engraftment of skeletal muscle stem cells in dystrophic muscles," Cell, 2008, 134: 37-47.
Cermak et al., "Efficient design and assembly of custom TALEN and other TAL effector-based constructs for DNA targeting," Nucleic Acids Res, 2011, 30: e82.
Chapdelaine et al., "Meganucleases can restore the reading frame of a mutual dystrophin," Gene therapy, 2010, 17: 846-858.
Cheng et al., "Multiplexed activation of endogenous genes by CRISPR-on, an RNA-guided transcriptional activator system," Cell Res, 2013, 23(10): 1163-1171.
Cho et al., "Analysis of off-target effects of CRISPR/Cas-derived RNA-guided endonucleases and nickases," Genome Res, 2014, 24: 132-141.
Cho et al., "Targeted genome engineering in human cells with the Cas9 RNA-guided endonuclease," Nat Biotechnol 2013, 31: 230-232.
Christian et al., "Targe ting DNA double-strand breaks with TAL effector nucleases," Genetics, 2010, 186: 757-761.

Cirak et al., "Exon skipping and dystrophin restoration in patients with Duchenne muscular dystrophy after systemic phosphorodiamidate morpholino oligomer treatment: anopen-label, phase 2, dose-escalation study," Lancet, 2011, 378: 595-605.
Congetai., "Multiplex Genome Engineering Using CRISPR/Cas Systems," Science, 2013, 339: 819-823.
Cornu et al., "DNA-binding specificity is a major determinant of the activity and toxicity of zinc-finger nucleases," Mol Ther, 2008, 16: 352-358.
Cornu et al., "Quantification of zinc finger nuclease-associated toxicity," Meth Mol Biol, 2010, 649: 237-245.
Cradick et al., "CRISPR/Cas9 systems targeting beta-globin and CCR5 genes have substantial off-target activity," Nucleic Acids Res, 2013, 41(20): 9584-92.
Darabi et al., "Human ES-and iPS-derived myogenic progenitors restore dystrophin and improve contractility upon transplantation in dystrophic mice," Cell Stem Cell, 2012, 10: 610-619.
Dezawa et al., "Bone marrow stromal cells generate muscle cells and repair muscle degeneration," Science Signaling, 2005, 309: 314.
Ding et al., "A Talen Genome-Editing System for Generating Human Stem Cell-Based Disease Models," Cell Stem Cell, 2013, 12: 238-251.
Ding et al., "Enhanced efficiency of human pluripotent stem cell genome editing through replacing TALENs with CRISPRs," Cell Stem Cell, 2013, 12: 393-394.
Dirks et al., "Triggered amplification by hybridization chain reaction," Proceedings of the National Academy of Sciences of the United States of America, 2004, 101(43): 15275-15278.
Doench et al., "Rational design of highly active sgRNAs for CRISPR-Cas9-mediated gene inactivation," Nature biotechnology, 2014, 32(12): 1262-1267.
Doudna et al., "Genome editing. The new frontier of genome engineering with CRISPR-Cas9," Science, 2014, 346, 1258096.
Doyle et al., "TAL Effector-Nucleotide Targeter (TALE-NT) 2.0: tools for TAL effector design and target prediction," Nucleic Acids Res, 2012, 40: W117-122.
Doyon et al., "Enhancing zinc-finger-nuclease activity with improved obligate heterodimeric architectures," Nat Methods, 2010, 8: 74-79.
Duan et al., "Genome-wide identification of CRISPR/Cas9 off-targets in human genome," Cell research, 2014, 24(8): 1009-12.
Edelstein et al., "Gene therapy clinical trials worldwide 1989-2004—an overview," J. Gene Med., 2004, 6: 597-602.
Esvelt et al., "Orthogonal Cas9 proteins for RNA-guided gene regulation and editing," Nature Methods, 2013, 10(11): 1116-21.
Farinelli et al., "Lentiviral vectors for the treatment of primary immunodeficiencies," J Inherit Metab Dis, 2014, 37: 525-533.
Farzadfard et al., "Tunable and Multifunctional Eukaryotic Transcription Factors Based onCRISPR/Cas," ACS Synth Biol, 2013, 604-613.
Flamm et al., "RNA folding at elementary step resolution," Rna, 2000, 6: 325-338.
Flanigan et al., "Mutational spectrumof DMD mutations in dystrophinopathy patients: application of modern diagnostic techniques to a large cohort," Human mutation, 2009, 30: 1657-1666.
Fonfara et al., "Phylogeny of Cas9 determines functional exchangeability of dual-RNA and Cas9 among orthologous type II CRISPR-Cas systems," Nucleic Acids Res, 2013, 42(4): 2577-2590.
Fu et al., "High-frequency off-target mutagenesis induced by CRISPR-Cas nucleases in human cells," Nat Biotechnol, 2013, 31(9): 822-6.
Fu et al., "Improving CRISPR-Cas nuclease specificity using truncated guide RNAs," Nat Biotechnol, 2014, 32: 279-284.
Gaj et al., "Targeted gene knockout by direct delivery of zinc-finger nuclease proteins," Nature Methods, 2012, 9(8): 805-807.
Gaj et al., "ZFN, TALEN, and CRISPR/Cas-based methods for genome engineering," Trends Biotechnol, 2013, 31: 397-405.
Garg et al., "Engineering synthetic TAL effectors with orthogonal target sites," Nucleic Acids Res, 2012, 40: 7584-7595.
Gasiunas et al., "Cas9-crRNA ribonucleoprotein complex mediates specific DNA cleavage for adaptive immunity in bacteria," Proceedings of the National Academy of Sciences of the United States of America, 2012, 109, E2579-2586.
GenBank Accession No. AK019325 (2010).

(56) References Cited

OTHER PUBLICATIONS

GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
Gertz et al., "Transposase mediated construction of RNA-seq libraries," Genome Res, 2012, 22: 134-141.
Gilbert et al., "CRISPR-mediated modular RNA-guided regulation of transcription in eukaryotes," Cell, 2013, 154, 442-451.
Gillespie, "A general method for numerically simulating the stochastic time evolution of coupled chemical reactions," Journal of computational physics, 1976, 22: 403-434.
Goemans et al., "Systemic administration of PR0051 in Duchenne's muscular dystrophy," The New England journal of medicine, 2011, 364: 1513-1522.
Gou et al., "A novel approach for the construction of multiple shRNA expression vectors," J Gene Med, 2007, 9(9): 751-63.
Gräslund et al., "Exploring strategies for the design of artificial transcription factors: targeting sites proximal to known regulatory regions for the induction of gamma-globin expression and the treatment of sickle cell disease," J Biol Chem, 2005, 280: 3707-3714.
Gregorevic et al., "Systemic delivery of genes to striated muscles using adeno-associated viral vectors," Nat Med, 2004, 10: 828-834.
Guo et al., "Directed evolution of an enhanced and highly efficient FokI cleavage domain for zinc finger nucleases," J Mol Biol, 2010, 400: 96-107.
Guschin et al., "A rapid and general assay for monitoring endogenous gene modification," Methods Mol Biol, 2010, 649: 247-256.
Hilton et al., "Epigenome editing by a CRISPR-Cas9-based acetyltransferase activates genes from promoters and enhancers," Nature biotechnology, 2015, 33(5): 510-519.
Hockemeyer et al., "Genetic engineering of human pluripotent cells using TALE nucleases," Nat Biotechnol, 2011, 29:731-734.
Hoffman et al., "Dystrophin: the protein product of the Duchenne muscular dystrophy locus," Cell, 1987, 51: 919.
Hou et al., "Efficient genome engineering in human pluripotent stem cells using Cas9 from Neisseria meningitidis," Proc Natl Acad Sci USA, 2013, 110: 15644-15649.
Howarth et al., "A monovalent streptavidin with a single femtomolar biotin binding site," Nature methods, 2006, 3(4): 267-273.
Hsu et al., "Development and Applications of CRISPR-Cas9 for Genome Engineering," Cell, 2014, 157, 1262-1278.
Hsu et al., "Dissecting Neural Function Using Targeted Genome Engineering Technologies", ACS Chem. Neurosci., 2012, 3:603-610.
Hsu et al., "DNA targeting specificity of RNA-guided Cas9 nucleases," Nature Biotechnology, 2013, 31: 827-832.
Humbert et al., "Targeted gene therapies: tools, applications, optimization", Critical Reviews in Biochemistry and Molecular Biology, 2012, 47(3): 264-281.
Hwang et al., "Efficient genome editing in zebrafish using CRISPR-Cas system," NatBiotechnol, 2013, 31(3): 227-9.
Jiang et al., "A Cas9-guide RNA complex preorganized for target DNA recognition," Science, 2015, 348, 1477-1481.
Jinek et al., "A programmable dual-RNA-guided DNA endonuclease in adaptive bacterial immunity," Science, 2012, 337: 816-821.
Jinek et al., "RNA-programmed genome editing in human cells," eLife, 2013, 2: e00471.
Jinek et al., "Structures of Cas9 endonucleases reveal RNA-mediated conformational activation," Science, 2014, 343(6176): 1247997.
Josephs et al., "Structure and specificity of the RNA-guided endonuclease Cas9 during DNA interrogation, target binding and cleavage," Nucleic Acids Research, 2015, 43(18): 8924-8941.
Joung et al., "TALENs: a widely applicable technology for targeted genome editing," Nature Reviews Molecular Cell Biology, 2013, 14: 49-55.
Kayali et al., "Site-directed gene repair of the dystrophin gene mediated by PNA-ssODNs," Human Molecular Genetics, 2010, 19(16): 3266-3281.
Kearns et al., "Cas9 effector-mediated regulation of transcription and differentiation in human pluripotent stem cells," Development, 2014, 141(1): 219-23.
Khodakov et al., "Protected DNA strand displacement for enhanced single nucleotide discrimination in doublestranded DNA," Scientific reports, 2015, 5: 8721.
Kim et al., "Surrogate reporters for enrichment of cells with nuclease-induced mutations," Nat Methods, 2011, 8: 941-943.
Kim et al., "TALENs and ZFNs are associated with different mutation signatures," Nat Methods, 2013, 10(3): 185.
Kimura et al., "Cell-lineage regulated myogenesis for dystrophin replacement: a novel therapeutic approach for treatment of muscular dystrophy," Hum Mol Genet, 2008, 17: 2507-2517.
Kleinstiver et al., "Engineered CRISPR-Cas9 nucleases with altered PAM specificities," Nature, 2015, 523(7561): 481-5.
Kleinstiver et al., "Genome-wide specificities of CRISPR-Cas Cpf1 nucleases in human cells," Nature Biotechnology, 2016, 34: 869-874.
Konermann et al., "Optical control of mammalian endogenous transcription and epigenetic states," Nature, 2013, 500(7463): 472-6.
Konieczny et al., "Gene and cell-mediated therapies for muscular dystrophy," Muscle Nerve, 2013, 47: 649-663.
Kubokawa et al., "Molecular characterization of the 5'-UTR of retinal dystrophin reveals a cryptic intron that regulates translational activity," Molecular Vision, 2010, 16: 2590-2597.
Kuscu et al., "Genome-wide analysis reveals characteristics of off-target sites bound by the Cas9 endonuclease," Nature biotechnology, 2014, 32(7): 677-83.
Kyte et al., "A Simple Method for Displaying the Hydropathic Character of a Protein," J. Mol. Biol., 1982, 157: 105-132.
Langmead et al., "Ultrafast and memory-efficient alignment of short DNA sequences to the human genome," Genome biology, 2009, 10: R25.
Larson et al., "CRISPR interference (CRISPRi) for sequence-editing control of gene expression," NatProtoc, 2013, 8(11): 2180-96.
Latta-Mahieu et al., "Gene transfer of a chimeric trans-activator is immunogenic and results in short-lived transgene expression," Human Gene Therapy, 2002, 13(13): 1611-1620.
Lattanzi et al., "High efficiency myogenic conversion of human fibroblasts by adenoviral vector-mediated MyoD gene transfer. An alternative strategy for ex vivo gene therapy of primary myopathies," The Journal of clinical investigation, 1998, 101: 2119-2128.
Lee et al., "Targeted chromosomal deletions in human cells using zinc finger nucleases," Genome research, 2010, 20: 81-89.
Lesnik et al., "Relative thermodynamic stability of DNA, RNA, and DNA: RNA hybrid duplexes: relationship with base composition and structure," Biochemistry, 1995, 34(34): 10807-10815.
Li etal, "In vivo genome editing restores haemostasis ina mouse model of haemophilia," Nature, 2011, 475: 217-221.
Li et al., "Marginal level dystrophin expression improves clinical outcome in a strain of dystrophin/utrophin double knockout mice," PLoS One, 2010, 5: e15286.
Li et al., "Modularly assembled designer TAL effector nucleases for targeted gene knockout and gene replacement in eukaryotes," Nucleic Acids Research, 2011, 39(14): 6315-6325.
Li et al., "Transcription activator-like effector hybrids for conditional control and rewiring of chromosomal transgene expression," Scientific reports, 2012, 2: 897.
Liang et al., "Engineeringbiological systems with synthetic RNA molecules," Mol Cell, 2011, 43: 915-926.
Liu et al., "Monte Carlo simulation for single RNA unfolding by force," Biophysical journal, 2005, 88(1): 76-84.
Lohmueller et al., "A tunable zinc finger-based framework for Boolean logic computation in mammalian cells," Nucleic Acids Res, 2012, 40: 5180-5187.

(56) References Cited

OTHER PUBLICATIONS

Lovric et al., "Terminal Differentiation of Cardiac and Skeletal Myocytes Induces Permissivity to AAV Transductionby Relieving Inhibition Imposed by DNA Damage Response Proteins," Molecular Therapy, 2012, 2087-2097.
Lu et al., "The status of exon skipping as a therapeutic approach to duchenne muscular dystrophy," Molecular Therapy, 2011, 19: 9-15.
Lund et al. "Promoter-targeted phage display selections with preassembled synthetic zinc finger libraries for endogenous gene regulation" Journal of Molecular Biology, 2004, 340: 599-613.
Luo et al., "Synthetic DNA delivery systems," Nature Biotechnology, 2000, 18: 33-37.
Machinek et al., "Programmable energy landscapes for kinetic control of DNA strand displacement," Nature communications, 2014, 5: 5324, 9 pages.
MacPherson et al., "Flexible guide—RNA design for CRISPR applications using Protospacer Workbench," Nature biotechnology, 2015, 33(8).
Maeder et al., "CRISPR RNA-guided activation of endogenous human genes," Nature Methods, 2013, 10, 977-979.
Maeder et al., "Robust, synergistic regulation of human gene expression using TALE activators," Nat Methods, 2013, 10(3): 243-245.
Maeder et al., "Robust, synergistic regulation of human gene expression using TALE activators," Nature Methods, 2013, 10(3): 243-246, including pp. 1/14-14/14 of Supplementary Material.
Maeder, "Targeted DNA demethylation and activation of endogenous genes using programmable TALE-TET1 fusion proteins," Nat Biotechnol, 2013, 31(12): 1137-42.
Mali et al., "Cas9 as a versatile tool for engineering biology," Nat Methods, 2013, 10(10): 957-63.
Mali et al., "CAS9 transcriptional activators for target specificity screening and paired nickases for cooperative genome engineering," Nat Biotechnol, 2013, 31(9): 833-8.
Mali et al., "RNA-Guided Human Genome Engineering via Cas9," Science, 2013, 339: 823-826.
Mamchaoui et al., "Immortalized pathological human myoblasts: towards a universal tool for the study of neuromuscular disorders," Skelet Muscle, 2011, 1: 1-11.
Mathews et al., "Expanded sequence dependence of thermodynamic parameters improves prediction of RNA secondary structure," Journal of Molecular Biology, 1999, 288(5): 911-940.
Mendell et al., "Dystrophin immunity in Duchenne's muscular dystrophy," New England Journal of Medicine, 2010, 363: 1429-1437.
Mendenhall et al., "Locus-specific editing of histone modification at endogenous enhancers," Nat Biotechnol, 2013, 31(12): 1133-6.
Mercer et al., "Regulation of Endogenous Human Gene Expression by Ligand-Inducible TALE Transcription Factors," ACS Synth Biol, 2013.
Miller et al., "A Tale nuclease architecture for efficient genome editing," Nat Biotechnol, 2011, 29: 143-148.
Moscou et al., "A simple cipher governs DNA recognitionby TAL effectors," Science, 2009, 326: 1501.
Murphy et al., "The in vitro transcription of the 7SK RNA gene by RNA polymerase III is dependable only on the presence of an upstream promoter," Cell, 1987, 51: 81-87.
Mussolino et al., "A novel TALE nuclease scaffold enables high genome editing activity in combination with low toxicity," Nucleic Acids Res, 2011, 39: 9283-9293.
Myslinski et al., "An unusually compact external promoter for RNA polymerase III transcription of the human H1RNA gene," Nucleic Acids Res, 2001, 29: 2502-2509.
Negroni et al., "In Vivo Myogenic Potential of Human CD133+ Muscle-derived Stem Cells: A Quantitative Study," Molecular Therapy, 2009, 17: 1771-1778.
Nishimasu et al., "Crystal structure ofcas9 in complex with guide RNA and target DNA," Cell, 2014, 156(5): 935-49.

Ohshima et al., "Nucleotide sequence of mouse genomic loci including a gene or pseudogene for U6 (4.85) nuclear RNA," Nucleic Acids Res, 1981, 9: 5145-5158.
Ousterout et al., "Reading frame correction by targeted genome editing restores dystrophin expression in cells from Duchenne muscular dystrophy patients," Mol Ther, 2013, 21: 1718-1726.
Paez-Espino et al., "CRISPR immunity drives rapid phage genome evolution in *Streptococcus thermophilus*," mBio, 2015, 6(2): e00262-15.
Palu et al. In pursuit of new developments for gene therapy of human diseases. J. Biotechnol., 1999, 68: 1-13.
Papayannakos et al., "Understanding lentiviral vector chromatin targeting: working to reduce insertional mutagenic potential for gene therapy," Gene Ther, 2013, 20(6): 581-8.
Park et al., "Phenotypic alteration of eukaryotic cells using randomized libraries of artificial transcription factors," Nat Biotechnol, 2003, 21: 1208-1214.
Pattanayak et al., "High-throughput profiling of off-target DNA cleavage reveals RNA-programmed Cas9 nuclease specificity," Nat Biotechnol, 2013, 31(9): 839-43.
Peault et al., "Stemand progenitor cells in skeletal muscle development, maintenance, and therapy," Molecular Therapy, 2007, 15: 867-877.
Penczek et al., "Three-dimensional reconstruction of single particles embedded in ice," Ultramicroscopy, 1992, 40, 33-53.
Perez et al., "Establishment of HIV-1 resistance in CD4+ T cells by genome editing using zinc-finger nucleases," Nature biotechnology, 2008, 26: 808-816.
Perez-Pinera et al., "Advances in targeted genome editing," Current Opinion in Chemical Biology, 2012, 16: 268-277.
Perez-Pinera et al., "Gene targeting to the ROSA26 locus directed by engineered zinc finger nucleases," Nucleic Acids Research, 2012, 40: 3741-3752.
Perez-Pinera et al., "RNA-guided gene activation by CRISPR-Cas9-based transcription factors," Nat Methods, 2013, 10: 973-976.
Perez-Pinera et al., "Synergistic and tunable human gene activationby combinations of synthetic transcription factors," Nat Methods, 2013, 10: 239-242.
Perez-Pinera et al., "Synergistic and tunable human gene activationby combinations of synthetic transcription factors," Nature Methods, 2013, 10(3): 239-244, including pp. 1/12-12-12 of Supplementary Material.
Perez-Pinera et al., "Synergistic Transcriptional Activationby Combinations of Engineered TALEs" presented at the American Society of Gene & Cell Therapy's 15th Annual Meeting in Philadelphia, Pennsylvania, May 19, 2012, Abstract 855.
Persons, "Lentiviral vector gene therapy: effective and safe?" Mol Ther, 2010, 18(5): 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23: 635-646.
Pichavant et al., "Current status of pharmaceutical and genetic therapeutic approaches to treat DMD," Molecular Therapy, 2011, 19: 830-840.
Pinello et al., "Analyzing CRISPR genome-editing experiments with CRISPResso," Nat Biotechnol, 2016, 34(7):695-697.
Polstein et al., "Light-inducible spatiotemporal control of gene activationby customizable zinc finger transcription factors," J Am Chem Soc, 2012, 134(40): 16480-3.
Popplewell et al., "Gene correction of a duchenne muscular dystrophy mutationby meganuclease-enhanced exon knock-in," Hum Gene Ther, 2013, 24: 692-701.
Qi et al., "Repurposing CRISPR as an RNA-guided platform for sequence-specific control of gene expression," Cell, 2013, 152: 1173-1183.
Ran et al., "Double nicking by RNA-guided CRISPR Cas9 for enhanced genome editing specificity," Cell, 2013, 154(6): 1380-9.
Ran et al., "Genome engineering using the CRISPR-Cas9 system," Nature Protocols, 2013, 8(11): 2281-2308.
Ratcliff et al., "A novel single-molecule study to determine protein-protein-protein association constants," Journal of the American Chemical Society, 2001, 123(24): 5632-5635.

(56) References Cited

OTHER PUBLICATIONS

Rebar et al., "Induction of angiogenesis in a mouse model using engineered transcription factors," Nat Med, 2002, 8: 1427-1432.
Reyon et al., "FLASH assembly of TALENs for high-throughput genome editing," Nat Biotechnol, 2012, 30: 460-465.
Rodriguez et al., "Clustering by fast search and find of density peaks," Science, 2014, 344(6191): 1492-1496.
Rousseau et al., "Endonucleases: tools to correct the dystrophin gene" The Journal of Gene Medicine, 2011, 13: 522-537.
Rutkauskas et al., "Directional R-loop formation by the CRISPR-Cas surveillance complex cascade provides efficient off-target site rejection," Cell reports, 2015, 10, 1534-1543.
Saito et al., "Specific activation of microRNA-127 with downregulation of the proto-oncogene BCL6 by chromatin-modifying drugs in human cancer cells," Cancer Cell, 2006, 9: 435-443.
Salmon et al., "Production and titration of lentiviral vectors," CurrProtoc Neurosci, 2006, Chapter 4: Unit 4 21.
SantaLucia et al., "Improved nearest-neighbor parameters for predicting DNA duplex stability," Biochemistry, 1996,35(11): 3555-3562.
Schmid-Burgk et al., "A ligation-independent cloning technique for high-throughput of transcription activator-like effector genes," Nat Biotechnol, 2012, 31: 76-81.
Scholze et al., "TAL effectors are remote controls for gene activation," Current Opinion in Microbiology, 2011, 14: 47-53.
Schreck et al., "DNA hairpins primarily promote duplex melting rather than inhibiting hybridization," 2014, arXiv preprint arXiv: 1408.4401.
Schreck et al., "DNA hairpins destabilize duplexes primarily by promoting melting rather than by inhibiting hybridization," Nucleic Acids Research, 2015, 43(13): 6181-6190.
Schultz et al., "Recombinant adeno-associated virus transduction and integration," Molecular Therapy, 2008, 16: 1189-1199.
Sebastiano et al., "In Situ Genetic Correction of the Sickle Cell Anemia Mutation in Human Induced Pluripotent Stem Cells Using Engineered Zinc Finger Nucleases," Stem Cells, 2011, 29: 1717-1726.
Seidel et al., "Chromatin-modifying agents in anti-cancer therapy," Biochimie, 2012, 94: 2264-2279.
Serra et al., "Predicting thermodynamic properties of RNA," Methods inEnzymology, 1995, 259: 242-261.
Seto et al., "Gene Replacement Therapies for Duchenne Muscular Dystrophy Using Adeno-Associated Viral Vectors," Current Gene Therapy, 2012, 12: 139-151.
Sharma et al., "Efficiency of nonho mologous DNA and joining varies among somatic tissues, despite similarity in mechanism," Cellular and Molecular Life Science, 2011, 68: 661-676.
Shlyakhtenko et al., "Silatrane-based surface chemistry for immobilization of DNA, protein-DNA complexes and other biological materials," Ultramicroscopy, 2003, 97: 279-287.
Silva et al., "Meganucleases and other tools for targeted genome engineering: perspective and challenges for gene therapy," Current gene therapy, 2011, 11: 11-27.
Şöllü et al., "Autonomous zinc-finger nuclease pairs for targeted chromosomal deletion," Nucleic acids research, 2010, 38: 8269-8276.
Song et al., "Dnase-seq: a high-resolution technique for mapping active gene regulatory elements across the genome from mammalian cells," Cold Spring Harbor protocols 2010, pdb prot5384.
Song et al., "Open chromatin defined by DNaseI and FAIRE identifies regulatory elements that shape cell-type identify," Genome Res, 2011, 21: 1757-1767.
Stemmer et al., "CCTop: An Intuitive, Flexible and Reliable CRISPR/Cas9 Target Prediction Tool," PLoS One, 2015, 10(4): e0124633.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sun et al., "Optimized TAL effector nucleases (TALENs) for use in treatment of sickle cell disease," Molecular bioSystems, 2012, 8: 1255-1263.
Sun et al., "Phage mutations in response to CRISPR diversification in a bacterial population," Environmental microbiology, 2013, 15(2): 463-470.
Szczelkun et al., "Direct observation of R-loop formation by single RNA-guided Cas9 and Cascade effector complexes," Proceedings of the National Academy of Sciences, 2014, 6 pages.
Szyf, "Epigenetics, DNA methylation, and chromatin modifying drugs," Annual Review of Pharmacology and Toxicology, 2009, 49: 243-263.
Taniguchi-Ikeda et al., "Pathogenic exon-trapping by SVA retro transposon and rescue in Fukuyama muscular dystrophy," Nature, 2011, 478: 127-131.
Tebas et al., "Gene editing of CCR5 in autologous CD4 T cells of persons infected with HIV," N Engl J Med, 2014, 370: 901-910.
Tedesco et al., "Repairing skeletal muscle: regenerative potential of skeletal muscle stem cells," J Clin Invest, 2010, 120: 11-19.
Tedesco et al., "Stem Cell-Mediated Transfer of a Human Artificial Chromosome Ameliorates Musculat Dystrophy," Science Translational Medicine, 2011, 3(96): 96ra78.
Tedesco et al., "Transplantation of Genetically Corrected Human iPSC-Derived Progenitors in Mice with Limb-Girdle Muscular Dystrophy," Science Translational Medicine, 2012, 4: 140ra189.
Tsai et al., "GUIDE-seq enables genome-wide profiling of off-target cleavage by CRISPR-Cas nucleases," Nature biotechnology, 2015, 33(2): 187-197.
Urnov et al., "Highly efficient endogenous human gene correction using designed zinc-finger nucleases," Nature, 2005, 435: 646-651.
Van Putten et al., "Low dystrophin levels in heart can delay heart failure in mdx mice," J Mol Cell Cardiol, 2014, 69C: 17-23.
Van Putten et al., "Low dystrophin levels increase survival and improve muscle pathology and function in dystrophin/utrophindouble-knockout mice," FASEB J, 2013, 27: 2484-2495.
Verma et al., "Gene Therapy: Twenty-first century medicine," Annual Review of Biochemistry, 2005, 74: 711-738.
Verma et al., "Gene therapy-promises, problems and prospects," Nature, 1997, 389: 239-242.
Vierbuchen et al., "Direct conversion of fibroblasts to functional neurons by defined factors," Nature, 2010, 463: 1035-1041.
Wang et al., "Adeno-associated virus vector carrying human minidystrophin genes effectively ameliorates muscular dystrophy in mdx mouse model," Proc Natl Acad Sci USA, 2000, 97(25): 13714-13719.
Wang et al., "One-Step Generation of Mice Carrying Mutations in Multiple Genes by CRISPR-Cas-Mediated Genome Engineering," Cell, 2013, 153(4): 910-8.
Wang et al., "Unbiased detection of off-target cleavage by CRISPR-Cas9 and TALENs using integrase-defective lentiviral vectors," Nature biotechnology, 2015, 33(2): 175-8.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wein et al., "Efficient bypass of mutations in dysferlin deficient patient cells by antisense-induced exon skipping," HumMutat, 2010, 31: 136-142.
Welch et al., "PTC124 targets genetic disorders caused by nonsense mutations," Nature, 2007, 447: 87-91.
Wiggins et al., "High flexibility of DNA on short length scales probed by atomic force microscopy," Nature nanotechnology, 2006, 1(2): 137-141.
Wu et al., "Genome-wide binding of the CRISPR endonuclease Cas9 in mammalian cells," Nature biotechnology, 2014, 32(7): 670-6.
Yan et al., "Drugging the Undruggable: Transcription Therapy for Cancer," Biochim Biophys Acta, 2013, 1835(1): 76-85.
Yang et al., "Determination ofprotein-DNA binding constants and specificities from statistical analyses of single molecules: MutS-DNA interactions," Nucleic acids research, 2005, 33(13): 4322-4334.
Yang et al., "Optimization of scarless human stemcell genome editing," Nucleic Acids Res, 2013, 41(19): 9049-9061.

(56) References Cited

OTHER PUBLICATIONS

Yin et al., "Programming biomolecular self-assembly pathways," Nature, 2008, 451(7176): 318-323.
Yusa et al., "Targeted gene correction of al-antitrypsin deficiency in induced pluripotent stem cells," Nature, 2011, 478: 391-394.
Zhang et al. "Efficient construction of sequence-specific TAL effectors for modulating mammalian transcription," Nat Biotechnol, 2011, 29: 149-153.
Zhu et al., "Cellular senescence in human telomerase reverse transcriptase and cyclin—dependent kinase 4: consequences in aging muscle and therapeutic strategies for muscular dystrophies," Aging cell, 2007, 6: 515-523.
Zou et al., "Site-specific gene correction of a point mutation in human iPS cells derived from an adult patient with sickle cell disease," Blood, 2011, 118: 4599-4608.
International Search Report and Written Opinion for Application No. PCT/US2016/048798 dated Feb. 27, 2017 (20 pages).
International Search Report and Written Opinion for Application No. PCT/US14/41190 dated Dec. 17, 2014 (14 pages).
Farasat, "Sequence-to-Function Models for Efficient Optimization of Metabolic Pathways and Genetic Circuits," Ph. D. Thesis, 2015, 254 pages.
Fu et al., Landscape of target: guide homology effects on Cas9-mediated cleavage, Nucleic Acids Research, 2014, 42 (22): 13778-13787.
Pykhozhij et al., "CRISPR MultiTargeter: A Web Tool to Find Common and Unique CRISPR Single Guide RNA Targets in a Set of Similar Sequences," PLoS One, 2015,10(3): e0119372.
Wiles et al., "CRISPR-Cas9 mediated genome editing and guide RNA design," Mammalian Genome, 2015, 26(9): 501-510.
European Patent Office Partial Supplementary Search Report for Application No. 16840171.9 dated Feb. 25, 2019 (20 pages).
Japanese Patent Office Action for Application No. 2018-510820 dated Sep. 23, 2020 (10 pages, English translation included).
Brazilian Patent Office Action for Application No. 112018003625-0 dated Nov. 10, 2020 (8 pages, English translation included).
Chinese Patent Office Action for Application No. 201680061639.8 dated Jul. 3, 2020 (8 pages, English translation included).
European Patent Office Action for Application No. 16840171.9 dated Aug. 17, 2020 (4 pages).
Israeli Patent Office Action for Application No. 257677 dated Apr. 29, 2021 (6 pages, English translation included).
Takeshima et al., "Mutation spectrum of the dystrophin gene in 442 Duchene/Becker muscular dystrophy cases from one Japanese referral center," Journal of Human Genetics, 2010, 55: 379-388.
Saudi Arabian Patent Office First Examination Report for Application No. 518390996 dated Jan. 27, 2021 (11 pages, English translation included).
European Patent Office Action for Application No. 16840171.9 dated Feb. 5, 2021 (4 pages).
Chinese Patent Office Action for Application No. 201680061639.8 dated Mar. 17, 2021 (17 pages).
O'Connell et al., "Programmable RNA recognition and cleavage by CRISPR/Cas9," Nature, 2014, 516: 263-266.
Dykeman, "An implementation of the Gillespie algorithm for RNA kinetics with logarithmic time update," Nucleic Acids Research, 2015, 45(12): 5708-5715.
Eurasian Patent Office Action for Application No. 201890565 dated Aug. 5, 2021 (9 pages, English translation included).
Saudi Arabian Patent Office Second Examination Report for Application No. 518390996 dated Aug. 30, 2021 (13 pages, English translation included).
Chinese Patent Office Action for Application No. 201680061639.8 dated Aug. 12, 2021 (10 pages, English translation included).
Arnold et al., "Genome-wide quantitative enhancer activity maps identified by STARR-seq," Science, 2013, 339(6123): 1074-1077.
Asokan et al., "The AAV Vector Toolkit: Poised at the Clinical Crossroads," Mol Ther, 2012, 20: 699-708.
Ayyanathan et al., "Regulated recruitment of HP1 to a euchromatic gene induces mitotically heritable, epigenetic gene silencing: a mammalian cell culture model of gene variegation," Genes Dev, 2003, 17: 1855-1869.
Bender et al., "Independent formation of DnaseI hypersensitive sites in the murine beta-globin locus control region," Blood, 2000, 95(11): 3600-3604.
Bernstein et al., "The NIH Roadmap Epigenomics Mapping Consortium," Nat Biotechnol, 2010, 28: 1045-1048.
Beverley, "Primer: making sense of T-cell memory," Nat. Clin Pract. Rheumatol., 2008, 4: 43-49.
Boshart et al., "A very strong enhancer is located upstream of an immediate early gene of human cytome galovirus," Cell, 1985, 41: 521-530.
Boyle et al., "High-resolution mapping and characterization of open chromatin across the genome," Cell, 2008, 132(2): 311-322.
Carrillo et al., "The Multiple Sequence Alignment Problem in Biology," SIAM J. Applied Math, 1988, 48: 1073.
Carter et al., "Long-range chromatin regulatory interactions in vivo," Nat Genet, 2002, 32: 623-626.
Chakraborty et al., "A CRISPR/Cas9-Based System for Reprogramming Cell Lineage Specification," Stem Cell Reports, 2014, 3: 940-947.
Chavez et al., "Comparison of Cas9 activators in multiple species," Nat Methods, 2016, 13: 563-67.
Chavez et al., "Highly efficient Cas9-mediated transcriptional programming," Nat Methods, 2015, 12: 326-328.
Chen et al., "Expanding the CRISPR imaging toolset with *Staphylococcus aureus* Cas9 for simultaneous imaging of multiple genomic loci," Nucleic Acids Research, 2016, 44(8): e75, 13 pages.
Chen et al., "Life and death of transcriptional co-activator p300," Epigenetics, 2011, 6: 957-961.
Chen et al., "Two upstream enhancers collaborate to regulate the spatial patterning and timing of MyoD transcription during mouse development," Dev Dyn, 2001, 221: 274-288.
Chew et al., "A multifunctional AAV-CRISPR-Cas9 and its host response," Nat Methods, 2016, 13: 868-874.
Choy et al., "Eukaryotic activators function during multiple steps of preinitiation complex assembly," Nature, 1993, 366:531-536.
Chu et al., "SV40 DNA transfection of cells in suspension: analysis of efficiency of transcription and translation of T-antigen," Gene, 1981, 13:197.
Cong et al., "Comprehensive interrogation of natural TALE DNA-binding modules and transcriptional repressor domains," Nat Commun, 2012, 3: 968.
Consortium, "An integrated encyclopedia of DNA elements in the human genome," Nature, 2012, 489: 57-74.
Crawford et al., "Genome-wide mapping of DNase hypersensitive sites using massively parallel signature sequencing (MPSS)," Genome Res, 2006, 16: 123-131.
Crocker et al., "TALE-mediated modulation of transcriptional enhancers in vivo," Nature Methods, 2013, 10: 762-767.
De Groote et al., "Epigenetic Editing: targeted rewriting of epigenetic marks to modulate expression of selected target genes," Nucleic Acids Res, 2012, 40(21): 10596-10613.
Dean et al., "Inducible transcription of five globin genes in K562 human leukemia cells," Proceedings of the National Academy of Sciences of the United States of America, 1983, 80: 5515-5519.
Deltcheva et al., "CRISPR RNA maturation by trans-encoded small RNA and host factor RNase III," Nature, 2011, 471(7340): 602-607.
Delvecchio et al., "Structure of the p300 catalytic core and implications for chromatin targeting and HAT regulation," Nat Struct Mol Biol, 2013, 20: 1040-1046.
Deng et al., "Reactivation of developmentally silenced globin genes by forced chromatin looping," Cell, 2014, 158: 849-860.
Dijkema et al., "Cloning and expression of the chromosomal immune interferon gene of the rat," Embo J., 1985, 4: 761-767.
Ding et al., "Permanent Alteration of PCSK9 Within Vivo CRISPR-Cas9 Genome Editing," Circulation Research, 2014, 115(5): 488-492.
Doench et al., "Optimized sgRNA design to maximize activity and minimize off-target effects of CRISPR-Cas9," Nat Biotechnol, 2016, 34: 184-191.

(56) References Cited

OTHER PUBLICATIONS

Dostie et al., "Chromosome Conformation Capture Carbon Copy (SC): a massively parallel solution for mapping interactions between genomic elements," Genome Research, 2006, 16: 1299-1309.
EBI Accession No. GSP: BCJ39961 (2016).
Egger et al., "Epigenetics in human disease and prospects for epigenetic therapy," Nature, 2004, 429: 457-463.
Ferretti et al., "Complete genome sequence of an M1 strain of *Streptococcus pyogenes*," Proc Natl Acad Sci US A, 2001, 98(8): 4658-4663.
Fine et al., "Trans-spliced Cas9 allows cleavage of HBB and CCR5 genes in human cells using compact expression cassettes," Sci Rep, 2015, 5: 10777.
Fontenot et al., "Regulatory Tcell lineage specification by the forkhead transcription factor foxp3," Immunity, 2005, 22: 329-341.
Gao et al., "Comparison of TALE designer transcription factors and the CRISPR/dCas9 in regulation of gene expression by targeting enhancers," Nucleic Acids Res, 2014, 42: e155.
Gao et al., "Reprogramming to Pluripotency Using Designer TALE Transcription Factors Targeting Enhancers," Stem Cell Reports, 2013, 1(2): 183-197.
Garriga-Canut et al., "Synthetic zinc finger repressors reduce mutant huntingtin expression in the brain of R6/2 mice," Proceedings of the National Academy of Sciences of the United States of America, 2012, 109: E3136-E3145.
Gersbach et al., "Activating human genes with zinc finger proteins, transcription activator-like effectors and CRISPR/Cas9 for gene therapy and regenerative medicine," Expert Opin Ther Targets, 2014, 18(8): 835-839.
Gersbach, "Genome engineering: the next genomic revolution," Nat Methods, 2014, 11: 1009-1011.
Gerstein et al., "Architecture of the human regulatory network derived from ENCODE data," Nature, 2012, 489: 91-100.
Gilbert et al., "Genome-Scale CRISPR-Mediated Control of Gene Repression and Activation," Cell, 2014, 159: 647-661.
Gorman et al., "The Rous sarcoma virus long terminal repeat is a strong promoter when introduced into a variety of eukaryotic cells by DNA-mediated transfection," Proc. Natl. Acad. Sci. U.S.A., 1982, 79: 6777.
Graham et al., "A new technique for the assay of infectivity of human adenovirus 5 DNA," Virol., 1973, 52: 456-467.
Grimmer et al., "Analysis of an artificial zinc finger epigenetic modulator: widespread binding but limited regulation," Nucleic Acids Research, 2014, 42: 10856-10868.
Groner et al., "KRAB-zinc finger proteins and KAPf can mediate long-range transcriptional repression through heterochromatin spreading," PLoS Genet, 2010, 6: e1000869.
Hamar et al., "Small interfering RNA targeting Fas protects mice against renal ischemia-reperfusion injury," PNAS, 2004, 101: 14883-14888.
Hardison et al., "Locus control regions of mammalian beta-globin gene clusters: combining phylogenetic analyses and experimental results to gain functional insights," Gene, 1997, 205: 73-94.
Hathaway et al., "Dynamics and memory of heterochromatin in living cells," Cell, 2012, 149: 1447-1460.
Heintzman et al., "Distinct and predictive chromatin signatures of transcriptional promoters and enhancers in the human genome," Nat Genet, 2007, 39: 311-318.
Hotta et al., "Isolation of human iPS cells using EOS lentiviral vectors to select for pluripotency," Nat Methods, 2009, 6: 370-376.
Hu et al., "Direct activation of human and mouse Oct4 genes using engineered TALE and Cas9 transcription factors," Nucleic Acids Res, 2014, 42: 4375-4390.
Ikonomi et al., "Levels of GATA-1/GATA-2 transcription factors modulate expression of embryonic and fetal hemoglobins," Gene, 2000, 261: 277-287.
Ji et al., "Engineered zinc-finger transcription factors activate OCT4 (POU5FI), SOX2, KLF4, c-MYC (MYC) and miR302/367," Nucleic Acids Res, 2014, 42: 6158-6167.
Jorg, "Engineering of the epigenome: synthetic biology to define functional causality and develop innovative therapies," Epigenomics, 2016, 8(2): 153-156.
Kabadi et al., "Multiplex CRISPR/Cas9-based genome engineering from a single lentiviral vector," Nucleic Acids Res, 2014, 42(19): e147.
Kearns et al., "Functional annotation of native enhancers with a Cas9-histone demethylase fusion," Nat Methods, 2015, 12(5): 401-403.
Keung et al., "Using targeted chromatin regulators to engineer combinatorial and spatial transcriptional regulation," Cell, 2014, 158: 110-120.
Khoury et al., "Efficient new cationic liposome formulation for systemic delivery of small interfering RNA silencing tumor necrosis factor a in experimental arthritis," Arthritis Rheumatol, 2006, 54: 1867-1877.
Kim et al., "Use of the human elongation factor la promoter as a versatile and efficient expression system," Gene, 1990, 91: 217.
Kim et al., "A Histone acetylation contributes to chromatin looping between the locus control region and globin gene by influencing hypersensitive site formation," Biochim Biophys Acta, 2013, 1829: 963-969.
Konermann et al., "Genome-scale transcriptional activation by an engineered CRISPRCas9 complex," Nature, 2015, 517:583-588.
Kotin, "Prospects for the use of adeno-associated virus as a vector for human gene therapy," Hum Gene Ther, 1994, 5: 793-801.
Kuscu et al., "Genome-wide analysis reveals characteristics of off-target sites bound by the Cas9 endonuclease," Nat Biotechnol, 2014, 32(7): 677-683.
La Russa et al., "The New State of the Art: Cas9 for Gene Activation and Repression," Molecular and Cellular Biology, 2015, 35(22): 3800-3809.
Landen et al., "Intraperitoneal delivery of liposomal siRNA for therapy of advanced ovarian cancer," Cancer Biol. Ther., 2006, 5(12): 1708-1713.
Langmead et al., "Fast gapped-read alignment with Bowtie 2," Nature methods, 2012, 9: 357-359.
Lee et al., "Role of satellite cells versus myofibers in muscle hypertrophy induced by inhibition of the myostatin/activin signaling pathway," Proc Natl Acad Sci US A, 2012, 109(35): E2353-E2360.
Lee, "Regulation of muscle mass by myostatin," Annu Rev Cell Dev Biol, 2004, 20: 61-86.
Li et al., "The role of chromatin during transcription," Cell, 2007, 128: 707-719.
Li et al., "Extensive promoter-centered chromatin interactions provide a topological basis for transcription regulation," Cell, 2012, 148: 84-98.
Li et al., "The Sequence Alignment/Map format and SAMtools," Bioinformatics, 2009, 25: 2078-2079.
Li et al., "Locus control regions," Blood, 2002, 100: 3077-3086.
Love et al., "Moderated estimation of fold change and dispersion for RNA-seq data with DESeq2," Genome Biology, 2014, 15: 550.
Magnenat et al., "In vivo selection of combinatorial libraries and designed affinity maturation of poly dactyl zinc finger transcription factors for ICAM-1 provides new insights into gene regulation," J Mol Biol, 2004, 341: 635-649.
Maniatis et al., "Regulation of inducible and tissue-specific gene expression," Science, 1987, 236: 1237.
Matsushita et al., "Adeno-associated virus vectors can be efficiently produced without helper virus," Gene Therapy, 1998, 5: 938.
McCarty et al, "Self-complementary recombinant adeno-associated virus (scAAV) vectors promote efficient transduction independently of DNA synthesis," Gene Ther, 2001, 8: 1248-1254.
McDowell et al., "A Structural and functional cross-talk between a distant enhancer and the epsilonglobin gene promoter shows interdependence of the two elements in chromatin," Molecular and Cellular Biology, 1999, 19: 7600-7609.
Memedula et al., "Sequential recruitment of HAT and SWI/SNF components to condensed chromatin by VP16," CurrBiol, 2003, 13: 241-246.
Mittler et al., "A novel docking site on Mediator is critical for activation by VP16 in mammalian cells," J, 2003, 22: 6494-6504.

(56) References Cited

OTHER PUBLICATIONS

Mizushima et al., "pEF-BOS, a powerful mammalian expression vector," Nucl. Acids. Res., 1990, 18: 5322.
Morrissey et al., "Activity of stabilized short interfering RNA in a mouse model of hepatitis B virus replication," Hepatol, 2005, 41: 1349-1356.
Muzycka, "Use of adeno-associated virus as a general transduction vector for mammalian cells," Curr. Top. Microbiol. Inmunol., 1992, 158: 97-129.
Nelson et al., "In vivo genome editing improves muscle function in a mouse model of Duchenne muscular dystrophy," Science, 2016, 351: 403-407.
Nissim et al., "Multiplexed and Programmable Regulation of Gene Networks with an Integrated RNA and CRISPR/Cas Toolkit in Human Cells," Mol Cell, 2014, 54: 698-710.
Nordhoff et al., "Comparative analysis of human, bovine, and murine Oct-4 upstream promoter sequences," Mamm Genome, 2001, 12: 309-317.
Ogryzko et al., "The transcriptional coactivators p300 and CBP are histone acetyltransferases," Cell, 1996, 87: 953-959.
Okkenhaug et al., "PI3K in lymphocyte development, differentiation and activation," Nat. Rev. Immunol., 2003, 3(4): 317-330.
Ong et al., "Enhancer function: new insights into the regulation of tissue-specific gene expression," Nature reviews. Genetics, 2011, 12: 283-293.
Osakabe et al., "FLAG-NLS-SpCas9-2A-GFBSD2 [Binary vector pEgP526-2A-GFBSD2]," National Center for Biotechnology Information, Genbank Entry, Retrieved from the Internet on Sep. 18, 2017 <https://www .ncbi.nlmnih gov/protein/BAVO1234>.
Polstein et al., "Genome-wide specificity of DNA-binding, gene regulation, and chromatin remodeling by TALE- and CRISPR/Cas9-based transcriptional activators," Genome Res, 2015, 25(8): 1158-1169.
Quinlan et al., "BEDTools: a flexible suite of utilities for comparing genomic features," Bioinformatics, 2010, 26: 841-842.
Rada-Iglesias et al., "A unique chromatin signature uncovers early developmental enhancers in humans," Nature, 2011, 470:279-283.
Rahdar et al., "Synthetic CRISPR RNA-Cas9-Guided Genome Editing in Human Cells," Proceedings to the National Academy of Sciences of USA, 2015, 112(51): E7110-E7117.
Ran et al., "In vivo genome editing using Staphylococcus aureus Cas9," Nature, 2015, 520: 186-191.
Reynolds et al., "NuRD-mediated deacetylation of H3K27 facilitates recruitment of Polycomb Repressive Complex 2 to direct gene repression," The EMBO Journal, 2012, 31: 593-605.
Riley, "PD-1 signaling in primary T cells," Immunological Reviews, 2009, 229: 114-125.
Rivenbark et al., "Epigenetic reprogramming of cancer cells via targeted DNA methylation." Epigenetics, 2012, 7: 350-360.
Schultz et al., "SETDBI: a novel KAP-1-associated histone H3, lysine 9-specific methyltransferase that contributes to HP1-mediated silencing of euchromatic genes by KRAB zinc-finger proteins," Genes & Development, 2002, 16: 919-932.
Smith et al., "Myostatin inhibitors as therapies for muscle wasting associated with cancer and other disorders," Curr Opin Support Palliat Care, 2013, 7: 352-360.
Snowden et al., "Gene-specific targeting of H3K9 methylation is sufficient for initiating repression in vivo," Curr Biol, 2002, 12: 2159-2166.
Soutschek et al., "Therapeutic silencing of an endogenous gene by systemic administration of modified siRNAs," Nature, 2004, 432: 173-178.
Spitz et al., "Transcription factors: from enhancer binding to developmental control," Nat. Rev. Genet., 2012, 13: 613-626.
Sripathy et al., "The KAP1 corepressor functions to coordinate the assembly of de novo HP1-demarcated microenvironments of heterochromatin required for KRAB zinc finger protein-mediated transcriptional repression," Molecular and Cellular Biology, 2006, 26: 8623-8638.
Sternberg et al., "Conformational Control of DNA Target Cleavage by CRISPR-Cas9," Nature, 2015, 527(7576): 110-113.
Sternberg et al., "DNA interrogation by the CRISPR RNA-guided endonuclease Cas9," Nature, 2014, 507: 62-67.
Su et al., "In vitro and in vivo mRNA delivery using lipid-enveloped pH-responsive polymer nanoparticles," Mol. Pharmaceutics, 2011, 8: 774-787.
Su et al., "Identification of biologically relevant enhancers in human erythroid cells," J Biol Chem, 2013, 288: 8433-8444.
Tabebordbar et al., "In vivo gene editing in dystrophic mouse muscle and muscle stem cells," Science, 2016, 351:407-411.
Takahashi et al., "Induction of pluripotent stem cells from adult human fibroblasts by defined factors," Cell, 2007, 1131: 861-872.
Tanenbaum et al., "A Protein-Tagging System for Signal Amplification in Gene Expression and Fluorescence Imaging," Cell, 2014, 159(3): 635-646.
Thakore et al., "Editing the epigenome: technologies for programmable transcription and epigenetic modulation," Nat Methods, 2016, 13: 127-137.
Thakore et al., "Highly specific epigenome editing by CRISPR-Cas9 repressors for silencing of distal regulatory elements," Nat Methods, 2015, 12: 1143-1149.
Thakore et al., "RNA-guided transcriptional silencing in vivo with S. aureus CRISPR-Cas9 repressors," Nature Communications, 2018, 9(1): 1674, 9 pages.
Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," Virol., 1994, 204: 304-311.
Thurman et al., "The accessible chromatin landscape of the human genome," Nature, 2012, 489: 75-82.
Tone et al., "Smad3 and NFAT cooperate to induce Foxp3 expression through its enhancer," Nat. Immunol., 2008, 9: 194-202.
Truong et al., "Development of an intein-mediated split-Cas9 system for gene therapy," Nucleic Acids Res., 2015, 43: 6450-6458.
Tuan et al., "Transcription of the hypersensitive site HS2 enhancer in erythroid cells," Proceedings of the National Academy of Sciences of the United States of America, 1992, 89: 11219-11223.
Uchida et al., "In Vivo Messenger RNA Introduction into the Central Nervous System Using Polyplex Nanomicelle," PLoS ONE, 2013, 8: e56220.
Uetsuki et al., "Isolation and characterization of the human chromosomal gene for polypeptide chain elongation factor-I alpha," J. Biol. Chem., 1989, 264: 5791.
Vakoc et al., "Proximity among distant regulatory elements at the beta-globin locus requires GATA-1 and FOG-1," Molecular Cell, 2005, 17: 453-462.
Visel et al., "ChIP-seq accurately predicts tissue-specific activity of enhancers," Nature, 2009, 457: 854-858.
Voss et al., "The role of enhancers in the regulation of cell-type-specific transcriptional control," Trends Biochem Sci., 1986, 11: 287.
Wagner et al., "A phase I/II trial of MYO-029 in adult subjects with muscular dystrophy," Ann Neurol, 2008, 63: 561-571.
Wang et al., "Efficient delivery of genome-editing proteins using bioreducible lipid nanoparticles," Proc Natl Acad Sci USA, 2016, 113(11): 2868-2873.
Wang et al., "Epstein-Barr virus nuclear protein 2 interacts with p300, CBP, and PCAF histone acetyltransferases inactivation of the LMP1 promoter," Proc Natl Acad Sci USA, 2000, 97: 430-435.
Wang et al., "Genome-wide mapping of HATs and HDACs reveals distinct functions inactive and inactive genes," Cell, 2009, 138: 1019-1031.
Whisstock et al., "Prediction of protein function from protein sequence," Q Rev Biophysics, 2003, 36(3): 307-340.
Youngblood et al., "Chronic virus infection enforces demethylation of the locus that encodes PD-1 in antigen-specific CD8 T cells," Immunity, 2011, 35: 400-412.
Zhang et al., "Adenovirus-Adeno-Associated Virus Hybrid for Large-Scale Recombinant Adeno-Associated Virus Production," Hum Gene Ther, 2009, 20: 922-929.
Zhang et al., "Model-based analysis of ChIP-Seq (MACS)," Genome Biology, 2008, 9: R137.

(56) References Cited

OTHER PUBLICATIONS

Zheng et al., "Role of conserved non-coding DNA elements in the Foxp3 gene in regulatory T-cell fate," Nature, 2010, 463: 808-812.
Zhou et al., "High-throughput screening of a CRISPR/Cas9 library for functional genomics in human cells," Nature, 2014, 509(7501): 487-491.
Zincarelli et al., "Analysis of AAV serotypes 1-9 mediated gene expression and tropism in mice after systemic injection," Mol Ther, 2008, 16: 1073-1080.
India Patent Office Examination Report for Application No. 201837008261 dated Mar. 9, 2022 (6 pages).

* cited by examiner

| Lane | | SEQ ID NO: |
|---|---|---|
| 3 | EJ-VEGF1-1_S | G TTCAC TTCG GGGTGGGGGAGTTTGCTCC | 296 |
| 4 | EJ-VEGF1-2_S | G TTCA TTCG GGGTGGGGGAGTTTGCTCC | 297 |
| 5 | EJ-VEGF1-3_S | G TCC TTCG GGGTGGGGGAGTTTGCTCC | 298 |
| 6 | EJ-VEGF1-4_S hairpin1 | G CTTCC TTCG GGGTGGGGGAGTTTGCTCC | 299 |
| 7 | EJ-VEGF1-5_S | G TTCC TTCG GGGTGGGGGAGTTTGCTCC | 300 |
| 8 | EJ-VEGF1-6_S | G CTCC TTCG GGGTGGGGGAGTTTGCTCC | 301 |

FIG. 31B

| Lane | | | SEQ ID NO: |
|---|---|---|---|
| 3 | EJ-VEGF3-1_S hp1 | G CACG TTCG GGTGAGTGAGTGTGTGCGTG | 309 |
| 4 | EJ-VEGF3-2_S hp2 | G TACG TTCG GGTGAGTGAGTGTGTGCGTG | 310 |
| 5 | EJ-VEGF3-3_S hp3 | G CATG TTCG GGTGAGTGAGTGTGTGCGTG | 311 |
| 6 | EJ-VEGF3-4_S | G TATG TTCG GGTGAGTGAGTGTGTGCGTG | 312 |
| 7 | EJ-VEGF3-5_S | G CGCG TTCG GGTGAGTGAGTGTGTGCGTG | 313 |
| 8 | EJ-VEGF3-6_S | G CGTG TTCG GGTGAGTGAGTGTGTGCGTG | 314 |

| | | | |
|---|---|---|---|
| Full | 22.17609557 | Full | 23.44021291 |
| EJ1 | 14.62010307 | EJ7 | 12.8315672 |
| EJ2 | 17.96688778 | EJ8 | 16.5260316 |
| EJ3 | 15.45320881 | EJ9 | 14.90816768 |
| EJ4 | 18.09621804 | EJ10 | 15.88223119 |
| EJ5 | 0 | EJ11 | 16.7829789 |
| EJ6 | 11.03398795 | EJ12 | 10.77677544 |

FIG. 39B

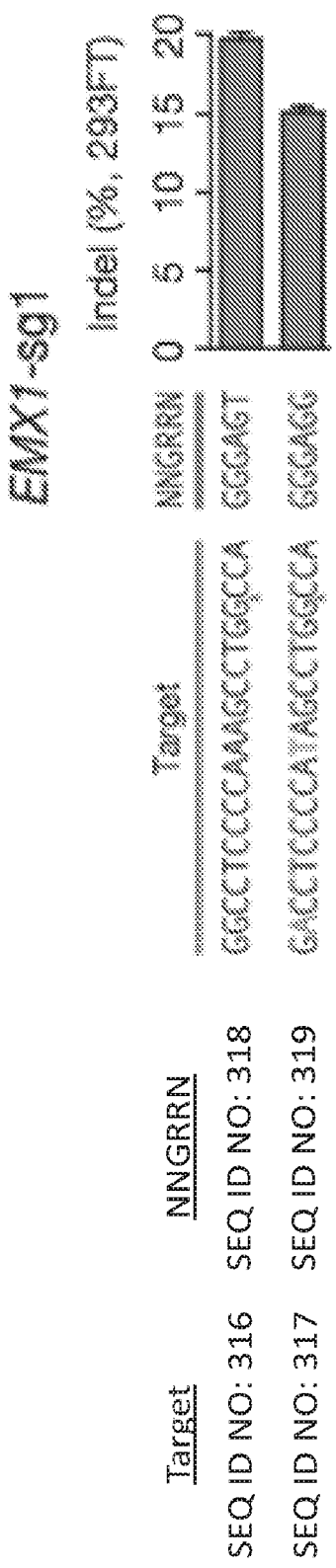

PAM sites labeled in YELLOW (for simplicity, only CCT PAM sites which match the PAM in the native AAVS1 target are labeled); sequences complementary to the protospacer labeled in BLACK, and sequences mismatched to protospacer sequences highlighted in ▨.

*sgRNA* (SEQ ID NO: 6):
GGGGCCACTAGGGACACGGAUguuuuagagcuagaaauaagcaaguuaaaauaaggcuagucccguuaucaacu
ugaaaaaguggcaccgagucggugcuuuu

*tru-gRNA* (SEQ ID NO: 7):
GGCCACTAGGGACACGGAUguuuuagagcuagaaauaagcaaguuaaaauaaggcuagucccguuaucaacuuga
aaaaguggcaccgagucggugcuuuu

*hp6-gRNA* (SEQ ID NO: 8):
ggGGCCCCuucgGGGGCCACTAGGGACACGGAUguuuuagagcuagaaauaagcaaguuaaaauaaggc
uaguccguuaucaacuugaaaaaguggcaccgagucggugcuuuu

*hp10-gRNA* (SEQ ID NO: 9):
ggUAGUGGCCCCuucgGGGGCCACTAGGGACACGGAUguuuuagagcuagaaauaagcaaguuaaaa
uaaggcuagucccguuaucaacugaaaaaguggcaccgagucgggugcuuuu

FIG. 45A

*AAVS1-derived substrate* (SEQ ID NO: 10):
CCAggatcagtgaaacgcaCCAgacagcccgtcagagcagctcaggttcTGGgagaggtagcgcaggTGGcCCAact
gagaaccgggcaggtcacgcatccccccttccctcCCAccccctgCCAagctctcctcCCAggatcctctcTGGctCCAt
cgtaagcaaacctagaggttcTGGctCCAggaaaTGGgggtgtgtcaCCAgataaggaatctg
cctaacaggaggTGGgggttagacCCAatatcaggagactaggaaggaggaggcctaaggaTGGggcttttctgtcaCCAt
<mark>TCTTGTCTCTAGTTGCCC</mark>actgTGGtCCAggTGGgaggggacacagattaaaagtacCCAgaaCCAgagCCAac
attaaccggcccTGGgaatatataaggTGGtCCAgctcgggacacaggatcccTGGgaggcagcaaacatgtgtcctgaag
TGGacataggggcccgggtTGGaggaagaagactagctgagctcTGGaagatgCCAtgacaggggcTG
GaagagctagcacagactagagaggtaagggggtagggagctgcCCAaatgaaaggagtgagaggtgacccgaatCCAc
aggagaacgggtgtCCAggaagaaagcaaggaTGGgaggTGGctaaaaCCAgggagacgggtactTGG
ggttgtCCAgaaaaacgtgatgatgcaggcctacaagaaaggggaggcgggacgcaagggagacatccgtcggagaaggCCAt
cctaagaaacgagaTGGcacaggccCCAgaaggaaggaaaaggaaaCCAgcgagtgaagacgcaTGGggtT
GCgtgaggaggagagatgccccggagaggacCCAgacacacgggggaggatccgtcagagagccgtcagagagagagagagacatcacgTGGagcagcgcg
agaaggaagtgctccggaaagagcatcctTGGgcagcaacacagagaggagcaagggaagaagagggagTGGgagcagaacgga
acctgaaggagccggcaggccaaggatcTGGgcCCAgccgtagaggtgacCCAgCCAcaagctgcagacagaaagcggc
acaagcCCAgggagaagaatgcaggtcaggtcagagaaagcaggaagcaggacctgccTGGgaagggaaacagTGGgtCCAgagggggc
gcagaagCCAgtagagctc

FIG. 45B

*Engineered substrate (SEQ ID NO. 11):* catgacgtgcagcaagcgcgctgacgcagcgcagctaatttatctatgtcttcgtcataacgtgatgcatatactctctgctagctgactcattcagctg
tactcactcgctgttgagtctcatacagcgcgagatcaaatgagtcatCCAATCGTCCCATGCCCGatcgtg
acactgcactgcagcgtacgcgacagagctagactcgtttcaatacagactagctactgcgtctgcagagcgctctcttgtcacttacatcg
aagtcaacgcgctcgcgttcagagatcttctCCAATGCTXXXXXXXXXcgctctcagcgtttgtgtctgtgc
gcgcacacagtctgtgctcgcttgcaactaaacgtagcgcttcagcgcatcgtcaaagagcgaaagagtcacagtgtctgttcacgtctct
atctttctagttctCCAATCGTCCCXXXXXXXXaagacagagtttcgcgaattcgcagcagcgcgatctctgct
cactgcaatctctgactgctgttttaagcaattctcgcagctcagcatgatgagtacttgcattacagcagcatgtctgCCAATCGTG
XXXXXXXXgcagcgtcagcagagctgatgagagtgcagcatcgcagacgcatcgcagagaagcacgaacgagcatctgta
gaaaatcgatcgacgcgcacttgcagagacaCCAXXXXXXXXXXXXcttgtctctcgttcgcatcaag
acacgctatttctgtctcttaaatgtttcaaaaacacacatcatgtcttcttcgtgcgaaagtaaagatatcgttcattcgagagacagagctagtct
CCTTAGCCCtgactctctgtcatttttgagctgcgaaagtaaagatatcgttcattcgagagacagagctagtct
cagttcttgcactgcctctcgatgctctcttagtgattcagcgcatcgtcg

FIG. 45C

"Nonsense" substrate (SEQ ID NO: 12):

gacctgcaggcatgcaagctTGGgctagcggagagtcagttcgcggtacTGGgaggaggcggcaacgtcgCCAgctgtctg
cacaggagaatccctgcTGGcgcataaagatgagacgcTGGagtacaaacgCCAgcTGGctgcactTGGcgacaagg
ttacgtatcaggagcgcctgaacgcgcTGGcgcagcaggcggataaattcgcacagcagcagcagcgggcaaaacgggccgCCAttg
atgcgaaaagccgggggctgactgaatacgtcatgtcagagcagagaaaaagaccTGGcggctgaagaCCAgcttcgcgggaacTGGaTG
ccgcTGGcgctgaataacgtcatgtcagagcagagaaaaagaccTGGcggctgaagaCCAgcttcgcgggaacTGGaTG
GcaggcctgaagtccggTGGCCATGGgctgaggCCAgctgaggtaccgctgaggattgctgaggtgtacagacgctcaa
gtcagaggTGGcgagagctcccggagTGGctcacagtcggTGGtccggcagtacaaTGGattacgtaagacggaaatcac
tcccgggtatatgaaagagacgaCCActgCCAgggacgaaagtgcaatgcggcatacctcagTGGCcgTGGagtgcaggtat
acagattaatccggcagctcgtcgttgatattgcttatgaaggctccggacagTGGcgacTGGcgtactgacgattcatcgtT
GCggtcggttataattctgattagCCAggtaacacagtgttatgacacggcacaggaaaaccgtacagaaactgcaCCAttcagctgaaagCCAgacgt
aTGGcagtaaacTGGcagttcaggagtcctgaaagtcctgaaagatccgaaagctgaCCAttcagctgaaagCCAgacgt
aacagcaCCAcggTGGTGGctgaacacggTGGgtcagagaatccggatgaagccgggcggttacagcaTGGatgTGG
agtacggtcagtacagtgtcatcctgcaggtgacggtttCCACCAtcgcacgccgggaCCAtcaccgtgtatgaagattcacaaac
cggggacgctg

FIG. 45D

COMPOSITIONS AND METHODS OF IMPROVING SPECIFICITY IN GENOMIC ENGINEERING USING RNA-GUIDED ENDONUCLEASES

CROSS-REFERENCE TO RELATED APPLICATIONS

This application is a national stage filing under 35 USC. § 371 of International Patent Application No. PCT/US2016/048798 Which claims priority to U.S. Provisional Application No. 62/209,466, filed Aug. 25, 2015, which are incorporated herein by reference in their entirety.

STATEMENT OF GOVERNMENT INTEREST

This invention was made with Government support under Federal Grant Nos. MCB1244297 and CBET1151035 awarded by the National Science Foundation and F32GM11250201, R01DA036865, and DP20D008586 awarded by the National Institutes of Health. The Government has certain rights to this invention.

SEQUENCE LISTING

The instant application includes a Sequence Listing which has been submitted electronically in ASCII format and is hereby incorporated by reference in its entirety. Said ASCII copy, created on Oct. 12, 2016, is named 028193-9240-WO00_SL.txt and is 149,501 bytes in size.

TECHNICAL FIELD

The present disclosure is directed to optimized guide RNAs (gRNAs) and methods of designing and using said gRNAs that have increased target binding specificity and reduced off-target binding.

BACKGROUND

RNA-guided endonucleases, notably the protein Cas9, have been hailed as a potential "perfect genomic engineering tool" because they can be directed by a single 'guide RNA' molecule to cut DNA with nearly any sequence. This ability has been recently exploited for a number of emerging biological and medical applications, generating tremendous excitement and promise for their future use. However, practical genomic engineering requires extremely precise control over the ability to target selectively and cut precise DNA sequences, lest off-target DNA become inadvertently damaged and mutated.

Cas9 is the endonuclease of the prokaryotic type II CRISPR (clustered, regularly interspaced, short palindromic repeats)—CRISPR-associated (Cas) response to invasive foreign DNA. During this response, Cas9 is first bound by a CRISPR RNA (crRNA): trans-activating crRNA (tracrRNA) duplex, and then directed to cleave DNA that contain 20 basepair (bp) 'protospacer' sites complementary to a variable 20 bp segment of the crRNA (FIG. 1A). Having bound a single-guide RNA (sgRNA), the Cas9-sgRNA complex binds to 20 bp 'protospacer' sequences in targeted DNA, provided that the protospacer is directly followed by a protospacer adjacent motif (PAM, here 'TGG'). Following binding, the Cas9 endonuclease produces double-strand breaks (triangles) within the protospacer. Essentially, the only constraint on sequences that Cas9 can target is that a short protospacer adjacent motif (PAM), such as 'NGG' in the case of *S. pyogenes* Cas9, must immediately follow the protospacer sites in the foreign DNA molecule. An analysis of crystallographic and biochemical experiments suggests that specificity in protospacer binding and cleavage is imparted first through the recognition of PAM sites by Cas9 protein itself, followed by strand invasion by the bound RNA complex and direct Watson-Crick base-pairing with the protospacer (FIG. 1A).

Cas9's ability to be modularly 'programmed' by a single RNA hairpin to target nearly any DNA site has recently generated tremendous excitement after CRISPR-Cas9 systems were re-appropriated for a number of heterologous biotechnological applications. Notably, a single-guide RNA (sgRNA) hairpin has been designed which combine the essential components of crRNA: tracrRNA duplexes into single functional molecules. With this sgRNA, Cas9 can be introduced into a variety of organisms to produce targeted double strand breaks in vivo for remarkably facile genomic engineering. Nuclease-null Cas9 (D10A/H840A, known as 'dCas9') and chimeric dCas9 derivatives have also been used to alter gene expression via targeted binding at or near promoter sites in vivo as well as to introduce targeted epigenetic modifications.

Off-target binding and cleavage by Cas9 is a concern as it can adversely affect its potential uses in practice. Significant efforts have been made to improve specificity of Cas9/dCas9 activity. First, the most widespread effort is largely accomplished through intelligent selection of target sequences without similar other sequences in the genome, although a recent survey found that these methods performed poorly in their ability to predict off-target cleavage. Additionally, efforts have also been made to directly engineer the protein itself, through introduction of point mutations which were found to modulate or increase specificity in PAM or protospacer binding. Cas9 derivatives which only nick a single strand of DNA rather than perform double stranded DNA cleavage are also used in pairs ('paired nickases'), with the assumption that the probability that off-target nicking at multiple sites that are close enough to each other to produce a double-strand break would be extremely rare. Finally, there has been some work in producing guide RNA variants themselves in an attempt to achieve greater specificity. Earlier efforts where 5'-extensions to guide RNAs were added in order to complement additional nucleotides beyond the protospacer did not show increased Cas9 cleavage specificity in vivo. Rather, they were digested back approximately to their standard length in living cells (FIG. 1A). For applications in genomic engineering, particularly for therapeutic applications, extreme specificity in the gene targeting is required, lest off-target DNA be damaged and unauthorized mutations occur. However, there have been several reports of off-target binding and cleavage by Cas9, which can adversely affect its potential uses in practice.

There remains a need for reducing off-target binding and increasing nuclease specificity using the CRISPR/Cas9 system.

SUMMARY OF THE INVENTION

The present invention is directed to a method of generating an optimized guide RNA (gRNA). The method comprises: a) identifying a target region of interest, the target region of interest comprising a protospacer sequence; b) determining a polynucleotide sequence of a full-length gRNA that targets the target region of interest, the full-length gRNA comprising a protospacer-targeting sequence or segment; c) determining at least one or more off-target sites for the full-length gRNA; d) generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment is at the 5' end of the polynucleotide sequence of the full-length gRNA, the first gRNA optionally comprising a linker between the 5' end of the polynucleotide sequence of the full-length gRNA and the RNA segment, the linker comprising a polynucleotide sequence having a length of N nucleotides, the first gRNA capable of invading the protospacer sequence and binding to a DNA sequence that is complementary to the protospacer sequence and forming a protospacer-duplex, and the first gRNA capable of invading an off-target site and binding to a DNA sequence that is complementary to the off-target site and forming an off-target duplex; e) calculating an estimate or computationally simulating the invasion kinetics and lifetime that the first gRNA remains invaded in the protospacer and off-target site duplexes, wherein the dynamics of invasion are estimated nucleotide-by-nucleotide by determining the energetic differences between further invasion of a different gRNA and re-annealing of the first gRNA to the DNA sequence that is complementary to the protospacer sequence; f) comparing the estimated lifetimes at the protospacer and/or off-target sites of the first gRNA with the estimated lifetimes of the full-length gRNA or a truncated gRNA (tru-gRNA) at the protospacer and/or off-target sites; g) randomizing 0 to N nucleotides in the linker and 0 to M nucleotides in the first gRNA and generating a second gRNA and repeating step (e) with the second gRNA; h) identifying an optimized gRNA based on a gRNA sequence that satisfy a design criteria; and i) testing the optimized gRNA in vivo to determine the specificity of binding.

The present invention is directed to a method of generating an optimized guide RNA (gRNA). The method comprises: a) identifying a target region of interest, the target region of interest comprising a protospacer sequence; b) determining a polynucleotide sequence of a full-length gRNA that targets the target region of interest, the full-length gRNA comprising a protospacer-targeting sequence or segment; c) determining at least one or more off-target sites for the full-length gRNA; d) generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment is at the 3' end of the polynucleotide sequence of the full-length gRNA, the first gRNA optionally comprising a linker between the 3' end of the polynucleotide sequence of the full-length gRNA and the RNA segment, the linker comprising a polynucleotide sequence having a length of N nucleotides, the first gRNA capable of invading the protospacer sequence and binding to a DNA sequence that is complementary to the protospacer sequence and forming a protospacer-duplex, and the first gRNA capable of invading an off-target site and binding to a DNA sequence that is complementary to the off-target site and forming an off-target duplex; e) calculating an estimate or computationally simulating the invasion kinetics and lifetime that the first gRNA remains invaded in the protospacer and off-target site duplexes, wherein the dynamics of invasion are estimated nucleotide-by-nucleotide by determining the energetic differences between further invasion of a different gRNA and re-annealing of the first gRNA to the DNA sequence that is complementary to the protospacer sequence; f) comparing the estimated lifetimes at the protospacer and/or off-target sites of the first gRNA with the estimated lifetimes of the full-length gRNA or a truncated gRNA (tru-gRNA) at the protospacer and/or off-target sites; g) randomizing 0 to N nucleotides in the linker and 0 to M nucleotides in the first gRNA and generating a second gRNA and repeating step (e) with the second gRNA; h) identifying an optimized gRNA based on a gRNA sequence that satisfy a design criteria; and i) testing the optimized gRNA in vivo to determine the specificity of binding.

The present invention is directed to an optimized gRNA generated by the methods described above.

The present invention is directed to an isolated polynucleotide encoding the optimized gRNA described above.

The present invention is directed to a vector comprising the isolated polynucleotide described above.

The present invention is directed to a cell comprising the isolated polynucleotide described above or the vector described above.

The present invention is directed to a kit comprising the isolated polynucleotide described above, the vector described above, or the cell described above.

The present invention is directed to a method of epigenomic editing in a target cell or a subject. The method comprises contacting a cell or a subject with an effective amount of the optimized gRNA molecule described above and a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

The present invention is directed to a method of site specific DNA cleavage in a target cell or a subject. The method comprises contacting a cell or a subject with an effective amount of the optimized gRNA molecule described above and a fusion protein or Cas9 protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

The present invention is directed to a method of genome editing in a cell. The method comprises administering to the cell an effective amount of the optimized gRNA molecule described above and a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

The present invention is directed to a method of modulating gene expression in a cell. The method comprises contacting the cell with an effective amount of the optimized gRNA described above and a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

BRIEF DESCRIPTION OF THE DRAWINGS

FIG. 2A shows a schematic of dCas9 bound to a single-guide RNA with a two nucleotide truncation from its 5'-end (tru-gRNA, purple). FIG. 2B shows a schematic and proposed mechanism of dCas9 bound to a single-guide RNA with 5'-end extension that forms a hairpin with the PAM-distal binding segment of its targeting region (hp-gRNA, blue). FIG. 2C shows single-site binding affinities ($K_A$) for dCas9 with tru-gRNA (purple, n=257) along the engineered DNA substrate (see FIG. 1D). Dashed line shows the single-site affinities of dCas9-sgRNA for comparison. FIG. 2D shows single-site binding affinities ($K_A$) for dCas9 with guide RNAs with 5'-hairpins that overlap the nucleotides complementary to the last six (hp6-gRNA, blue) or ten (hp10-gRNA, green) PAM-distal nucleotides of the protospacer.

FIG. 3A shows fraction of bound DNA occupied by Cas9/dCas9 along the DNA substrates, with colours representing populations of Cas9/dCas9 clustered according to their structures (by mean-squared difference after alignment, see text). Different features on DNA that were used for site-specific analysis of Cas9/Cas9 structural properties labelled as: non-specific sequences ($\alpha$; '20 MM'), sites containing 10 PAM-distal mismatches within the protospacer ($\beta$, '10 MM'), sites containing 5 PAM-distal mismatches within the protospacer ($\gamma$, '5 MM'), or the full protospacer site ($\delta$ or $\epsilon$ for dCas9 or Cas9, respectively; '0 MM'). The ensemble average of the primary clusters are displayed in FIG. 3C and color-coded according to the clustered structures they represent. FIG. 3B shows volume vs. height of Cas9/dCas9 observed, color-coded by the cluster to which each protein was assigned. Dashed lines delineate regions likely composed of aggregates (top right) or streptavidin labels adsorbed near DNA (bottom left). For comparison—mean height of streptavidin end-labels: 0.92 nm±0.006 nm (SEM); mean volume of streptavidin end-labels: 0.110×10$^4$ nm$^3$±0.002×10$^4$ nm$^3$ (SEM); n=1941. FIG. 3D shows mean volumes and heights of Cas9/dCas9 with sgRNAs (red circles, with red labels for Cas9 and blue labels for dCas9) or tru-gRNAs (purple circles) bound at each feature on the substrates. Note that dCas9 with tru-gRNAs are only expected to interact the first 3 or 8 PAM-distal mismatches of the 5 MM and 10 MM sites (labelled '3 MM' and '8 MM' here, respectively). For standard errors of mean volumes and heights, see Table 2. For Cas9/dCas9 with sgRNAs, their structural properties at each feature are statistically distinct ($\delta$–$\epsilon$, $\alpha$–$\epsilon$: p<0.05; $\alpha$–$\beta$: p<0.005; $\beta$–$\gamma$, $\gamma$–$\delta$: p<<0.0005. Hotelling's $T^2$ test).

FIG. 4A shows a schematic of strand invasion of the protospacer (green) by the guide RNA (red) for KMC experiments. The R-loop is highlighted. Transition rates for invasion ($v_f$ for the rate of m→m+1, where m is the extent of the strand invasion or, equivalently, the length of the R-loop) or duplex re-annealing ($v_r$ for the rate of m→m~1) are a function of the nearest-neighbour DNA:DNA and RNA:DNA hybridization energies. See text and Supplementary Methods for details. FIG. 4B shows Fractional time that the R-loop is of size m for sg-RNAs (red) or tru-gRNA (purple) derived from KMC experiments 'at equilibrium' (simulation initiated at m=20 or 18, respectively). Simulation run until t≥10,000 (arbitrary units). FIG. 4C shows kinetic Monte Carlo time course of the R-loop 'breathing' for sgRNA (red) and tru-gRNA (purple) after full invasion (simulation initiated at m=20 or 18, respectively). Asterisks highlight the starting position for the simulation. (insert) Histogram of the respective lifetimes during which the R-loop is ≥16 bp long. FIG. 4D shows proposed model for the mechanisms governing Cas9/dCas9 specificity, based on results of AFM imaging and kinetic Monte Carlo (KMC) experiments (see main text). Cas9/dCas9 binds to the PAM and the guide RNA invades into the PAM-adjacent protospacer duplex. During this strand invasion, the guide RNA must displace the complementary strand of the protospacer. Competition between invasion and re-annealing of the duplex results in a dynamic ('breathing') R-loop structure. The stability of the 14$^{th}$-17$^{th}$ sites of the protospacer-guide RNA interaction, which is dramatically increased by binding at the 19$^{th}$ and 20$^{th}$ sites, promotes a conformational change in the Cas9/dCas9 that authorizes DNA cleavage in Cas9.

FIGS. 5A-5B show fractional occupancy by time of R-loop lengths m for sgRNA (FIG. 5A) or tru-gRNA (FIG. 5B) during invasion derived from KMC experiments (initiated atm=10, highlighted by asterisk). White X's indicate positions of mismatches. Simulation run until t≥10,000 (arbitrary units) and the results are averaged over 100 trials. FIG. 5C shows representative KMC time courses for strand invasion (starting at m=10) with a mismatched site at m=14 (arrow) for sgRNA (red) and tru-gRNA (purple). While sgRNAs are largely stably invaded after bypassing a mismatch, tru-gRNAs are repeatedly re-trapped behind the mismatch as a result of the inherent volatility of their R-loops (see FIG. 4).

FIG. 6A shows log$_{10}$(p-value) of the correlations between Cas9 cutting frequency and stability of R-loop at sites m (fraction of time the guide RNA remains bound to the protospacer at site m, see text) during strand invasion initiated at site m. (i) Stability at sites m 10 to m 14 is highly anti-correlated with the probability that the guide RNA will fall off the protospacer prior to traversing the mismatch (FIG. 5B), while (ii) sites m−14 to m−17 are associated (from AFM images) with the conformational change which induces cleavage activity. Colour corresponds to the correlation coefficient. FIG. 6B shows experimental cutting frequency does not correlate significantly with estimated guide RNA—protospacer equilibrium binding free energies ($\Delta G^0_{37}$) (left), while it does with stability of site m−14 during strand invasion (right). Error bars are standard errors of the mean occupancy time at site m−14. For these kinetic Monte Carlo experiments, max(t)−100 (arbitrary units). Colour bar is used to show the location of the mismatched (MM) site.

FIG. 7A shows that for the single guide RNA (sgRNA), the first few nucleotides of the RNA (which bind to the 18th-20th sites of the protospacer) stabilize R-loop breathing and binding at the 14th-17th sites of the protospacer, allow efficient conformational transition to the active state to permit cleavage. However, this increased stability imparted by these bases allows for transient stabilization at mismatched sites and the conformational change permitting cleavage. In many cases, having traversed a mismatch, R-loops remain stably fully-invaded. FIG. 7B shows that for guide RNAs with the first few (here 2) nucleotides truncated (tru-gRNA), the reduced stability of the R-loop (characterized by significant volatility) decreases the probability of maintaining the active conformation. When there are mismatched sites in the protospacer, the volatility of the R-loop ensures that it will becomes quickly and repeatedly 're-trapped' behind the mismatch and greatly hindered at those sites. FIG. 7C shows that while 'simple' extensions of the 5'-end of the guide RNA to target the protospacer and adjoining sites beyond the protospacer was found to be digested back to approximately sgRNA length in vivo (FIG. 7A), guide RNAs with 5'-hairpins complementary to 'PAM-distal'-targeting segments (hp-gRNAs) are anticipated to remain protected within the structure of the Cas9/dCas9 prior to invasion. After binding a PAM site and initiating strand invasion by the hp-gRNA, upon binding to a full protospacer the hairpin is opened and full strand invasion can occur. If there are PAM-distal mismatches at the target site, then it is more energetically favorable for the hairpin to remain closed and strand invasion is hindered. The ability for Cas9-hp-gRNAs to cleave RNA remains to be verified.

FIG. 11A shows a representative widefield image of dCas9 bound to engineered DNA. FIG. 11B shows a close-up of boxed region. White arrows are monovalent streptavidin and red arrows are dCas9 proteins. FIGS. 11C-11D show an example of extraction from original image (FIG. 11C) and isolation (FIG. 11D) of Cas9/dCas9 structures. This extraction was repeated for each isolated protein bound to the DNA, then aligned pair-wise through iterative translation, rotation, and reflection to minimize their mean-squared topological difference. From these minimized mean-squared differences a distance matrix was composed, clustered each protein according to the method of Laio and Rodriguez (2014) Science (New York, N.Y.), 344, 1492-1496, then mapped the populations of structures by cluster back to their sites on the DNA (FIG. 2A, FIGS. 10A-10C).

FIG. 14A shows a schematic model of strand invasion of DNA protospacers by guide RNAs. See also FIG. 4A. Guide RNA is presumed to dissociated when $m=1$. FIG. 14B shows the calculated probability distribution of dissociation times for a guide RNA initially invaded up to $m=5$ for protospacers with different numbers of contiguous PAM-distal mismatches. The length of these dissociation times can be viewed as an approximation of dCas9 binding propensity at those sites. The asterisk highlights the dissociation times for the population of guide RNAs which initially fails to fully invade after initial invasion to $m=5$. The invaded RNAs are highly unstable at protospacer sites with 15 PAM-distal mismatches (15 MM), and experimentally we rarely observe Cas9/dCas9 bound at these sites (FIG. 1D). The invaded RNA (prior to dissociation) at protospacer sites with 10 or 5 PAM-distal mismatches (10 MM and 5 MM) are calculated to remain for significantly longer than those at 15 MM sites, but within an order of magnitude of each other; we find their binding propensity to be approximately equal and lower than full protospacer sites (0 MM) in AFM experiments. The probability density functions were calculated using a Q-matrix method as described (Sakmann et al. (1995) Single-channel recording, Springer; 2nd ed.), using the sequence-specific transition rates between the m states ($v_f$ and $v_r$, see Supplementary Methods). FIG. 14C shows examination of the estimated half-lives of RNA-protospacer binding at protospacers with different numbers of PAM-distal mismatches suggests there are roughly three regimes within which the stabilities of the invaded RNA are similar: those with >11 PAM-distal mismatches (low stability); those with between 3 and 11 PAM-distal mismatches (medium stability); and those with <3 PAM-distal mismatches (high stability). The results are qualitatively similar to the distribution of dCas9 on the engineered substrate observed via AFM (FIG. 1D).

FIG. 16A shows statistical power and strength of the correlations between stability of R-loop sites (from kinetic Monte Carlo, see main text) and experimental cleavage frequency from Hsu et al. (2013) Nature Biotechnology, 31, 827-832 decrease with increasing simulation length ($max(t)=100$ to $max(t)=1000$, arbitrary units). This result suggests that the kinetics of strand invasion can be an important predictor of off-target cleavage rate. FIG. 16B shows correlation between fractions of time the R-loop is of size m vs. the probability that the kinetic Monte Carlo trial predicts that the invading strand will dissociate before traversing the mismatch. Binding at sites 10-14-15 is very strongly anti-correlated (~0.5-0.85) with the probability of dissociation before traversing the mismatch, while from the AFM imaging experiments we find that binding at sites $\sim\geq 16$ are associated with a conformational change in the Cas9/dCas9.

FIG. 26A shows hairpin 1 which is a 6 bp 5'-hairpin. FIG. 26B shows hairpin 2 which is a 5 bp 5'-hairpin on 18 nt (truncated) gRNA. FIG. 26C shows hairpin 3 which is a 3 bp 5'-hairpin.

FIG. 25A shows Hairpin 4—Computationally-derived hairpin designed to discriminate against Off-target site 2 while maintaining on-target activity. FIG. 25B shows Hairpin 5-4 bp 5'-hairpin (gRNA normally has significant 3' secondary structure).

FIG. 44A shows a hairpin designed to target EMX1 gene.

FIG. 44B shows the EMX1-sg1 sequence of the hairpin of FIG. 44A.

FIG. 45A-45D show DNA/RNA Sequences.

DETAILED DESCRIPTION

Figures 1A, 1B, 1C, 1D:
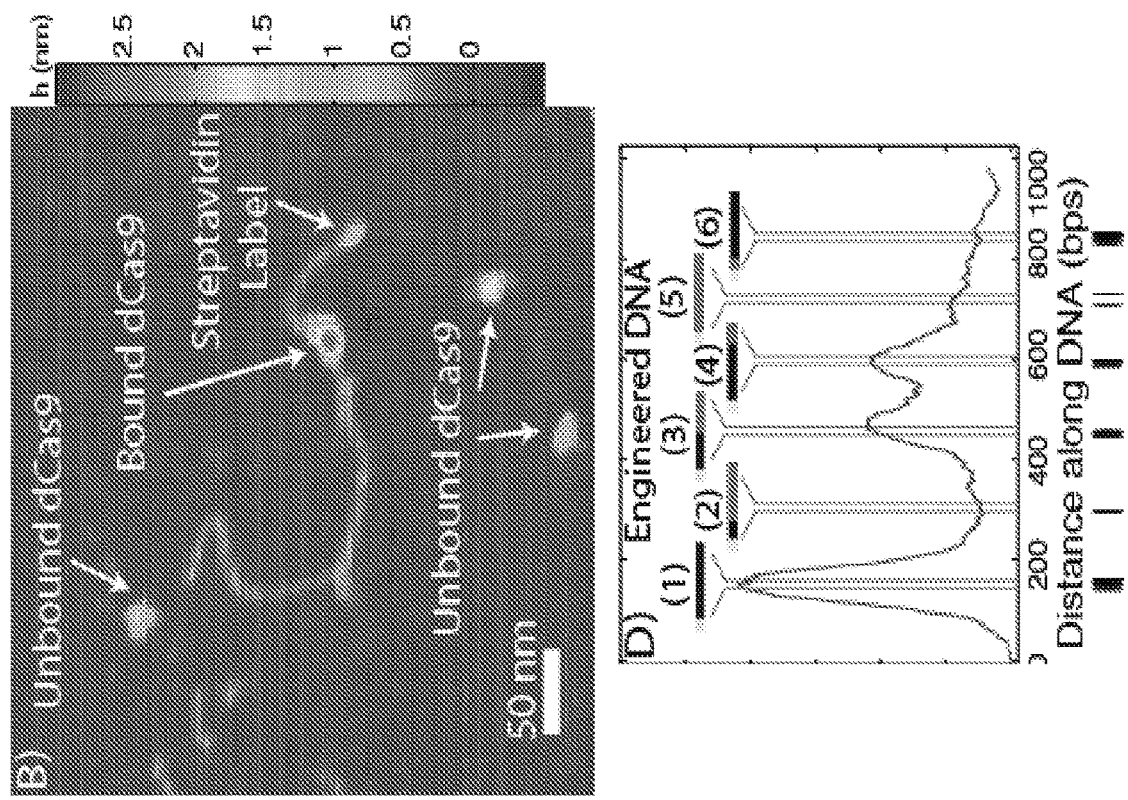
FIG. 1A shows a schematic representation of Cas9 activity.
FIG. 1B shows an atomic force microscopy (AFM) image of dCas9-sgRNA bound at the protospacer sequence within a single streptavidin-labeled DNA molecule derived from the human AAVS1 locus.
FIGS. 1C-1D show fraction of bound DNA occupied by Cas9/dCas9-sgRNA along an AAVS1-derived (FIG. 1C) or an engineered DNA substrate (FIG. 1D) designed with a series of fully-complementary and partially-complementary protospacer sequences. Vertical lines represent the (23 bp) segments where each significant feature is located on the respective substrates.

Disclosed herein are composition and methods for site specific DNA targeting and epigenomic gene editing and/or transcriptional regulation, such as DNA cleavage and gene activation or repression. The present invention is directed to a modular method for designing and using optimized guide RNAs that have hairpin structures (hpgRNA) that can be easily incorporated into the existing biotechnology infrastructure and which results in a controlled decrease of off-target activity, all while maintaining the ability to target the correct DNA sequence specifically. The methods described herein provide a novel approach to engineering the optimized gRNA to perform significantly better than other available methods and can be used in combination with other protein-specific means of improving increasing specifically for highly improved performance.

The disclosed methods and optimized gRNAs have the great advantage of being easily adapted to current methodologies and infrastructures already in place to perform RNA-guided genomic engineering. In some embodiments, Cas9, dCas9, or Cpf1 are delivered into a cell using viral vectors along with vectors coding for the transcription of the optimized gRNAs in the cell. The current invention would require only a few additional nucleotides to the vector coding for the optimized gRNA, which can be easily accommodated by the current and standard practices. Like truncated guide RNAs (tru-gRNAs), the optimized gRNAs or hpgRNAs can be used in combination with paired nickases, for example, or other modifications of the endonucleases themselves to further improve specificity. A series of experiments were performed in vitro which showed that the use of the optimized gRNAs produced using the methods described herein increased the specificity in DNA binding relative to the best available gRNA options (see FIG. 2). The use of the optimized gRNA abolishes or significantly weakens activity at targets containing only a few mismatched DNA sequences, which tend to be the sites at which off-target activity by RNA-guided endonucleases occurs. The optimized gRNA also provide specificity of cleavage activity in mammalian cells at sites which are known to induce off-target activity even in the best known improvements to the guide RNAs. The invention is a generally-applicable method to decrease off-target activity by RNA-guided endonucleases, particularly Cas9, by engineering changes the structural design of the guide RNA.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease, such as Cas9.

"Chromatin" as used herein refers to an organized complex of chromosomal DNA associated with histones.

"Cis-regulatory elements" or "CREs" as used interchangeably herein refers to regions of non-coding DNA which regulate the transcription of nearby genes. CREs are found in the vicinity of the gene, or genes, they regulate. CREs typically regulate gene transcription by functioning as binding sites for transcription factors. Examples of CREs include promoters, enhancers, super-enhancers, silencers, insulators, and locus control regions.

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

"Demethylases" as used herein refers to an enzyme that removes methy (CH3-) groups from nucleic acids, proteins (in particular histones), and other molecules. Demethylase enzymes are important in epigenetic modification mechanisms. The demethylase proteins alter transcriptional regulation of the genome by controlling the methylation levels that occur on DNA and histones and, in turn, regulate the chromatin state at specific gene loci within organisms. "Histone demethylase" refers to a methylase that removes methy groups from histones. There are several families of histone demethylases, which act on different substrates and play different roles in cellular function. The Fe(II)-dependent lysine demethylases may be a JMJC demethylase. A JMJC demethylase is a histone demethylase containing a JumonjiC (JmjC) domain. The JMJC demethylase may be a member of the KDM3, KDM4, KDM5, or KDM6 family of histone demethylases.

"DNase I hypersensitive sites" or "DHS" as used interchangeably herein refers to docking sites for the transcription factors and chromatin modifiers, including p300 that coordinate distal target gene expression.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Endogenous gene" as used herein refers to a gene that originates from within an organism, tissue, or cell. An endogenous gene is native to a cell, which is in its normal genomic and chromatin context, and which is not heterologous to the cell. Such cellular genes include, e.g., animal genes, plant genes, bacterial genes, protozoal genes, fungal genes, mitochondrial genes, and chloroplastic genes. An "endogenous target gene" as used herein refers to an endogenous gene that is targeted by an optimized gRNA and CRISPR/Cas9-based system or CRISPR/Cpf1-based system.

"Enhancer" as used herein refers to non-coding DNA sequences containing multiple activator and repressor binding sites. Enhancers range from 50 bp to 1500 bp in length and may be either proximal, 5' upstream to the promoter, within any intron of the regulated gene, or distal, in introns of neighboring genes, or intergenic regions far away from the locus, or on regions on different chromosomes. More than one enhancer may interact with a promoter. Similarly, enhancers may regulate more than one gene without linkage restriction and may "skip" neighboring genes to regulate more distant ones. Transcriptional regulation may involve elements located in a chromosome different to one where the promoter resides. Proximal enhancers or promoters of neighboring genes may serve as platforms to recruit more distal elements.

"Duchenne Muscular Dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exon 51" as used herein refers to the $51^{st}$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Full-length gRNA" or "standard gRNA" as used interchangeably herein refers to a gRNA that includes a "scaffold" and a protospacer-targeting sequence or segment that is typically 20 nucleotides in length.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

"Genome" as used herein refers to the complete set of genes or genetic material present in a cell or organism. The genome includes DNA or RNA in RNA viruses. The genome includes both the genes, (the coding regions), the noncoding DNA and the genomes of the mitochondria and chloroplasts.

"guide RNA," "gRNA," "single gRNA," and "sgRNA" as used interchangeably herein refer to a short synthetic RNA composed of a "scaffold" sequence necessary for Cas9-binding or Cpf1-binding and a user-defined "spacer" or "targeting sequence" (also referred to herein as a protospacer-targeting sequence or segment) which defines the genomic target to be modified. "hpgRNA," "hp-gRNA," and "optimized gRNA" as used interchangeably herein refer to a gRNA that has additional nucleotides at either the 5'-end or 3'-end that can form a secondary structure with all or part of the protospacer-targeting sequence or segment.

"Histone acetyltransferases" or "HATs" are used interchangeably herein refers to enzymes that acetylate conserved lysine amino acids on histone proteins by transferring an acetyl group from acetyl CoA to form ε-N-acetyllysine. DNA is wrapped around histones, and, by transferring an acetyl group to the histones, genes can be turned on and off. In general, histone acetylation increases gene expression as it is linked to transcriptional activation and associated with euchromatin. Histone acetyltransferases can also acetylate non-histone proteins, such as nuclear receptors and other transcription factors to facilitate gene expression.

"Histone deacetylases" or "HDACs" as used interchangeably herein refers to a class of enzymes that remove acetyl groups ($O=C-CH_3$) from an ε-N-acetyl lysine amino acid on a histone, allowing the histones to wrap the DNA more tightly. HDACs are also called lysine deacetylases (KDAC), to describe their function rather than their target, which also includes non-histone proteins.

"Histone methyltransferase" or "HMTs" as used interchangeably herein refers to histone-modifying enzymes (e.g., histone-lysine N-methyltransferases and histone-arginine N-methyltransferases), that catalyze the transfer of one, two, or three methyl groups tolysine and arginine residues of histone proteins. The attachment of methyl groups occurs predominantly at specific lysine or arginine residues on histones H3 and H4.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the site specific nuclease, such as with a CRISPR/Cas9-based system or CRISPR/Cpf1-based system, then the cellular machinery will repair the break by homologous recombination, which is enhanced several orders of magnitude in the presence of DNA cleavage. When the homologous DNA piece is absent, non-homologous end joining may take place instead.

"Genome" as used herein refers to the complete set of genes or genetic material present in a cell or organism. The genome includes DNA or RNA in RNA viruses. The genome includes both the genes, (the coding regions), the noncoding DNA and the genomes of the mitochondria and chloroplasts.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Insulators" as used herein refers to a genetic boundary element that blocks the interaction between enhancers and promoters. By residing between the enhancer and promoter, the insulator may inhibit their subsequent interactions. Insulators can determine the set of genes an enhancer can influence. Insulators are needed where two adjacent genes on a chromosome have very different transcription patterns and the inducing or repressing mechanisms of one does not interfere with the neighboring gene. Insulators have also been found to cluster at the boundaries of topological association domains (TADs) and may have a role in partitioning the genome into "chromosome neighborhoods"—genomic regions within which regulation occurs. Insulator activity is thought to occur primarily through the 3D structure of DNA mediated by proteins including CTCF. Insulators are likely to function through multiple mechanisms. Many enhancers form DNA loops that put them in close physical proximity to promoter regions during transcriptional activation. Insulators may promote the formation of DNA loops that prevent the promoter-enhancer loops from forming. Barrier insulators may prevent the spread of heterochromatin from a silenced gene to an actively transcribed gene.

"Invasion" as used herein refers to the disruption of a DNA duplex at a protospacer region in a target region of a target gene, such as by a gRNA that binds to the DNA sequence that is complementary to the protospacer.

"Invasion kinetics" as used herein refers to the rate at which invasion proceeds. Invasion kinetics can refer to the rate at which the guide RNA invades the duplex, either to "full invasion" such that the protospacer is completely invaded, or the rate at which the segment of protospacer DNA bound to the guide RNA expands as it is displaced from its complementary strand and bound to the guide RNA nucleotide-by-nucleotide from its PAM-proximal region through to full invasion.

"Lifetime" as used herein refers to period of time that a gRNA remains invaded in the region in a target region of a target gene.

"Locus control regions" as used herein refers to a long-range cis-regulatory element that enhances expression of linked genes at distal chromatin sites. It functions in a copy number-dependent manner and is tissue-specific, as seen in the selective expression of (3-globin genes in erythroid cells. Expression levels of genes can be modified by the LCR and gene-proximal elements, such as promoters, enhancers, and silencers. The LCR functions by recruiting chromatin-modifying, coactivator, and transcription complexes. Its sequence is conserved in many vertebrates, and conservation of specific sites may suggest importance in function.

"Mismatched" or "MM" as used interchangeably herein refers to mismatched bases that include a G/T or A/C pairing. Mismatches are commonly due to tautomerization of bases during G2. The damage is repaired by recognition of the deformity caused by the mismatch, determining the template and non-template strand, and excising the wrongly incorporated base and replacing it with the correct nucleotide.

"Modulate" as used herein may mean any altering of activity, such as regulate, down regulate, upregulate, reduce, inhibit, increase, decrease, deactivate, or activate.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called micro-homologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease, such as a cas9, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"On-target site" as used herein refers to the target region or sequence in a genome to which the gRNA is intended to target. Ideally, the on-target site has perfect homology (100% identity or homology) to the target DNA sequence with no homology elsewhere in the genome.

"Off-target site" as used herein refers to a region of the genome which has partial homology or partial identity to the on-target site or target region of the gRNA, but which the gRNA is not intended or designed to target.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"p300 protein," "EP300," or "E1A binding protein p300" as used interchangeably herein refers to the adenovirus E1A-associated cellular p300 transcriptional co-activator protein encoded by the EP300 gene. p300 is a highly conserved acetyltransferase involved in a wide range of cellular processes. p300 functions as a histone acetyltransferase that regulates transcription via chromatin remodeling and is involved with the processes of cell proliferation and cell differentiation.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Primary cell" as used herein refers to cells taken directly from living tissue (e.g. biopsy material). Primary cells can be established for growth in vitro. These cells have undergone very few population doublings and are therefore more representative of the main functional component of the tissue from which they are derived in comparison to continuous (tumor or artificially immortalized) cell lines thus representing a more representative model to the in vivo state. Primary cells may be taken from different species, such as mouse or humans.

"Protospacer sequence" or "protospacer segment" as used interchangeably herein refers to a DNA sequence targeted by the Cas9 nuclease or Cpf1 nuclease in the CRISPR bacterial adaptive immune system. In the CRISPR/Cas9 system, the protospacer sequence is typically followed by a protospacer-adjacent motif (PAM); the PAM is at the 5'-end. In the CRISPR/Cpf1 system, PAM is followed by the protospacer sequence; the PAM is at the 3'-end.

"Protospacer-targeting sequence" or "protospacer-targeting segment" as used interchangeably herein refers to a nucleotide sequence of a gRNA that corresponds to the protospacer sequence and facilitates targeting of the CRISPR/Cas9-based system or CRISPR/Cpf1-based system to the protospacer sequence.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs, or anywhere in the genome, from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, hormones, toxins, drugs, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Protospacer adjacent motif" or "PAM" as used herein refers to a DNA sequence immediately following the DNA sequence targeted by the Cas9 or immediately before the DNA sequence targeted by the Cpf1 nuclease in the CRISPR bacterial adaptive immune system. PAM is a component of the invading virus or plasmid, but is not a component of the bacterial CRISPR locus. Cas9 and Cpf1 will not successfully bind to or cleave the target DNA sequence if it is not followed by or preceded by the PAM sequence, respectively. PAM is an essential targeting component (not found in bacterial genome) which distinguishes bacterial self from non-self DNA, thereby preventing the CRISPR locus from being targeted and destroyed by nuclease.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

"Silencers" or "repressors" as used interchangeably herein refer to a DNA sequence capable of binding transcription regulation factors and preventing genes from being expressed as proteins. A silencer is a sequence-specific element that induces a negative effect on the transcription of its particular gene. There are many positions in which a silencer element can be located in DNA. The most common position is found upstream of the target gene where it can help repress the transcription of the gene. This distance can vary greatly between approximately −20 bp to −2000 bp upstream of a gene. Certain silencers can be found downstream of a promoter located within the intron or exon of the gene itself. Silencers have also been found within the 3 prime untranslated region (3' UTR) of mRNA. There are two main types of silencers in DNA, which are the classical silencer element and the non-classical negative regulatory element (NRE). In classical silencers, the gene is actively repressed by the silencer element, mostly by interfering with general transcription factor (GTF) assembly. NREs passively repress the gene, usually by inhibiting other elements that are upstream of the gene.

"Skeletal muscle" as used herein refers to a type of striated muscle, which is under the control of the somatic nervous system and attached to bones by bundles of collagen fibers known as tendons. Skeletal muscle is made up of individual components known as myocytes, or "muscle cells", sometimes colloquially called "muscle fibers." Myocytes are formed from the fusion of developmental myoblasts (a type of embryonic progenitor cell that gives rise to a muscle cell) in a process known as myogenesis. These long, cylindrical, multinucleated cells are also called myofibers.

"Skeletal muscle condition" as used herein refers to a condition related to the skeletal muscle, such as muscular dystrophies, aging, muscle degeneration, wound healing, and muscle weakness or atrophy.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Super enhancer" as used herein refers to a region of the mammalian genome comprising multiple enhancers that is collectively bound by an array of transcription factor proteins to drive transcription of genes involved in cell identity. Super-enhancers are frequently identified near genes important for controlling and defining cell identity and can be used to quickly identify key nodes regulating cell identity. Enhancers have several quantifiable traits that have a range of values, and these traits are generally elevated at super-enhancers. Super-enhancers are bound by higher levels of transcription-regulating proteins and are associated with genes that are more highly expressed. Expression of genes associated with super-enhancers is particularly sensitive to perturbations, which may facilitate cell state transitions or explain sensitivity of super-enhancer-associated genes to small molecules that target transcription.

"Target enhancer" as used herein refers to enhancer that is targeted by a gRNA and CRISPR/Cas9-based system. The target enhancer may be within the target region.

"Target gene" as used herein refers to any nucleotide sequence encoding a known or putative gene product. The target gene may be a mutated gene involved in a genetic disease.

The "target region", "target sequence," "protospacer," or "protospacer sequence" as used interchangeably herein refers to the region of the target gene to which the CRISPR/Cas9-based system or CRISPR/Cpf1-based system targets.

"Transcribed region" as used herein refers to the region of DNA that is transcribed into single-stranded RNA molecule, known as messenger RNA, resulting in the transfer of genetic information from the DNA molecule to the messenger RNA. During transcription, RNA polymerase reads the template strand in the 3' to 5' direction and synthesizes the RNA from 5' to 3'. The mRNA sequence is complementary to the DNA strand.

"Target regulatory element" as used herein refers to a regulatory element that is targeted by a gRNA and CRISPR/Cas9-based system. The target regulatory element may be within the target region.

"Transcribed region" as used herein refers to the region of DNA that is transcribed into single-stranded RNA molecule, known as messenger RNA, resulting in the transfer of genetic information from the DNA molecule to the messenger RNA. During transcription, RNA polymerase reads the template strand in the 3' to 5' direction and synthesizes the RNA from 5' to 3'. The mRNA sequence is complementary to the DNA strand.

"Transcriptional Start Site" or "TSS" as used interchangeably herein refers to the first nucleotide of a transcribed DNA sequence where RNA polymerase begins synthesizing the RNA transcript.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"tru gRNA" as used herein refers to a full-length guide RNA with nucleotides truncated from their 5'-end, typically 2 nucleotides.

"Trans-regulatory elements" as used herein refers to regions of non-coding DNA which regulate the transcription of genes distant from the gene from which they were transcribed. Trans-regulatory elements may be on the same or different chromosome from the target gene. Examples of trans-regulatory elements include enhancers, super-enhancers, silencers, insulators, and locus control regions.

"Variant" used herein with respect to a nucleic acid means (i) a portion or fragment of a referenced nucleotide sequence (including nucleotide sequences that have insertions or deletions as compared to the referenced nucleotide sequences); (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode Cas9 and at least one optimized gRNA nucleotide sequence of any one of SEQ ID NOs: 149-315, 321-323, and 326-329.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. CRISPR System

The CRISPR system is a microbial nuclease system involved in defense against invading phages and plasmids that provides a form of acquired immunity. The CRISPR loci in microbial hosts can contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the single guide RNA ("sgRNA"), and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the CRISPR RNA ("crRNA"), i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed chimeric sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

An engineered form of the Type II effector system of *Streptococcus pyogenes* was shown to function in human cells for genome engineering. In this system, the Cas9 protein was directed to genomic target sites by a synthetically reconstituted "guide RNA" ("gRNA", also used interchangeably herein as a chimeric sgRNA, which for Cas9 is a crRNA-tracrRNA fusion that obviates the need for RNase III and crRNA processing in general.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9-based system is the straightforward ability to simultaneously target multiple distinct genomic loci by co-expressing a single Cas9 protein with two or more sgRNAs. For example, the *Streptococcus pyogenes* Type II system naturally prefers to use an "NGG" sequence, where "N" can be any nucleotide, but also accepts other PAM sequences, such as "NAG" in engineered systems (Hsu et al. (2013) *Nature Biotechnology*, 31, 827-832). Similarly, the Cas9 derived from *Neisseria meningitidis* (NmCas9) normally has a native PAM of NNNNGATT, but has activity across a variety of PAMs, including a highly degenerate NNNNGNNN PAM (Esvelt et al. *Nature Methods* (2013) doi:10.1038/nmeth.2681).

3. CRISPR/Cas9-Based System

Provided herein are CRISPR/Cas9 systems that include an optimized gRNA, such as a hairpin gRNA (also referred herein as "hpgRNA" or "hp-gRNA"), that allow improved DNA targeting for use in epigenomic editing and transcriptional regulation, such as specifically cleaving a target region of interest, such as a target gene, or activating or repressing gene expression of a target gene. The optimized gRNAs provide increased target binding specificity, while having decreased off-target binding and off-target activity of the CRISPR/Cas9-based and CRISPR/Cpf1-based systems by modulating lifetimes at off-target locations so as to minimize any activity at those off-target sites.

The optimized gRNA can modulate the Cas9-fusion protein activities by modulating the Cas9 lifetime at these locations and modulating the overall invasion kinetics without regard to second domain activity. In addition, gRNA binding to the protospacer at the 5'-end of the protospacer targeting segment may also be involved with Cas9 cleavage. The decreased binding to off-target sites would limit the potential for full invasion/cleavage at these off-target sites. An engineered form of the Type II effector system of *Streptococcus pyogenes* was shown to function in human cells for genome engineering. In this system, the Cas9 protein was directed to genomic target sites by a synthetically reconstituted "guide RNA" ("gRNA", also used interchangeably herein as a chimeric single guide RNA ("sgRNA")), which for Cas9 is a crRNA-tracrRNA fusion that obviates the need for RNase III and crRNA processing in general. Provided herein are CRISPR/Cas9-based systems for use in genome editing and treating genetic diseases. The CRISPR/Cas9-based systems may be designed to target any gene, including genes involved in a genetic disease, aging, tissue regeneration, or wound healing. The CRISPR/Cas9-based systems may include a Cas9 protein or Cas9 fusion protein and at least one optimized gRNA, as described below. The Cas9 fusion protein may, for example, include a domain that has a different activity that what is endogenous to Cas9, such as a transactivation domain.

The target gene may have a mutation such as a frameshift mutation or a nonsense mutation. If the target gene has a mutation that causes a premature stop codon, an aberrant splice acceptor site or an aberrant splice donor site, the CRISPR/Cas9-based system may be designed to recognize and bind a nucleotide sequence upstream or downstream from the premature stop codon, the aberrant splice acceptor site or the aberrant splice donor site. The CRISPR-Cas9-based system may also be used to disrupt normal gene splicing by targeting splice acceptors and donors to induce skipping of premature stop codons or restore a disrupted reading frame. The CRISPR/Cas9-based system may or may not mediate off-target changes to protein-coding regions of the genome.

i. Cas9

The CRISPR/Cas9-based system may include a Cas9 protein or a Cas9 fusion protein. Cas9 protein is an endonuclease that cleaves nucleic acid and is encoded by the CRISPR loci and is involved in the Type II CRISPR system. The Cas9 protein may be from any bacterial or archaea species, such as Streptococcus pyogenes. The Cas9 protein may be mutated so that the nuclease activity is inactivated. An inactivated Cas9 protein from Streptococcus pyogenes (iCas9, also referred to as "dCas9") with no endonuclease activity has been recently targeted to genes in bacteria, yeast, and human cells by gRNAs to silence gene expression through steric hindrance. As used herein, "iCas9" and "dCas9" both refer to a Cas9 protein that has the amino acid substitutions D10A and H840A and has its nuclease activity inactivated. In some embodiments, an inactivated Cas9 protein from Neisseria meningitides, such as NmCas9, may be used. For example, the CRISPR/Cas9-based system may include a iCas9 of SEQ ID NO: 1.

ii. Cas9 Fusion Protein

The CRISPR/Cas9-based system may include a fusion protein of a Cas9 protein that does not have nuclease activity, such as dCas9, and a second domain. The second domain may include a transcription activation domain, such as a VP64 domain or p300 domain, transcription repression domain, such as KRAB domain, nuclease domain, transcription release factor domain, histone modification domain, nucleic acid association domain, acetylase domain, deacetylase domain, methylase domain, such as a DNA methylase domain, demethylase domain, phosphorylation domain, ubiquitylation domain, or sumoylation domain. The second domain may be a modifier of DNA methylation or chromatin looping.

In some embodiments, the fusion protein can include a dCas9 domain and a transcriptional activator. For example, the fusion protein can include the amino acid sequence of SEQ ID NO: 2. In other embodiments, the fusion protein can include a dCas9 domain and a transcriptional repressor. For example, the fusion protein comprises the amino acid sequence of SEQ ID NO:3. In further aspects, the fusion protein can include a dCas9 domain and a site-specific nuclease that is different from Cas9 nuclease activity.

The fusion protein may comprise two heterologous polypeptide domains, wherein the first polypeptide domain comprises a Cas protein and the second polypeptide domain has does not have nuclease activity. The fusion protein may include a Cas9 protein or a mutated Cas9 protein, as described above, fused to a second polypeptide domain that has nuclease activity. The second polypeptide domain may have nuclease activity that is different from the nuclease activity of the Cas9 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

(1) CRISPR/Cas9-Based Gene Activation System

The CRISPR/Cas9-based system can be a CRISPR/Cas9-based gene activation system that can activate regulatory element function with exceptional specificity of epigenome editing. The CRISPR/Cas9-based gene activation system can be used to screen for enhancers, insulators, silencers, and locus control regions that can be targeted to increase or decrease target gene expression. This technology can be used to assign function to putative regulatory elements identified through genomic studies such as the ENCODE and the Roadmap Epigenomics projects.

The CRISPR/Cas9-based gene activation system may activate gene expression by modifying DNA methylation, chromatin looping or catalyzing acetylation of histone H3 lysine 27 at its target sites, leading to robust transcriptional activation of target genes from promoters and proximal and distal enhancers. The CRISPR/Cas9-based gene activation system is highly specific and may be guided to the target gene using as few as one guide RNA. The CRISPR/Cas9-based gene activation system may activate the expression of one gene or a family of genes by targeting enhancers at distant locations in the genome.

(a) Histone Acetyltransferase (HAT) Protein

The CRISPR/Cas9-based gene activation system may include a histone acetyltransferase protein, such as a p300 protein, CREB binding protein (CBP; an analog of p300), GCN5, or PCAF, or fragment thereof. Acetylating histones in regulatory elements using a programmable CRISPR/Cas9-based fusion protein is an effective strategy to increase the expression of target genes. A CRISPR/Cas9-based histone acetyltransferase that can be targeted to any site in the genome is uniquely capable of activating distal regulatory elements. The histone acetyltransferase protein may include a human p300 protein or a fragment thereof. The histone acetyltransferase protein may include a wild-type human p300 protein or a mutant human p300 protein, or fragments thereof. The histone acetyltransferase protein may include the core lysine-acetyltransferase domain of the human p300 protein, i.e., the p300 HAT Core (also known as "p300 Core").

(b) CRISPR/dCas9$^{p300\ Core}$ Activation System

The p300 protein regulates the activity of many genes in tissues throughout the body. The p300 protein plays a role in regulating cell growth and division, prompting cells to mature and assume specialized functions (differentiate) and preventing the growth of cancerous tumors. The p300 protein may activate transcription by connecting transcription factors with a complex of proteins that carry out transcription in the cell's nucleus. The p300 protein also functions as a histone acetyltransferase that regulates transcription via chromatin remodeling.

The dCas9$^{p300\ Core}$ fusion protein is a potent and easily programmable tool to synthetically manipulate acetylation at targeted endogenous loci, leading to regulation of proximal and distal enhancer-regulated genes. The p300 Core acetylates lysine 27 on histone H3 (H3K27ac) and may provide H3K27ac enrichment. The fusion of the catalytic core domain of p300 to dCas9 may result in substantially higher transactivation of downstream genes than the direct fusion of full-length p300 protein despite robust protein expression. The dCas9$^{p300\ Core}$ fusion protein may also exhibit an increased transactivation capacity relative to dCas9$^{VP64}$, including in the context of the Nm-dCas9 scaffold, especially at distal enhancer regions, at which dCas9$^{VP64}$ displayed little, if any, measurable downstream transcriptional activity. Additionally, the dCas9$^{P300\ Core}$ displays precise and robust genome-wide transcriptional specificity. dCas9$^{P300}$ Core may be capable of potent transcriptional activation and co-enrichment of acetylation at promoters targeted by the epigenetically modified enhancer.

The dCas9$^{P300\ Core}$ may activate gene expression through a single gRNA that target and bind a promoter and/or a characterized enhancer. This technology also affords the ability to synthetically transactivate distal genes from putative and known regulatory regions and simplifies transactivation via the application of a single programmable effector and single target site. These capabilities allow multiplexing to target several promoters and/or enhancers simultaneously. The mammalian origin of p300 may provide advantages over virally-derived effector domains for in vivo applications by minimizing potential immunogenicity.

Gene activation by dCas9$^{P300-Core}$ is highly specific for the target gene. In some embodiments, the p300 Core includes amino acids 1048-1664 of SEQ ID NO: 2 (i.e., SEQ ID NO: 4). In some embodiments, the CRISPR/Cas9-based gene activation system includes a dCas9$^{P300\ Core}$ fusion protein of SEQ ID NO: 2 or an Nm-dCas9$^{P300\ Core}$ fusion protein of SEQ ID NO: 5.

(2) CRISPR/Cas9-Based Gene Repression System

The CRISPR/Cas9-based system can be a CRISPR/Cas9-based gene repression system which can inhibit regulatory element function with exceptional specificity of epigenome editing. In some embodiments, the CRISPR/Cas9-based gene repression system, such as one that include dCas9$^{KRAB}$, can interfere with distal enhancer activity by highly specific remodeling of the epigenetic state of targeted genetic loci.

(a) CRISPR/dCas9$^{KRAB}$ Gene Repression System

The dCas9$^{KRAB}$ repressor is a highly specific epigenome editing tool that can be used in loss-of-function screens to study gene function and discover targets for drug development. The dCas9$^{KRAB}$ has exceptional specificity to target a particular enhancer, silence only the target genes of that enhancer, and create a repressive heterochromatin environment at that site. dCas9-$^{KRAB}$ can be used to screen for novel regulatory elements within the endogenous genomic context by silencing proximal or distal regulatory elements and corresponding gene targets. The specificity of dCas9-KRAB repressors allows it to be used for transcriptome-wide specificity for silencing endogenous genes. Epigenetic mechanisms for disruption at targeted locus such as histone methylation.

The KRAB domain, a common heterochromatin-forming motif in naturally occurring zinc finger transcription factors, has been genetically linked to dCas9 to create an RNA-guided synthetic repressor, dCas9$^{KRAB}$. The Kruppel-associated box ("KRAB") recruits heterochromatin-forming factors: Kap1, HP1, SETDB1, NuRD. It induces H3K0 trimethylation, histone deacetylation. KRAB-based synthetic repressors can effectively silence the expression of single genes and have been employed to repress oncogenes, inhibit viral replication, and treat dominant negative diseases.

4. CRISPR/Cpf1-Based System

The disclosed optimized gRNA may be used with a Clustered Regularly Interspaced Short Palindromic Repeats from *Prevotella* and *Francisella* 1 or ("CRISPR/Cpf1") system. CRISPR/Cpf1 system, a DNA-editing technology analogous to the CRISPR/Cas9 system, is found in *Prevotella* and *Francisella* bacteria and prevents genetic damage from viruses. Cpf1 is an RNA-guided endonuclease of a class II CRISPR/Cas system containing a 1,300 amino acid protein. Cpf1 genes are associated with the CRISPR locus, coding for an endonuclease that use a guide RNA to find and cleave viral DNA. Cpf1 is a smaller and simpler endonuclease than Cas9 and has a smaller sgRNA molecule (proximately half as many nucleotides as Cas9) as functional Cpf1 does not need the tracrRNA and only crRNA is required. Examples of Cpf1 that can be used with the optimized gRNA include Cpf1 from *Acidaminococcus* and *Lachnospiraceae* bacterial.

The Cpf1 loci encode Cas1, Cas2 and Cas4 proteins more similar to types I and III than from type II systems. The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Cpf1 does not have a HNH endonuclease domain, and the N-terminal of Cpf1 does not have the alfa-helical recognition lobe of Cas9. Cpf1 CRISPR-Cas domain architecture shows that Cpf1 is functionally unique, being classified as Class 2, type V CRISPR system.

The CRISPR/Cpf1 system consists of a Cpf1 enzyme and a guide RNA that finds and positions the complex at the correct spot on the double helix to cleave target DNA. CRISPR/Cpf1 systems activity has three stages: adaptation, formation of crRNAs and interference. During the adaptation stage, Cas1 and Cas2 proteins facilitate the adaptation of small fragments of DNA into the CRISPR array. The formation of crRNAs stage involves processing of pre-crRNAs producing of mature crRNAs to guide the Cas protein. In the interference stage, the Cpf1 is bound to a crRNA to form a binary complex to identify and cleave a target DNA sequence.

The Cpf1-crRNA complex cleaves target DNA or RNA by identification of a protospacer adjacent motif 5'-YTN-3' (where "Y" is a pyrimidine and "N" is any nucleobase) or 5'-TTN-3', in contrast to the G-rich PAM targeted by Cas9. The PAM targeted by Cpf1 is on the 5' side of the guide RNA, in contrast to the PAM targeted by Cas9, which is on the 3' side of the guide RNA. After identification of PAM, Cpf1 introduces a sticky-end-like DNA double-stranded break of 4 or 5 nucleotides overhang in contrast to the blunt end cuts of Cas9 thereby enhancing the efficiency of genetic insertions and specificity during NHEJ or HDR. TTN PAM sites are more useful for human genomic engineering than GGN PAM sites because the human genome is more T-rich than G-rich. Protospacer-targeting segment of the gRNA for Cpf1 is at its extreme 3'-end, while Cas9 gRNAs are at its extreme 5' end.

5. gRNA

The CRISPR/Cas9-based system or CRISPR/Cpf1-based system may include at least one gRNA, such as an optimized gRNA as described herein, which targets a nucleic acid sequence. The gRNA provides the specific targeting of the CRISPR/Cas9-based system or CRISPR/Cpf1-based system to a target region or gene. For the CRISPR/Cas9-based system, the gRNA is a fusion of two noncoding RNAs: a crRNA and a tracrRNA. The gRNA or sgRNA may target any desired DNA sequence by exchanging the sequence encoding a 20 bp protospacer which confers targeting specificity through complementary base pairing with the desired DNA target. gRNA mimics the naturally occurring crRNA:tracrRNA duplex involved in the Type II Effector system. This duplex, which may include, for example, a 42-nucleotide crRNA and a 75-nucleotide tracrRNA, acts as a guide for the Cas9 to cleave the target nucleic acid. The gRNA may target and bind a target region of a target gene. For the CRISPR/Cpf1-based system, the gRNA is a crRNA.

The CRISPR/Cas9-based system or CRISPR/Cpf1-based system may include at least one gRNA, such as an optimized gRNA described herein, wherein the gRNAs target different DNA sequences. The target DNA sequences may be overlapping. The target sequence or protospacer is followed by a PAM sequence at the 3' end of the protospacer. Different Type II systems have differing PAM requirements. For example, the *Streptococcus pyogenes* Type II system uses an "NGG" sequence, where "N" can be any nucleotide.

6. Methods of Generating an Optimized Guide RNA (gRNA)

The present disclosure is directed towards methods of generating optimized gRNAs, such as hairpin gRNAs (also referred to herein as "hpgRNA" and "hp-gRNA"). The optimized gRNA includes a nucleotide sequence of a full-length gRNA and nucleotides added to the 5' end or the 3' end of the full-length gRNA. In some embodiments, the full-length gRNA can be designed using a program such as SgRNA designer, CRISPR MultiTargeter, or SSFinder. The nucleotides added to the 5' end for the CRISPR/Cas9 system or the 3' end for the CRISPR/Cpf1 system of the full-length gRNA can form secondary structures by hybridizing or partially hybridizing to the nucleotides in the protospacer-targeting sequence of the full-length gRNA. The secondary structure modulates DNA binding or cleavage by disrupting invasion of the DNA duplex by the gRNA. The secondary structure influences the invasion kinetics of the gRNA rather than the binding energy of the gRNA with the complementary DNA strand. As described in the examples below, guide RNAs of type II CRISPR-Cas systems bind to protospacers through a Cas9-facilitated process known as 'strand invasion,' where the Cas9 protein itself first binds to and melts the protospacer adjacent motif (PAM) through direct interactions, followed by base-pairing of the 3'-end of the gRNA with the PAM-adjacent nucleotides (the 'seed' region) then proceeding nucleotide-by-nucleotide from the 3'- of the gRNA to the 5'-end base-pairing with the protospacer. A similar mechanism is used with the CRISPR/Cpf1 system.

The nucleotides added to the 5' end or 3' end of the full-length gRNA are not merely added to hybridize with the protospacer-targeting segment of the guide RNA (hairpins) to block access to the protospacer at thermodynamic equilibrium. As described in the examples, the equilibrium thermodynamic secondary structure properties (such as melting temperature of the gRNA secondary structure) are not at all correlated with the specificity of the guide RNA. Rather, in the case of cleavage and in subsequent computational work for Cas9 binding (as measured through ChIP-Seq in cells (see doi:10.1038/nbt.2916; doi:10.1038/nbt.2889)), there is a significant and substantial correlation between those and estimated strand invasion kinetics, and the structure, design, and function of guide RNAs which modulate strand invasion into the protospacer that are necessarily different than hairpins designed to compete thermodynamically for binding at equilibrium with on- and off-target sites. For example, secondary structure elements which are designed to be stable at equilibrium (such as an RNA which forms a hairpin-like structure containing internal rG-rU wobble pairs within the stem) may become rapidly destabilized during strand invasion (for example, as the rG-rU wobble pairs become the terminal base-pair of the stem as adjacent nucleotides invade the protospacer, incurring a significant energetic penalty on the RNA secondary structure, modulating the strand invasion and binding kinetics by an entirely separate mechanism than by merely blocking access to the protospacer at thermodynamic equilibrium. Secondary structures that are stable at equilibrium but rapidly destabilized during strand invasion, can be designed using the methods described herein in such a way that discriminate between on- and off-target sites with minimal thermodynamic energetic differences between the sites (a result of a single internal mismatch, say) that cannot be practically discriminated by cis-blocking or thermodynamic competition. Where invasion of the on-target site destabilizes the hairpin containing G-U wobble pairs and the sites are discriminated kinetically by invasion. For example, the VEGFA1 sites described in the examples below (the target site is GGGTGGGGGGAGTTTGCTCC, and the off-target site 2 is GG<u>A</u>TGG<u>A</u>GGGAGTTTGCTCC; mismatches underlined) were able to make reduce off-target cleavage by 93% and 98% compared to a standard or full-length guide RNA or truncated guide RNA, respectively, using the computationally designed secondary structures which account for strand invasion.

Additionally, the nucleotides may be added to the 5' end or 3' end of a full-length gRNA to disrupt a 'naturally-occurring' secondary structure on the protospacer targeting segment of the gRNA in the 'seed' region to enhance the initiation of strand invasion by the guide RNA. Hence, the addition of these nucleotides which form secondary structures that alter strand invasion by hybridizing partially hybridizing nucleotides in the protospacer-targeting sequence to modulate DNA binding or cleavage represent a different class of guide RNA modification.

The optimized gRNAs are designed to minimize binding at an off-target site and to allow binding to a protospacer sequence. In some embodiments, the off-target site is a known or predicted off-target site. In some embodiments, the methods involve identifying a target region of interest, the target region of interest comprising a protospacer sequence; determining a polynucleotide sequence of a full-length gRNA that targets the target region of interest, the full-length gRNA comprising a protospacer-targeting sequence or segment; determining at least one or more off-target sites for the full-length gRNA; generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment is at the 5' end of the polynucleotide sequence of the full-length gRNA, the first gRNA optionally comprising a linker between the 5' end of the polynucleotide sequence of the full-length gRNA and the RNA segment, the linker comprising a polynucleotide sequence having a length of N nucleotides, the first gRNA capable of invading the protospacer sequence and binding to a DNA sequence that is complementary to the protospacer sequence and forming a protospacer-duplex, and the first gRNA capable of invading an off-target site and binding to a DNA sequence that is complementary to the off-target site and forming an off-target duplex; calculating an estimate or computationally simulating the invasion kinetics and lifetime that the first gRNA remains invaded in the protospacer and off-target site duplexes, wherein the dynamics of invasion are estimated nucleotide-by-nucleotide by determining the energetic differences between further invasion of a different gRNA and re-annealing of the first gRNA to the DNA sequence that is complementary to the protospacer sequence; comparing the estimated lifetimes at the protospacer and/or off-target sites of the first gRNA with the estimated lifetimes of the full-length gRNA or a truncated gRNA (tru-gRNA) at the protospacer and/or off-target sites; randomizing 0 to N nucleotides in the linker and 0 to M nucleotides in the first gRNA and generating a second gRNA and repeating step (e) with the second gRNA; identifying an optimized gRNA based on a gRNA sequence that satisfy a design criteria; and testing the optimized gRNA in vivo to determine the specificity of binding.

In some embodiments, the methods involve identifying a target region of interest, the target region of interest comprising a protospacer sequence; determining a polynucleotide sequence of a full-length gRNA that targets the target region of interest, the full-length gRNA comprising a protospacer-targeting sequence or segment; determining at least one or more off-target sites for the full-length gRNA; generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment is at the 3' end of the polynucleotide sequence of the full-length gRNA, the first gRNA optionally comprising a linker between the 3' end of the polynucleotide sequence of the full-length gRNA and the RNA segment, the linker comprising a polynucleotide sequence having a length of N nucleotides, the first gRNA capable of invading the protospacer sequence and binding to a DNA sequence that is complementary to the protospacer sequence and forming a protospacer-duplex, and the first gRNA capable of invading an off-target site and binding to a DNA sequence that is complementary to the off-target site and forming an off-target duplex; calculating an estimate or computationally simulating the invasion kinetics and lifetime that the first gRNA remains invaded in the protospacer and off-target site duplexes, wherein the dynamics of invasion are estimated nucleotide-by-nucleotide by determining the energetic differences between further invasion of a different gRNA and re-annealing of the first gRNA to the DNA sequence that is complementary to the protospacer sequence; comparing the estimated lifetimes at the protospacer and/or off-target sites of the first gRNA with the estimated lifetimes of the full-length gRNA or a truncated gRNA (tru-gRNA) at the protospacer and/or off-target sites; randomizing 0 to N nucleotides in the linker and 0 to M nucleotides in the first gRNA and generating a second gRNA and repeating step (e) with the second gRNA; identifying an optimized gRNA based on a gRNA sequence that satisfy a design criteria; and testing the optimized gRNA in vivo to determine the specificity of binding.

In some embodiments, the energetics of further invasion of a different gRNA is determined by determining the energetics of at least one of (I) breaking a DNA-DNA base-pairing, (II) forming an RNA-DNA base-pair, (III) energetic difference resulting from disrupting or forming different secondary structure within the uninvaded guide RNA, and (IV) forming or disrupting interactions between the displaced DNA strand that is complementary to the protospacer and any unpaired guide RNA nucleotides which are not involved in secondary structures. In some embodiments, the energetics of re-annealing of the first gRNA to the DNA sequence that is complementary to the protospacer sequence is determined by determining the energetics of at least one of (I) forming a DNA-DNA base-pairing, (II) breaking an RNA-DNA base-pair, (III) energetic difference resulting from disrupting or forming different secondary structure within the newly uninvaded guide RNA, and (IV) forming or disrupting interactions between the displaced DNA strand that is complementary to the protospacer and any unpaired guide RNA nucleotides which are not involved in secondary structures. In some embodiments, the method further comprises determining the energetic considerations from at least one of (V) base-pairing across mismatches, (VI) interactions with the Cas9 protein, and/or (VII) additional heuristics, wherein the additional heuristics relate to binding lifetime, extent of invasion, stability of invading guide RNA, or other calculated/simulated properties of gRNA invasion to Cas9 cleavage activity.

The CRISPR/Cas9-based system or CRISPR/Cpf1-based system can use gRNA, such as an optimized gRNA described herein, of varying sequences and lengths. In some embodiments, a full-length gRNA may comprise a protospacer-targeting segment which corresponds to the polynucleotide sequence of the target DNA sequence (i.e., protospacer). In some embodiments, the protospacer-targeting segment may have at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 30 nucleotides, or at least 35 nucleotides. The gRNA may target at least one of a promoter region, an enhancer region, a repressor region, an insulator region, a silencer region, a region involved in DNA looping with the promoter region, a gene splicing region, or the transcribed region of the target gene. In some embodiments, the full-length gRNA comprises a protospacer-targeting segment having between about 15 and 20 nucleotides.

In some embodiments, the RNA segment comprises between 2 and 20 nucleotides, between 3 and 10 nucleotides, or between 5 and 8 nucleotides. In some embodiments, the RNA segment comprises between 2 and 20 nucleotides, between 3 and 10 nucleotides, or between 5 and 8 nucleotides that complement the protospacer-targeting sequence. In some embodiments, M is between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10. For example, M can be 1, 2, 3, 4, 5, 6, 7, 8, 9, 10, 11, 12, 13, 14, 15, 16, 17, 18, 19, or 20. In some embodiments, the RNA segment can have between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10 nucleotides, some of which or all of which complement the protospacer-targeting sequence. In some embodiments, the RNA segment can have 1, 2, 3, 4, 5, 6, 7, 8, 9, 10, 11, 12, 13, 14, 15, 16, 17, 18, 19, or 20 nucleotides.

In some embodiments, N is between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10. For example, N can be 1, 2, 3, 4, 5, 6, 7, 8, 9, 10, 11, 12, 13, 14, 15, 16, 17, 18, 19, or 20. In some embodiments, the linker comprises between 1 and 20 nucleotides, between 3 and 10 nucleotides, or between 5 and 8 nucleotides. For example, the linker can have between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10 nucleotides, some of which or all of which complement the protospacer-targeting sequence. In some embodiments, the linker can have 1, 2, 3, 4, 5, 6, 7, 8, 9, 10, 11, 12, 13, 14, 15, 16, 17, 18, 19, or 20 nucleotides. In some embodiments, the linker can include a stabilizing linker, such as a tetraloop. Examples of tetraloop, include but are not limited to ANYA, CUYG, GNRA, UMAC and UNCG.

In some embodiments, the RNA segment and/or protospacer-targeting sequence provide a secondary structure. In some embodiments, the secondary structure is formed by partially hybridizing the protospacer-targeting sequence with the RNA segment. In some embodiments, the secondary structure modulates DNA binding or cleavage by Cas9 by disrupting invasion of the protospacer duplex or off-target duplex by the optimized gRNA. In some embodiments, the secondary structure keeps the 5'-end of the gRNA stably within the protein and protects the optimized gRNA within the Cas9 to prevent degradation In some embodiments, the secondary structure is formed by hybridizing all or part of the RNA segment to nucleotides in the 5' end of the protospacer-targeting sequence or segment, nucleotides in the middle of the protospacer-targeting sequence or segment, and/or nucleotides in the 3'-end of the protospacer-targeting sequence or segment. In some embodiments, contiguous segments of the RNA segment hybridize to the protospacer-targeting sequence or segment. In some embodiments, non-contiguous segment of the RNA segment hybridize to the protospacer-targeting sequence or segment. In some embodiments, the secondary structure is a hairpin.

In some embodiments, the secondary structure is stable at room temperature or 37° C. In some embodiments, overall equilibrium free energy of the secondary structure is less than about 2 kcal/mol at a temperature between about 4° C. and about 50° C., such as room temperature or 37° C. For example, the overall equilibrium free energy of the secondary structure can be less than about 10 kcal/mol, less than about 5 kcal/mol, less than about 4 kcal/mol, less than about 3 kcal/mol, less than about 2 kcal/mol, less than about 1 kcal/mol, or less than about 0.5 kcal/mol at a temperature between about 4° C. and about 50° C., between about 4° C. and about 40° C., between about 4° C. and about 37° C., between about 4° C. and about 30° C., between about 4° C. and about 25° C., between about 4° C. and about 20° C., between about 4° C. and about 10° C., between 5° C. and about 50° C., between about 5° C. and about 40° C., between about 5° C. and about 37° C., between about 5° C. and about 30° C., between about 5° C. and about 25° C., between about 5° C. and about 20° C., between about 5° C. and about 10° C., between about 10° C. and about 50° C., between about 10° C. and about 40° C., between about 10° C. and about 37° C., between about 10° C. and about 30° C., between about 10° C. and about 25° C., between about 10° C. and about 20° C., between about 20° C. and about 50° C., between about 20° C. and about 40° C., between about 20° C. and about 37° C., between about 20° C. and about 30° C., between about 25° C. and about 50° C., between about 25° C. and about 40° C., between about 25° C. and about 37° C., or between about 25° C. and about 30° C. In some embodiments, the RNA segment hybridizes or forms non-canonical base pairs with at least two nucleotides of the protospacer-targeting sequence or segment. In some embodiments, the non-canonical base pair is rU-rG.

In some embodiments, between 1 and 20 nucleotides are randomized in the linker. For example, between 1 and 20, between 1 and 15, between 1 and 10, between 1 and 9, between 1 and 8, between 1 and 7, between 1 and 6, between 1 and 5, between 1 and 4, between 1 and 3, between 1 and 2, between 2 and 20, between 2 and 15, between 2 and 10, between 2 and 9, between 2 and 8, between 2 and 7, between 2 and 6, between 2 and 5, between 2 and 4, between 3 and 20, between 3 and 15, between 3 and 10, between 3 and 9, between 3 and 8, between 3 and 7, between 3 and 6, between 3 and 5, between 3 and 4, between 4 and 20, between 4 and 15, between 4 and 10, between 4 and 9, between 4 and 8, between 4 and 7, between 4 and 6, between 4 and 5, between 5 and 20, between 5 and 15, between 5 and 10, between 5 and 9, between 5 and 8, between 5 and 7, between 5 and 6, between 6 and 20, between 6 and 15, between 6 and 10, between 6 and 9, between 6 and 8, between 6 and 7, between 7 and 20, between 7 and 15, between 7 and 10, between 7 and 9, between 7 and 8, between 8 and 20, between 8 and 15, between 8 and 10, between 8 and 9, between 9 and 20, between 9 and 15, or between 9 and 10, between 10 and 20, between 10 and 15, or between 15 and 20 nucleotides may be randomized in the linker.

In some embodiments, the between 1 and 20 nucleotides are randomized in the RNA segment. For example, between 1 and 20, between 1 and 15, between 1 and 10, between 1 and 9, between 1 and 8, between 1 and 7, between 1 and 6, between 1 and 5, between 1 and 4, between 1 and 3, between 1 and 2, between 2 and 20, between 2 and 15, between 2 and 10, between 2 and 9, between 2 and 8, between 2 and 7, between 2 and 6, between 2 and 5, between 2 and 4, between 3 and 20, between 3 and 15, between 3 and 10, between 3 and 9, between 3 and 8, between 3 and 7, between 3 and 6, between 3 and 5, between 3 and 4, between 4 and 20, between 4 and 15, between 4 and 10, between 4 and 9, between 4 and 8, between 4 and 7, between 4 and 6, between 4 and 5, between 5 and 20, between 5 and 15, between 5 and 10, between 5 and 9, between 5 and 8, between 5 and 7, between 5 and 6, between 6 and 20, between 6 and 15, between 6 and 10, between 6 and 9, between 6 and 8, between 6 and 7, between 7 and 20, between 7 and 15, between 7 and 10, between 7 and 9, between 7 and 8, between 8 and 20, between 8 and 15, between 8 and 10, between 8 and 9, between 9 and 20, between 9 and 15, or between 9 and 10, between 10 and 20, between 10 and 15, or between 15 and 20 nucleotides may be randomized in the RNA segment.

In some embodiments, step (g) is repeated X number of times, thereby generating X number of gRNAs and repeating step (e) with each X number of gRNAs, wherein X is between 0 to 20. In some embodiments, X can be is between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10. For example, X can be 1, 2, 3, 4, 5, 6, 7, 8, 9, 10, 11, 12, 13, 14, 15, 16, 17, 18, 19, or 20.

In some embodiments, the invasion kinetics and lifetime are calculated using kinetic Monte Carlo method or Gillespie algorithm. In some embodiment, the invasion kinetics and lifetime can be determined using 'deterministic' methods such as differential equations which model strand invasion, which are known to one of skill in the art. The kinetic Monte Carlo (KMC) method is a Monte Carlo method computer simulation intended to simulate the time evolution of some processes occurring in nature. The processes are typically processes that occur with known transition rates among states. These known transition rates are inputs to the KMC algorithm. The Gillespie algorithm (also known as the Doob-Gillespie algorithm) generates a statistically correct trajectory (possible solution) of a stochastic equation. The Gillespie algorithm can be used to simulate increasingly complex systems. The algorithm is particularly useful for simulating reactions within cells where the number of reagents typically number in the tens of molecules (or less). Mathematically, it is a variety of a dynamic Monte Carlo method and similar to the kinetic Monte Carlo methods. The Gillespie algorithm allows a discrete and stochastic simulation of a system with few reactants because every reaction is explicitly simulated. A trajectory corresponding to a single Gillespie simulation represents an exact sample from the probability mass function that is the solution of the master equation.

In some embodiments, the design criteria can be specificity, modulation of binding lifetime, and/or estimated cleavage specificity. For example, the optimized gRNA may be designed to have a binding lifetime greater than or equal to that of the full gRNA at an on-target site, and/or a binding lifetime less than or equal to that of the full-length gRNA at an off-target site. In some embodiments, the optimized gRNA is selected to have a binding lifetime less than or equal to that of the full-length gRNA to at least three off-target sites, wherein the off-target sites are predicted to be the closest off-target sites or predicted to have the highest identity to the on-target sites. In some embodiments, the design criteria comprises a lifetime or cleavage rate at an off-target site that is less than or equal to the lifetime or cleavage rate of a full-length gRNA or truncated gRNA at the off-target site and/or a predicted on-target activity rate that is greater than 10% of the predicted on-target activity rate of a full-length gRNA or truncated gRNA.

In some embodiments, the optimized gRNA is tested in step i) using a mismatch-sensitive nuclease to determine CRISPR activity, such as using surveyor assay or T7 endonuclease I (T7E1) assay, or next-gen sequencing techniques, such as Illumina MiSeq or GUIDE-Seq. In some embodiments, the optimized gRNA is tested in step i) using a reporter assay, wherein the Cas9-fusion protein activity alters the expression of a reporter protein, such as GFP. GUIDE-Seq is an assay that has been devised to assay off-target cleavages.

In some embodiments, the target region can be determined based on a sequence's proximity to a PAM sequence using a program, such as CRISPR design (Ran, et al. *Nature Protocols* (2013) 8:2281-2308) and CCTop (Stemmer, *PLoS One* (2015) 10:e0124633) tools. In some embodiments, the target sites can include promoters, DNAse I hypersensitivity sites, Transposase-Accessible Chromatin sites, DNA methylation sites, transcription factor binding sites, epigenetic marks, expression quantitative trait loci, and/or regions associated with human traits or phenotypes in genetic association studies. The target sites can be determined by DNase-sequencing (DNase-seq), Assay for Transposase-Accessible Chromatin with high throughput sequencing (ATAC-seq), ChIP-sequencing, self-transcribing active regulatory region sequencing (STARR-Seq), single molecule real time sequencing (SMRT), Formaldehyde-Assisted Isolation of Regulatory Elements sequencing (FAIRE—seq), micrococcal nuclease sequencing (MNase-seq), reduced representation bisulfite sequencing (RRBS-seq), whole genome bisulfite sequencing, methyl-binding DNA immunoprecipitation (MEDIP-seq), or genetic association studies. In some embodiments, the off-target site can be determined using CasOT (PKU Zebrafish Functional Genomics group, Peking University), CHOPCHOP (Harvard University), CRISPR Design, (Massachusetts Institute of Technology), CRISPR Design tool (The Broad Institute of Harvard and MIT), CRISPR/Cas9 gRNA finder (University of Colorado), CRISPRfinder (Université Paris-Sud), E-CRISP (DKFZ German Cancer Research Center), CRISPR gRNA Design tool (DNA 2.0), PROGNOS (Emory University/Georgia Institute of Technology), ZiFiT (Massachusetts General Hospital). Examples of tools that can be used to determine target regions and off-target sites are described in International Patent Application No. WO2016109255, which is incorporated herein by reference in its entirety.

7. Target Gene

As disclosed herein, the CRISPR/Cas9-based system or CRISPR/Cpf1-based system may be designed to target and cleave any target gene. For example, the gRNA, such as the optimized gRNA described herein, may target and bind a target region in a target gene. The target gene may be an endogenous gene, a transgene, or a viral gene in a cell line. In some embodiments, the target gene may be a known gene. In some embodiments, the target gene is an unknown gene. The gRNA may target any nucleic acid sequence. The nucleic acid sequence target may be DNA. The DNA may be any gene. For example, the gRNA may target a gene, such as DMD, EMX1, or VEGFA.

In some aspects, the target gene is a disease-relevant gene. In some embodiments, the target cell is a mammalian cell. In some embodiments, the genome includes a human genome. In some embodiments, the target gene may be a prokaryotic gene or a eukaryotic gene, such as a mammalian gene. For example, the CRISPR/Cas9-based system or CRISPR/Cpf1-based system may target a mammalian gene, such as DMD (dystrophin gene), EMX1, VEGFA, IL1RN, MYOD1, OCT4, HBE, HBG, HBD, HBB, MYOCD (Myocardin), PAX7 (Paired box protein Pax-7), FGF1 (fibroblast growth factor-1) genes, such as FGF1A, FGF1B, and FGF1C. Other target genes include, but not limited to, Atf3, Axud1, Btg2, c-Fos, c-Jun, Cxcl1, Cxcl2, Edn1, Ereg, Fos, Gadd45b, Ier2, Ier3, Ifrd1, I11b, I16, Irf1, Junb, Lif, Nfkbia, Nfkbiz, Ptgs2, Slc25a25, Sqstm1, Tieg, Tnf, Tnfaip3, Zfp36, Birc2, Cc12, Cc120, Cc17, Cebpd, Ch25h, CSF1, Cx3cl1, Cxcl10, Cxcl5, Gch, Icam1, Ifi47, Ifngr2, Mmp10, Nfkbie, Npal1, p21, Relb, Ripk2, Rnd1, Slpr3, Stx11, Tgtp, T1r2, Tmem140, Tnfaip2, Tnfrsf6, Vcam1, 1110004C05Rik (GenBank accession number BC010291), Abcal, AI561871 (GenBank accession number BI143915), AI882074 (GenBank accession number BB730912), Artsl, AW049765 (GenBank accession number BCO26642.1), C3, Casp4, Cc15, Cc19, Cdsn, Enpp2, Gbp2, H2-D1, H2-K, H2-L, Ifit1, Il13ra1, Illrl1, Lcn2, Lhfp12, LOC677168 (GenBank accession number AK019325), Mmp13, Mmp3, Mt2, Nafl, Ppicap, Prnd, Psmb10, Saa3, Serpina3g, Serpinfl, Sod3, Statl, Tapbp, U90926 (GenBank accession number NM 020562), Ubd, A2AR (Adenosine A2A receptor), B7-H3 (also called CD276), B7-H4 (also called VTCN1), BTLA (B and T Lymphocyte Attenuator; also called CD272), CTLA-4 (Cytotoxic T-Lymphocyte-Associated protein 4; also called CD152), IDO (Indoleamine 2,3-dioxygenase) KIR (Killer-cell Immunoglobulin-like Receptor), LAG3 (Lymphocyte Activation Gene-3), PD-1 (Programmed Death 1 (PD-1) receptor), TIM-3 (T-cell Immunoglobulin domain and Mucin domain 3), and VISTA (V-domain Ig suppressor of T cell activation. In some embodiments, the target gene is DMD (dystrophin), EMXJ, or VEGFA gene.

8. Compositions for Genome Editing

The present invention is directed to compositions for genome editing, genomic alteration or altering gene expression of a target gene. The compositions include an optimized gRNA generated by the disclosed method with a a CRISPR/Cas9-based system or CRISPR/Cpf1-based system. In some embodiments, the gRNA can discriminate between on- and off-target sites with minimal thermodynamic energetic differences between the sites and provide increased specificity. In some embodiments, the optimized gRNA modulates strand invasion into the protospacer.

The increase in specificity is achieved by adding an extension to the 5'-end or 3'-end of a full-length or standard gRNA such that it forms a 'hairpin' structure that is self-complementary to the segment of the full-length or standard gRNA which targets the protospacer, e.g., the protospacer-targeting sequence. See FIG. 1B and FIG. 2B. The hairpins serve as a kinetic barrier to strand invasion of the protospacer, but the hairpins are displaced during strand invasion of the full target sites so full invasion can occur.

Figures 2A, 2B:
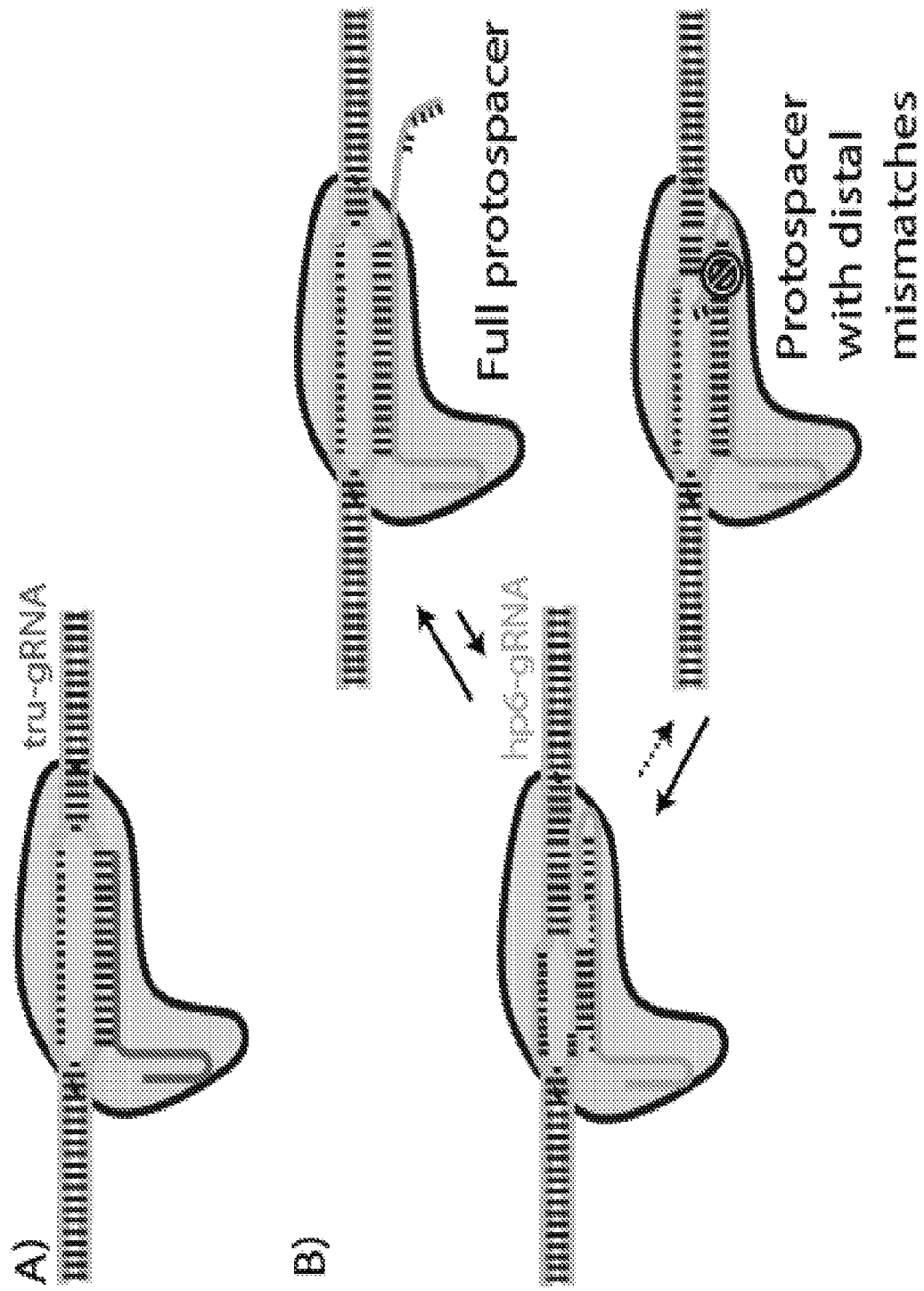
FIGS. 2A-2D show modulation of binding affinity and specificity by guide RNA variants.
Figures 2C, 2D:
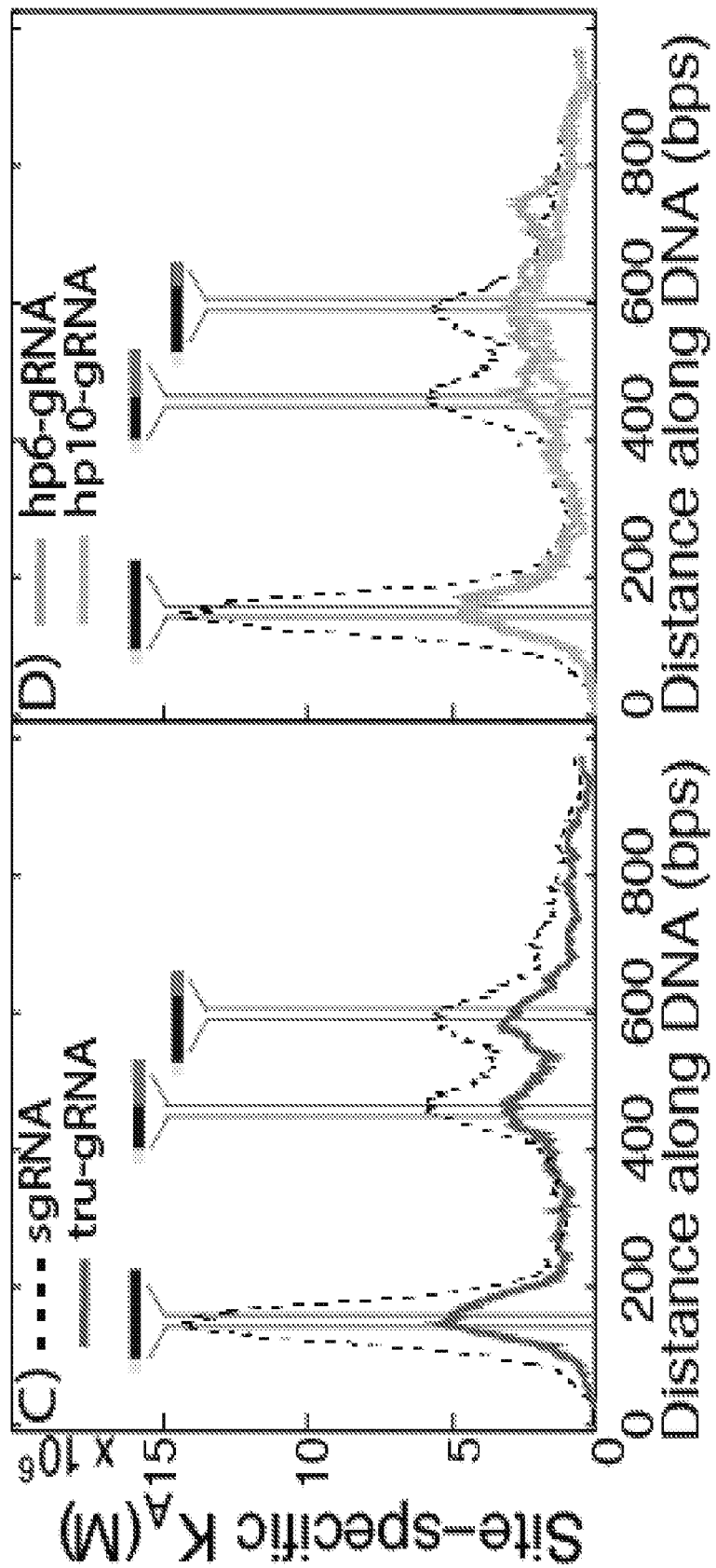

As shown in FIG. 2D, binding by dCas9 to full protospacers preferentially occurs, strongly suggesting that the hairpins are in fact displaced during invasion. The disclosed optimized gRNAs that are hairpins were designed to increase specificity in binding to targeted sites by inhibiting invasion if there were mismatches between the target and the PAM-distal targeting region of the guide RNA. In those cases, it is more energetically favorable for the hairpins to remain closed, and the presence of the hairpin likely promotes melting and detachment of Cas9/dCas9 from those sites.

Optimized gRNAs with 5'-hairpins or 3'-hairpins (hpgRNAs) significantly enhanced specificity in binding compared to both standard guide RNAs and the best available guide RNA variants (see examples), and abolished or significantly weakened binding at protospacer sites containing mismatches. Increasing lengths of the hairpin increased the specificity of dCas9 binding. Optimized gRNA and hpgRNAs can be used to tune Cas9/dCas9 or Cpf1 binding affinities and specificity. Based on the size and structure of the hairpin, the hairpin of hpgRNAs could be accommodated within the DNA-binding channel of Cas9/dCas9 molecule and protected from degradation. In some embodiments, the hairpin length, loop length, and loop composition may be changed to allow for more fine control of these properties. In some embodiments, the hairpin length can be between about 1 and about 20 nucleotides or between about 3 to about 10 nucleotides. For example, the hairpin length can be between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10. For example, the hairpin length can be 1, 2, 3, 4, 5, 6, 7, 8, 9, 10, 11, 12, 13, 14, 15, 16, 17, 18, 19, or 20 or about 5 to about 8 nucleotides.

In some embodiments, the loop length can be between about 1 and about 20 nucleotides, between about 3 to about 10 nucleotides, or between about 5 to about 8 nucleotides. For example, the loop length can be between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10. In some embodiments, the loop length can be 1, 2, 3, 4, 5, 6, 7, 8, 9, 10, 11, 12, 13, 14, 15, 16, 17, 18, 19, or 20 or about 5 to about 8 nucleotides.

In some embodiments, the loop composition can be between about 1 and about 20 nucleotides, between about 3 to about 10 nucleotides, or about 5 to about 8 nucleotides. For example, the loop composition can be between 1 and 20, between 1 and 19, between 1 and 18, between 1 and 17, between 1 and 16, between 1 and 15, between 1 and 14, between 1 and 13, between 1 and 12, between 1 and 11, between 1 and 10, between 1 and 9, between 1 and 8, between 1 and 7, between 1 and 6, between 1 and 5, between 2 and 20, between 2 and 19, between 2 and 18, between 2 and 17, between 2 and 16, between 2 and 15, between 2 and 14, between 2 and 13, between 2 and 12, between 2 and 11, between 2 and 10, between 2 and 9, between 2 and 8, between 2 and 7, between 2 and 6, between 2 and 5, between 3 and 20, between 3 and 19, between 3 and 18, between 3 and 17, between 3 and 16, between 3 and 15, between 3 and 14, between 3 and 13, between 3 and 12, between 3 and 11, between 3 and 10, between 3 and 9, between 3 and 8, between 3 and 7, between 3 and 6, between 3 and 5, between 4 and 20, between 4 and 19, between 4 and 18, between 4 and 17, between 4 and 16, between 4 and 15, between 4 and 14, between 4 and 13, between 4 and 12, between 4 and 11, between 4 and 10, between 4 and 9, between 4 and 8, between 4 and 7, between 4 and 6, between 4 and 5, between 5 and 20, between 5 and 19, between 5 and 18, between 5 and 17, between 5 and 16, between 5 and 15, between 5 and 14, between 5 and 13, between 5 and 12, between 5 and 11, between 5 and 10, between 5 and 9, between 5 and 8, between 5 and 7, between 5 and 6, between 6 and 20, between 6 and 19, between 6 and 18, between 6 and 17, between 6 and 16, between 6 and 15, between 6 and 14, between 6 and 13, between 6 and 12, between 6 and 11, between 6 and 10, between 6 and 9, between 6 and 8, between 6 and 7, between 7 and 20, between 7 and 19, between 7 and 18, between 7 and 17, between 7 and 16, between 7 and 15, between 7 and 14, between 7 and 13, between 7 and 12, between 7 and 11, between 7 and 10, between 7 and 9, between 7 and 8, between 8 and 20, between 8 and 19, between 8 and 18, between 8 and 17, between 8 and 16, between 8 and 15, between 8 and 14, between 8 and 13, between 8 and 12, between 8 and 11, between 8 and 10, between 8 and 9, between 9 and 20, between 9 and 19, between 9 and 18, between 9 and 17, between 9 and 16, between 9 and 15, between 9 and 14, between 9 and 13, between 9 and 12, between 9 and 11, or between 9 and 10. In some embodiments, the loop composition can be 1, 2, 3, 4, 5, 6, 7, 8, 9, 10, 11, 12, 13, 14, 15, 16, 17, 18, 19, or 20 or about 5 to about 8 nucleotides.

The compositions may include a may include viral vector and a CRISPR/Cas9-based system or CRISPR/Cpf1-based system with at least one gRNA, such as an optimized gRNA described herein. In some embodiments, the composition includes a modified AAV vector and a nucleotide sequence encoding a CRISPR/Cas9-based system with at least one gRNA, such as an optimized gRNA described herein. The composition may further comprise a donor DNA or a transgene. These compositions may be used in genome editing, genome engineering, and correcting or reducing the effects of mutations in genes involved in genetic diseases.

The target gene may be involved in differentiation of a cell or any other process in which activation, repression, or disruption of a gene may be desired, or may have a mutation such as a deletion, frameshift mutation, or a nonsense mutation. If the target gene has a mutation that causes a premature stop codon, an aberrant splice acceptor site or an aberrant splice donor site, the CRISPR/Cas9-based system or CRISPR/Cpf1-based system with at least one gRNA, such as an optimized gRNA described herein, may be designed to recognize and bind a nucleotide sequence upstream or downstream from the premature stop codon, the aberrant splice acceptor site or the aberrant splice donor site. The CRISPR/Cas9-based system or CRISPR/Cpf1-based system with at least one gRNA, such as an optimized gRNA described herein, may also be used to disrupt normal gene splicing by targeting splice acceptors and donors to induce skipping of premature stop codons or restore a disrupted reading frame. The CRISPR/Cas9-based system or CRISPR/Cpf1-based system with at least one gRNA, such as an optimized gRNA described herein, may or may not mediate off-target changes to protein-coding regions of the genome.

In some embodiments, the CRISPR/Cas9-based system induces or represses the gene expression of a target gene by at least about 1 fold, at least about 2 fold, at least about 3 fold, at least about 4 fold, at least about 5 fold, at least about 6 fold, at least about 7 fold, at least about 8 fold, at least about 9 fold, at least about 10 fold, at least 15 fold, at least 20 fold, at least 30 fold, at least 40 fold, at least 50 fold, at least 60 fold, at least 70 fold, at least 80 fold, at least 90 fold, at least 100 fold, at least about 110 fold, at least 120 fold, at least 130 fold, at least 140 fold, at least 150 fold, at least 160 fold, at least 170 fold, at least 180 fold, at least 190 fold, at least 200 fold, at least about 300 fold, at least 400 fold, at least 500 fold, at least 600 fold, at least 700 fold, at least 800 fold, at least 900 fold, at least 1000 fold, at least 1500 fold, at least 2000 fold, at least 2500 fold, at least 3000 fold, at least 3500 fold, at least 4000 fold, at least 4500 fold, at least 5000 fold, at least 600 fold, at least 7000 fold, at least 8000 fold, at least 9000 fold, at least 10000 fold, at least 100000 fold compared to a control level of gene expression. A control level of gene expression of the target gene may be the level of gene expression of the target gene in a cell that is not treated with any CRISPR/Cas9-based system.

a. Modified Lentiviral Vector

The compositions for genome editing, genomic alteration or altering gene expression of a target gene may include a modified lentiviral vector. The modified lentiviral vector includes a first polynucleotide sequence encoding a DNA targeting system and a second polynucleotide sequence encoding at least one sgRNA. The first polynucleotide sequence may be operably linked to a promoter. The promoter may be a constitutive promoter, an inducible promoter, a repressible promoter, or a regulatable promoter.

The second polynucleotide sequence encodes at least 1 gRNA, such as an optimized gRNA described herein. For example, the second polynucleotide sequence may encode at least 1 gRNA, at least 2 gRNAs, at least 3 gRNAs, at least 4 gRNAs, at least 5 gRNAs, at least 6 gRNAs, at least 7 gRNAs, at least 8 gRNAs, at least 9 gRNAs, at least 10 gRNAs, at least 11 gRNA, at least 12 gRNAs, at least 13 gRNAs, at least 14 gRNAs, at least 15 gRNAs, at least 16 gRNAs, at least 17 gRNAs, at least 18 gRNAs, at least 19 gRNAs, at least 20 gRNAs, at least 25 gRNA, at least 30 gRNAs, at least 35 gRNAs, at least 40 gRNAs, at least 45 gRNAs, or at least 50 gRNAs. The second polynucleotide sequence may encode between 1 gRNA and 50 gRNAs, between 1 gRNA and 45 gRNAs, between 1 gRNA and 40 gRNAs, between 1 gRNA and 35 gRNAs, between 1 gRNA and 30 gRNAs, between 1 gRNA and 25 different gRNAs, between 1 gRNA and 20 gRNAs, between 1 gRNA and 16 gRNAs, between 1 gRNA and 8 different gRNAs, between 4 different gRNAs and 50 different gRNAs, between 4 different gRNAs and 45 different gRNAs, between 4 different gRNAs and 40 different gRNAs, between 4 different gRNAs and 35 different gRNAs, between 4 different gRNAs and 30 different gRNAs, between 4 different gRNAs and 25 different gRNAs, between 4 different gRNAs and 20 different gRNAs, between 4 different gRNAs and 16 different gRNAs, between 4 different gRNAs and 8 different gRNAs, between 8 different gRNAs and 50 different gRNAs, between 8 different gRNAs and 45 different gRNAs, between 8 different gRNAs and 40 different gRNAs, between 8 different gRNAs and 35 different gRNAs, between 8 different gRNAs and 30 different gRNAs, between 8 different gRNAs and 25 different gRNAs, between 8 different gRNAs and 20 different gRNAs, between 8 different gRNAs and 16 different gRNAs, between 16 different gRNAs and 50 different gRNAs, between 16 different gRNAs and 45 different gRNAs, between 16 different gRNAs and 40 different gRNAs, between 16 different gRNAs and 35 different gRNAs, between 16 different gRNAs and 30 different gRNAs, between 16 different gRNAs and 25 different gRNAs, or between 16 different gRNAs and 20 different gRNAs. Each of the polynucleotide sequences encoding the different gRNAs may be operably linked to a promoter. The promoters that are operably linked to the different gRNAs may be the same promoter. The promoters that are operably linked to the different gRNAs may be different promoters. The promoter may be a constitutive promoter, an inducible promoter, a repressible promoter, or a regulatable promoter. At least one gRNA may bind to a target gene or loci. If more than one gRNA is included, each of the gRNAs binds to a different target region within one target loci or each of the gRNA binds to a different target region within different gene loci.

b. Adeno-Associated Virus Vectors

AAV may be used to deliver the compositions to the cell using various construct configurations. For example, AAV may deliver a CRISPR/Cas9-based system or CRISPR/Cpf1-based system and gRNA expression cassettes on separate vectors. Alternatively, if the small Cas9 proteins, derived from species such as *Staphylococcus aureus* or *Neisseria meningitidis*, are used then both the Cas9 and up to two gRNA expression cassettes may be combined in a single AAV vector within the 4.7 kb packaging limit.

The composition, as described above, includes a modified adeno-associated virus (AAV) vector. The modified AAV vector may be capable of delivering and expressing the CRISPR/Cas9-based system or CRISPR/Cpf1-based system in the cell of a mammal. For example, the modified AAV vector may be an AAV-SASTG vector (Piacentino et al. (2012) *Human Gene Therapy* 23:635-646). The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151).

9. Target Cells

As disclosed herein, the gRNA, such as an optimized gRNA described herein, may be used with a CRISPR/Cas9 system with any type of cell. In some embodiments, the cell is a bacterial cell, a fungal cell, an archaea cell, a plant cell or an animal cell, such as a mammalian cell. In some embodiments, this may be an organ or an animal organism. In some embodiments, the cell may be any cell type or cell line, including but not limited to, 293-T cells, 3T3 cells, 721 cells, 9 L cells, A2780 cells, A2780ADR cells, A2780cis cells, A172 cells, A20 cells, A253 cells, A431 cells, A-549 cells, ALC cells, B16 cells, B35 cells, BCP-1 cells, BEAS-2B cells, bEnd.3 cells, BHK-21 cells, BR 293 cells, BxPC3 cells, C2C12 cells, C3H-10T1/2 cells, C6/36 cells, Cal-27 cells, CHO cells, COR-L23 cells, COR-L23/CPR cells, COR-L23/5010 cells, COR-L23/R23 cells, COS-7 cells, COV-434 cells, CIVIL T1 cells, CMT cells, CT26 cells, D17 cells, DH82 cells, DU145 cells, DuCaP cells, EL4 cells, EM2 cells, EM3 cells, EMT6/AR1 cells, EMT6/AR10.0 cells, FM3 cells, H1299 cells, H69 cells, HB54 cells, HB55 cells, HCA2 cells, HEK-293 cells, HeLa cells, Hepa1c1c7 cells, HL-60 cells, HMEC cells, HT-29 cells, Jurkat cells, J558L cells, JY cells, K562 cells, Ku812 cells, KCL22 cells, KG1 cells, KYO1 cells, LNCap cells, Ma-Mel 1, 2, 3 . . . 48 cells, MC-38 cells, MCF-7 cells, MCF-10A cells, MDA-MB-231 cells, MDA-MB-468 cells, MDA-MB-435 cells, MDCK II cells, MDCK II cells, MG63 cells, MOR/0.2R cells, MONO-MAC 6 cells, MRC5 cells, MTD-1A cells, MyEnd cells, NCI-H69/CPR cells, NCI-H69/LX10 cells, NCI-H69/LX20 cells, NCI-H69/LX4 cells, NIH-3T3 cells, NALM-1 cells, NW-145 cells, OPCN/OPCT cells, Peer cells, PNT-1A/PNT 2 cells, Raji cells, RBL cells, RenCa cells, RIN-5F cells, RMA/RMAS cells, Saos-2 cells, Sf-9 cells, SiHa cells, SkBr3 cells, T2 cells, T-47D cells, T84 cells, THP1 cells, U373 cells, U87 cells, U937 cells, VCaP cells, Vero cells, WM39 cells, WT-49 cells, X63 cells, YAC-1 cells, YAR cells, GM12878, K562, H1 human embryonic stem cells, HeLa-S3, HepG2, HUVEC, SK-N-SH, IMR90, A549, MCF7, HMEC or LHCM, CD14+, CD20+, primary heart or liver cells, differentiated H1 cells, 8988T, Adult_CD4_naive, Adult_CD4_Th0, Adult_CD4_Th1, AG04449, AG04450, AG09309, AG09319, AG10803, AoAF, AoSMC, BC_Adipose_UHN00001, BC_Adrenal_Gland_H12803N, BC_Bladder_01-11002, BC_Brain_H11058N, BC_Breast_02-03015, BC_Colon_01-11002, BC_Colon_H12817N, BC_Esophagus_01-11002, BC_Esophagus_H12817N, BC_Jejunum_H12817N, BC_Kidney_01-11002, BC_Kidney_H12817N, BC_Left_Ventricle_N41, BC_Leukocyte_UHN00204, BC_Liver_01-11002, BC_Lung_01-11002, BC_Lung_H12817N, BC_Pancreas_H12817N, BC_Penis_H12817N, BC_Pericardium_H12529N, BC_Placenta_UHN00189, BC_Prostate_Gland_H12817N, BC_Rectum_N29, BC_Skeletal_Muscle 01-11002, BC_Skeletal_Muscle H12817N, BC_Skin_01-11002, BC_Small_Intestine_01-11002, BC_Spleen_H12817N, BC_Stomach_01-11002, BC_Stomach_H12817N, BC_Testis_N30, BC_Uterus_BN0765, BE2_C, BG02ES, BG02ES-EBD, BJ, bone_marrow_HS27a, bone_marrow_HS5, bone_marrow_MSC, Breast_OC, Caco-2, CD20+RO01778, CD20+_RO01794, CD34+_Mobilized, CD4+_Naive_Wb_11970640, CD4+_Naive_Wb78495824, Cerebellum_OC, Cerebrum_frontal_OC, Chorion, CLL, CMK, Colo829, Colon_BC, Colon_OC, Cord_CD4_naive, Cord_CD4_Th0, Cord_CD4_Th1, Decidua, Dnd41, ECC-1, Endometrium_OC, Esophagus_BC, Fibrobl, Fibrobl_GM03348, FibroP, FibroP_AG08395, FibroP_AG08396, FibroP_AG20443, Frontal_cortex_OC, GC_B_cell, Gliobla, GM04503, GM04504, GM06990, GM08714, GM10248, GM10266, GM10847, GM12801, GM12812, GM12813, GM12864, GM12865, GM12866, GM12867, GM12868, GM12869, GM12870, GM12871, GM12872, GM12873, GM12874, GM12875, GM12878-XiMat, GM12891, GM12892, GM13976, GM13977, GM15510, GM18505, GM18507, GM18526, GM18951, GM19099, GM19193, GM19238, GM19239, GM19240, GM20000, H0287, Hi-neurons, H7-hESC, H9ES, H9ES-AFP-, H9ES-AFP+, H9ES-CM, H9ES-E, H9ES-EB, H9ES-EBD, HAc, HAEpiC, HA-h, HAL, HAoAF, HAoAF_6090101.11, HAoAF_6111301.9, HAoEC, HAoEC_7071706.1, HAoEC_8061102.1, HA-sp, HBMEC, HBVP, HBVSMC, HCF, HCFaa, HCH, HCH_0011308.2P, HCH_8100808.2, HCM, HConF, HCPEpiC, HCT-116, Heart_OC, Heart_STL003, HEEpiC, HEK293, HEK293T, HEK293-T-REx, Hepatocytes, HFDPC, HFDPC_0100503.2, HFDPC_0102703.3, HFF, HFF-Myc, HFL11W, HFL24W, HGF, HHSEC, HIPEpiC, HL-60, HMEpC, HMEpC_6022801.3, HMF, hMNC-CB, hMNC-CB_8072802.6, hMNC-CB_9111701.6, hMNC-PB, hMNC-PB_0022330.9, hMNC-PB_0082430.9, hMSC-AT, hMSC-AT_0102604.12, hMSC-AT_9061601.12, hMSC-BM, hMSC-BM_0050602.11, hMSC-BM_0051105.11, hMSC-UC, hMSC-UC_0052501.7, hMSC-UC_0081101.7, HMVEC-dAd, HMVEC-dBl-Ad, HMVEC-dBl-Neo, HMVEC-dLy-Ad, HMVEC-dLy-Neo, HMVEC-dNeo, HMVEC-LBl, HMVEC-LLy, HNPCEpiC, HOB, HOB_0090202.1, HOB_0091301, HPAEC, HPAEpiC, HPAF, HPC-PL, HPC-PL_0032601.13, HPC-PL_0101504.13, HPDE6-E6E7, HPdLF, HPF, HPIEpC, HPIEpC_9012801.2, HPIEpC_9041503.2, HRCEpiC, HRE, HRGEC, HRPEpiC, HSaVEC, HSaVEC_0022202.16, HSaVEC_9100101.15, HSMM, HSMM_emb, HSMM_FSHD, HSMMtube, HSMMtube_emb, HSMMtube_FSHD, HT-1080, HTR8svn, Huh-7, Huh-7.5, HVMF, HVMF_6091203.3, HVMF_6100401.3, HWP, HWP_0092205, HWP_8120201.5, iPS, iPS_CWRU1, iPS_hFib2_iPS4, iPS_hFib2_iPS5, iPSNIHi11, iPS_NIHi7, Ishikawa, Jurkat, Kidney_BC, Kidney_OC, LHCN-M2, LHSR, Liver_OC, Liver_STL004, Liver_STL011, LNCaP, Loucy, Lung_BC, Lung_OC, Lymphoblastoid_cell_line, M059J, MCF10A-Er-Src, MCF-7, MDA-MB-231, Medullo, Medullo_D341, Mel_2183, Melano, Monocytes-CD14+, Monocytes-CD14+_RO01746, Monocytes-CD14+_RO01826, MRT_A204, MRT_G401, MRT_TTC549, Myometr, Naive_B_cell, NB4, NH-A, NHBE, NHBE_RA, NHDF, NHDF_0060801.3, NHDF_7071701.2, NHDF-Ad, NHDF-neo, NHEK, NHEM.f_M2, NHEM.f_M2_5071302.2, NHEM.f_M2_6022001, NHEM_M2, NHEM_M2_7011001.2, NHEM_M2_7012303, NHLF, NT2-D1, Olf_neurosphere, Osteobl, ovcar-3, PANC-1, Pancreas_OC, PanIsletD, PanIslets, PBDE, PBDEFetal, PBMC, PFSK-1, pHTE, Pons_OC, PrEC, ProgFib, Prostate, Prostate_OC, Psoas_muscle_OC, Raji, RCC_7860, RPMI-7951, RPTEC, RWPE1, SAEC, SH-SY5Y, Skeletal_Muscle_BC, SkMC, SKMC, SkMC_8121902.17, SkMC_9011302, SK-N-MC, SK-N-SH_RA, Small_intestine_OC, Spleen_OC, Stellate, Stomach_BC, T_cells_CD4+, T-47D, T98G, TBEC, Th1, Th1_Wb33676984, Th1_Wb54553204, Th17, Th2, Th2_Wb33676984, Th2_Wb54553204, Treg_Wb78495824, Treg_Wb83319432, U20S, U87, UCH-1, Urothelia, WERI-Rb-1, and WI-38. In some embodiments, the target cell can be any cell, such as a primary cell, a HEK293 cell, 293Ts cell, SKBR3 cell, A431 cell, K562 cell, HCT116 cell, HepG2 cell, or K-Ras-dependent and K-Ras-independent cell groups.

10. Methods of Epigenomic Editing

The present disclosure relates to a method of epigenomic editing in a target cell or a subject with a CRISPR/Cas9-based system or CRISPR/Cpf1-based system. The method can be used to activate or repress a target gene. The method includes contacting a cell or a subject with an effective amount of the optimized gRNA molecule, as described herein, and a CRISPR/Cas9-based system or CRISPR/Cpf1-based system. In some embodiments, the optimized gRNA is encoded by a polynucleotide sequence and packaged into a lentiviral vector. In some embodiments, the lentiviral vector comprises an expression cassette comprising a promoter operably linked to the polynucleotide sequence encoding the sgRNA. In some embodiments, the promoter operably linked to the polynucleotide encoding the optimized gRNA is inducible.

11. Methods of Site-Specific DNA Cleavage

The present disclosure relates to a method of site specific DNA cleavage in a target cell or a subject with a CRISPR/Cas9-based system or CRISPR/Cpf1-based system. The method includes contacting a cell or a subject with an effective amount of the optimized gRNA molecule, as described herein, and a CRISPR/Cas9-based system or CRISPR/Cpf1-based system. In some embodiments, the optimized gRNA is encoded by a polynucleotide sequence and packaged into a lentiviral vector. In some embodiments, the lentiviral vector comprises an expression cassette comprising a promoter operably linked to the polynucleotide sequence encoding the sgRNA. In some embodiments, the promoter operably linked to the polynucleotide encoding the optimized gRNA is inducible.

The number of gRNA administered to the cell or sample may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs.

The gRNA may comprise a complementary polynucleotide sequence of the target DNA sequence followed by a PAM sequence. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. The PAM sequence may be "NGG", where "N" can be any nucleotide. The gRNA may target at least one of the promoter region, the enhancer region or the transcribed region of the target gene. In some embodiments, the gRNA targets a nucleic acid sequence having a polynucleotide sequence of at least one of SEQ ID NOs: 13-148, 316, 317, or 320. The gRNA may include a nucleic acid sequence of at least one of SEQ ID NOs: 149-315, 321-323, or 326-329.

12. Methods of Correcting a Mutant Gene and Treating a Subject

The present disclosure is also directed to a method of correcting a mutant gene in a subject. The method comprises administering to a cell of the subject the composition, as described above. Use of the composition to deliver the CRISPR/Cas9-based system or CRISPR/Cpf1-based system with at least one gRNA, such as an optimized gRNA described herein, to the cell may restore the expression of a full-functional or partially-functional protein with a repair template or donor DNA, which can replace the entire gene or the region containing the mutation. The CRISPR/Cas9-based system or CRISPR/Cpf1-based system with at least one gRNA, such as an optimized gRNA described herein, may be used to introduce site-specific double strand breaks at targeted genomic loci. Site-specific double-strand breaks are created when the CRISPR/Cas9-based system or CRISPR/Cpf1-based system with at least one gRNA, such as an optimized gRNA described herein, binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with a CRISPR/Cas9-based system or CRISPR/Cpf1-based system with at least one gRNA, such as an optimized gRNA described herein, without a repair template, which can efficiently correct the reading frame and restore the expression of a functional protein involved in a genetic disease. The disclosed CRISPR/Cas9-based system or CRISPR/Cpf1-based system with at least one gRNA, such as an optimized gRNA described herein, may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active the CRISPR/Cas9-based system or CRISPR/Cpf1-based system with at least one gRNA, such as an optimized gRNA described herein, with an efficient gene editing method for the treatment of genetic diseases caused by mutations in nonessential coding regions that cause frameshifts, premature stop codons, aberrant splice donor sites or aberrant splice acceptor sites.

a. Nuclease Mediated Non-Homologous End Joining

Restoration of protein expression from an endogenous mutated gene may be through template-free NHEJ-mediated DNA repair. In contrast to a transient method targeting the target gene RNA, the correction of the target gene reading frame in the genome by a transiently expressed CRISPR/Cas9-based system or CRISPR/Cpf1-based system with at least one gRNA, such as an optimized gRNA described herein, may lead to permanently restored target gene expression by each modified cell and all of its progeny.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment. NHEJ-based gene correction using a CRISPR/Cas9-based system or CRISPR/Cpf1-based system, as well as other engineered nucleases including meganucleases and zinc finger nucleases, may be combined with other existing ex vivo and in vivo platforms for cell- and gene-based therapies, in addition to the plasmid electroporation approach described here. For example, delivery of a CRISPR/Cas9-based system or CRISPR/Cpf1-based system by mRNA-based gene transfer or as purified cell permeable proteins could enable a DNA-free genome editing approach that would circumvent any possibility of insertional mutagenesis.

b. Homology-Directed Repair

Restoration of protein expression from an endogenous mutated gene may involve homology-directed repair. The method as described above further includes administrating a donor template to the cell. The donor template may include a nucleotide sequence encoding a full-functional protein or a partially-functional protein. For example, the donor template may include a miniaturized dystrophin construct, termed minidystrophin ("minidys"), a full-functional dystrophin construct for restoring a mutant dystrophin gene, or a fragment of the dystrophin gene that after homology-directed repair leads to restoration of the mutant dystrophin gene.

13. Methods of Genome Editing

The present disclosure is also directed to genome editing with the CRISPR/Cas9-based system or CRISPR/Cpf1-based system described above to restore the expression of a full-functional or partially-functional protein with a repair template or donor DNA, which can replace the entire gene or the region containing the mutation. The CRISPR/Cas9-based system or CRISPR/Cpf1-based system may be used to introduce site-specific double strand breaks at targeted genomic loci. Site-specific double-strand breaks are created when the CRISPR/Cas9-based system or CRISPR/Cpf1-based system binds to a target DNA sequences using the gRNA, thereby permitting cleavage of the target DNA. The CRISPR/Cas9-based system and CRISPR/Cpf1-based system has the advantage of advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with CRISPR/Cas9-based system or CRISPR/Cpf1-based system without a repair template, which can efficiently correct the reading frame and restore the expression of a functional protein involved in a genetic disease. The disclosed CRISPR/Cas9-based system or CRISPR/Cpf1-based system and methods may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cas9-based system or CRISPR/Cpf1-based system with an efficient gene editing method for the treatment of genetic diseases caused by mutations in nonessential coding regions that cause frameshifts, premature stop codons, aberrant splice donor sites or aberrant splice acceptor sites.

The present disclosure provides methods of correcting a mutant gene in a cell and treating a subject suffering from a genetic disease, such as DMD. The method may include administering to a cell or subject a CRISPR/Cas9-based system or CRISPR/Cpf1-based system, a polynucleotide or vector encoding said CRISPR/Cas9-based system or CRISPR/Cpf1-based system, or composition of said CRISPR/Cas9-based system or CRISPR/Cpf1-based system as described above. The method may include administering a CRISPR/Cas9-based system or CRISPR/Cpf1-based system, such as administering a Cas9 protein, a Cpf1 protein, a Cas9 fusion protein containing a second domain, a nucleotide sequence encoding said Cas9 protein, Cpf1 protein, or Cas9 fusion protein, and/or at least one gRNA, wherein the gRNAs target different DNA sequences. The target DNA sequences may be overlapping. The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNA, at least 15 different gRNA, at least 20 different gRNA, at least 30 different gRNA, or at least 50 different gRNA, as described above. The gRNA may include a nucleic acid sequence of at least one of SEQ ID NOs: 149-315, 321-323, or 326-329. The method may involve homology-directed repair or non-homologous end joining.

14. Constructs and Plasmids

The compositions, as described above, may comprise genetic constructs that encodes the CRISPR/Cas9-based system or CRISPR/Cpf1-based system, as disclosed herein. The genetic construct, such as a plasmid, may comprise a nucleic acid that encodes the CRISPR/Cas9-based system or CRISPR/Cpf1-based system, such as the Cas9 protein, the Cpf1 protein, and Cas9 fusion proteins and/or at least one of the optimized gRNAs as described herein. The compositions, as described above, may comprise genetic constructs that encodes the modified AAV vector and a nucleic acid sequence that encodes the CRISPR/Cas9-based system or CRISPR/Cpf1-based system with at least one gRNA, such as an optimized gRNA described herein. The genetic construct, such as a plasmid, may comprise a nucleic acid that encodes the CRISPR/Cas9-based system or CRISPR/Cpf1- based system with at least one gRNA, such as an optimized gRNA described herein. The compositions, as described above, may comprise genetic constructs that encodes the modified lentiviral vector, as disclosed herein. The genetic construct, such as a plasmid, may comprise a nucleic acid that encodes a Cas9-fusion protein and at least one sgRNA. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the fusion protein, such as a Cas9-fusion protein, in the cell of a mammal. The vector may be recombinant. The vector may comprise heterologous nucleic acid encoding the Cas9-fusion protein. The vector may be a plasmid. The vector may be useful for transfecting cells with nucleic acid encoding the Cas9-fusion protein, which the transformed host cell is cultured and maintained under conditions wherein expression of the Cas9-fusion protein system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based system or CRISPR/Cpf1-based system and may further comprise an initiation codon, which may be upstream of the CRISPR/Cas9-based system or CRISPR/Cpf1-based system coding sequence, and a stop codon, which may be downstream of the CRISPR/Cas9-based system or CRISPR/Cpf1-based system coding sequence. The initiation and termination codon may be in frame with the CRISPR/Cas9-based system or CRISPR/Cpf1-based system coding sequence. The vector may also comprise a promoter that is operably linked to the CRISPR/Cas9-based system or CRISPR/Cpf1-based system coding sequence. The promoter operably linked to the CRISPR/Cas9-based system or CRISPR/Cpf1-based system coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the CRISPR/Cas9-based system or CRISPR/Cpf1-based system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the CRISPR/Cas9-based system or CRISPR/Cpf1-based system, i.e., the Cas9 protein, the Cpf1 protein, or Cas9 fusion protein coding sequence or sgRNA, such as an optimized gRNA described herein. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based system or CRISPR/Cpf1-based system, including the nucleic acid sequence encoding the Cas9 protein, the Cpf1 protein, or Cas9 fusion protein and the nucleic acid sequence encoding the at least one gRNA comprising the nucleic acid sequence of at least one of SEQ ID NOs: 149-315, 321-323, or 326-329.

15. Pharmaceutical Compositions

The composition may be in a pharmaceutical composition. The pharmaceutical composition may comprise about 1 ng to about 10 mg of DNA encoding the CRISPR/Cas9-based system, CRISPR/Cpf1-based system, or CRISPR/Cas9-based system protein component, i.e., the Cas9 protein, the Cpf1 protein, or Cas9 fusion protein. The pharmaceutical composition may comprise about 1 ng to about 10 mg of the DNA of the modified AAV vector and nucleotide sequence encoding the CRISPR/Cas9-based system with at least one gRNA, such as an optimized gRNA described herein. The pharmaceutical composition may comprise about 1 ng to about 10 mg of the DNA of the modified lentiviral vector. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred.

Stabilizers include gelatin and albumin. In some embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

16. Constructs and Plasmids

The compositions, as described above, may comprise genetic constructs that encodes the CRISPR/Cas9-based system or CRISPR/Cpf1-based system, as disclosed herein. The genetic construct, such as a plasmid or expression vector, may comprise a nucleic acid that encodes the CRISPR/Cas9-based system or CRISPR/Cpf1-based system, and/or at least one gRNA, such as an optimized gRNA described herein. The compositions, as described above, may comprise genetic constructs that encodes the modified lentiviral vector and a nucleic acid sequence that encodes the CRISPR/Cas9-based system or CRISPR/Cpf1-based system, as disclosed herein. The genetic construct, such as a plasmid, may comprise a nucleic acid that encodes the CRISPR/Cas9-based system or CRISPR/Cpf1-based system. The compositions, as described above, may comprise genetic constructs that encodes a modified lentiviral vector. The genetic construct, such as a plasmid, may comprise a nucleic acid that encodes the CRISPR/Cas9-based system or CRISPR/Cpf1-based system and at least one sgRNA such as an optimized gRNA described herein. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the fusion protein, such as the CRISPR/Cas9-based system or CRISPR/Cpf1-based system, in the cell of a mammal. The vector may be recombinant. The vector may comprise heterologous nucleic acid encoding the fusion protein, such as the CRISPR/Cas9-based system. The vector may be a plasmid. The vector may be useful for transfecting cells with nucleic acid encoding the CRISPR/Cas9-based system or CRISPR/Cpf1-based system, which the transformed host cell is cultured and maintained under conditions wherein expression of the CRISPR/Cas9-based system or CRISPR/Cpf1-based system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based system or CRISPR/Cpf1-based system and may further comprise an initiation codon, which may be upstream of the CRISPR/Cas9-based system or CRISPR/Cpf1-based system coding sequence, and a stop codon, which may be downstream of the CRISPR/Cas9-based system or CRISPR/Cpf1-based system coding sequence. The initiation and termination codon may be in frame with the CRISPR/Cas9-based system or CRISPR/Cpf1-based system coding sequence. The vector may also comprise a promoter that is operably linked to the CRISPR/Cas9-based system or CRISPR/Cpf1-based system coding sequence. The CRISPR/Cas9-based system or CRISPR/Cpf1-based system may be under the light-inducible or chemically inducible control to enable the dynamic control of in space and time. The promoter operably linked to the CRISPR/Cas9-based system or CRISPR/Cpf1-based system coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the CRISPR/Cas9-based system or CRISPR/Cpf1-based system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the CRISPR/Cas9-based system or CRISPR/Cpf1-based system and/or sgRNA, such as an optimized gRNA described herein. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based system or CRISPR/Cpf1-based system and the nucleic acid sequence encoding the at least one gRNA, such as an optimized gRNA described herein.

In some embodiments, the gRNA, such as an optimized gRNA described herein, is encoded by a polynucleotide sequence and packaged into a lentiviral vector. In some embodiments, the lentiviral vector includes an expression cassette. The expression cassette can includes a promoter operably linked to the polynucleotide sequence encoding the gRNA, such as an optimized gRNA described herein. In some embodiments, the promoter operably linked to the polynucleotide encoding the gRNA is inducible.

i. Adeno-Associated Virus Vectors

The composition, as described above, includes a modified adeno-associated virus (AAV) vector. The modified AAV vector may have enhanced cardiac and skeletal muscle tissue tropism. The modified AAV vector may be capable of delivering and expressing the CRISPR/Cas9-based system or CRISPR/Cpf1-based system with at least one gRNA, such as an optimized gRNA described herein, in the cell of a mammal. For example, the modified AAV vector may be an AAV-SASTG vector (Piacentino et al. (2012) Human Gene Therapy 23:635-646). The modified AAV vector may deliver nucleases to skeletal and cardiac muscle in vivo. The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151).

17. Methods of Delivery

Provided herein is a method for delivering the CRISPR/Cas9-based system or CRISPR/Cpf1-based system and the optimized gRNA described herein for providing genetic constructs and/or proteins of the CRISPR/Cas9-based system or CRISPR/Cpf1-based system. The delivery of the CRISPR/Cas9-based system or CRISPR/Cpf1-based system and the optimized gRNA described herein may be the transfection or electroporation of the CRISPR/Cas9-based system or CRISPR/Cpf1-based system and the optimized gRNA described herein as one or more nucleic acid molecules that is expressed in the cell and delivered to the surface of the cell. The CRISPR/Cas9-based system or CRISPR/Cpf1-based system protein may be delivered to the cell. The nucleic acid molecules may be electroporated using BioRad Gene Pulser Xcell or Amaxa Nucleofector IIb devices or other electroporation device. Several different buffers may be used, including BioRad electroporation solution, Sigma phosphate-buffered saline product #D8537 (PBS), Invitrogen OptiMEM I (OM), or Amaxa Nucleofector solution V (N. V.). Transfections may include a transfection reagent, such as Lipofectamine 2000.

The vector encoding a CRISPR/Cas9-based system or CRISPR/Cpf1-based system protein may be delivered to the modified target cell in a tissue or subject by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus.

The nucleotide encoding a CRISPR/Cas9-based system or CRISPR/Cpf1-based system protein may be introduced into a cell to induce gene expression of the target gene. For example, one or more nucleotide sequences encoding the CRISPR/Cas9-based system or CRISPR/Cpf1-based system directed towards a target gene may be introduced into a mammalian cell. Upon delivery of the CRISPR/Cas9-based system or CRISPR/Cpf1-based system to the cell, and thereupon the vector into the cells of the mammal, the transfected cells will express the CRISPR/Cas9-based system or CRISPR/Cpf1-based system. The CRISPR/Cas9-based system or CRISPR/Cpf1-based system may be administered to a mammal to induce or modulate gene expression of the target gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

Methods of introducing a nucleic acid into a host cell are known in the art, and any known method can be used to introduce a nucleic acid (e.g., an expression construct) into a cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. In some embodiments, the composition may be delivered by mRNA delivery and ribonucleoprotein (RNP) complex delivery.

18. Routes of Administration

The compositions may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus. The composition may be injected into the skeletal muscle or cardiac muscle. For example, the composition may be injected into the tibialis anterior muscle.

19. Kits

Provided herein is a kit, which may be used for site-specific DNA binding. The kit comprises a composition, as described above, and instructions for using said composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The composition may include a modified lentiviral vector and a nucleotide sequence encoding a CRISPR/Cas9-based system and the optimized gRNA, as described above. The CRISPR/Cas9-based system, as described above, may be included in the kit to specifically bind and target a particular regulatory region of the target gene.

20. Examples

The foregoing may be better understood by reference to the following examples, which are presented for purposes of illustration and are not intended to limit the scope of the invention.

Example 1

Materials and Methods

Materials.

Tris-HCl (pH 7.6) buffer was obtained from Corning Life Sciences. L-glutamic acid monopotassium salt monohydrate, dithiothreitol (DTT), and magnesium chloride were obtained from Sigma Aldrich Co., LLC.

Cloning of Cas9, dCas9, and sgRNA Expression Plasmids;

Plasmids encoding Cas9, dCas9, and sgRNAs which target the AAVS1 locus of human chromosome 19 were cloned, expressed, and purified using standard techniques. The DNA substrates used for imaging—(i) a 1198 bp substrate derived from a segment of the AAVS1 locus of human chromosome 19; (ii) an 'engineered' 989 bp DNA substrate containing a series of six full, partial, or mismatched target sites; and (iii) a 1078 bp 'nonsense' substrate containing no homology to the protospacer (>3 bp)—were also generated using standard techniques. The plasmids encoding wild-type Cas9 and dCas9 were obtained from Addgene (plasmid 39312 and plasmid 47106). Plasmids for the expression of Cas9 and dCas9 in bacteria were cloned using Gateway Cloning (Life Technologies). Briefly, PCR was used to amplify Cas9 and dCas9 genes and to add flanking attL1 and attL2 sites. BP recombination was performed to transfer these genes to a shuttle vector, after which LP recombination was performed to transfer these genes to pDest17, which adds an N-terminal hexa-histidine tag (Life Technologies). The plasmids encoding the chimeric sgRNA and sgRNA variants (described below) were cloned as previously described (Perez-Pinera et al., (2013) *Nature methods*, 10, 973-976).

Expression and Purification of Cas9, dCas9.

Plasmids encoding Cas9 or dCas9 were transformed into SoluBL21 competent cells (Genlantis) according to standard techniques (Sambrook, J., Fritsch, E. F. and Maniatis, T. (1989) Molecular cloning. *Cold spring harbor laboratory press* New York.). Single colonies were used to inoculate 25 mL starter cultures. 25 mL starter cultures were grown overnight and used to inoculate 1 L cultures. Inoculated 1 L cultures were grown for 5 hours at 25° C. after which the temperature was dropped to 16° C. and protein expression induced by the addition of 0.1 mM IPTG. Induced cultures were grown for another 12 hours at 16° C. Cells were harvested by centrifugation at 4000×g and stored at −80° C. for long-term storage.

Cell pellets were resuspended in 30 mL of Lysis Buffer (50 mM Tris-HCl, 500 mM NaCl, 10 mM $MgCl_2$, 10% v/v glycerol, 0.2% Triton-1000, and 1 mM PMSF). The cell suspension was lysed by sonication at 30% duty cycle for 5 minutes. The suspension was then centrifuged for 30 minutes at 12,000×g. The supernatant was then taken and incubated with Ni-NTA resin (Qiagen) for 30 minutes under gentle agitation. The resin was then loaded onto a column, washed with Wash Buffer (35 mM imidizole, 50 mM Tris-HCl, 500 mM NaCl, 10 mM $MgCl_2$, 10% v/v glycerol), and eluted with Elution Buffer (120 mM imidizole, 50 mM Tris-HCl, 500 mM NaCl, 10 mM $MgCl_2$, 10% v/v glycerol). Ultracel-30 k centrifugal filters were then used to exchange solvents to the Storage Buffer (50 mM Tris-HCl, 500 mM NaCl, 10 mM $MgCl_2$, 10% v/v glycerol). The samples were then aliquoted and frozen at −80° C. Representative polyacrylamide SDS gels of purified Cas9 and dCas9 are presented in FIG. 51, indicating approximately >95% purity.

Expression and Purification of sgRNA and Guide RNA Variants.

Guide RNAs were in vitro transcribed using the MEGAshortscript T7 Transcription Kit (Life Technologies. DNA templates with a T7 promoter were generated via PCR from guide RNA plasmids and reactions were set up following the manufacturer's instructions. The T7 templates for the guide RNAs with 2 nucleotides truncated from their 5'-ends (tru-gRNAs) and those with 5' extensions that form hairpins (hp-gRNAs) were generated by PCR off of the standard gRNA plasmids. The RNA was then purified using phenol-chloroform extraction using standard techniques (Sambrook et al. (1989) Molecular cloning. *Cold spring harbor laboratory press* New York).

Generation of DNA Substrates.

Genomic DNA was extracted and purified from HEK293T cell line using the DNeasy kit (Qiagen), following the manufacturer's protocol. The AAVS1 locus was then amplified using PCR. The 1198 bp AAVS1-derived substrate was constructed via direct PCR from genomic DNA using primers from Integrated DNA Technologies (IDT): 5'-\Bt\-CCAGGATCAGTGAAACGCAC-3' and 5'-GAGCTC-TACTGGCTTCTGCG-3', where \Bt\ represents a biotinylation of the primer at the 5'-end. The 'engineered' DNA substrate, which contains a series of PAMs and full or partial protospacer sites, was ordered as two gBlock fragments each containing an EcoRI restriction site on one end. Substrates were digested, ligated together, and then enriched via PCR with primers (Integrated DNA Technologies, IDT): 5'-\Bt\-CATGACGTGCAGCAAGC-3' and 5'-CGACGATGCGCT-GAATC-3'. To construct a 'nonsense' substrate containing no sites exhibiting homology (greater than 3 bp) to the protospacer: a 690 bp DNA construct was synthesized (GeneScript, Inc.) containing a series of restriction sites, and an addition length of DNA from lambda DNA (New England Biolabs) was sub-cloned into the construct; the 1078 bp substrate was then PCR amplified using primers (IDT): 5'-\Bt\-GACCTGCAGGCATGCAAGCTTGG-3' and 5'-CAGCGTCCCCGGTTGTGAATCT-3'. All DNA was gel purified, diluted to 25 nM in working buffer (20 mM Tris-HCl (pH 7.6), 100 mM potassium glutamate, 5 mM $MgCl_2$, and 0.4 mM DTT) and incubated with 40× excess monomeric streptavidin (Howarth et al., (2006) *Nature methods*, 3, 267-273) for 10 minutes prior to incubation with Cas9/dCas9.

Figures 8A, 8B:
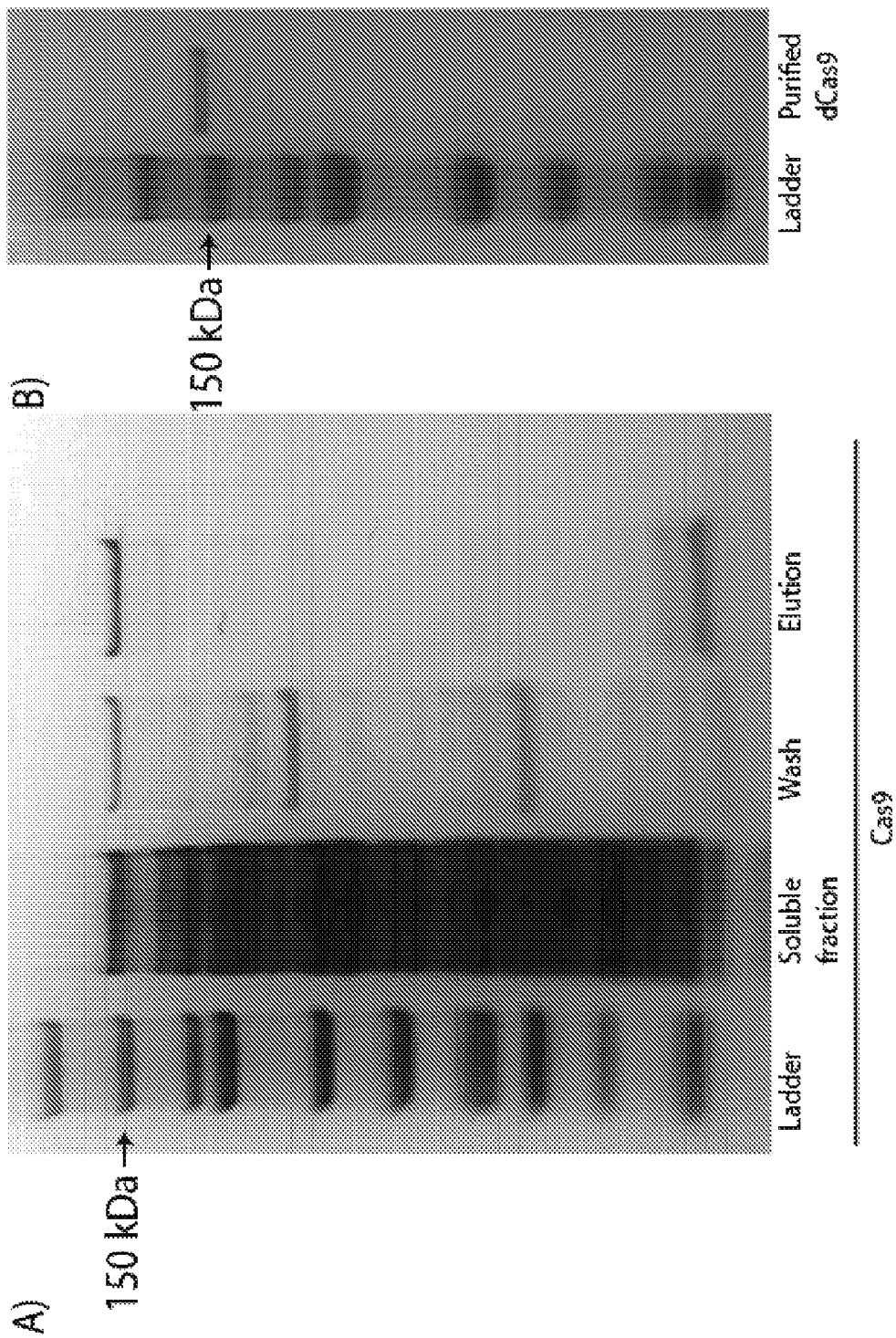
FIGS. 8A-8B show purity of expressed Cas9 and dCas9 in SDS gel of purified Cas9 (FIG. 8A) and dCas9 (FIG. 8B) products (nominal molecular weight: 160 kDa). Eluted bands show product is ~95% pure.

Sodium dodecyl sulfate-polyacrylamide gels of purified Cas9 and dCas9 are presented in FIGS. 8A-8B, indicating approximately 95% purity.

Atomic Force Microscopy.

Atomic force microscopy (AFM) was performed in air using a Bruker (née Veeco) Nanoscope V Multimode with RTSEP (Bruker) probes (nominal spring constant 40 N/m, resonance frequency, 300 kHz). Prior to experiments, protein and guide RNAs were mixed in 1:1.5 ratio for 10 minutes. Protein and DNA were mixed in a solution of working buffer for at least 10 minutes (up to 35 minutes) at room temperature, deposited for 8 seconds on freshly cleaved mica (Ted Pella, Inc.) that had been treated with 3-aminopropylsiloxane (prepared as previously described (24)), rinsed with ultra-pure (>17 MS2) water, and dried in air. Proteins were centrifuged briefly prior to incubation with DNA. When the standard sgRNA was used, at least four preparations for each experimental condition were imaged, and at least two for experiments with the other guide RNA variants. In general images were acquired with pixel resolution of 1024×1024 over 2.75 micron square areas or 2048×2048 over 5.5 micron square areas at 1-1.5 line/s for each sample. Images of several thousand (~2500-6000) DNA molecules were resolved for each experimental condition.

DNA Tracing and Refinement with Sub-Pixel Resolution.

Acquired AFM images were flattened and leveled (plane-wise, by line, and by $3^{rd}$ order polynomial leveling) using an open-source image analysis software for scanning probe microscopy, Gwyddion (http://gwyddion.net/), and then exported to MATLAB (Mathworks, Inc.). 151×151 pixel (405 nm×405 nm) regions containing each DNA molecule were sorted by inspection for a clearly identifiable streptavidin label, the presence of at least one bound Cas9/dCas9 molecule, and an unambiguous end-to-end path to ensure lack of aggregation or overlap with other DNA molecules. The contour of the DNA was traced by hand and the estimated boundaries of the streptavidin and Cas9/dCas9 were marked. The trace was then algorithmically refined using a method based on Wiggins et al. (2006) *Nature nanotechnology*, 1, 137-141. Starting at the weighted centroid of the streptavidin ($x_1$), the position of next element on the backbone ($x_2$) is estimated by stepping 2.5 nm toward the nearest hand-traced points beyond the estimated boundary of the streptavidin. An 11-pixel line is drawn on a two-fold linear interpolation of the image of the DNA perpendicularly to the ($x_1$-$x_2$) line segment at $x_2$. $x_2$ is relocated to the position on the normal line with the maximum topographical height then adjusted to the 2.5 nm from $x_1$ on the new ($x_1$-$x_2$) line. The positions of $x_3 \ldots x_n$ are then iteratively estimated using the nearest hand-traced points to generate the initial guess for the next backbone position then corrected as before, and the correction process continues until the point $x_n$ is less than 2.5 nm from the end of the traced DNA molecule. When the refined trace enters the estimated boundary of a Cas9/dCas9 molecule at $x_1$, the position of the DNA is instead estimated as the point on a cubic Hermite spline (using points $x_{i-1}$, $x_i$, $x_j$, and $x_{j+1}$, where is the first point of the hand-drawn trace beyond the estimated Cas9/dCas9 boundary) located 2.5 nm from $x_1$.

Upon completion of the trace, the height of the DNA along the contour is extracted (relative to the median pixel height of the local region). The estimated boundaries of the streptavidin and Cas9/dCas9 were iteratively expanded or retracted around the original estimate until they expanded to a contiguous region greater than ($\mu_d+\sigma_d$), where $\mu_d$ and $\sigma_d$ are the mean and standard deviation of the height of the traced DNA beyond the estimated positions of bound proteins, and the estimate converges.

To account for any instrumental hysteresis which may distort the apparent length of DNA, the length of the DNA was normalized, and only DNA molecules originally measured to be 20% of their expected length (given the known number of base-pairs, 0.33 nm per base-pair) were used for further analysis (for the AAVS1 substrate-number traced: 804; nominal length: 1198 bp, mean length recorded: 1283 bp, std. dev: 154 bp; for the engineered substrate-number traced: 1520, nominal length: 986 bp, mean length recorded: 1071 bp, std. dev: 124 bp; for the 'nonsense' substrate-number traced: 616, nominal length: 1078 bp, mean length recorded: 1217 bp, std. dev: 135 bp). This step prevented us from improperly analyzing, e.g., two DNA molecules which appeared collinear, DNA which may have fragmented, or DNA which may have been cleaved by Cas9 and separated (which was rare, see main text).

The binding histograms of FIGS. 1C-1D, FIG. 2C-2D, and FIG. 9 were generated by mapping the relative location of each bound protein to the bases overlapped (nearest-neighbor interpolation) by the protein and summing the total number of proteins bound to each site (if a single Cas9/dCas9 could be interpreted as being in contact with multiple (k) sites, each region of contact was weighed by 1/k in the binding histogram). Peaks in the binding histogram were fit to the empirical Gaussian $\exp(-((x-\mu)/w)^2)$, where $\mu$ is the mean peak position and w is the peak width parameter (w=$\sqrt{2}\sigma$, with a the standard deviation), using MATLAB.

Determination of dCas9 Apparent Dissociation Constants.

Apparent dissociation constants of dCas9 with different guide RNA variants were determined as previously described (Yang et al. (2005) *Nucleic Acids Res.*, 33, 4322-4334). Briefly, at known solution concentrations of dCas9-guide RNA ($[dCas9]_0$) and DNA molecules ($[DNA]_0$), the respective numbers of 'engineered' DNA molecules were counted with and without proteins bound (fraction of DNA bound by proteins $\Theta_{dCas9}$). After tracing DNA with bound proteins (see above) the average number of proteins bound per DNA molecule ($n_{dCas9}$) was determined. Overall dissociation constants are calculated as $K_{d, DNA}=[DNA][dCas9]/[DNA\cdot dCas9]=(1-\Theta_{dCas9})\ ([dCas9]_0-n_{dCas9}\ [DNA]_0)/(\Theta_{dCas9})$ The protospacer-specific dissociation constants $K_{d,protospacer}$ are calculated similarly using instead $\Theta_{dCas9,protospacer}$, the fractions of DNA with dCas9 bound within one peak width of the Gaussian fit in their respective binding histograms (i.e., see Table 1), as are the site-specific association constants $K_{a,ss}=K_{d,ss}^{-1}$ using the fractions of each site on the DNA with a bound dCas9 $\Theta_{dCas9,ss}$.

Protein Alignment and Clustering.

Images of Cas9 and dCas9 proteins which were isolated and appeared only to contact the DNA at a single location were extracted. These features were selected as those with features greater than $(\mu_d+2\sigma_d)$ which fit entirely within a 134 nm×134 nm bounding box, where $\mu_d$ and $\sigma_d$ are the mean and standard deviation of the DNA height to which the proteins are bound; this step essentially had the effect of removing most of the aggregated/densely packed Cas9/dCas9 from the set as well as those proteins from images with larger extrinsic noise. After four-fold nearest-neighbor interpolation, features of the protein with topographical height greater than $(\mu_d+\sigma_d)$ were each aligned by repeated translation, rotation, and reflection with respect to one another to minimize the mean-squared difference between their topographical heights. A distance matrix was composed of these minimized mean-square difference, then the proteins with standard sgRNA were clustered according to this criterion using the method of Rodriguez and Laio (27); proteins with the guide RNA variants were clustered according to the closest Cas9/dCas9 structure with the standard sgRNA. Ensemble average structures were extracted by performing a reference-free alignment across each member of individual clusters following the method of Penczek, Radermacher, and Frank (28). Properties of Cas9/dCas9 populations at each feature (such as protospacer sites) on the DNA were determined using proteins bound within one peak width of the Gaussian distributions fit to the binding histograms (i.e., see Table 1).

Kinetic Monte Carlo (KMC) of Guide RNA Strand Invasion and R-Loop 'Breathing'.

Kinetic Monte Carlo (KMC) experiments to simulate strand invasion by the guide RNAs at protospacer sites were performed using a Gillespie-type (continuous time, discrete state) ((Gillespie (1976) *Journal of computational physics*, 22, 403-434) algorithm implemented in MATLAB. Strand invasion is modeled as a one-dimensional random walk in a position-dependent potential determined by the relative nearest-neighbor dependent DNA:DNA and RNA:DNA binding free energies. See, e.g., FIG. 4A. That is, the guide RNA is base-paired with the protospacer up to protospacer site m ($1 \geq m \geq 20$ for sgRNA and $1 \geq m \geq 18$ for a truncated sgRNA (tru-gRNA)) and, to first-order, the forward rate (rate of additional guide RNA invasion) $v_f$ is estimated using the symmetric approximation to be $\exp(-(\Delta G \degree (m+1)_{RNA:DNA} - \Delta G \degree (m+1)_{DNA:DNA})/2RT)$, where R is Boltzmann's constant, T is the temperature (here 37° C. to correspond with parameter set that was used), $\Delta G \degree (m+1)_{RNA:DNA}$ is free energy of the base-pairing between the RNA and protospacer at site m+1 and $\Delta G \degree (m+1)_{DNA:DNA}$ is the free energy of the base-pairing between the protospacer and its complementary DNA strand (the ½ corrective term is included to satisfy detailed balance). $v_f$ at state m=20 or 18 for sgRNA or tru-gRNA was set to 0. The reverse rate (rate of re-hybridization between the protospacer and its complementary DNA strand) $v_r$ is calculated similarly as proportional to $\exp(-(\Delta G \degree (m)_{DNA:DNA} - \Delta G \degree (m)_{RNA:DNA})/2RT)$; if state m=1, the simulation was halted (signifying guide RNA-protospacer dissociation). Starting at time t=0 (in arbitrary time units), for each iteration of the algorithm, the m-dependent rates are determined and two random numbers $r_1$ and $r_2$ are generated from a uniform distribution between 0 and 1. t is advanced by $\Delta t=\log(r_1)/(v_f+v_r)$. State m is increased to m+1 if $r_2 \geq v_f/(v_f+v_r)$ or decreased to m−1 otherwise. For 'equilibrium' measurements of R-loop breathing, m was initiated at m=20 (or 18 in the case of tru-gRNA) and the algorithm iterated until t 10,000. For measurements of 'invasion' kinetics' dynamics (such as in the presence of mismatched base-pairs), m was initiated at m=10 (up to t=1000).

Free energy parameters are derived from the literature from experiments at 1M NaCl at 37° C. Sequence-dependent DNA:DNA hybridization free energies $\Delta G \degree (x)_{DNA:DNA}$ were obtained from SantaLucia et al. (1996) *Biochemistry*, 35, 3555-3562; sequence-dependent RNA:DNA hybridization free energies $\Delta G \degree (x)_{RNA:DNA}$ were obtained from Sugimoto et al. (1995) *Biochemistry*, 34, 11211-11216; and $\Delta G(x)_{RNA:DNA}$ values in cases of introduced point mismatches rG.dG, rC.dC, rA.dA, and rU.dT were obtained from Watkins et al. (2011) *Nucleic acids research*, 39, 1894-1902 (under slightly higher salt conditions). The sequence of the protospacer used is 'ATCCTGTCCC TAGTGGCCCC' (SEQ ID NO: 336), the AAVS1 target site as in the AFM experiments; the sequence of the protospacer complementary DNA is 'GGGGCCACTAGGGACAG-GAT' (SEQ ID NO: 337), and the sequence of the guide RNA was either 'GGGGCCACUAGGGACAGGAU' (SEQ ID NO: 338) for sgRNA or 'GGCCACUAGGGACAG-GAU' (SEQ ID NO: 339) for the truncated RNA.

Correlations between R-loop stability derived from KMC and experimental Cas9 cleavage rates. To analyze correlations between guide RNA—protospacer interactions and Cas9 cleavage rates in vivo, the sequences of guide RNAs and targeted DNA from Hsu et al. (2013) *Nature biotechnology*, 31, 827-832 and their experimentally determined maximum likelihood estimate (MLE) cutting frequencies by Cas9 were extracted. The sequences of guide RNAs and targeted DNA from Hsu et al. (2013) *Nature Biotechnology*, 31, 827-832 with single-nucleotide PAM-distal ($\geq 10$ bp away from the PAM site) mismatches of type rG.dG, rC.dC, rA.dA, and rU.dT and the experimentally determined maximum likelihood estimate (MLE) cutting frequencies by Cas9 at those sites were imported (n=136) into the KMC script. Simulations of strand invasion initiated at m=10 were repeated 1000 times for each sequence (up to t=100) to obtain the mean fraction of time $m \geq 16$ and correlated with the empirical cleavage rates. Significance was determined by bootstrapping the mean fraction of occupancy with the MLE cutting frequencies via permutation 100,000 times, then recalculating correlation coefficients and p-values. Guide RNA—protospacer binding free energies were estimated by summing over the nearest neighbor energies using the parameter sets listed above and corrected with a ~3.1 kcal mol$^{-1}$ initiation factor.

dCas9-Tru-gRNA and dCas9-Hp-gRNA Data for Comparison with dCas9-sgRNA Structural Properties.

When comparing height and volume measurements of the proteins across experiments, the AFM imaging conditions should remain mostly consistent so as not to introduce artifacts. This does not generally present an issue, for example, when comparing heights and volumes of dCas9 bound to different sites on the engineered DNA molecules, but presents a challenge when comparing the structural properties of dCas9/Cas9 when using different guide RNAs or DNA substrates. As a control, the heights and volumes of the streptavidin proteins used to label the ends of the traced DNA molecules were used, which should remain unchanged across all experimental conditions, for the different experiments. For experiments with sgRNAs, mean heights of the streptavidins differed by less than 0.1 nm (mean difference: 0.087 nm; standard deviation of differences: 0.052 nm) and their mean volumes (1098 nm$^3$) differed by less than 15 nm$^3$ (mean difference: 14.461 nm$^3$; standard deviation of differences: 10.419 nm$^3$). However, the mean heights and volumes between the experiments with tru-gRNA and the hp-gRNAs differed from those with sgRNAs by up to 0.14 nm and 225 nm$^3$, respectively. To directly compare the results of these experiments, the heights of dCas9 with tru-gRNA and hp-gRNAs on engineered DNA were shifted by their difference in mean heights relative to those with sgRNAs and the volumes scaled by the percent difference of the mean volumes.

Example 2

Figures 9A, 9B, 9C:
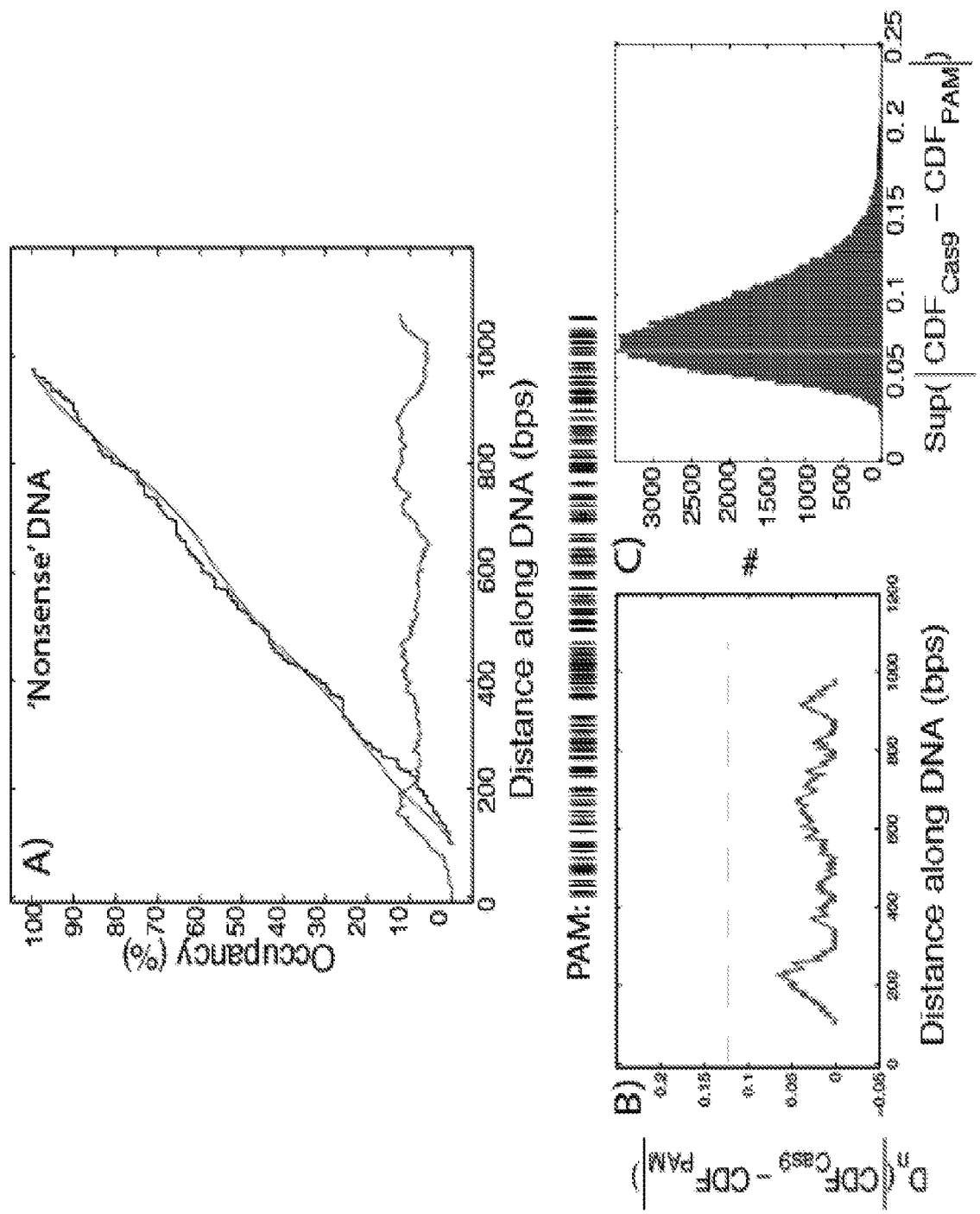
FIGS. 9A-9C show additional images of Cas9/dCas9 bound to DNA. A) Binding distribution of dCas9 to substrate containing no homology to the AAVs1 protospacer sequence (compare with FIG. 1) (n=443). Overlaid is the cumulative distribution (CDF) of PAM sites ($CDF_{PAM}$, black) and CDF of bases bound by dCas9 (red, $CDF_{Cas9}$). Comparison begins 100 bases from each end to avoid artifacts introduced by overlap with streptavidin tag (a criteria for DNA selection) and binding to exposed blunt ends of DNA (resulting in expected increase in non-specific binding). B) Absolute difference $D_n$ between CDF of protein binding and of PAM sites. Dashed line is Kolmogorov-Smirnov criterion for goodness-of-fit of two distributions. C) CDF of binding was compared to CDF of PAM distributions from 100,000 randomly generated sequences with same probabilities of G, A, T, and C using MATLAB. Vertical red line is experimental $Sup(D_n)$, indicating that experimental dCas9 binding more closely matches the experimental PAM distribution than it does to 71.20% of generated sequences.
Figures 10A, 10B, 10C:
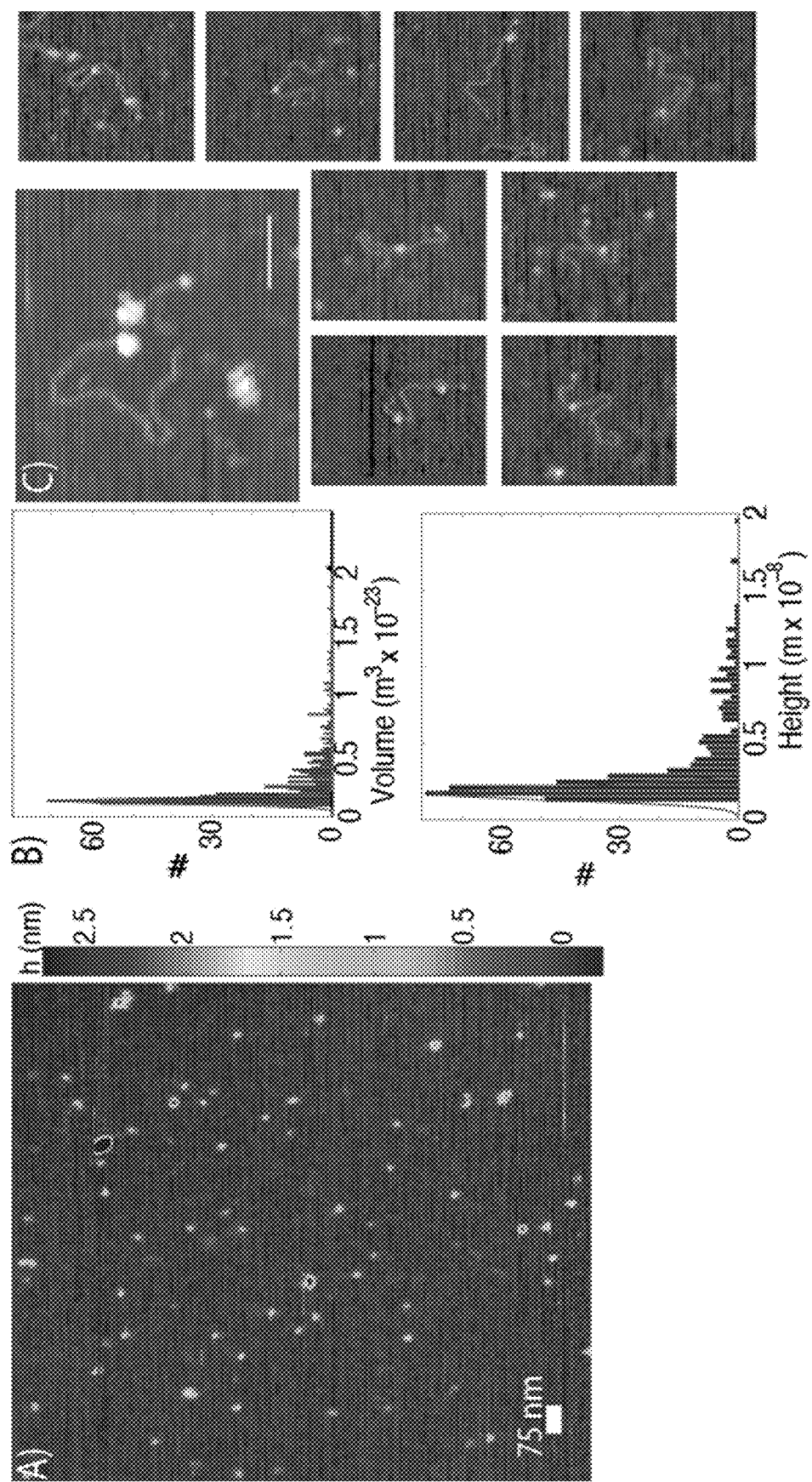
FIGS. 10A-10C show binding to 'nonsense' substrate containing no homology (>3 bp) to protospacer sequence. (A) Images of dCas9 alone. (B) Histogram (n=423) of volume (left) and height (right) of dCas9 imaged alone with Gaussian fit to primary peaks. From the Gaussian fits: mean height is 1.746 nm (95% confidence: 1.689 nm-1.802 nm) with standard deviation 0.441 nm, and mean volume is 1302 nm$^3$ (95% confidence: 1266 nm$^3$-1337 nm$^3$) with standard deviation 259.1 nm$^3$ (note that because the dCas9 here do not have a DNA within its binding channel, their recorded volumes may appear artificially low because of decreased mechanical resistance to the AFM probe). The heights were measured relative to the median value of a 10-pixel area surrounding each protein, and the volumes recorded as the contiguous features greater than twice the standard deviation of the local background heights. (C) Additional representative images of dCas9 bound to DNA which has been labeled at one end with a monovalent streptavidin.
Figures 11A, 11B, 11C, 11D:
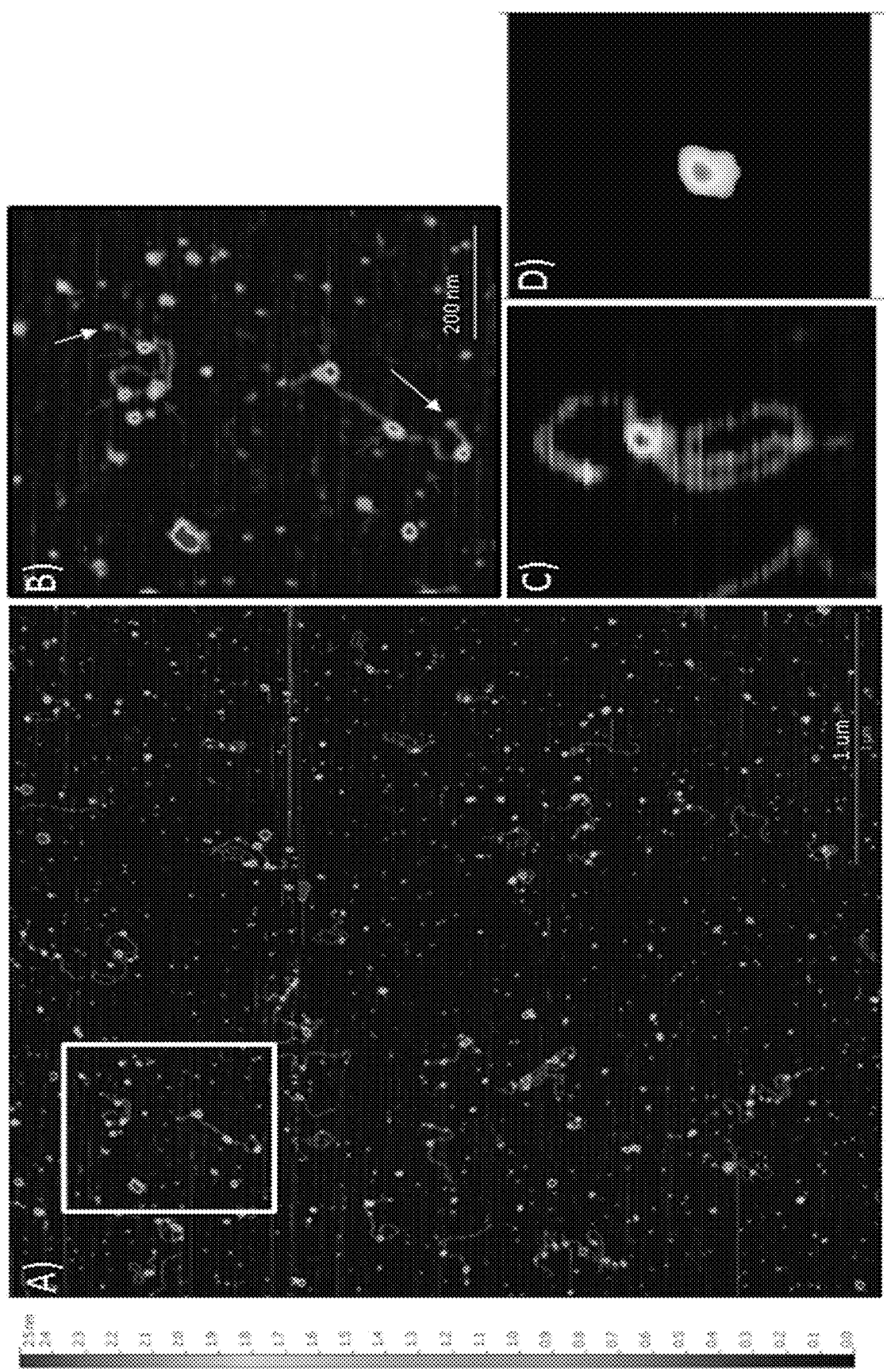
FIGS. 11A-11D show a representative figure of dCas9-sgRNA bound to RNA and example of processing of protein structural properties.

Atomic Force Microscopy Captures Cas9/dCas9 Binding Specifically and Non-Specifically Along Engineered DNA Substrates with High Resolution The analysis of crystallographic and biochemical experiments suggests that specificity in protospacer binding and cleavage is imparted first through the recognition of PAM sites by Cas9 itself, followed by strand invasion by the bound RNA complex and direct Watson-Crick base-pairing with the protospacer (FIG. 1A), although a complete mechanistic picture has yet to emerge. To directly probe the relative propensities to bind to protospacer and off-target sites with single-molecule resolution, 50 nM Cas9-sgRNA or dCas9-sgRNA complexes targeting the AAVS1 locus of human chromosome 19 were imaged by AFM in air after incubation with one of three DNA substrates (2.5 nM):

(i) a 1198 bp segment of the AAVS1 locus containing the complete target site following a PAM (hre 'TGG') (FIG. 1C);

(ii) a 989 bp engineered DNA substrate containing a series of six complete, partial, or mismatched target sites each separated by approximately 150 bp (FIG. 1D). Mismatches at these sites could span both the 'seed' (PAM-proximal, approximately 12 bp) and 'non-seed' (PAM-distal) regions of the protospacer. The only PAM sites in this engineered substrate were at these explicitly designed locations; and (iii) a 1078 bp 'nonsense' DNA with no homology (beyond 3 bp sequences) with the target sequence (FIGS. 9A-9C).

FIG. 1C shows that dCas9 and Cas9 exhibit nearly identical binding distributions on the AAVS1 substrate (n=404 and n=250, respectively). FIG. 1D shows that on the engineered substrate (n=536) dCas9 binds with the highest propensity to the complete protospacer with no mismatched (MM) sites (peak 1, later referred to as the full or '0 MM' site) and also to sites with 5 or 10 mismatched bases distal to the PAM site (third and fourth feature from streptavidin label, referred to later as the '5 MM' or '10 MM' sites, respectively) albeit with the reduced affinity. Sites containing greater numbers of mismatches (second and fifth feature), or which possess two PAM-proximal mismatched nucleotides (sixth feature) are bound at significantly lower rates. (below) Distribution of PAM ('TGG') sites in each substrate.

Structurally, *S. pyogenes* Cas9 is a 160 kDa monomeric protein approximately 10 nm×10 nm×5 nm (from crystal structures), roughly divided into two lobe-like halves each containing a nuclease domain. Consistent with the x-ray structures, dCas9—sgRNA imaged via AFM appears as large ovular structures (FIGS. 10A-10C), after incubating Cas9 or dCas9 with DNA these structures bound along DNA were observed and assigned to be Cas9 or dCas9, respectively (FIG. 1B, FIGS. 10A-10C, and FIGS. 11A-11D). To unambiguously determine the sequence of the sites bound by Cas9 and dCas9, the biotinylated DNA molecules were labelled at one end with monovalent streptavidin tag prior to AFM imaging. DNA molecules that were observed with bound Cas9 or dCas9 proteins were selected for further analysis and traced with sub-pixel resolution according to a modified protocol adapted from that of Wiggins et al. (25), and the sites bound by Cas9/dCas9 were extracted (see Supplementary Methods for details).

This method proved remarkably robust (Table 1): on the DNA bound by Cas9 or dCas9, a distinct enrichment of proteins centred precisely at the location of protospacer sites with an adjoining PAM (within the expected 23 bp, FIG. 1C-D) is observed and manifest as sharp peaks. No such obvious peaks are observed in the DNA substrate containing no target sites (FIGS. 9A-9C). Standard deviation of the peak widths ranged from 36-60 bp, which is a significant improvement compared with binding experiments using single-molecule fluorescence that result in peak width standard deviations σ of approximately 1000 bp). The mean apparent Cas9/dCas9 'footprint' on DNA covering 78.1 bp±37.9 bp; this broadening of the apparent footprint over the ~20 bp footprint of Cas9 on DNA determined by biochemical and crystallographic methods is a well-established result of imaging convolution with the width of the AFM tip. Previously, it had been observed in vitro that Cas9 remains bound to targeted DNA for extended periods (>10 min) after putative DNA cleavage as a single-turnover endonuclease, and could not be displaced from the cleaved strands without harsh chemical treatment. Most of the DNA molecules observed with bound Cas9 appeared as full-length AAVS1-derived substrates, with only a small (~5%) percentage of substrates that have been both cleaved and separated. After these DNA molecules were traced, Cas9 was observed to bind to these 'full-length' substrates with nearly an identical distribution as was dCas9 (two-sided Komolgorov-Smirnov test, significance level 5%) (FIG. 1C).

TABLE 1

Peaks recorded in binding histograms of FIGS. 1C-D for Cas9/dCas9-sgRNA and FIG. 2C for dCas9 with sgRNAs possessing 2 nt truncation at 5'-end (tru-gRNA), based on empirical fit to Gaussian $\propto \exp(-((x - \mu)/w)^2)$

| Guide RNA: | sgRNA[a] | tru-gRNA[b] | sgRNA | |
|---|---|---|---|---|
| Substrate: | Engineered DNA: | Engineered DNA: | AAVs1-derived DNA: | |
| Total DNA molecules traced:[c] | n = 536 | n = 257 | n = 404 | n = 250 |

TABLE 1-continued

Peaks recorded in binding histograms of FIGS. 1C-D for Cas9/dCas9-sgRNA and FIG. 2C for dCas9 with sgRNAs possessing 2 nt truncation at 5'-end (tru-gRNA), based on empirical fit to Gaussian $\propto \exp(-((x-\mu)/w)^2)$

| Location name: | Full site | 10MM site[d] | 5MM site[e] | Full site | 10MM site[f] | 5MM site[g] | Full site | Full site |
|---|---|---|---|---|---|---|---|---|
| Cas9/dCas9 | dCas9 | dCas9 | dCas9 | dCas9 | dCas9 | dCas9 | dCas9 | Cas9 |
| Location:[h] | 144-167 | 452-465 | 592-610 | 144-167 | 452-465 | 592-610 | 316-339 | 316-339 |
| Peak $\mu$[i] | 151.3 | 467.6 | 600.6 | 159.0 | 462.9 | 592.0 | 327.7 | 315.0 |
| (95% conf.): | (151.1, 151.6) | (466.6, 468.5) | (599.5, 601.7) | (158.2, 159.7) | (462.1, 463.6) | (590.9, 593.0) | (327.3, 328.2) | (314.4, 315.7) |
| Peak width[j] $w = \sqrt{2}\sigma$ | 51.46 | 57.5 | 70.8 | 53.98 | 54.44 | 67.88 | 84.10 | 58.7 |
| (95% conf.): | (51.53, 52.38) | (55.84, 59.16) | (68.72, 72.89) | (52.2, 55.76) | (52.07, 6.81) | (64.27, 71.49) | (83.12, 85.27) | (56.8, 60.63) |
| # dCas9[k]: | 287 | 180.5 | 211.9 | 84.5 | 58.75 | 74.33 | | |
| #/(2w) (scaled to density at full site, 95% conf.): | 1 | 0.5688 | 0.5399 | 1 | 0.6894 | 0.6994 | | |

[a]Standard single-guide RNA (sgRNA)
[b]Single-guide RNA with 2 nt truncated from 5'-end (tru-gRNA)
[c]Numbers of DNA molecules observed with both monovalent streptavidin label and bound protein which were then traced (see Supporting Methods for details).
[d]Target site with 10 PAM-distal mismatched nucleotides
[e]Targeted site with 5 PAM-distal mismatched nucleotides
[f]On the engineered DNA substrate, tru-gRNA is expected to interact with only the first 8 of the 10 PAM-distal mismatched nucleotides at the 10MM site.
[g]On the engineered DNA substrate, tru-gRNA is expected to interact with only the first 3 of the 5 PAM-distal mismatched nucleotides at the 5MM site.
[h]bp from streptavidin-labelled end (from PAM to end of site)
[i]Peak maximum in binding histogram (from Gaussian fit)
[j]Peak width is $\sqrt{2}\sigma$, with $\sigma$ as the standard deviation
[k]Number of dCas9 molecules observed within 1 peak width ($\sqrt{2}\sigma$) of binding site. If Cas9/dCas9 appeared to contact DNA at n sites, that molecule is weighted by 1/n. If molecules overlapped both 10MM and 5MM sites, # was weighted by an additional ½.

By examining the occupancies of dCas9 bound to different locations along the engineered substrate, the relative binding propensities of dCas9 to various mismatched and partial target sites could be determined (FIG. 1D, Table 1). The overall dissociation constant between dCas9 and the entire DNA substrate was estimated to be 2.70 nM (±1.58 nM, 95% confidence, Table 2). The dCas9 dissociation constant specifically at the site of the full (perfectly-matched) protospacer (within one peak width in the binding histogram) located substrate to be 44.67 nM (±1.04 nM, 95% confidence). Earlier electrophoretic mobility shift assays (EMSA) had estimated dCas9-sgRNA binding to protospacer sites on short DNA molecules (~50 bp) to be between 0.5 nM and 2 nM. While the increase in dissociation constant at protospacer sites observed may be related the presence of multiple off-target sites on the engineered DNA substrate, it is typical that dissociation constants determined by AFM are nearly an order of magnitude higher than those determined by traditional assays (26). This difference is often attributed to nonspecific interactions of proteins to the blunt ends of the shorter DNA that are not accounted for in EMSA.

TABLE 2

Apparent dissociation constants for dCas9 with different guide RNA variants from the 989 bp 'engineered' DNA substrates (e.g., FIGS. 1D, 2C, and 2D) that contain a series of fully- and partially- complementary protospacer sites

| Guide RNA variant | Overall dissociation constant between dCas9 and the engineered DNA substrate (±95% confidence) | Protospacer-specific dissociation constant for dCas9 and the full target on the engineered substrate (±95% confidence) |
|---|---|---|
| sgRNA[a] | 2.70 nM (±1.58 nM) | 44.67 nM (±1.04 nM) |
| tru-gRNA[b] | 17.89 nM (±0.45 nM) | 136.4 nM (±2.30 nM) |
| hp6-gRNA[c] | 16.61 nM (±0.40 nM) | 164.4 nM (±13.63 nM) |
| hp10-gRNA[d] | 35.84 nM (±0.63 nM) | 164.8 nM (±15.60 nM) |

[a]Full-length single-guide RNA (sgRNA)
[b]Truncated sgRNA (first two nt at 5'- truncated)
[c]sgRNA with additional 5'- hairpin which overlaps six PAM-distal targeting nts (see text)
[d]sgRNA with additional 5'- hairpin which overlaps ten PAM-distal targeting nts (see text)

On the engineered substrate, dCas9 is relatively tolerant to distal mismatches (exhibiting 50-60% binding propensity relative to complete target site, FIG. 1D and Table 1), and has the same apparent affinity (within confidence) toward target sites containing 5 and 10 distal mismatches (MMs). However, binding to protospacer sites containing only two PAM-adjacent mismatches occurred with similar propensity as to sites with 15 or even 20 (PAM site alone) distal mismatches (approximately 5-10% binding propensity relative to perfect target, approximately that of the background binding signal), a finding consistent with previous biochemical studies. While there are no PAM sites on the engineered substrate except adjacent to the protospacer sites, on the AAVS1-derived substrate there is a distinct 'shoulder peak' of enhanced Cas9 and dCas9 binding near the AAVS1 target that is particularly enriched in PAM sites. On the 'nonsense' substrate and the segments of the AAVS1-derived substrate away from target sites, subtle enrichments of dCas9 closely mirrored the distribution of PAM sites (two-sided Komolgorov-Smirnov test, significance level 5%) and dCas9 distribution on the 'nonsense' substrate more closely reflected the experimental PAM distribution than it did to 71.20% of 100,000 randomly generated sequences with the same dA, dT, dC, and dG distributions (FIGS. 9A-9C). As dCas9 binding along the 'nonsense' substrate (with 879 PAM sites in 1079 bp) corresponds so well with PAM site distribution, this was interpreted as a measurement of real dCas9-PAM interactions. The mean single-site dissociation constant for dCas9 binding along the 'nonspecific' substrate was estimated to be approximately 867 nM (standard deviation±209 nM). This can be understood as an estimate of the dCas9 binding dissociation constant on DNA with no protospacer homology.

Example 3 sgRNAs with a two nucleotide truncation at their 5'-ends (tru-gRNAs) do not increase binding specificity of dCas9 in vitro Cas9 was found to still exhibit cleavage activity even if up to four nucleotides of the guide (protospacer-targeting) segment of the sgRNA or crRNA were truncated from their 5'-ends and Fu et al. (21) recently showed that use of sgRNAs with these 5'-truncations (optimally by 2-3 nucleotides) can actually result in orders-of-magnitude increase in Cas9 cleavage fidelity in vivo. It was suggested that the increased sensitivity to mismatched sites (MM) using these truncated sgRNAs (termed 'tru-gRNAs', FIG. 2A) was a result of its reduced binding energy between the guide RNA and protospacer sites. This implies that the binding energy imparted by the additional 5'-nucleotides on the sgRNA could compensate for any mismatched nucleotides and stabilize the Cas9 at incorrect sites, while the tru-gRNAs would be relatively less stable on the DNA if there are mismatches.

As a test of this proposed mechanism, dCas9 was imaged with a tru-gRNA with a two nucleotide 5'-truncation relative to the sgRNA used previously. The dCas9-tru-gRNA complexes were incubated with the engineered substrates that contained a series of full and partial protospacer sites. Again a distinct peak was found precisely at the full protospacer site (FIG. 2C and Table 1), although the apparent association constant relative to dCas9 with a full sgRNA at this site decreases considerably (i.e., dissociation constant increases, see Table 2). However, relative to binding at full protospacer sites, off-target binding by dCas9 with the tru-gRNA at the protospacer sites with PAM-distal mismatches actually increases when compared to dCas9 with sgRNAs (FIG. 2C and Table 1). Similar to dCas9 with sgRNA, dCas9 with tru-gRNA binds to protospacers with either 10 or 5 PAM-distal mismatched sites with approximately equal propensities (note that the tru-gRNA is only expected to interact with the first 8 and 3 mismatches at those sites, respectively). These results suggest that increased cleavage fidelity using tru-gRNAs is not necessarily imparted by a relative reduction of binding propensity at off-target sites or a reduction in relative stability in the presence of mismatches. Rather, while there may be some 'threshold' effects where reduction of the association constant below ~4-5×10$^6$ M effectively abolishes cleavage activity in vivo, these and additional results presented below suggest that the increased specificity exhibited by the tru-gRNAs may be influenced by discrimination in the cleavage mechanism itself. Furthermore, these findings would suggest that while tru-gRNAs can improve specificity in cleavage of active Cas9, they may not improve specificity in their binding activity for applications involving dCas9 (or chimeric derivatives) in vivo.

Additionally, previous reports have shown that tru-gRNAs, which have 5'-truncations (optimally by 2-3 nucleotides), in their protospacer-targeting segment can result in orders-of-magnitude increase in Cas9 cleavage fidelity in vivo (FIG. 2A), the results shown in the Examples indicate that the truncated gRNAs do not improve specificity in dCas9 binding (FIG. 2C). FIG. 2C shows the binding affinity of dCas9 with a standard gRNA (dashed line) compared with the binding affinity of a dCas9 with a tru-gRNA (trugRNA, purple line) on a DNA molecule which contains a full protospacer (site i) as well as protospacer sites with 5 and 10 PAM-distal mismatches (sites ii and iii, respectively). FIG. 2C shows the standard guide RNAs retain significant ability to bind to these off-target sites (containing mismatches), and that trugRNAs exhibit no relative enhancement in binding specificity at sites which contained mismatches in the 5 10 nucleotides at the PAM distal end of the protospacer. The binding distribution of dCas9 with tru-gRNAs exhibits distinct peaks in its affinity exactly at the protospacer sites with 10 PAM-distal mismatches and 5 PAM-distal mismatches, demonstrating that it does not have increased binding specificity relative to full sgRNAs (see Table 1). The 'peaks' in the binding histogram are indicative of specific, stable binding at these off-target sites. In fact, binding at the off-target sites by dCas9-trugRNAs actually increases relative to binding to the protospacer compared to the standard guide RNA. This promiscuous binding may limit their utility for dCas9 and chimeric dCas9 derivatives. It may also reflect the off-target cleavage reported for this system which, while improved relative to the standard guide RNAs, was still significant at some off-target sites. For comparison, we found no specific binding of the hpgRNAs at these sites with mismatches (FIG. 2D). hpgRNAs bound at these sites with approximately the same affinity as they do nonspecifically to DNA with no homology to the protospacer, with a ~22% decrease in the maximum observed off-target binding affinities relative to the truncated gRNAs. Additionally, based on the narrow geometry of the Cas9 DNA-binding channel, we expect that the presence of an unopened hairpin at mismatched protospacers may inhibit the conformational change in Cas9 necessary to perform cleavage (FIG. 1B).

Significant efforts have been made to characterize this off-target activity—and to improve specificity of Cas9/dCas9 through intelligent selection of protospacer target sequences; optimization of sgRNA structure, for example, by truncation of first two 5'-nucleotides in the sgRNA; and use of 'dual-nicking' Cas9 enzymes—but a clear understanding of the precise mechanism of RNA-guided cleavage as it relates to the structural biology of Cas9 will be essential to developing Cas9 derivatives and guide RNAs with increased fidelity for their emerging applications in medicine and biology.

Pursuant to this goal, here we use atomic force microscopy (AFM) to resolve individual *S. pyogenes* Cas9 and dCas9 proteins as they bind to targets along engineered DNA substrates after incubation with different sgRNA variants. This technique allows us to directly resolve both the binding site and structure of individual Cas9/dCas9 proteins simultaneously, providing a wealth of mechanistic information regarding Cas9/dCas9 specificity with single-molecule resolution. Consistent with traditional biochemical studies, we find that significant binding by Cas9/dCas9 with sgRNAs occurs at sites containing up to 10 mismatched base-pairs in the target sequence. However, while use of guide RNAs with two nucleotides truncated from their 5'-end (tru-gRNA) had previously shown to result in up to 5000-fold decrease in off-target mutagenesis by Cas9 in vivo, we find similar specificities in vitro for dCas9 with tru-gRNA binding to mismatched targets as with standard sgRNA. The addition of a hairpin to the 5'-end of the sgRNA which partially overlaps the target-binding region of the guide RNA is found to increase dCas9 specificity at the cost of overall decreased binding propensity to DNA. Our results indicate that overall stability of guide RNA-DNA binding does not necessarily govern specificity in Cas9 cleavage when mismatches are located more than 10 bp away from the PAM.

Example 4

Guide RNAs with 5'-Hairpins Complementary to 'PAM-Distal'-Targeting Segments (Hp-gRNAs) Modulate the Absolute Binding Propensity and Profile of dCas9s Bound to DNA with Mismatched Protospacers In Vitro dCas9 specificity may be increased by extending the 5'-end of the sgRNA such that it formed a hairpin structure which overlapped the 'PAM-distal'-targeting (or 'non-seed') segment of the sgRNA (FIG. 2B). After a PAM site is bound and strand invasion of the DNA by the guide RNA has initiated, the hairpin is opened upon binding to a full protospacer and full strand invasion can occur. If there are PAM-distal mismatches at the target site, then it is more energetically favourable for the hairpin to remain closed and strand invasion is hindered. Similar topologies have been used recently for 'dynamic DNA circuits' which are driven by strand invasion. In those systems, the hairpins serve as kinetic barriers to invasion, with oligonucleotide invasion rates slowed several orders of magnitude in cases of attempted invasion by targets with mismatches. The hairpins here may be displaced during invasion of the full target sites, but inhibit invasion if there were mismatches between the target and the non-seed targeting region of the guide RNA (FIG. 2B). In those cases, it is more energetically favourable for the hairpins to remain closed. While previous efforts which had added 5'-extensions to sgRNAs in order to complement additional nucleotides beyond the protospacer, these guide RNAs did not show increased Cas9 cleavage specificity in vivo. Rather, they were digested back approximately to their standard length in living cells. Based on the size and structure of the hairpin, the hairpin may be accommodated within the DNA-binding channel of Cas9/dCas9 molecule and protected from degradation.

sgRNAs were generated with 5'-hairpins (hp-gRNAs) which overlapped the nucleotides complementary to the last six (hp6-gRNA) or ten (hp10-gRNA) PAM-distal sites of the protospacer. By mapping the observed binding locations of dCas9-hp-gRNAs on the engineered DNA substrate (FIG. 2D), sharp peaks were observed precisely at the protospacer site (PAM and protospacer located at sites 144-167, with binding peak at site 154.0 (95% confidence: 153.3-154.8) for dCas9-hp6-gRNA and at 158.3 (95% confidence: 157.6-158.9) for dCas9-hp10-gRNA). The specific peaks at the sites with 5 and 10 distal mismatches are significantly flattened, with dCas9 and hp10-gRNA exhibiting substantially decreased affinity for off-target sites (22% drop relative to dCas9 with tru-gRNA). The peaks in affinity at the full protospacer sites imply that the hairpins indeed open upon full invasion. n=243 for hp6-gRNA and n=212 for hp10-gRNA. dCas9 with hp-gRNAs show a similar drop in affinity for the target site as with tru-gRNAs, however, in contrast to dCas9 with tru-gRNAs, dCas9 with hp-RNAs do not present any sharp binding peaks at off-target sites which would otherwise indicate strong, specific binding. With hp6-gRNA, there was an enrichment of binding around the sites of protospacers with 5 or 10 mismatched PAM-distal sites. Because they lack the sharp binding peaks observed with sgRNA and tru-gRNA, these enrichments are not likely indicative of specific binding, but rather may indicate that the dCas9 had dissociated from these sites upon adsorption to the surface. This would indicate very weak binding at those off-target sites in the case of hp6-gRNA.

In the case of hp10-gRNA, binding to these mismatched sites is approximately at the level of the non-specific binding elsewhere on the substrate, representing a 22% decrease in the maximum observed off-target binding affinity relative to the tru-gRNAs (decrease in the maximum observed association constant from to $3.18 \times 10^6$ M to $2.48 \times 10^6$ M, FIG. 2D). This increase in specificity of hp10-gRNA is also reflected by a similar binding dissociation constant as hp6-gRNA to the protospacer sites but a significant increase in the overall dissociation constant to the entire (specific+non-specific) engineered substrate relative (Table 2).

The distinct enrichment precisely at the complete protospacer sites suggests that upon invasion of full protospacer sites the hairpins in the hp-gRNAs are in fact opening, as the nucleotides which bind the PAM-distal sites of the protospacer would otherwise be trapped within the hairpin. A likely mechanism for the improvement of binding specificity is that, when unopened at protospacer sites with PAM-distal mismatches, the presence of the hairpin promotes melting of the guide RNA from these off-target sites. The results suggest that the hp-gRNAs can be used to tune Cas9/dCas9 binding affinities and specificity, and further manipulation of hairpin length, loop length, and loop composition may allow for more fine control of these properties.

Example 5

Figure 12A:
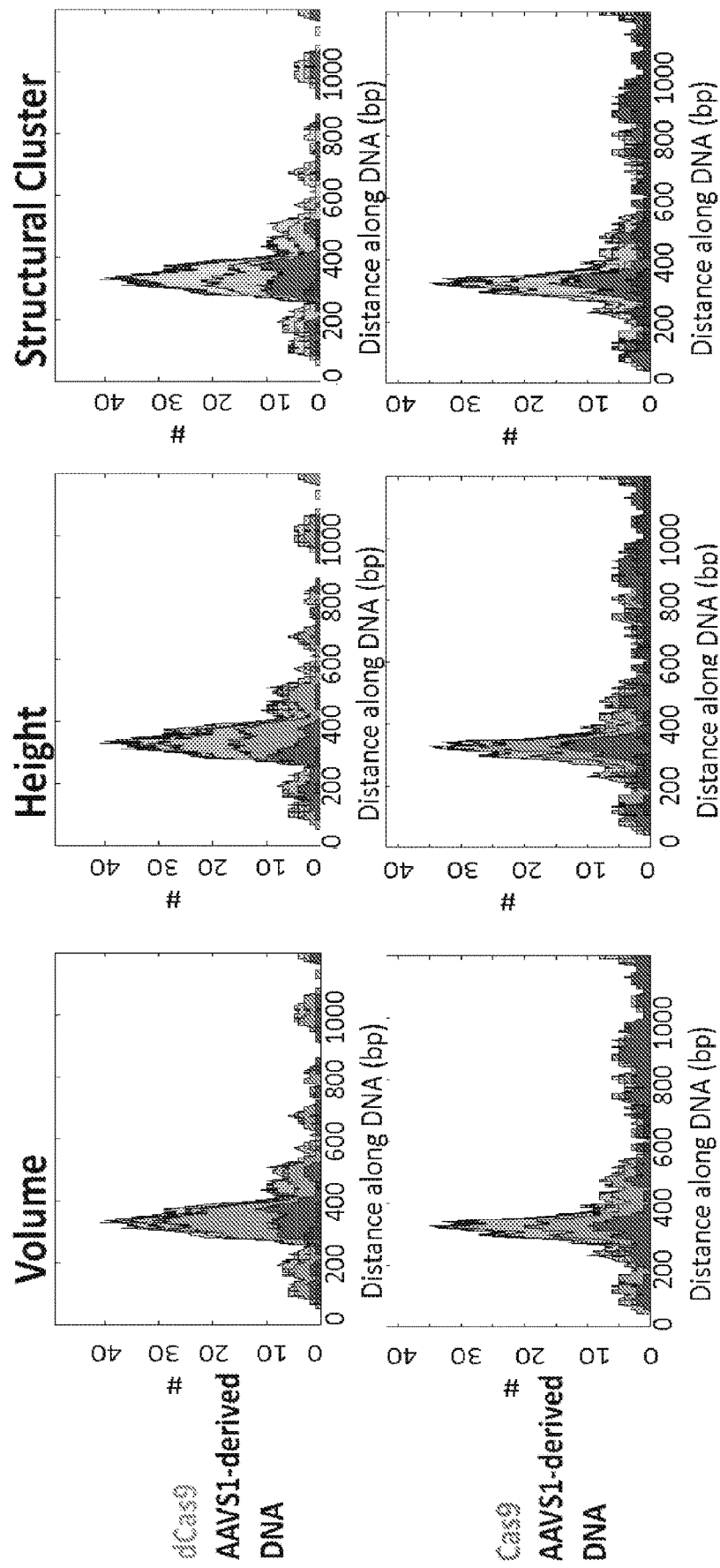
FIGS. 12A-12B show properties of Cas9/dCas9-sgRNAs mapped to their respective binding sites. Upper: Stacked histograms of the volume (left), maximum heights (middle), and structures (clustered by mean squared difference) after alignment (right, see text) for all experimental conditions. Populations are colored according to binned volume, height or structural cluster as in the scatter plot below. The binding distribution of extracted Cas9/dCas9 molecules (FIGS. 10A-10C) closely matches that of the entire dataset (FIG. 1C-1D, FIGS. 8A-8B), indicating that the selection procedure is unbiased and the selected proteins are representative of the whole data set. Lower: Scatter plot of volume vs. maximum height of all Cas9/dCas9 color-coded by binned (left) volume, (middle) maximum height, and (right) structural cluster.
Figure 12B:
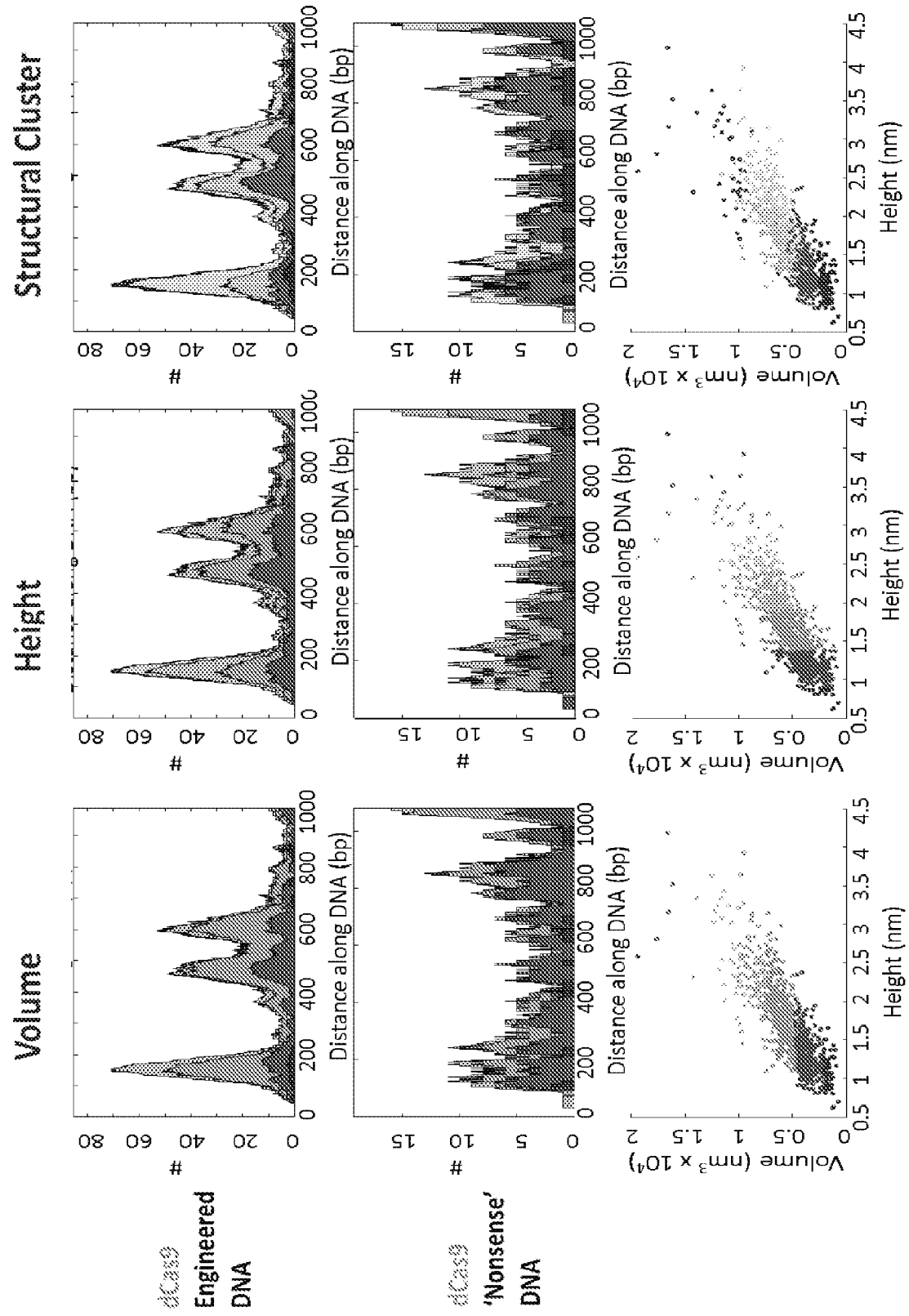

Cas9 and dCas9 Undergo a Progressive Structural Transition as they Bind to DNA Sites that Increasingly Match the Targeted Protospacer Sequence It was observed using negative-stain transmission electron microscopy (TEM) that, upon binding sgRNA, the structure of dCas9 compacts and rotates to open a putative DNA-binding channel between its two lobes. After binding to DNA containing the PAM and protospacer sequence, dCas9 undergoes a second structural reorientation to an expanded conformation. The role of this second transition was suggested to be related to strand invasion by sgRNA or to align the two major Cas9 nuclease sites with the two separated DNA strands. However, these studies were performed only in the presence or absence of DNA containing fully-matched protospacer sequences, and examining the transition between these conformations at partially matched protospacer sites can provide insights into the mechanism of off-target binding and cleavage. Therefore, in addition to determining relative binding propensities, AFM imaging was used to capture these putative conformational transitions by Cas9 and dCas9 as they bind to DNA at sites of various complementarity to the protospacer. We extracted the volumes and maximum topographical heights of Cas9 and dCas9 proteins with sgRNAs which appeared isolated on the DNA (n=839) and mapped these values to their respective binding sites on DNA (FIG. 3, FIGS. 11A-11D, and FIGS. 12A-12B). The binding site distribution is nearly identical to the distribution of the full data set, indicating that this selection was unbiased and representative. The recorded image of each of these proteins was extracted (FIGS. 11C-11D) and aligned pair-wise by iterative rotation, reflection, and translation. The protein structures was clustered according to their pair-wise mean-squared topographical difference (FIGS. 12A-12B and Table 3). A pronounced advantage of this technique is that it naturally clusters any monovalent streptavidin or any aggregated Cas9/dCas9 proteins that co-localize on the surface with the DNA separately from those assigned to be individual Cas9/dCas9 molecules, allowing for an unbiased analysis of the structural properties of these proteins on DNA. Analysis of the distribution of binding sites by either the putative streptavidin molecules or aggregated proteins reveals that they are both rare and uniformly distributed along the DNA and hence did not interfere with analysis of the binding site distributions (FIGS. 12A-12B).

Figures 3A, 3B:
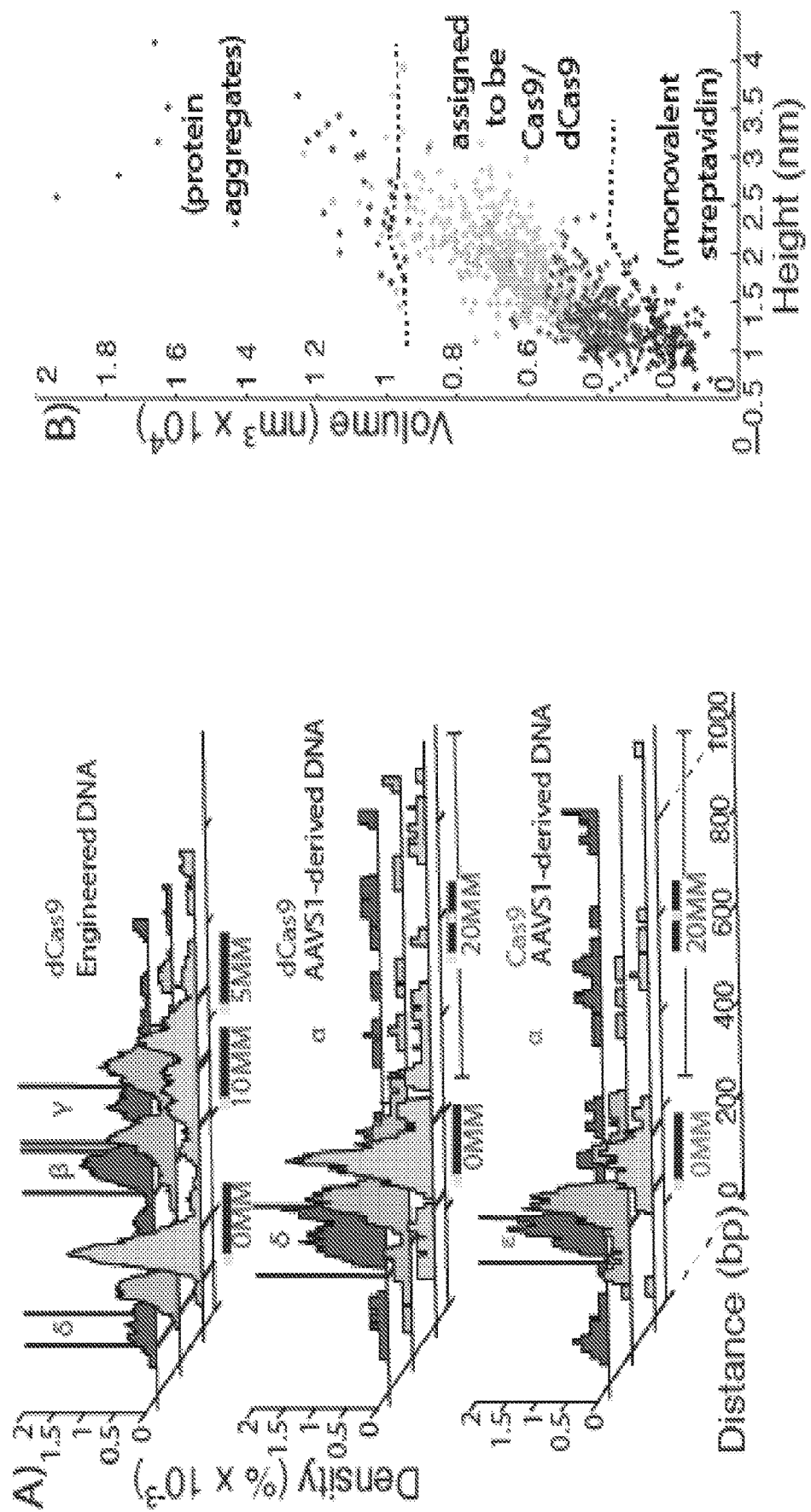
FIGS. 3A-3D show Cas9 undergoes a progressive conformational transition as it binds to sites that increasingly match the protospacer sequence.
Figures 3C, 3D:
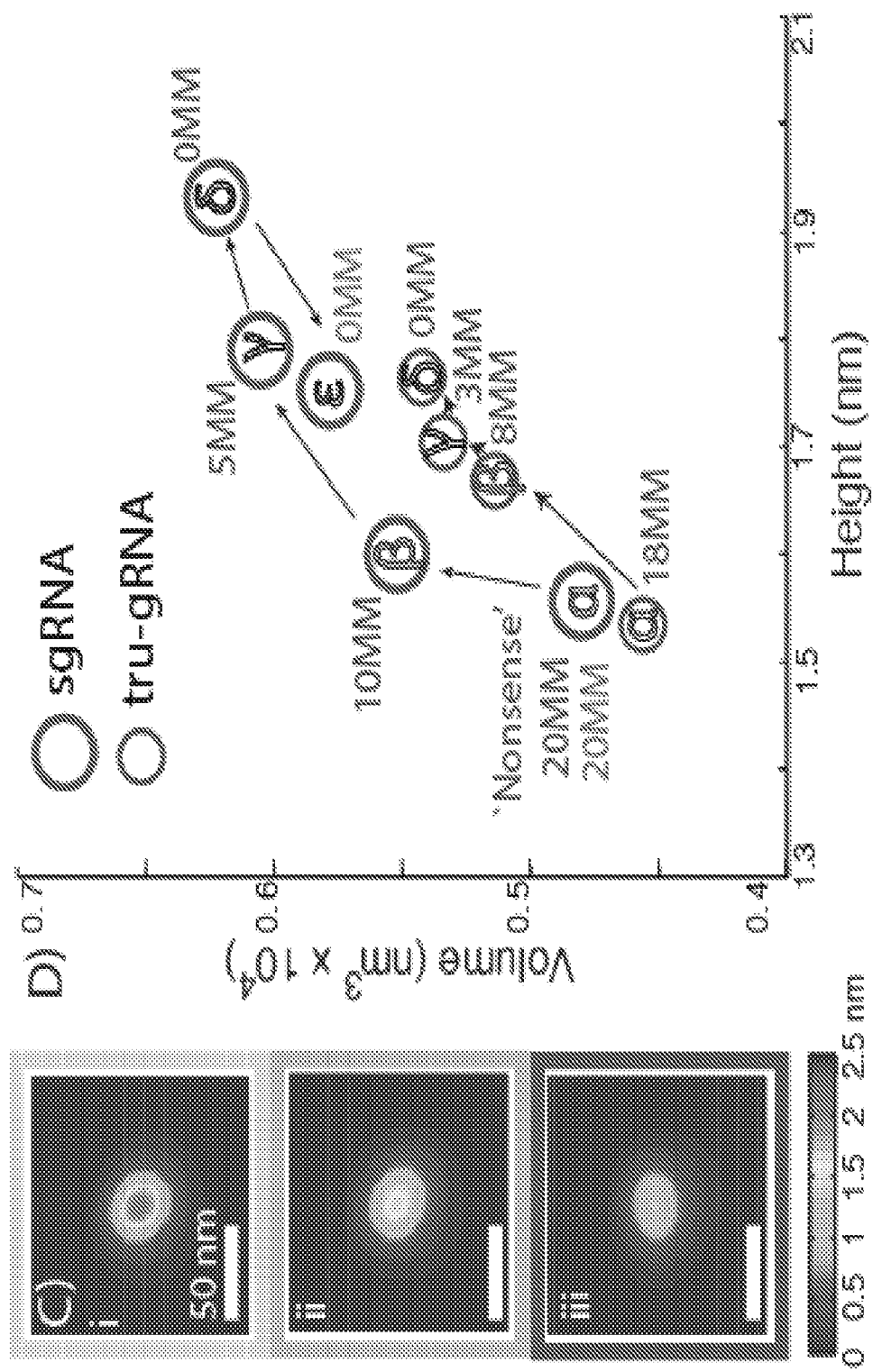

At sites containing no homology to targets, such as on the 'nonsense' DNA substrate, dCas9 molecules with sgRNAs were predominately smaller and egg-shaped (FIG. 3C(iii), and Table 3). But as dCas9 proteins bind to increasingly complementary target sequences (FIG. 3(α—S)), their height and volume significantly increase (FIGS. 3D and 12A-12B, Table 2) relative to non-specific binding, reaching a maximum size at the protospacer sequence. This increase is likewise accompanied by a shift in the population of dCas9 (FIGS. 3A, and 12A-12B, Table 2) from structures clustering with the flatter and egg-shaped conformations (FIG. 3C(ii) and C3(iii), blue and green) to those which increasingly cluster with slightly rounder structures possessing a large, central bulge (FIG. 3C(i), yellow). This latter observed conformation is likely the expanded conformation previously observed via TEM and recently by size exclusion chromatography, and is presumably the active state where the nuclease domains of Cas9 are positioned properly around the DNA such that cleavage could occur most efficiently.

Catalytically active Cas9 undergoes a significant increase in size as it binds to the protospacer sequence as well (FIG. 3(c)); however there is a small, but statistically significant, decrease in size relative to dCas9, and the conformation of Cas9 at full protospacer sites tends to cluster with the flatter (green) structures. As we do not concurrently monitor whether the DNA has been cleaved at the time of imaging, it is unclear if this represents another conformational change after DNA cleavage or is a result of the mutational differences between Cas9 and dCas9; however as binding and strand invasion have been previously determined to be the rate-limiting steps it is likely that the DNA within the Cas9 is cleaved during these measurements.

TABLE 3

Properties of dCas9/Cas9 with different guide RNA variants at fully-, and partially-, and non-complementary protospacer sites

| Site | DNA | Guide RNA | $n^a$ | Mean Volume ($nm^3 \times 10^4$) ± $SEM^b$ | Mean Height (nm) ± SEM |
|---|---|---|---|---|---|
| Protospacer (dCas9) | Engineered + $AAVsI^c$ | sgRNA | 201<br>Y: 41% (±6.8%)<br>G: 22% (±5.8%)<br>B: 21% (±5.6%) | 0.6226 ± 0.016 | 1.932 ± 0.041 |
| Protospacer (Cas9) | AAVsI | sgRNA | 65<br>Y: 17% (±9.1%)<br>G: 32% (±11.4%)<br>B: 26% (±10.7%) | 0.5784 ± 0.035 | 1.753 ± 0.076 |
| 10MM (dCas9) | Engineered | sgRNA | 76<br>Y: 25% (±8.9%)<br>G: 31% (±9.7%)<br>B: 34% (±9.9%) | 0.5510 ± 0.011 | 1.601 ± 0.026 |
| 5MM (dCas9) | Engineered | sgRNA | 85<br>Y: 34% (±8.8%)<br>G: 34% (±8.8%)<br>B: 25% (±8.1%) | 0.6055 ± 0.024 | 1.790 ± 0.049 |
| Non-specific (Cas9 + dCas9) | AAVsI + $Nonsense^c$ | sgRNA | 274<br>Y: 21% (±4.8%)<br>G: 17% (±4.5%)<br>B: 39% (±5.8%) | 0.4780 ± 0.015 | 1.553 ± 0.034 |
| Protospacer $(dCas9)^d$ | Engineered | tru-$gRNA^g$ | 47<br>Y: 26% (±12.5%)<br>G: 17% (±10.7%)<br>B: 34% (±13.6%) | 0.5421 ± 0.041 | 1.761 ± 0.079 |
| (10MM) $(dCas9)^{d,e}$ | Engineered | tru-gRNA | 32<br>Y: 13% (±11.5%)<br>G: 38% (±16.7%)<br>B: 19% (±13.5%) | 0.5123 ± 0.049 | 1.665 ± 0.099 |
| (5MM) $(dCas9)^{d,f}$ | Engineered | tru-gRNA | 34<br>Y: 18% (±12.8%)<br>G: 29% (±15.3%)<br>B: 24% (±14.2%) | 0.5346 ± 0.048 | 1.705 ± 0.084 |
| Non-specific (dCas9) | Engineered | tru-gRNA | 72<br>Y: 14% (±8.0%)<br>G: 17% (±8.6%)<br>B: 29% (±10.5%) | 0.4554 ± 0.035 | 1.532 ± 0.059 |
| Protospacer (dCas9) | Engineered | hp6-$gRNA^g$ | 47<br>Y: 26% (±12.5%)<br>G: 17% (±10.7%)<br>B: 34% (±13.6%) | 0.5940 ± 0.043 | 1.860 ± 0.109 |
| Non-specific (dCas9) | Engineered | hp6-gRNA | 32<br>Y: 13% (±11.5%)<br>G: 38% (±16.7%)<br>B: 19% (±13.5%) | 0.4656 ± 0.024 | 1.572 ± 0.047 |

TABLE 3-continued

Properties of dCas9/Cas9 with different guide RNA variants at fully-, and partially-, and non-complementary protospacer sites

| Site | DNA | Guide RNA | n[a] | Mean Volume ($nm^3 \times 10^4$) ± SEM[b] | Mean Height (nm) ± SEM |
|---|---|---|---|---|---|
| Protospacer (dCas9) | Engineered | hp10-gRNA[g] | 47<br>Y: 26% (±12.5%)<br>G: 17% (±10.7%)<br>B: 34% (±13.6%) | 0.6304 ± 0.038 | 1.837 ± 0.076 |
| Nonspecific (dCas9) | Engineered | hp10-gRNA | 32<br>Y: 13% (±11.5%)<br>G: 38% (±16.7%)<br>B: 19% (±13.5%) | 0.5181 ± 0.027 | 1.644 ± 0.050 |

[a]Total molecules observed within two standard deviations of those sites. Below: fraction of population in the main three structural clusters (±95% binomial confidence) coloured as in FIG. 2 in main text (Y = yellow cluster, G = green cluster, B = light blue cluster). Full distribution of properties by cluster in FIGS. 12A-12B.
[b]Standard error of the mean
[c]Standard error of the mean
[d]Rejected null hypothesis of height-volume distributions' being different (p > 0.05; Hotelling's $T^2$ test)
[e]On the engineered DNA substrate, tru-gRNA is expected to interact with only the first 8 of the 10 PAM-distal mismatched nucleotides at the 10MM site (labelled '8MM' in FIG. 3D).
[f]On the engineered DNA substrate, tru-gRNA is expected to interact with only the first 3 of the 5 PAM-distal mismatched nucleotides at the 5MM site (labelled '3MM' in FIG. 3D).
[g]See Supplementary Comment 1 in Supporting Information regarding correction of the heights and volumes of proteins with tru-gRNA and hp-gRNAs so they could be compared to those with sgRNA.

Example 6

Interactions Between the Guide RNA and the Target DNA at or Near the 16th Protospacer Site Stabilize the Cas9/dCas9 Conformational Change AFM imaging directly reveals that although dCas9/Cas9 retains a significant propensity to bind protospacer sites with up to ten distal mismatches, binding to DNA sites that are increasingly complementary to the protospacer drives an increasing shift in the population of dCas9/Cas9 proteins toward what appear to be the active conformation. Notably, we see similar shift in structure between off-target sites and perfectly-matched sites for dCas9 with hp-gRNAs as well (Table 2 and FIG. 13). The presence of complementary PAM-distal sequences is known to be associated with increased stability of Cas9 on DNA. It was also recently found that Cas9 binding to single-stranded DNA with increasing PAM-distal complementarity to the protospacer (from 10 to 20 sites) resulted in an increased change of protein size. This was also then associated with a transition of Cas9 activity from nicking behaviour to full cleavage. Here, we directly can determine the volumes of Cas9/dCas9 bound onto double-stranded DNA sites. An analysis of the structural properties of individual Cas9/dCas9 proteins on double-stranded DNA reveals a steady conformational transition with increasingly matched target sequences that is consistent with a 'conformational gating' mechanism, where sgRNA base-pairing with these distal sites also stabilizes the active conformation so that efficient cleavage may occur, whereas binding to sites with numerous distal mismatches shifts the equilibrium away from the active structure (i.e., see FIG. 4D).

Figure 13:
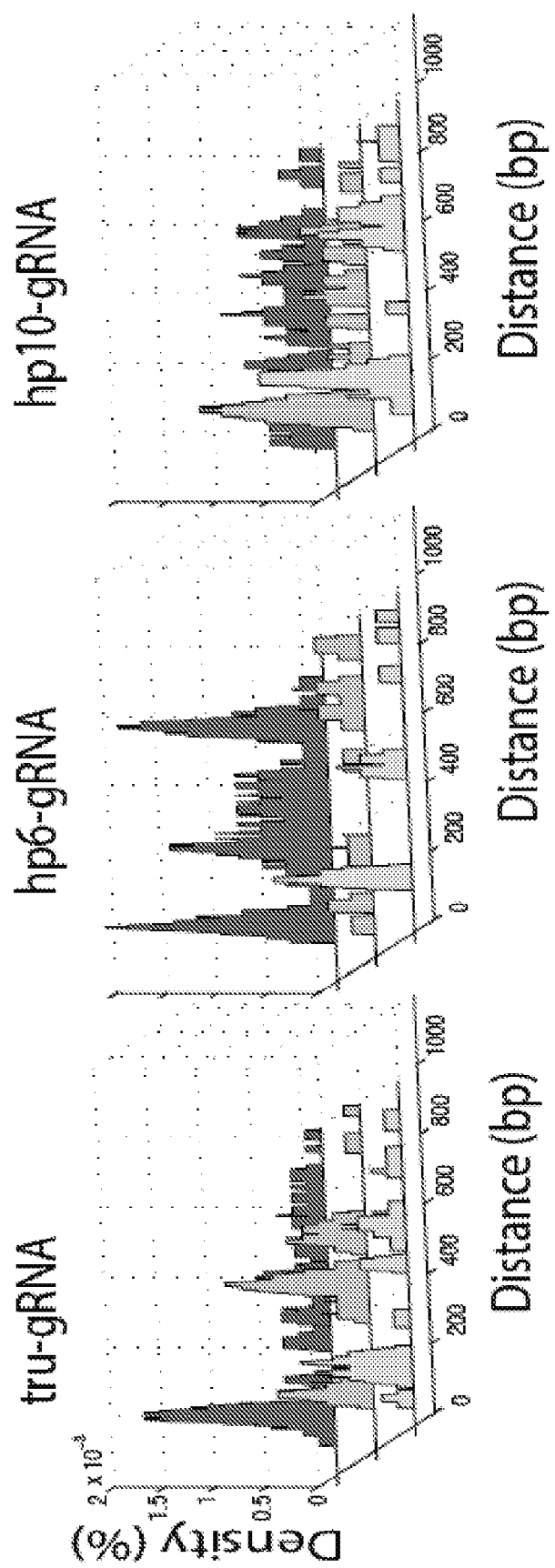
FIG. 13 shows structural properties of Cas9/dCas9 with tru-gRNA and hp-gRNAs at their respective binding sites. Fraction of bound DNA occupied by Cas9/dCas9 with along the engineered DNA substrate, with colors representing populations of Cas9/dCas9 clustered according to their structures (see FIG. 3C). Protein structures were classified according to the dCas9/Cas9 with sgRNA that they most closely resembled (by mean-squared difference after alignment, see text). For reference, on the engineered DNA substrates, location of full protospacer site: 144-167 bp; location of 10 MM (8 MM) site: 452-465 bp; location of 5 MM (3 MM) site: 592-610 bp. Similar trends as was seen with dCas9/Cas9 with sgRNAs were seen: as dCas9 binds to sites which increasingly match the mismatch, the fraction of population clustering with the largest (yellow) group increases, although this effect is depressed in tru-gRNA, with a sizable fraction of the population clustering with smaller (green and blue) populations even at the full protospacer site. The effect for hp10-gRNA is particularly pronounced, emphasizing that it has poor affinities for off-target sites.

Along these lines, we see this effect is dramatically muted for dCas9 with the tru-gRNA (FIG. 3D and Table 3), with a smaller shifts between the structural populations within which the proteins cluster (FIG. 13). Additionally, while we see a statistical difference between the height-volume properties of dCas9-tru-gRNAs that are non-specifically bound and those bound at full or partial protospacer sites (p<0.05; Hotelling's $T^2$ test), at sites that increasingly match the protospacer (10 MM, 5 MM, and full protospacer sites) their structural properties are not statistically differentiable (FIG. 3D and Table 3). It was recently postulated that while invasion of the first 10 bp of the protospacer initiates a conformational change in Cas9, full invasion of the protospacer by the guide RNA helps to drive a further shift to the complete active state. We therefore hypothesized the observed depression of the conformational change at increasingly matched protospacer sites for dCas9 with tru-gRNAs (relative to those with sgRNAs) was a result of the decreased stability of these guide RNAs at PAM-distal sites.

Figures 4A, 4B, 4C:
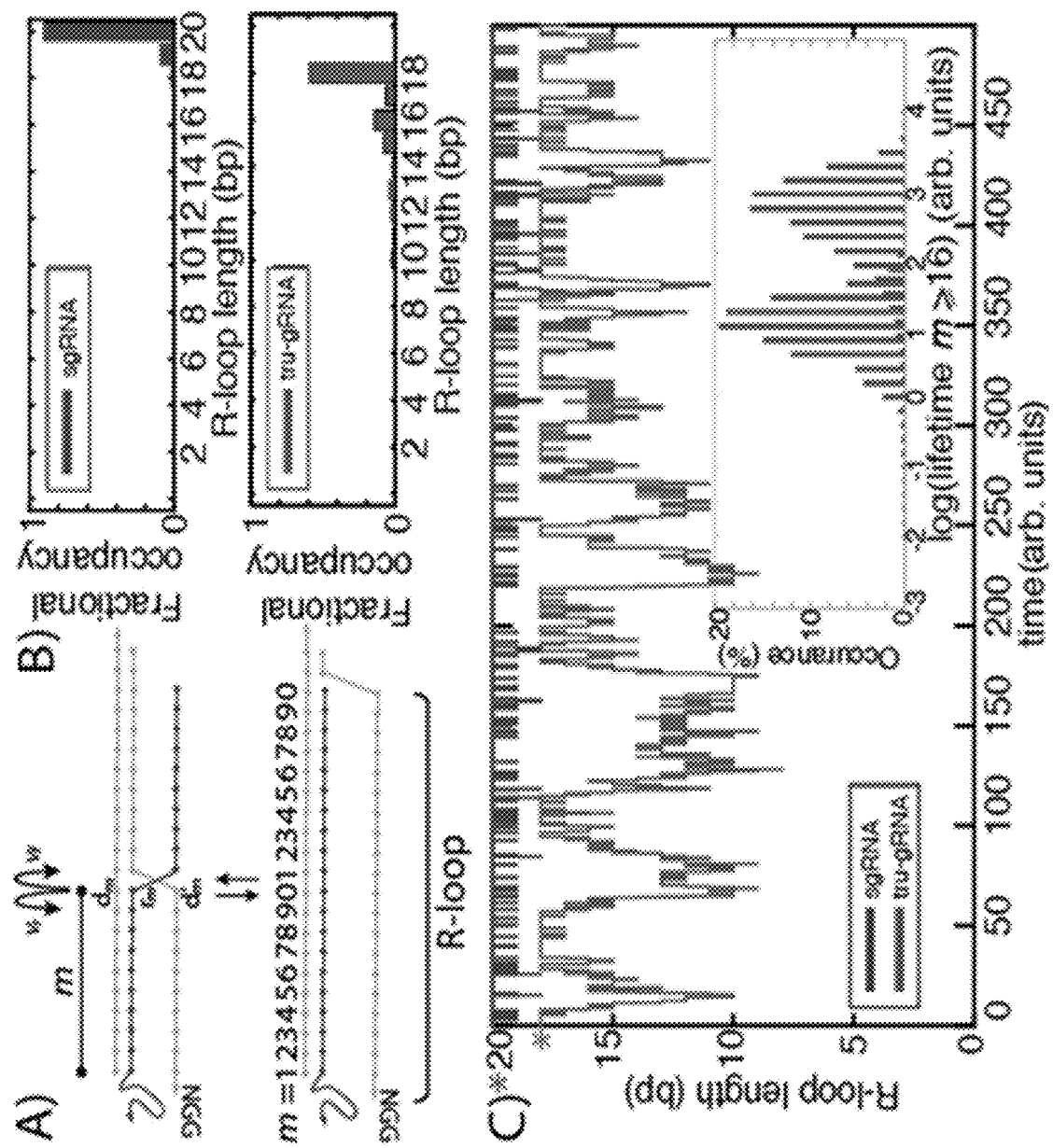
FIGS. 4A-4D show Kinetic Monte Carlo (KMC) experiments revealing differences in the stability of the R-loop, or the structure formed by the protospacer duplex with an invading guide RNA, within stably bound Cas9 for different guide RNA variants.

To investigate the relative stabilities of sgRNAs and tru-gRNAs at these sites, we performed a kinetic Monte Carlo (KMC) study of the dynamic structure of the R-loop— that is, the structure formed by the invading guide RNA bound to a segment of contiguous DNA, exposing a single-stranded loop of the that segment's complementary DNA (FIG. 4A)—during and after strand invasion. See Supplementary Methods for more detail. Briefly, using a Gillespie-type algorithm, we modelled the strand invasion of the guide RNA bound up to protospacer site m as a sequential, nucleotide-by-nucleotide competition between invasion (breaking of base-pairing between the protospacer and its complementary DNA strand, then replacement with a protospacer-guide RNA base-pair) and re-annealing (the reverse), with sequence-dependent rates of invasion and re-annealing $v_f$ and $v_r$, respectively (FIG. 4A). To first-order, we approximate the transition rate from state m to m+1, $v_f$, to be proportional to $\exp(-(\Delta G° (m+1)_{RNA:DNA} - \Delta G° (m+1)_{DNA:DNA})/2RT)$, where $\Delta G° (m+1)_{RNA:DNA}$ is free energy of the base-pairing between the RNA and protospacer at site m+1 and $\Delta G° (m+1)_{DNA:DNA}$ is the free energy of the base-pairing between the protospacer and its complementary DNA strand at m+1 (R is the ideal gas constant, T is the temperature, and the 1/2 term is added to satisfy detailed balance). $v_r$ is estimated similarly as proportional to $\exp(-(\Delta G° (m)_{DNA:DNA} - \Delta G° (m)_{RNA:DNA})/2RT)$. Transition rates of this type have been previously used for computational studies of nucleotide base-pairing and stability, and here they allowed us to capture the general dynamics of the R-loop in a sequence-dependent manner.

In general, RNA:DNA base-pairs are energetically stronger than DNA:DNA base-pairs, and at equilibrium we see from the KMC trajectories that the guide RNAs are stably bound to the protospacer, as expected (FIG. 4C). However, while sgRNA is quite stable and remains nearly totally invaded—during 95% of simulated time course, the strand remains invaded up to the $19^{th}$ protospacer site (FIG. 4B)— tru-gRNA exhibits significant fluctuations of protospacer re-annealing at PAM-distal sites (FIGS. 4B and 4C). Because the only difference between the dCas9-sgRNA and dCas9-tru-gRNA is a simple truncation of two 5'-nucleotides from the guide RNA, and because we see an inhibition of the conformational change by dCas9-sgRNA at sites containing 5 PAM-distal mismatches, these results suggest that the conformational change to a fully active state is stabilized by interactions between the guide RNA and protospacer near the $16^{th}$ site of the protospacer, which is disrupted by the instability of the tru-gRNA in that region. In fact, the KMC experiments show that the mean lifetime between full invasion and re-annealing of the DNA back to the $16^{th}$ site is decreased by two orders of magnitude when replacing the sgRNA with the tru-gRNA (FIG. 4C inset). This result is consistent with the earlier finding that while Cas9 activity with tru-gRNA variants with 2 or 3 nucleotide (nt) truncations was modulated depending on sequence context, and that cleavage in all tested cases was dramatically reduced by ~90%-100% by 4 nt truncations and abolished after a 5 nt truncation. The conformational change to the protein activate state is stabilized by these interactions at or near the $16^{th}$ site of the protospacer. This finding is supported by gRNA stability at the $14^{th}$-$17^{th}$ protospacer positions, which was estimated from additional KMC experiments described below and correlated with experimental off-target cleavage in vivo (see below) while stability of the guide RNA at protospacer sites 18-20 was not.

Example 7

Figures 5A, 5B:
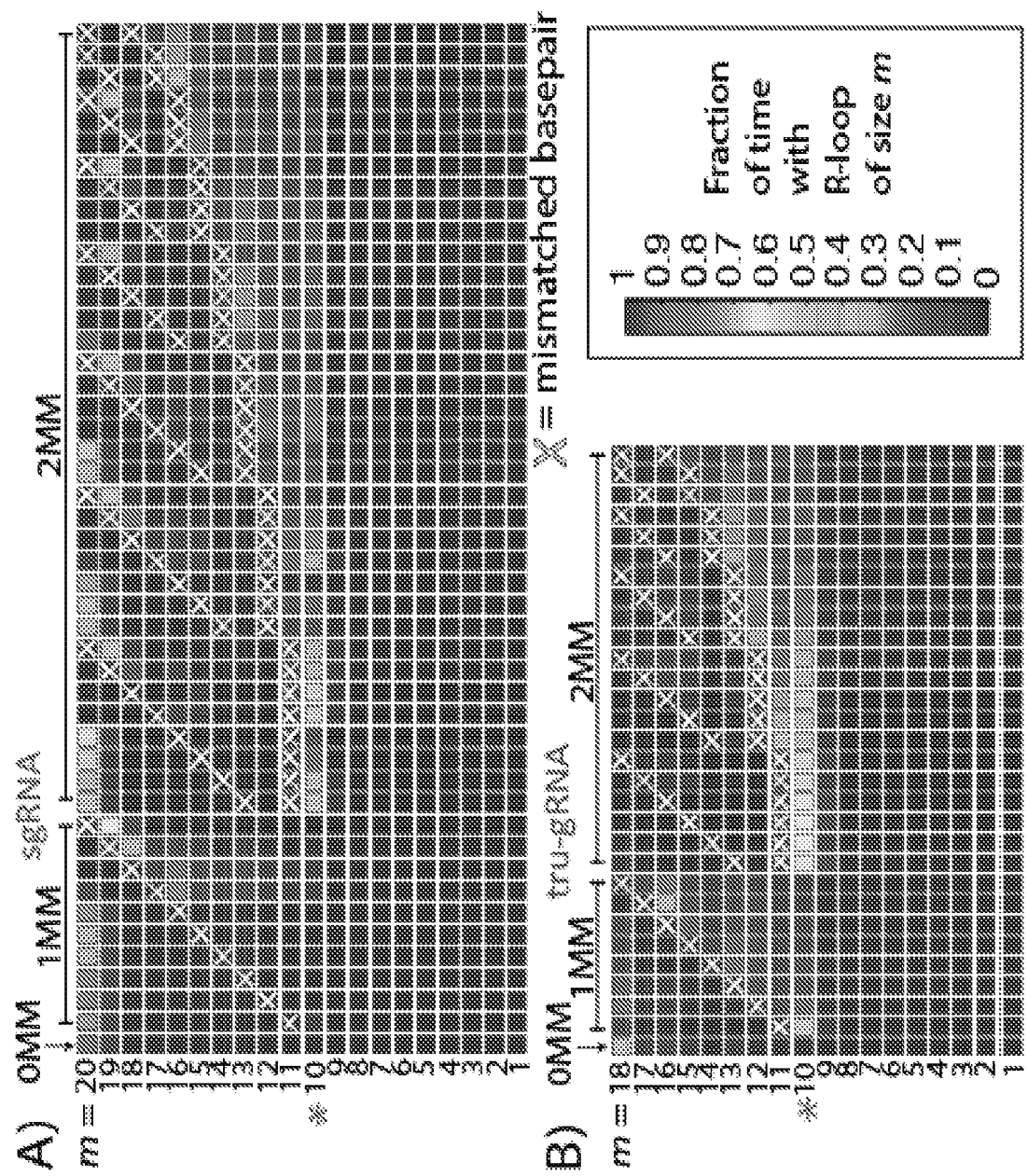
FIGS. 5A-5C show Kinetic Monte Carlo (KMC) experiments reveal differences in ability to traverse mismatches (MINI) and invade the protospacer depending on guide RNA structure.

Fluctuations of the Guide RNA-Protospacer R-Loop Suggest a Mechanism of Mismatch Tolerance by Cas9/dCas9 and of Increased Specificity in Cleavage by Tru-gRNAs To investigate mechanisms by which Cas9 or dCas9 can tolerate or become sensitized to mismatches in protospacers, we performed a series of KMC experiments using the AAVS1 protospacer site where one or two PAM-distal (≥10 bp away from the PAM) mismatches were introduced (FIG. 5). Cas9 is generally more tolerant of PAM-distal mismatches than PAM-proximal mismatches. However, Hsu et al. (2013) Nature Biotechnology, 31, 827-832 identified significant and varying differences in estimated Cas9 cleavage rates at protospacers containing PAM-distal mismatches depending on sequence context, type of mismatch, and site of the mismatch. Based on our AFM and earlier KMC experiments, we hypothesized the differences in cleavage rates may similarly be a result of different stabilities of the guide RNA near the $16^{th}$ site of the protospacer. For these simulations, we only examined sequences with protospacers-guide RNA pairs which would result in isolated rG.dG, rC.dC, rA.dA, and rU.dT mismatches, for which the sequence context-dependent thermodynamic data is the most complete and suitable for our KMC model. The effects of these mismatched base-pairs are not expected to lower the overall binding energy between sgRNA and the protospacer dramatically (Table 4); for example, single rG.dG, rC.dC, rA.dA, and rU.dT mismatches lower RNA:DNA melting temperatures on average by 1.7° C. Rather, their effect is expected to be kinetic rather than thermodynamic in nature by hindering strand displacement at the mismatch. Hence we initiated the kinetic Monte Carlo experiments as proceeding from the $10^{th}$ protospacer site (initial R-loop length m=10), such as would be occurring during strand invasion.

TABLE 4

Sequences and Maximum Likelihood Estimate (MLE) Cutting Frequencies from Hsu et al. (2013) Nature Biotechnology, 31, 827-832 used for correlation analysis (mismatch site in target sequence bold).

| Target sequence | SEQ ID NO | Protospacer-targeting region of Guide RNA | SEQ ID NO | MLE Cutting Frequency (Hsu et al. (2013)) | Estimated $\Delta G°_{37}$ (kcal/mol) |
|---|---|---|---|---|---|
| TTCTTCTTCTGCTCGG ACTC | 13 | GUGUCCGAGCAGAAGA AGAA | 149 | 0.10384 | -32.16 |
| TTCTTCTTCTGCTCGG ACTC | 14 | GACUCCGAGCAGAAGA AGAA | 150 | 0.12609 | -31.4 |
| TTCTTCTTCTGCTCGG ACTC | 15 | GAGACCGAGCAGAAGA AGAA | 151 | 0.13145 | -32.69 |
| TTCTTCTTCTGCTCGG ACTC | 16 | GAGUGCGAGCAGAAGA AGAA | 152 | 0.097464 | -32.33 |
| TTCTTCTTCTGCTCGG ACTC | 17 | GAGUCGGAGCAGAAGA AGAA | 153 | 0.12704 | -33.43 |
| TTCTTCTTCTGCTCGG ACTC | 18 | GAGUCCCAGCAGAAGA AGAA | 154 | 0.079556 | -31.37 |
| TTCTTCTTCTGCTCGG ACTC | 19 | GAGUCCGUGCAGAAGA AGAA | 155 | 0.11197 | -32.36 |
| TTCTTCTTCTGCTCGG ACTC | 20 | GAGUCCGACCAGAAGA AGAA | 156 | 0.04788 | -31.9 |

TABLE 4-continued

Sequences and Maximum Likelihood Estimate (MLE) Cutting Frequencies from Hsu et al. (2013) Nature Biotechnology, 31, 827-832 used for correlation analysis (mismatch site in target sequence bold).

| Target sequence | SEQ ID NO | Protospacer-targeting region of Guide RNA | SEQ ID NO | MLE Cutting Frequency (Hsu et al. (2013)) | Estimated ΔG°$_{37}$ (kcal/mol) |
|---|---|---|---|---|---|
| TTCTTCTTCTGCTCGG ACTC | 21 | GAGUCCGAGGAGAAGA AGAA | 157 | 0.085461 | −32.83 |
| TTCTTCTTCTTGCTCGG ACTC | 22 | GAGUCCGAGCUGAAGA AGAA | 158 | 0.074938 | −32.22 |
| TTCTTCTTCTGCTCGG ACTC | 23 | GUGUCCGAGCAGAAGA AGAA | 159 | 0.15588 | −32.16 |
| TTCTTCTTCTGCTCGG ACTC | 24 | GACUCCGAGCAGAAGA AGAA | 160 | 0.11015 | −31.4 |
| TTCTTCTTCTGCTCGG ACTC | 25 | GAGACCGAGCAGAAGA AGAA | 161 | 0.11435 | −32.69 |
| TTCTTCTTCTGCTCGG ACTC | 26 | GAGUGCGAGCAGAAGA AGAA | 162 | 0.15072 | −32.33 |
| TTCTTCTTCTGCTCGG ACTC | 27 | GAGUCGGAGCAGAAGA AGAA | 163 | 0.11567 | −33.43 |
| TTCTTCTTCTGCTCGG ACTC | 28 | GAGUCCAGCAGAAGA AGAA | 164 | 0.070181 | −31.37 |
| TTCTTCTTCTGCTCGG ACTC | 29 | GAGUCCGUGCAGAAGA AGAA | 165 | 0.10538 | −32.36 |
| TTCTTCTTCTGCTCGG ACTC | 30 | GAGUCCGACCAGAAGA AGAA | 166 | 0.064145 | −31.9 |
| TTCTTCTTCTGCTCGG ACTC | 31 | GAGUCCGAGGAGAAGA AGAA | 167 | 0.085148 | −32.83 |
| TTCTTCTTCTGCTCGG ACTC | 32 | GAGUCCGAGCUGAAGA AGAA | 168 | 0.064903 | −32.22 |
| CCCTAGTCATTGGAGG TGAC | 33 | GACACCUCCAAUGACUA GGG | 169 | 0.062949 | −32.19 |
| CCCTAGTCATTGGAGG TGAC | 34 | GUGACCUCCAAUGACUA GGG | 170 | 0.063313 | −31.73 |
| CCCTAGTCATTGGAGG TGAC | 35 | GUCUCCUCCAAUGACUA GGG | 171 | 0.068655 | −31.72 |
| CCCTAGTCATTGGAGG TGAC | 36 | GUCAGCUCCAAUGACUA GGG | 172 | 0.073003 | −32 |
| CCCTAGTCATTGGAGG TGAC | 37 | GUCACGUCCAAUGACUA GGG | 173 | 0.037401 | −32.63 |
| CCCTAGTCATTGGAGG TGAC | 38 | GUCACCACCAAUGACUA GGG | 174 | 0.038197 | −32.11 |
| CCCTAGTCATTGGAGG TGAC | 39 | GUCACCUGCAAUGACUA GGG | 175 | 0.041758 | −31.63 |
| CCCTAGTCATTGGAGG TGAC | 40 | GUCACCUCGAAUGACUA GGG | 176 | 0.067751 | −32.23 |
| CCCTAGTCATTGGAGG TGAC | 41 | GUCACCUCCUAUGACUA GGG | 177 | 0.031653 | −31.62 |
| CCCTAGTCATTGGAGG TGAC | 42 | GUCACCUCCAUUGACUA GGG | 178 | 0.027161 | −31.77 |
| ATGGGGAGGACATCG ATGTC | 43 | GUCAUCGAUGUCCUCCC CAU | 179 | 0.027124 | −31.26 |

TABLE 4-continued

Sequences and Maximum Likelihood Estimate (MLE) Cutting Frequencies
from Hsu et al. (2013) Nature Biotechnology, 31, 827-832 used for correlation
analysis (mismatch site in target sequence bold).

| Target sequence | SEQ ID NO | Protospacer-targeting region of Guide RNA | SEQ ID NO | MLE Cutting Frequency (Hsu et al. (2013)) | Estimated ΔG°$_{37}$ (kcal/mol) |
|---|---|---|---|---|---|
| ATGGGGAGGACATCG ATGTC | 44 | GAGAUCGAUGUCCUCCC CAU | 180 | 0.022366 | -31.7 |
| ATGGGGAGGACATCG ATGTC | 45 | GACUUCGAUGUCCUCCC CAU | 181 | 0.01127 | -30.92 |
| ATGGGGAGGACATCG ATGTC | 46 | GACAACGAUGUCCUCCC CAU | 182 | 0.011836 | -31.44 |
| ATGGGGAGGACATCG ATGTC | 47 | GACAUGGAUGUCCUCCC CAU | 183 | 0.009146 | -31.83 |
| ATGGGGAGGACATCG ATGTC | 48 | GACAUCCAUGUCCUCCC CAU | 184 | 0.006333 | -30.27 |
| ATGGGGAGGACATCG ATGTC | 49 | GACAUCGUUGUCCUCCC CAU | 185 | 0.006232 | -31.06 |
| ATGGGGAGGACATCG ATGTC | 50 | GACAUCGAAGUCCUCCC CAU | 186 | 0.007085 | -31.64 |
| ATGGGGAGGACATCG ATGTC | 51 | GACAUCGAUCUCCUCCC CAU | 187 | 0.001545 | -30.32 |
| ATGGGGAGGACATCG ATGTC | 52 | GACAUCGAUGACCUCCC CAU | 188 | 0.00025 | -31.59 |
| ATCACATCAACCGGTG GCGC | 53 | GGGCCACCGGUUGAUG UGAU | 189 | 0.15963 | -35.23 |
| ATCACATCAACCGGTG GCGC | 54 | GCCCCACCGGUUGAUGU GAU | 190 | 0.14121 | -32.17 |
| ATCACATCAACCGGTG GCGC | 55 | GCGGCACCGGUUGAUG UGAU | 191 | 0.18743 | -33.43 |
| ATCACATCAACCGGT GGCGC | 56 | GCGCGACCGGUUGAUG UGAU | 192 | 0.1634 | -33.63 |
| ATCACATCAACCGGT GGCGC | 57 | GCGCCUCCGGUUGAUGU GAU | 193 | 0.15877 | -33.12 |
| ATCACATCAACCGGT GGCGC | 58 | GCGCCAGCGGUUGAUG UGAU | 194 | 0.029249 | -33.4 |
| ATCACATCAACCGGT GGCGC | 59 | GCGCCACGGGUUGAUG UGAU | 195 | 0.12208 | -34.13 |
| ATCACATCAACCGGT GGCGC | 60 | GCGCCACCGUUGAUGU GAU | 196 | 0.051622 | -31.57 |
| ATCACATCAACCGGT GGCGC | 61 | GCGCCACCGCUUGAUGU GAU | 197 | 0.004914 | -31.74 |
| ATCACATCAACCGGTG GCGC | 62 | GCGCCACCGGAUGAUGU GAU | 198 | 0.032227 | -33.79 |
| GAGTTTCTCATCTGTG CCCC | 63 | GGGCCACAGAUGAGAA ACUC | 199 | 0.015879 | -33.54 |
| CCAGCTTCTGCCGTTT GTAC | 64 | GUUCAAACGGCAGAAG CUGG | 200 | 0.037469 | -33.17 |
| CCAGCTTCTGCCGTTT GTAC | 65 | GUACUAACGGCAGAAG CUGG | 201 | 0.059921 | -32.92 |
| CCAGCTTCTGCCGTTT GTAC | 66 | GUACAAACGGGAGAAG CUGG | 202 | 0.032605 | -33.43 |

TABLE 4-continued

Sequences and Maximum Likelihood Estimate (MLE) Cutting Frequencies
from Hsu et al. (2013) Nature Biotechnology, 31, 827-832 used for correlation
analysis (mismatch site in target sequence bold).

| Target sequence | SEQ ID NO | Protospacer-targeting region of Guide RNA | SEQ ID NO | MLE Cutting Frequency (Hsu et al. (2013)) | Estimated $\Delta G°_{37}$ (kcal/mol) |
|---|---|---|---|---|---|
| TTCCTCCTCCAGCTTCTGCC | 67 | GCCAGAAGCUGGAGGAGGAA | 203 | 0.000481 | -35.94 |
| TTCCTCCTCCAGCTTCTGCC | 68 | GGCACAAGCUGGAGGAGGAA | 204 | 0.041538 | -37.4 |
| TTCCTCCTCCAGCTTCTGCC | 69 | GGCAGAACCUGGAGGAGGAA | 205 | 0.047874 | -37.5 |
| TTCCTCCTCCAGCTTCTGCC | 70 | GGCAGAAGCAGGAGGAGGAA | 206 | 0.050381 | -38.61 |
| TTCCTCCTCCAGCTTCTGCC | 71 | GGCAGAAGCUCGAGGAGGAA | 207 | 0.006459 | -36.92 |
| CCGGTTGATGTGATGGGAGC | 72 | GCACCCAUCACAUCAACCGG | 208 | 0.03967 | -33.31 |
| CCGGTTGATGTGATGGGAGC | 73 | GCUCCCUUCACAUCAACCGG | 209 | 0.033426 | -32.52 |
| CCGGTTGATGTGATGGGAGC | 74 | GCUCCCAACACAUCAACCGG | 210 | 0.035651 | -33.04 |
| CCGGTTGATGTGATGGGAGC | 75 | GCUCCCAUCAGAUCAACCGG | 211 | 0.03209 | -33.3 |
| GCAGCAAGCAGCACTCTGCC | 76 | GGCAGUGUGCUGCUUGCUGC | 212 | 0.004014 | -32.46 |
| GCAGCAAGCAGCACTCTGCC | 77 | GGCAGAGUGCAGCUUGCUGC | 213 | 0.000219 | -33.11 |
| GCTTGGGCCCACGCAGGGGC | 78 | GCCCCAGCGUGGGCCCAAGC | 214 | 0.001487 | -38.81 |
| GCTTGGGCCCACGCAGGGGC | 79 | GCCCCUGCCUGGGCCCAAGC | 215 | 0.003322 | -36.77 |
| GCTTCGTGGCAATGCGCCAC | 80 | GUGGCCCAUUGCCACGAAGC | 216 | 0.000463 | -32.67 |
| GCTTGGGCCCACGCAGGGGC | 81 | GCCCCUGCGUCGGCCCAAGC | 217 | 0 | -37.12 |
| AAGCTGGACTCTGGCCACTC | 82 | GAGUGGCCUGAGUCCAGCUU | 218 | 0.010169 | -33.02 |
| TTCTTCTTCTGCTCGGACTC | 83 | GAGACCGAGCAGAAGAAGAA | 219 | 0.084395 | -32.69 |
| TTCTTCTTCTGCTCGGACTC | 84 | GAGUCCGAGGAGAAGAAGAA | 220 | 0.051852 | -32.83 |
| TTCTTCTTCTGCTCGGACTC | 85 | GAGUCCGAGCUGAAGAAGAA | 221 | 0.050685 | -32.22 |
| GAGTTTCTCATCTGTGCCCC | 86 | GGGGCACAGUUGAGAAACUC | 222 | 0.004503 | -34.16 |
| TTCCTCCTCCAGCTTCTGCC | 87 | GGCAGAAGGUGGAGGAGGAA | 223 | 0.006035 | -38.83 |
| TTCCTCCTCCAGCTTCTGCC | 88 | GGCAGAAGCAGGAGGAGGAA | 224 | 0.011364 | -38.61 |
| AGCAGAAGAAGAAGGGCTCC | 89 | GGAGCCCUUGUUCUUCUGCU | 225 | 0.007206 | -29.83 |

TABLE 4-continued

Sequences and Maximum Likelihood Estimate (MLE) Cutting Frequencies
from Hsu et al. (2013) Nature Biotechnology, 31, 827-832 used for correlation
analysis (mismatch site in target sequence bold).

| Target sequence | SEQ ID NO | Protospacer-targeting region of Guide RNA | SEQ ID NO | MLE Cutting Frequency (Hsu et al. (2013)) | Estimated ΔG°$_{37}$ (kcal/mol) |
|---|---|---|---|---|---|
| AAGCTGGACTCTGGC CACTC | 90 | GAGUGGCCUGAGUCCA GCUU | 226 | 0 | −33.02 |
| CCCTAGTCATTGGAGG TGAC | 91 | GACACCUCCAAUGACUA GGG | 227 | 0.053611 | −32.19 |
| CCCTAGTCATTGGAGG TGAC | 92 | GUGACCUCCAAUGACUA GGG | 228 | 0.05399 | −31.73 |
| CCCTAGTCATTGGAGG TGAC | 93 | GUCUCCUCCAAUGACUA GGG | 229 | 0.070404 | −31.72 |
| CCCTAGTCATTGGAGG TGAC | 94 | GUCAGCUCCAAUGACUA GGG | 230 | 0.067678 | −32 |
| CCCTAGTCATTGGAGG TGAC | 95 | GUCACGUCCAAUGACUA GGG | 231 | 0.03597 | −32.63 |
| CCCTAGTCATTGGAGG TGAC | 96 | GUCACCACCAAUGACUA GGG | 232 | 0.025207 | −32.11 |
| CCCTAGTCATTGGAGG TGAC | 97 | GUCACCUGCAAUGACUA GGG | 233 | 0.056019 | −31.63 |
| CCCTAGTCATTGGAGG TGAC | 98 | GUCACCUCGAAUGACUA GGG | 234 | 0.065347 | −32.23 |
| CCCTAGTCATTGGAGG TGAC | 99 | GUCACCUCCUAUGACUA GGG | 235 | 0.063769 | −31.62 |
| CCCTAGTCATTGGAGG TGAC | 100 | GUCACCUCCAUUGACUA GGG | 236 | 0.052644 | −31.77 |
| ATGGGGAGGACATCG ATGTC | 101 | GUCAUCGAUGUCCUCCC CAU | 237 | 0.020295 | −31.26 |
| ATGGGGAGGACATCG ATGTC | 102 | GAGAUCGAUGUCCUCCC CAU | 238 | 0.012126 | −31.7 |
| ATGGGGAGGACATCG ATGTC | 103 | GACUUCGAUGUCCUCCC CAU | 239 | 0.007202 | −30.92 |
| ATGGGGAGGACATCG ATGTC | 104 | GACAACGAUGUCCUCCC CAU | 240 | 0.010912 | −31.44 |
| ATGGGGAGGACATCG ATGTC | 105 | GACAUGGAUGUCCUCCC CAU | 241 | 0.009292 | −31.83 |
| ATGGGGAGGACATCG ATGTC | 106 | GACAUCCAUGUCCUCCC CAU | 242 | 0.006125 | −30.27 |
| ATGGGGAGGACATCG ATGTC | 107 | GACAUCGUUGUCCUCCC CAU | 243 | 0.007805 | −31.06 |
| ATGGGGAGGACATCG ATGTC | 108 | GACAUCGAAGUCCUCCC CAU | 244 | 0.010174 | −31.64 |
| ATGGGGAGGACATCG ATGTC | 109 | GACAUCGAUCUCCUCCC CAU | 245 | 0.003595 | −30.32 |
| ATGGGGAGGACATCG ATGTC | 110 | GACAUCGAUGACCUCCC CAU | 246 | 0.000206 | −31.59 |
| ATCACATCAACCGGTG GCGC | 111 | GGGCCACCGGUUGAUG UGAU | 247 | 0.18977 | −35.23 |
| ATCACATCAACCGGTG GCGC | 112 | GCCCCACCGGUUGAUGU GAU | 248 | 0.13525 | −32.17 |

TABLE 4-continued

Sequences and Maximum Likelihood Estimate (MLE) Cutting Frequencies
from Hsu et al. (2013) Nature Biotechnology, 31, 827-832 used for correlation
analysis (mismatch site in target sequence bold).

| Target sequence | SEQ ID NO | Protospacer-targeting region of Guide RNA | SEQ ID NO | MLE Cutting Frequency (Hsu et al. (2013)) | Estimated $\Delta G°_{37}$ (kcal/mol) |
|---|---|---|---|---|---|
| ATCACATCAACCGGTGGCGC | 113 | GCGGCACCGGUUGAUGUGAU | 249 | 0.14749 | -33.43 |
| ATCACATCAACCGGTGGCGC | 114 | GCGCGACCGGUUGAUGUGAU | 250 | 0.13952 | -33.63 |
| ATCACATCAACCGGTGGCGC | 115 | GCGCCUCCGGUUGAUGUGAU | 251 | 0.13949 | -33.12 |
| ATCACATCAACCGGTGGCGC | 116 | GCGCCAGCGGUUGAUGUGAU | 252 | 0.031221 | -33.4 |
| ATCACATCAACCGGTGGCGC | 117 | GCGCCACGGGUUGAUGUGAU | 253 | 0.14776 | -34.13 |
| ATCACATCAACCGGTGGCGC | 118 | GCGCCACCCGUUGAUGUGAU | 254 | 0.050539 | -31.57 |
| ATCACATCAACCGGTGGCGC | 119 | GCGCCACCGCUUGAUGUGAU | 255 | 0.003982 | -31.74 |
| ATCACATCAACCGGTGGCGC | 120 | GCGCCACCGGAUGAUGUGAU | 256 | 0.015494 | -33.79 |
| GAGTTTCTCATCTGTGCCCC | 121 | GGGCCACAGAUGAGAAACUC | 257 | 0.025334 | -33.54 |
| CCAGCTTCTGCCGTTTGTAC | 122 | GUUCAAACGGCAGAAGCUGG | 258 | 0.062094 | -33.17 |
| CCAGCTTCTGCCGTTTGTAC | 123 | GUACUAACGGCAGAAGCUGG | 259 | 0.080429 | -32.92 |
| CCAGCTTCTGCCGTTTGTAC | 124 | GUACAAACGGGAGAAGCUGG | 260 | 0.032505 | -33.43 |
| TTCCTCCTCCAGCTTCTGCC | 125 | GCCAGAAGCUGGAGGAGGAA | 261 | 0.00117 | -35.94 |
| TTCCTCCTCCAGCTTCTGCC | 126 | GGCACAAGCUGGAGGAGGAA | 262 | 0.034381 | -37.4 |
| TTCCTCCTCCAGCTTCTGCC | 127 | GGCAGAACCUGGAGGAGGAA | 263 | 0.059128 | -37.5 |
| TTCCTCCTCCAGCTTCTGCC | 128 | GGCAGAAGCAGGAGGAGGAA | 264 | 0.05162 | -38.61 |
| TTCCTCCTCCAGCTTCTGCC | 129 | GGCAGAAGCUCGAGGAGGAA | 265 | 0.007682 | -36.92 |
| CCGGTTGATGTGATGGGAGC | 130 | GCACCCAUCACAUCAACCGG | 266 | 0.093725 | -33.31 |
| CCGGTTGATGTGATGGGAGC | 131 | GCUCCCUUCACAUCAACCGG | 267 | 0.075435 | -32.52 |
| CCGGTTGATGTGATGGGAGC | 132 | GCUCCCAACACAUCAACCGG | 268 | 0.091723 | -33.04 |
| CCGGTTGATGTGATGGGAGC | 133 | GCUCCCAUCAGAUCAACCGG | 269 | 0.070319 | -33.3 |
| GCAGCAAGCAGCACTCTGCC | 134 | GGCAGUGUGCUGCUUGCUGC | 270 | 0.006754 | -32.46 |
| GCAGCAAGCAGCACTCTGCC | 135 | GGCAGAGUGCAGCUUGCUGC | 271 | 0.000545 | -33.11 |

TABLE 4-continued

Sequences and Maximum Likelihood Estimate (MLE) Cutting Frequencies from Hsu et al. (2013) Nature Biotechnology, 31, 827-832 used for correlation analysis (mismatch site in target sequence bold).

| Target sequence | SEQ ID NO | Protospacer-targeting region of Guide RNA | SEQ ID NO | MLE Cutting Frequency (Hsu et al. (2013)) | Estimated $\Delta G°_{37}$ (kcal/mol) |
|---|---|---|---|---|---|
| GCTTGGGCCCACGCAGGGGC | 136 | GCCCCAGCGUGGGCCCAAGC | 272 | 0.004676 | -38.81 |
| GCTTGGGCCCACGCAGGGGC | 137 | GCCCCUGCCUGGGCCCAAGC | 273 | 0.001918 | -36.77 |
| GCTTCGTGGCAATGCGCCAC | 138 | GUGGCCCAUUGCCACGAAGC | 274 | 0.001045 | -32.67 |
| GCTTGGGCCCACGCAGGGGC | 139 | GCCCCUGCGUCGGCCCAAGC | 275 | 0 | -37.12 |
| AAGCTGGACTCTGGCCACTC | 140 | GAGUGGCCUGAGUCCAGCUU | 276 | 0.008891 | -33.02 |
| TTCTTCTTCTGCTCGGACTC | 141 | GAGACCGAGCAGAAGAAGAA | 277 | 0.091861 | -32.69 |
| TTCTTCTTCTGCTCGGACTC | 142 | GAGUCCGAGGAGAAGAAGAA | 278 | 0.062783 | -32.83 |
| TTCTTCTTCTGCTCGGACTC | 143 | GAGUCCGAGCUGAAGAAGAA | 279 | 0.044444 | -32.22 |
| GAGTTTCTCATCTGTGCCCC | 144 | GGGGCACAGUUGAGAAACUC | 280 | 0.0053 | -34.16 |
| TTCCTCCTCCAGCTTCTGCC | 145 | GGCAGAAGGUGGAGGAGGAA | 281 | 0.00714 | -38.83 |
| TTCCTCCTCCAGCTTCTGCC | 146 | GGCAGAAGCAGGAGGAGGAA | 282 | 0.019945 | -38.61 |
| AGCAGAAGAAGAAGGGCTCC | 147 | GGAGCCCUUGUUCUUCUGCU | 283 | 0.007996 | -29.83 |
| AAGCTGGACTCTGGCCACTC | 148 | GAGUGGCCUGAGUCCAGCUU | 284 | 0.006102 | -33.02 |

Figure 4D:
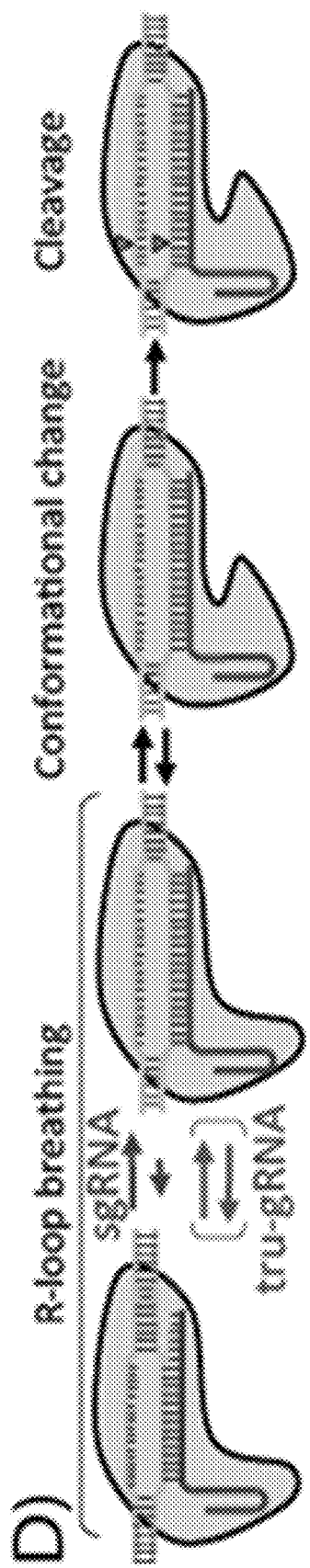
Figure 5C:
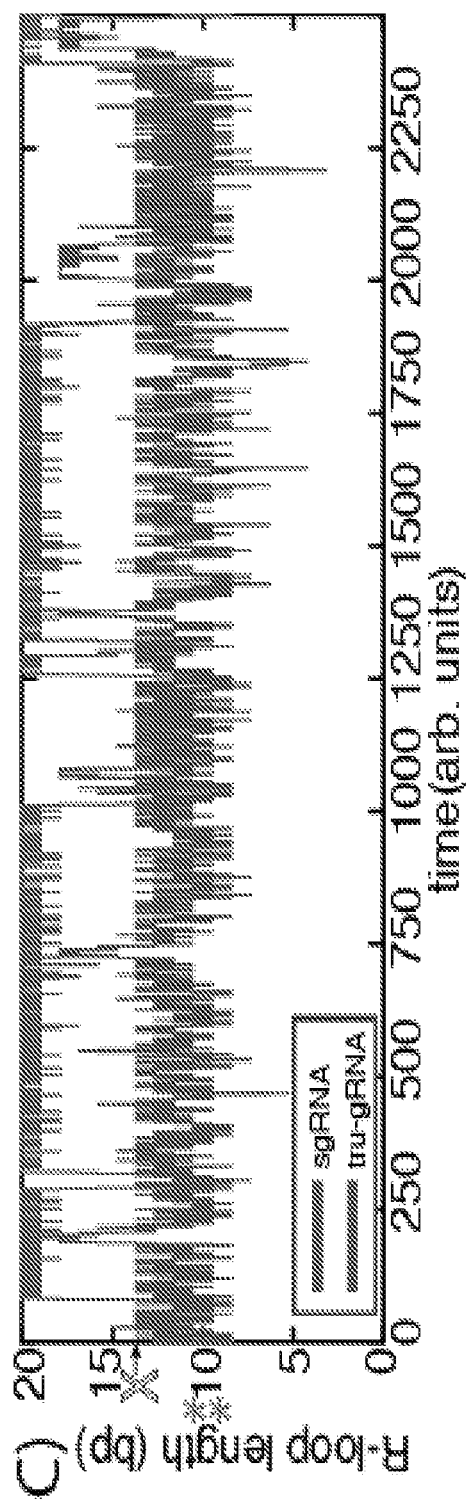
Figures 14A, 14B, 14C:
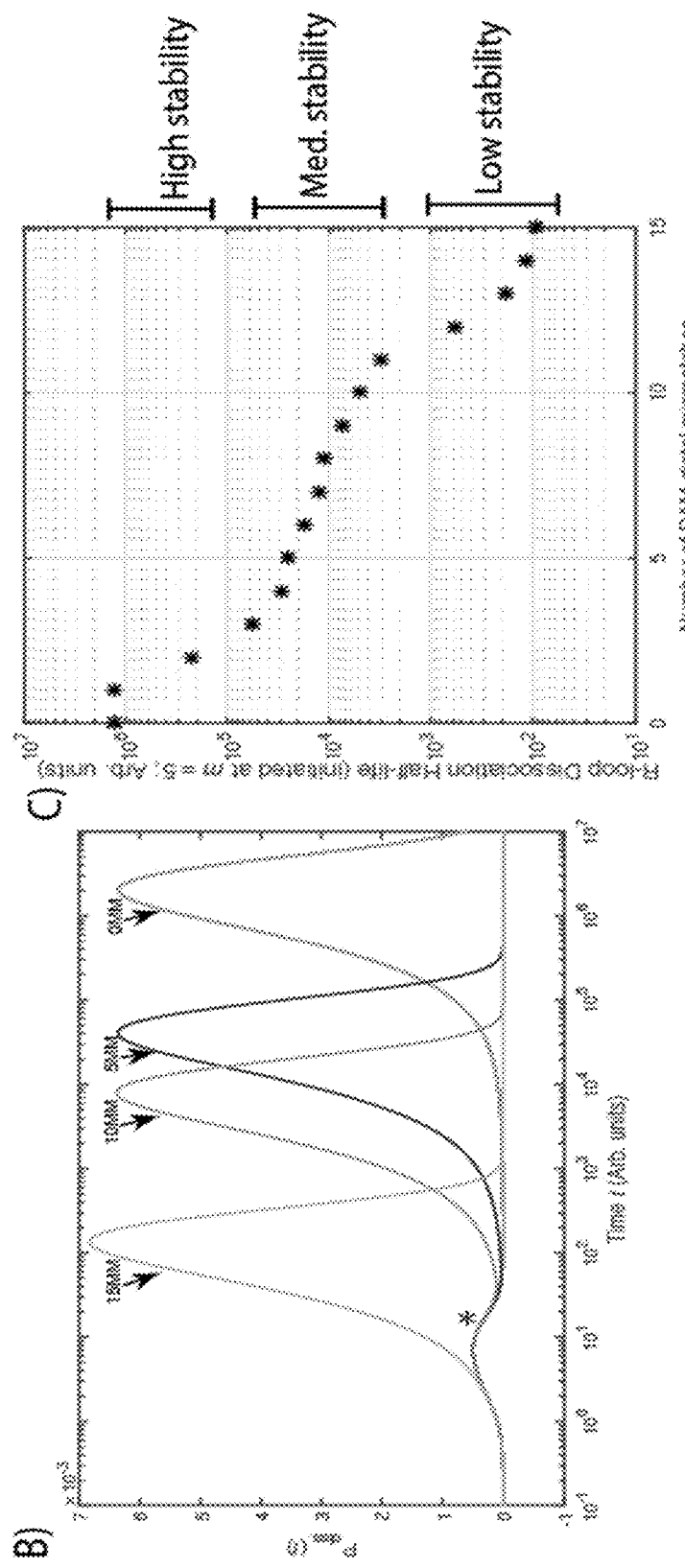
FIGS. 14A-14C show model of the strand invasion of DNA protospacers by guide RNAs, and estimated binding stabilities of RNA invaded into protospacers with PAM-distal mismatches.

KMC experiments were then performed to investigate the kinetics of strand invasion in the presence of PAM-distal mismatches. In all cases (1000 trials each), the guide RNAs remain quite stably bound even when there are mismatches (i.e., are not observed to completely melt off) and are often able to quickly bypass these sites to complete full invasion (FIG. 5C and FIGS. 14A-14C), although the mean first passage time of total strand invasion varied significantly depending on the position of the mismatch site (FIGS. 14A-14C). The R-loops are quite stable during invasion (FIG. 5A), as the sgRNAs are often able to remain fully invaded even in the presence of multiple mismatches. The results qualitatively resemble those of earlier in vitro studies of dCas9/Cas9 binding and cleavage on mismatched targets. However, in the case of tru-gRNAs (FIG. 5B), the R-loops are often trapped behind the mismatch sites. The mean first passage time across mismatches is similar for both sgRNAs and tru-gRNAs (FIGS. 14A-14C), but an inspection of the time courses for the KMC reveals that, because of the inherent volatility of the R-loop for tru-gRNAs, tru-gRNAs are often quickly 're-trapped' behind the mismatch (FIG. 5C). For sgRNAs, this re-trapping is much less frequent. Hence, in combination with AFM imaging, the results of the KMC experiments suggest that the origin of increased tru-gRNA specificity lies not in discrimination during binding but rather in the volatility of its R-loop (FIG. 4D) such that it becomes repeatedly trapped behind mismatches even after initially bypassing them, making Cas9 less likely to assume the active conformation. For sgRNAs, once a mismatch is bypassed it can remain fully invaded with relatively little perturbation, suggesting a mechanism of mismatch tolerance.

Example 8

Stabilities of the Guide RNA Interaction with the 14th-17th Positions of the Protospacer are Correlated with Experimental Off-Target Cas9 Cleavage Rates, while Overall Guide RNA—Protospacer Binding Energies are not To verify whether the stabilities of the R-loop at or near the $16^{th}$ position of the protospacer—which was implicated by AFM studies to be connected to the conformational change in Cas9—are associated with Cas9 activity in vivo, we performed a kinetic Monte Carlo (KMC) analysis of R-loop stability on the sequences used by Hsu et al. (2013) *Nature Biotechnology*, 31, 827-832. The data set of Hsu et al. (2013) *Nature Biotechnology,* 31, 827-832 consisted of measurements of the cleavage frequency at fifteen different protospacer targets containing various point mutations vs. the guide RNA that were performed to investigate cleavage specificity by Cas9. This data set contained 136 protospacer-guide RNA pairs that possessed a single, isolated mismatch of type rG.dG, rC.dC, rA.dA, and rU.dT in the PAM-distal region (Table 4), which we investigated using KMC methods initiated at R-loop size m=10 to simulate invasion. The inclusion of a single mismatched site from this set decreased the magnitude of their overall guide RNA-protospacer binding free energy on average by about only 6% relative to perfectly matched targets although, as mentioned, there was a wide distribution Cas9 cutting frequencies observed for these guide-RNA protospacer pairs whose origin was not obvious.

Figures 6A, 6B:
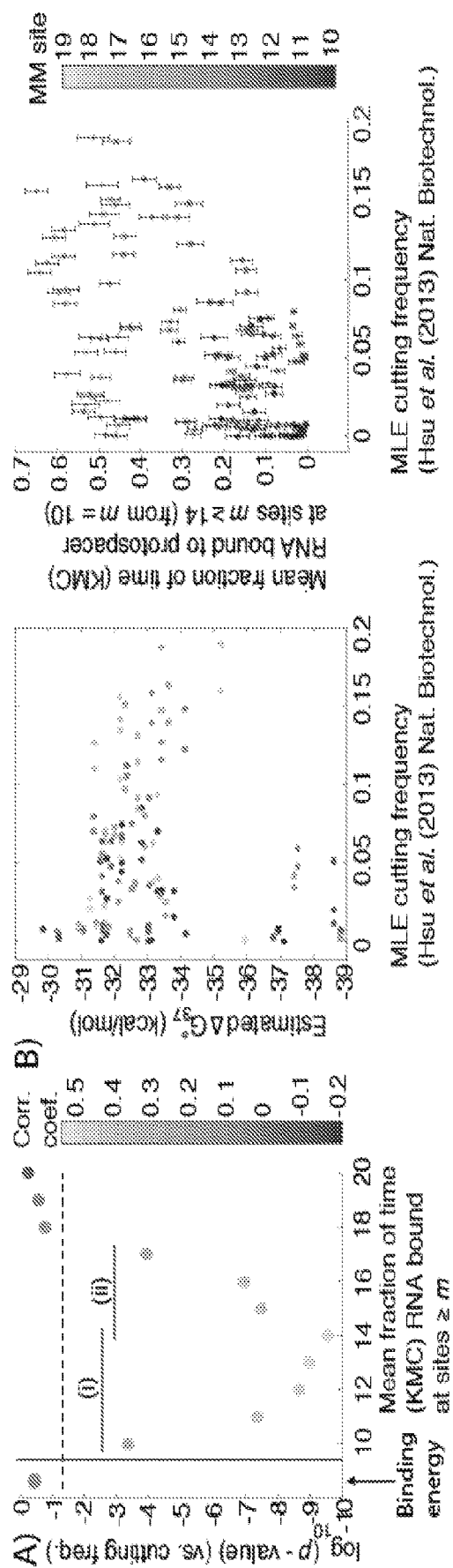
FIGS. 6A-6B show experimental (Hsu et al. (2013) *Nature biotechnology*, 31, 827-832) cutting frequencies at target sites containing a single rG·dG, rC·dC, rA-dA, and rU·dT mismatch in the PAM-distal region (≥10$^{th}$ protospacer site) are correlated with stabilities of the R-loop determined from kinetic Monte Carlo experiments.
Figure 15:
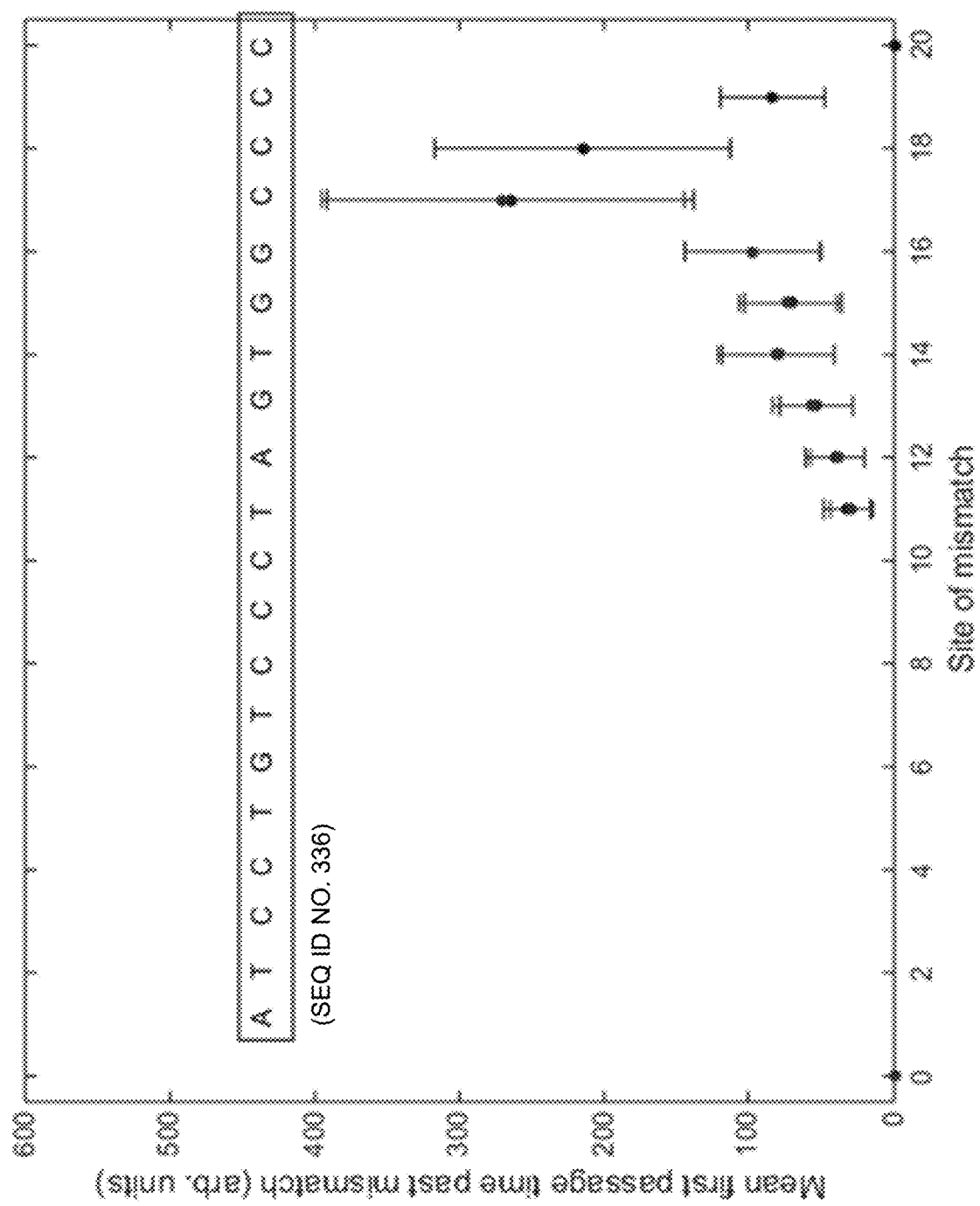
FIG. 15 shows simulated mean first passage times to traverse the mismatched site during strand invasion by sgRNA and tru-gRNA. Simulated (kinetic Monte Carlo) mean first passage times to traverse the mismatched site during strand invasion by sgRNA (blue) and tru-gRNA (red) for different positions of the mismatched site. Error bars are standard deviations of recorded first passage times. Sequence of protospacer (AAVS1 site) in box.

The mean fraction of time the RNA was bound stably to each site of the protospacer was determined for each guide RNA over 1000 trials, which was then correlated to the maximum-likelihood estimated cleavage activity of Cas9 (Table 4, FIG. 6, and FIG. 15). A moderate (0.433) but statistically significant ($p<1\times10^{-6}$) correlation was found between guide RNA stability at the $16^{th}$ protospacer position and reported off-target cleavage activity. Notably, no statistically significant correlation was found between cleavage rate and the predicted DNA:RNA binding energies alone (0.0786; p=0.3631) (FIGS. 6A and 6B). In addition to R-loop stability at the $16^{th}$ position, a significant correlation is also found for stability the $17^{th}$ protospacer site and reported cleavage (Table 5), but this was not the case for sites $\geq 18^{th}$ site (FIG. 6). While the kinetic Monte Carlo model presented here is based on a relatively simple model of strand invasion, these results further suggest that stability of the $16^{th}$-$17^{th}$ sites of the protospacer, and hence the concomitant conformational changes we observed, are associated with Cas9 cleavage activity in vivo (FIG. 4D).

TABLE 5

Correlations between experimental (Hsu et al. (2013) *Nature Biotechnology*, 31, 827-832) cutting frequencies at target sites containing a single rG · dG, rC · dC, rA · dA, and rU · dT mismatch in the PAM-distal region ($\geq 10^{th}$ protospacer site)[a] and measures of guide RNA - protospacer stability

| | | $\log_{10}$(p-value) | Correlation coefficient |
|---|---|---|---|
| Hsu et al. (2013) estimated cutting frequency vs. guide RNA - protospacer binding energy[b] | | −0.4400 | (0.0786) |
| Hsu et al estimated cutting frequency vs. position of mismatch site | | −5.8258 | 0.3990 |
| Hsu et al estimated cutting frequency vs. fractional time guide RNA bound at sites ≥ the $m^{th}$ protospacer site in a simulated R-loop (KMC)[c] | m = 14 | −9.5550 | 0.5078 |
| | m = 15 | −7.4854 | 0.4522 |
| | m = 16 | −6.9510 | 0.4333 |
| | m = 17 | −3.9270 | 0.3191 |
| | m = 18 | −0.7639 | (0.1159) |
| | m = 19 | −0.5546 | (0.1058) |
| | m = 20 | −0.2346 | (−0.0176) |

[a]n = 136.
[b]See Table 4 for details.
[c]See text for details. Max(t) = 100.

Figures 16A, 16B:
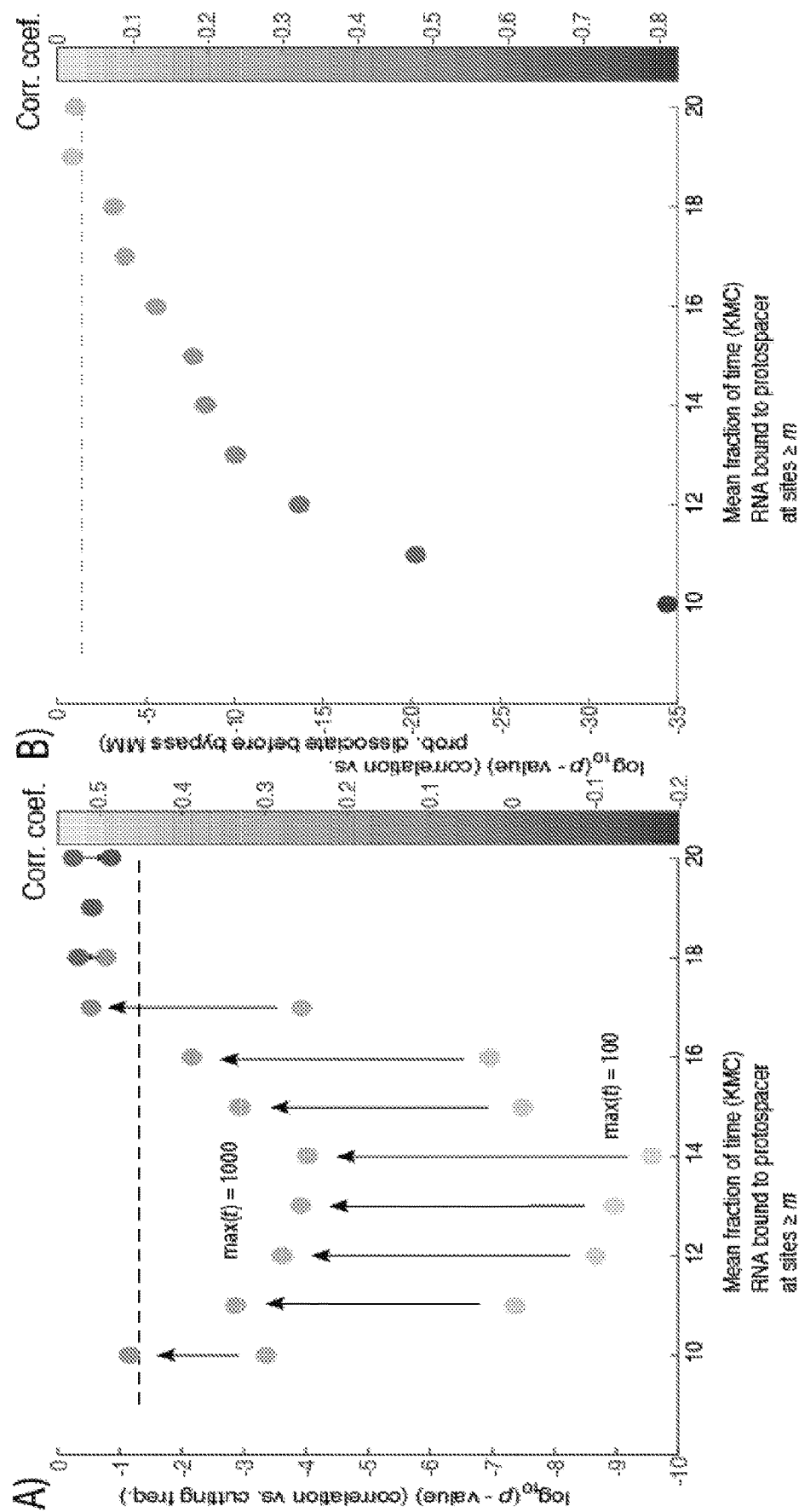
FIGS. 16A-16B shows correlations between Cas9 cleavage frequency (Hsu et al. (2013) Nature Biotechnology, 31, 827-832) and measures of R-loop stability derived from kinetic Monte Carlo.

We limited most of our analysis to interactions with the $16^{th}$-$18^{th}$ nucleotides of the protospacer because of the observed structural differences between dCas9 with tru-gRNAs and sgRNA. However, we also observe an increase of the strength and statistical significance of the correlations between cleavage and the stability of the $14^{th}$ and $15^{th}$ protospacer sites (FIG. 6), with greatest significance for the correlation at the $14^{th}$ site. Because the R-loop is a dynamic structure (FIG. 4D), it is possible that interactions with these sites are those critical ones believed to be responsible for DNA cleavage. Truncation of the guide RNA by 4 or 5 nucleotides may abolish cleavage activity by sufficiently destabilizing the R-loop at the $14^{th}$ or $15^{th}$ position in much the same way that the tru-gRNA destabilized the R-loop at the $16^{th}$-$17^{th}$ sites. However, because in our model $14^{th}$ and $15^{th}$ sites are necessarily invaded whenever the $16^{th}$ site is bound by sgRNA, it is likely that these positions are additionally informative because they are also more strongly anti-correlated with the probability of sgRNA dissociation from the duplex prior to bypassing the mismatched site (FIG. 6Ai and FIG. 16B), another mechanism by which cleavage would fail to occur. At present, there is no crystallographic evidence which directly relates strand invasion to the observed conformational change believed to authorize cleavage. However, based on the evidence provided by AFM experiments presented here and the results of the kinetic Monte Carlo simulations, we conclude that stability of the guide gRNA at the $14^{th}$-$17^{th}$ sites of the protospacer during invasion is critical for this conformational change and, ultimately, the specificity of Cas9 cleavage.

Furthermore, the R-loop as a dynamic structure in competition between strand invasion and DNA re-annealing can be useful in understanding mechanisms of off-target cleavage and mismatch tolerance. No statistically significant correlation was found between cleavage rate and the predicted DNA-RNA binding energies alone (FIG. 6B), suggesting that the kinetics of strand invasion can be considered when attempting to determine Cas9 activity at off-target sites. While cleavage is abolished when 4 or 5 nucleotides are truncated from the guide RNA, Cas9 is still able to cleave DNA with up to 6 distal-mismatch sites. Transient, non-specific interactions at these PAM-distal sites could sufficiently stabilize the conformational shifts necessary for cleavage. Since we see minority populations of dCas9-sgRNA at partial protospacer sites with similar structures to those at the full protospacer (yellow, FIG. 3C(i)), this population may represent the fraction of Cas9 in a transiently-stabilized active conformation. As such, this population may be responsible for off-target cleavage.

Figures 7A, 7B, 7C:
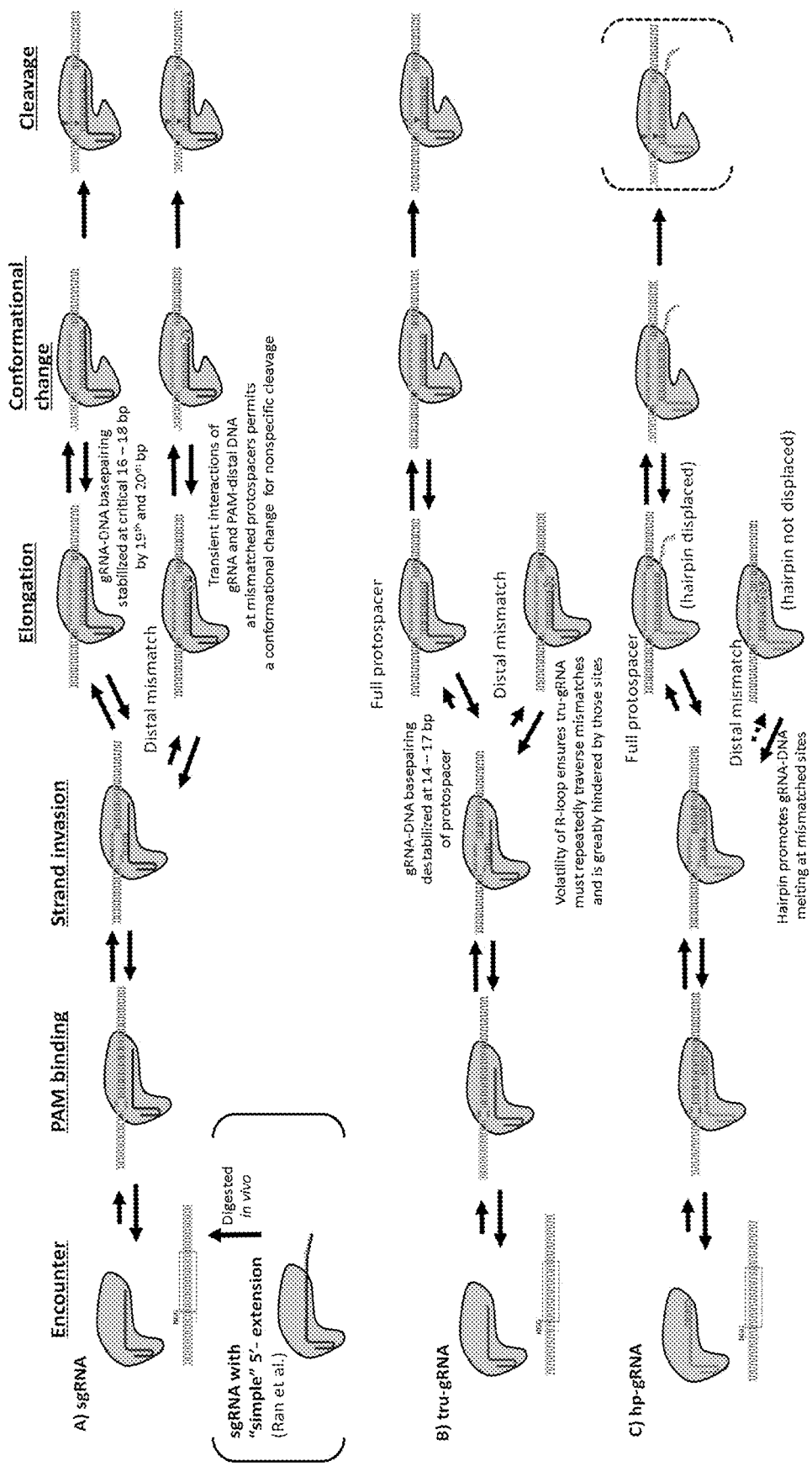
FIGS. 7A-7C show a summary of proposed mechanisms by which the structure of the guide RNA affects Cas9/dCas9 specificity.

While Cas9/dCas9 binding specificity is largely determined by interactions with the PAM-proximal region, DNA cleavage specificity is likely governed by a conformational change to an activated structure that is stabilized by guide RNA interactions at the $14^{th}$-$17^{th}$ bp region of the protospacer (FIG. 4D). Kinetic Monte Carlo experiments reveal that the R-loop formed during strand invasion of the guide RNA can be quite a dynamic structure even when the guide RNA remains stably bound, which suggests a mechanism for the improved specificity of tru-gRNAs, and an origin of off-target cleavage via transient stability of the guide RNA-protospacer at the critical region around mismatched sites. The proposed mechanisms for the effects of each of the sgRNA variants on Cas9/dCas9 specificity are summarized in FIG. 7.

Using AFM, hp-gRNAs were found to significantly weakened or abolished specific binding at homologous targets. hp-gRNAs may be valuable for modulating dCas9 binding affinity and specificity in their potential applications in biology and medicine. Specifically, based on the narrow geometry of the Cas9 binding channel, the presence of an unopened hairpin at mismatched protospacers may inhibit the conformational change by Cas9 to the active state. The opening of the hairpin in hp-gRNAs upon binding could also be used as a binding-dependent signal in vivo, for example, to nucleate dynamic DNA/RNA structures only upon binding to specific sites.

Earlier guide RNA truncation studies raised the question of why do natural Cas9 systems employ a crRNA which targets 20 bp protospacer sites when only a guide sequence of 16 nucleotides is required for cleavage and the additional nucleotides (>18) do not improve cleavage specificity in vivo. These results suggest that presence of the 'extra' 5'-nucleotides which bind to the $19^{th}$ and $20^{th}$ protospacer sites buffer this transient re-annealing at the critical $14^{th}$-$17^{th}$ sites of the protospacer, allowing efficient conformational change to the active state and subsequent cleavage to occur. The results of AFM and KMC experiments suggest that stability of the guide RNA at these sites shifts the equilibrium structure of Cas9 toward the active conformation upon full invasion (FIG. 4A), while the volatility of R-loops for 'truncated' guide RNAs reduces the pressure to shift the equilibrium to the active state. The promiscuous activity of Cas9 with sgRNAs vs. tru-gRNAs might also hold evolutionary advantages in its role as an agent of adaptive immunity in prokaryotes to invasive DNA, since the DNA of invading phages undergo rapid point mutations at sites targeted by Cas9 in order to avoid cleavage.

The design of guide RNA sequences for Cas9/dCas9 applications in vivo has focused primarily on avoiding targets with multiple sites with similar sequences in the genome. However, a recent study exploring off-target cleavage found that current methods for predicting off-target activity were largely ineffective. The stability of the R-loop during invasion correlates with off-target cleavage rates significantly better than guide RNA-protospacer binding energies alone or the position of the mismatch (another important criteria used in guide RNA design, Table 3). The stability of the R-loop at shorter times after the initiation of invasion was correlated with experimental cleavage rate much better than was the long-term stability in the KMC experiments (FIG. 16A), suggesting that the kinetics of strand invasion is a factor in off-target activity prediction.

Example 9

In Vivo Testing

Figure 17:
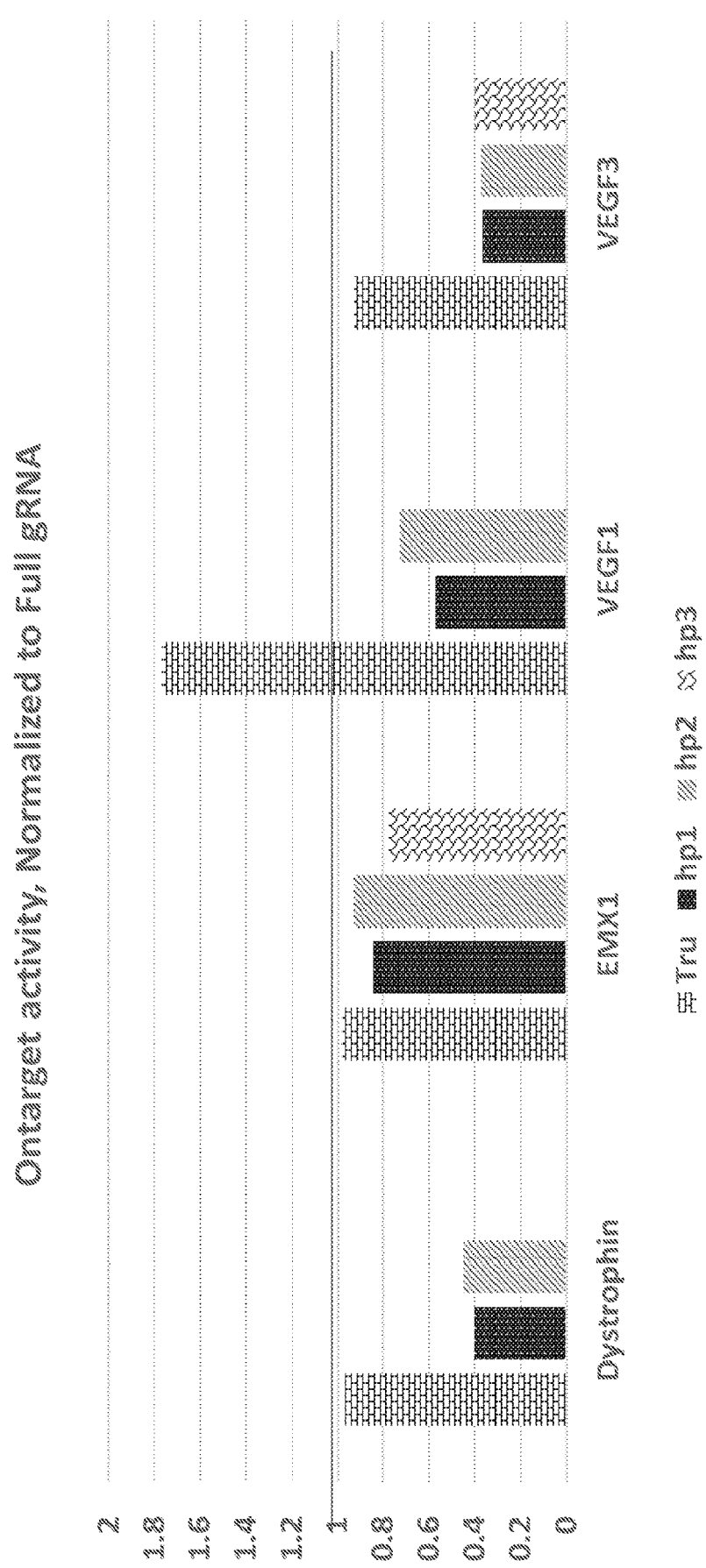
FIG. 17 shows a summary of Deep-Seq data, comparing ontarget activities.
Figure 18:
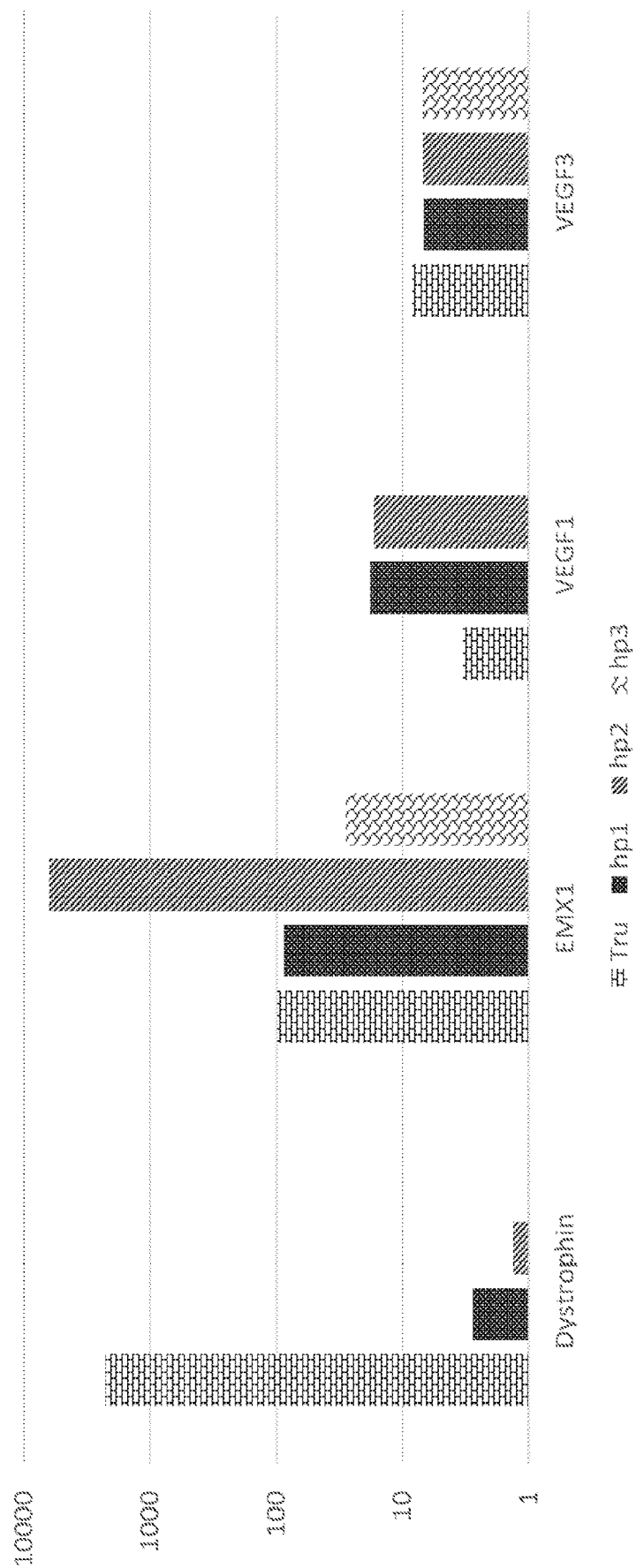
FIG. 18 shows a summary of Deep-Seq data, comparing specificity increases.
Figure 19:
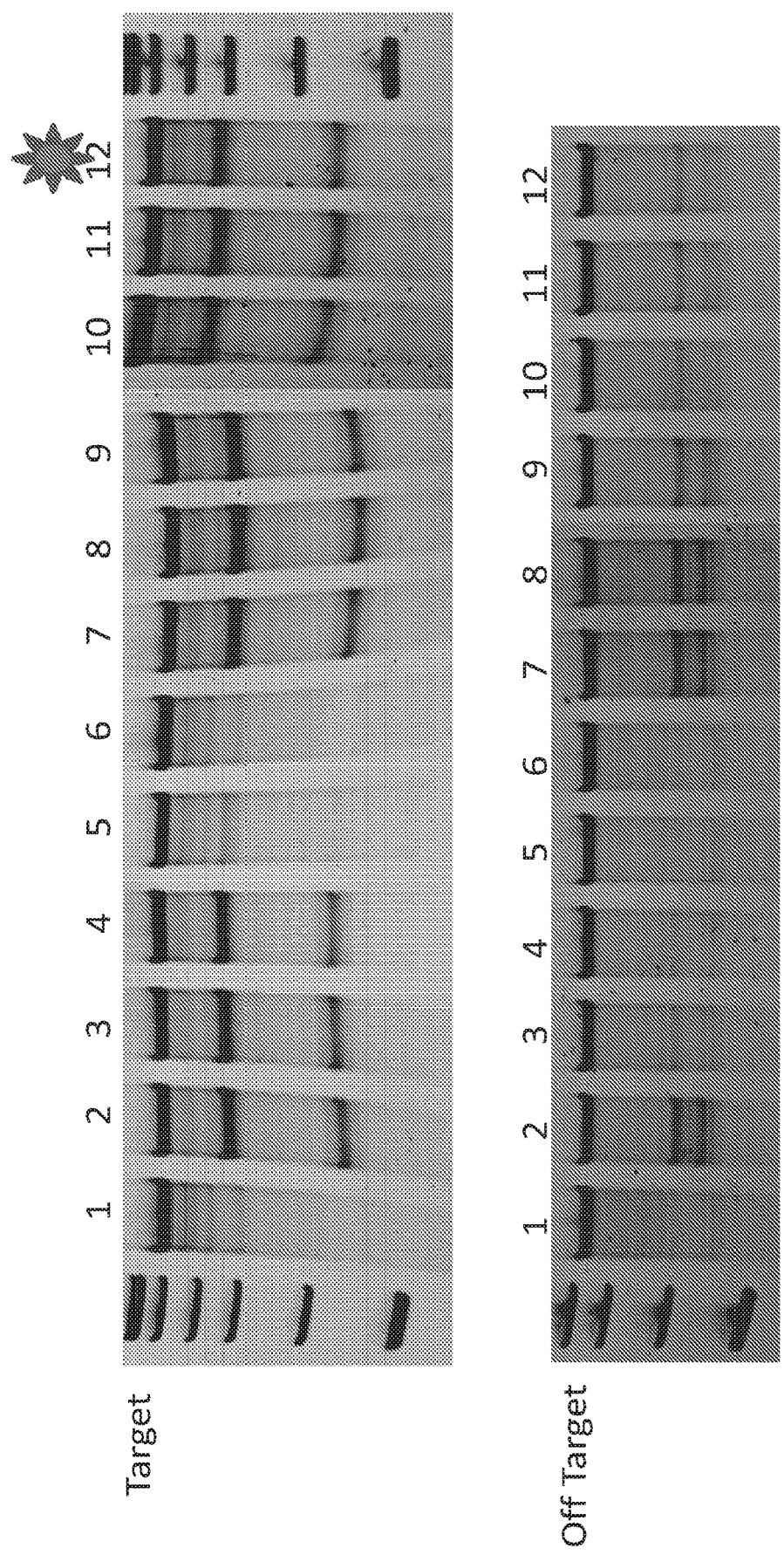
FIG. 19 shows protospacer1, Dystrophin; Lane 1 shows GFP Control; Lane 2 shows Full gRNA; Lane 3 shows Tru-gRNA 19 nt; Lane 4 shows Tru-gRNA 18 nt; Lane 5 shows Tru-gRNA 17 nt; Lane 6 shows Tru-gRNA 16 nt; Lane 7 shows Hp-gRNA 4 bp; Lane 8 shows Hp-gRNA 5 bp; Lane 9 shows Hp-gRNA 6 bp; Lane 10 shows Hp-gRNA 7 bp; Lane 11 shows Hp-gRNA 8 bp; and Lane 12 shows Hp-gRNA 9 bp, hairpin 1 (Lane 12, 9 nt hp)—GtgagtaggttcgCCTACTCAGACTGTTACTC (SEQ ID NO: 335), wherein italicized is part of hairpin and underlined is the hairpin loop.
Figure 20:
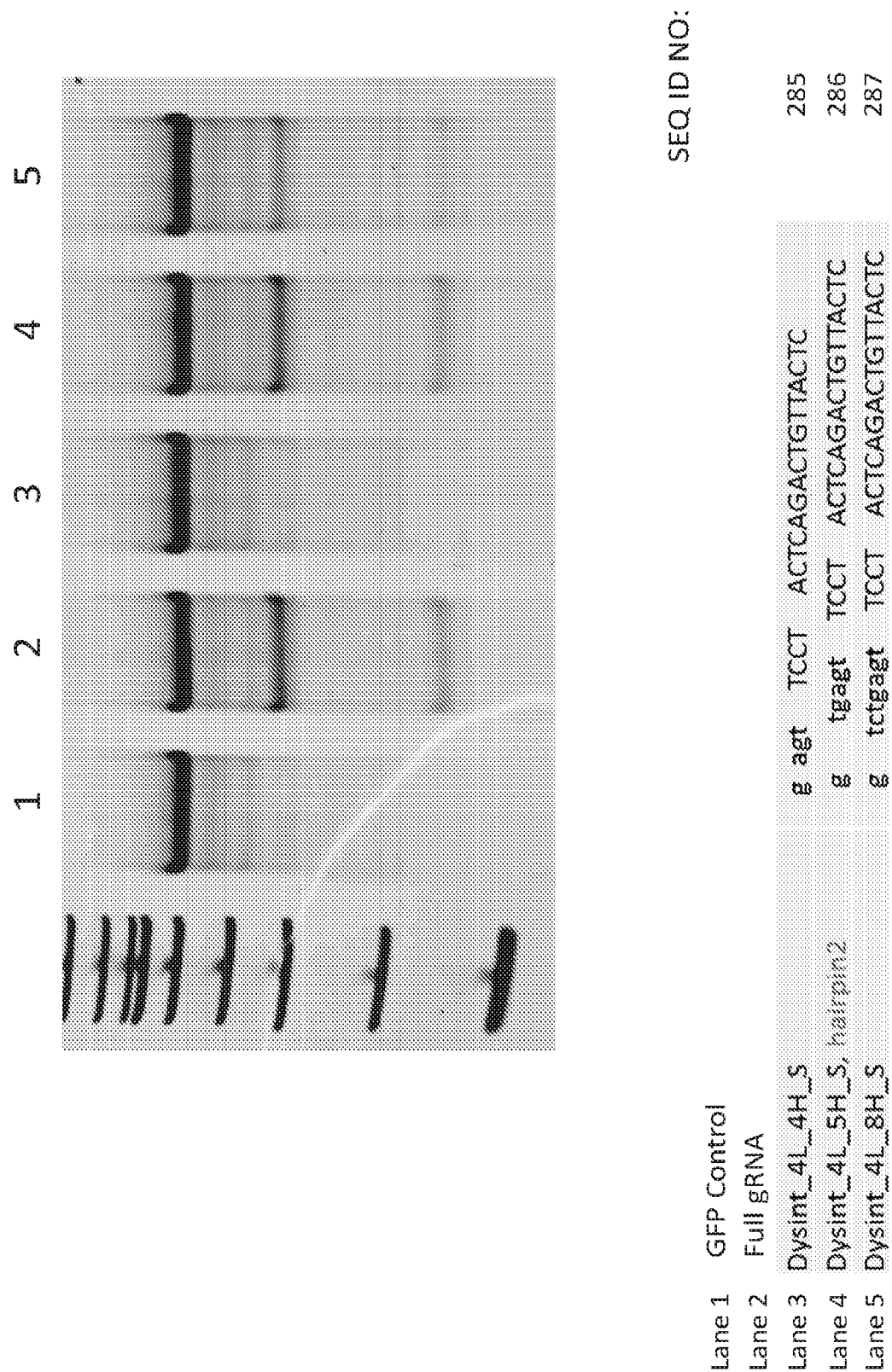
FIG. 20 shows protospacer1, Dystrophin, internal loops
Figure 21A:
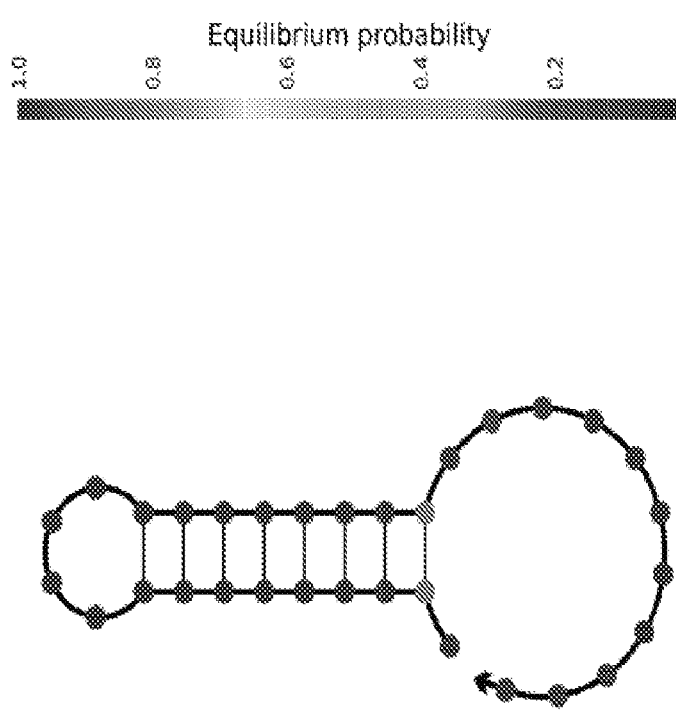
FIG. 21 shows Calculated secondary structures of the 5'-ends of the protospacer-targeting segments of hp-gRNAs used for Deep Seq experiments (using NuPack software suite). Colors are probability of each nucleotide existing in that secondary structure at equilibrium.
Figure 21B:
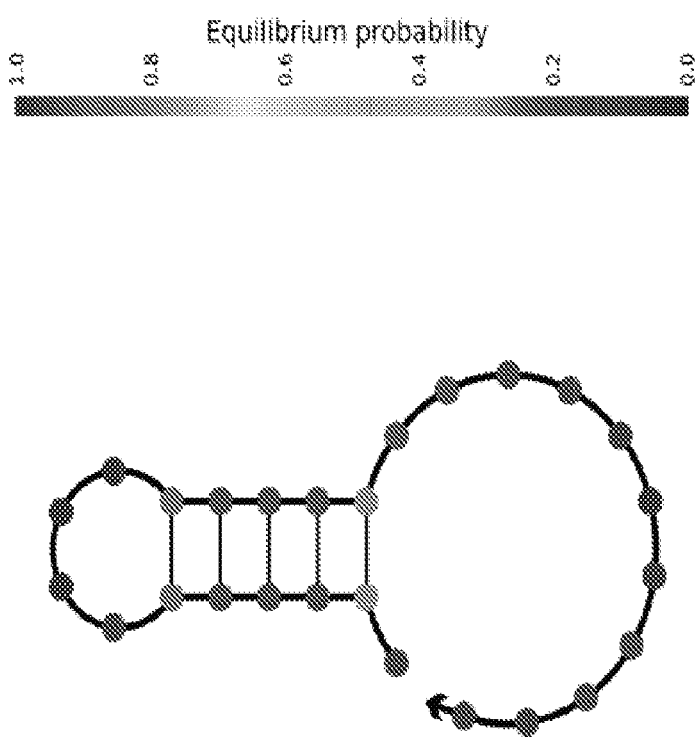
Figure 22:
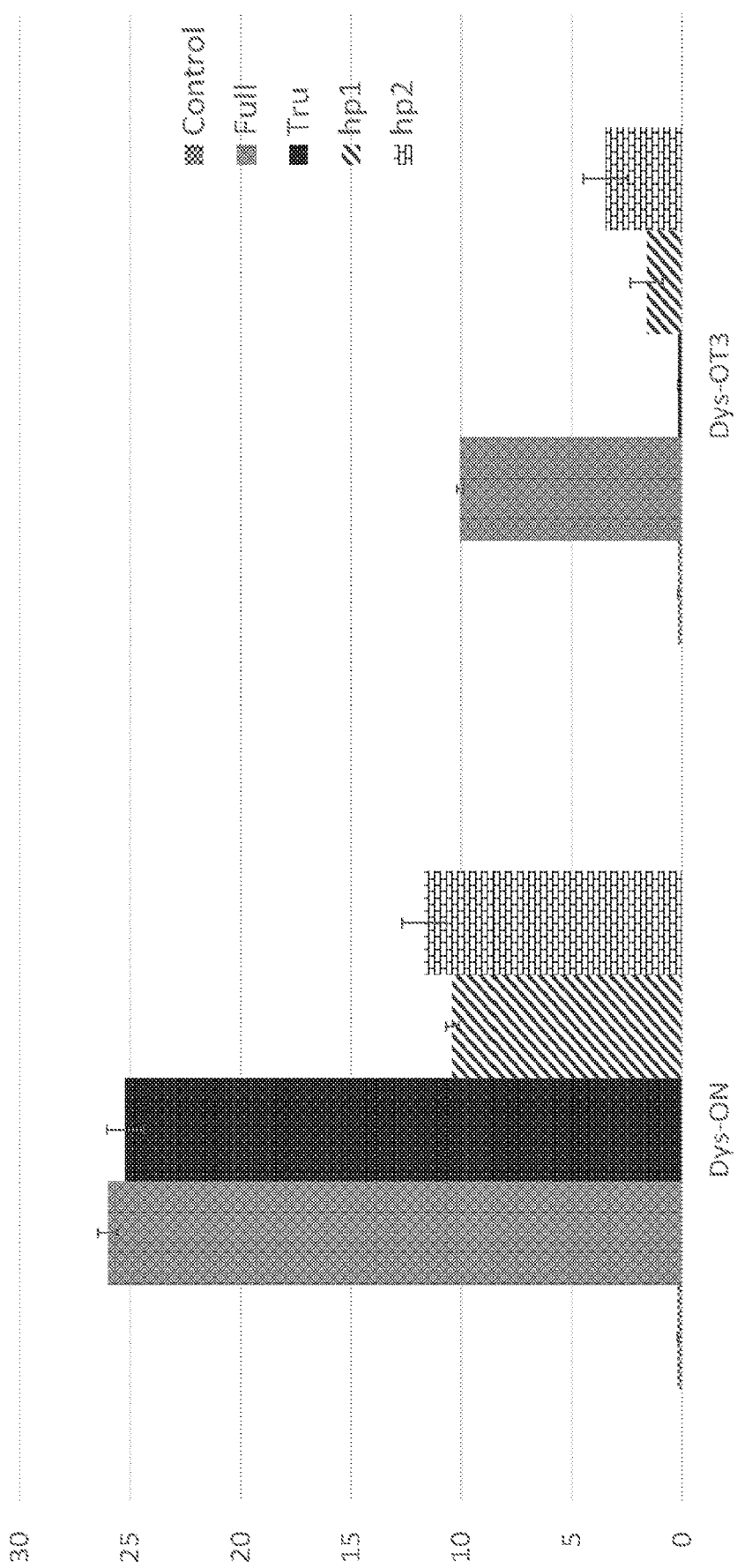
FIG. 22 shows Dystrophin, indel rates, all sites
Figure 23:
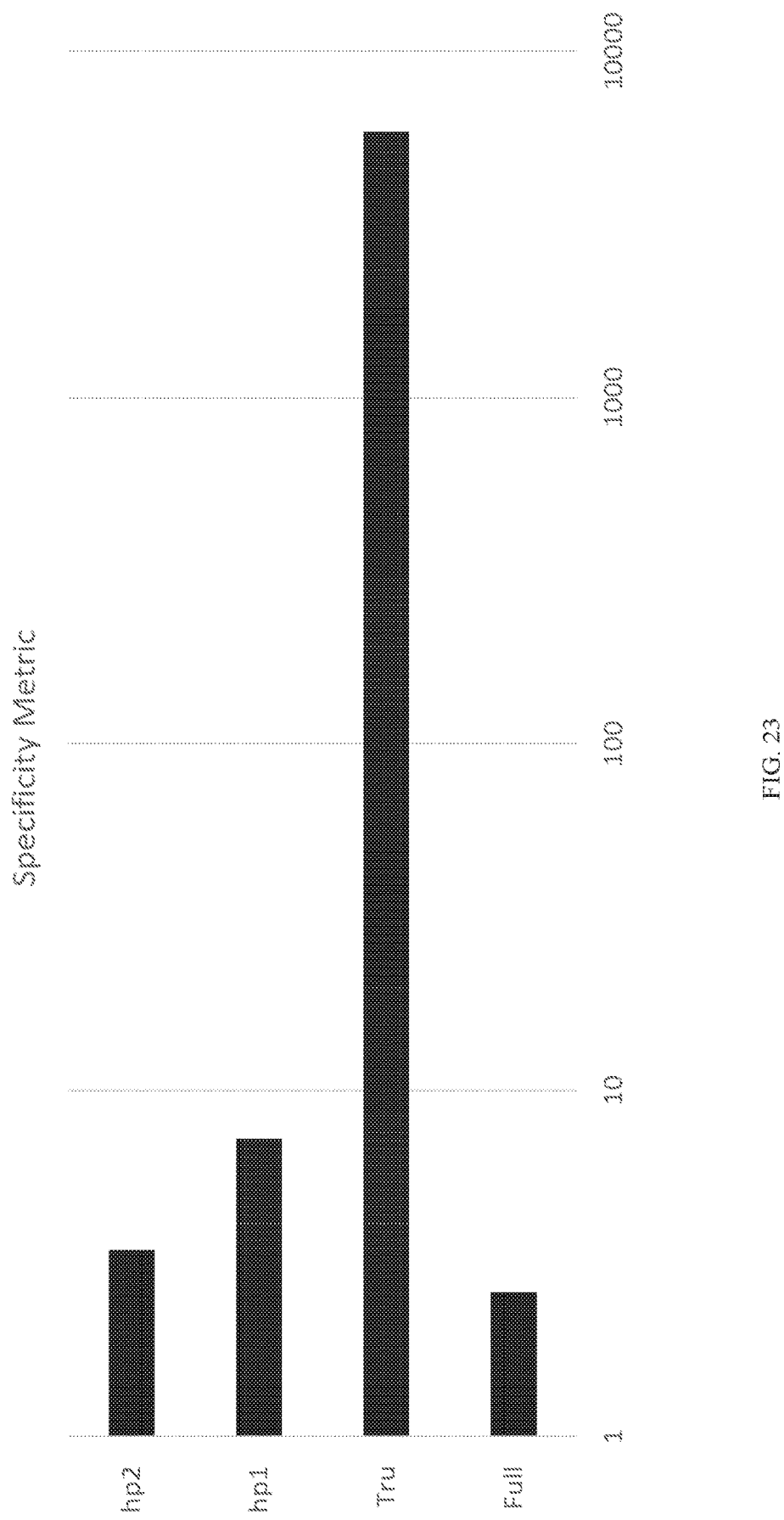
FIG. 23 shows Dystrophin, ontarget/sum(offtargets).
Figure 24:
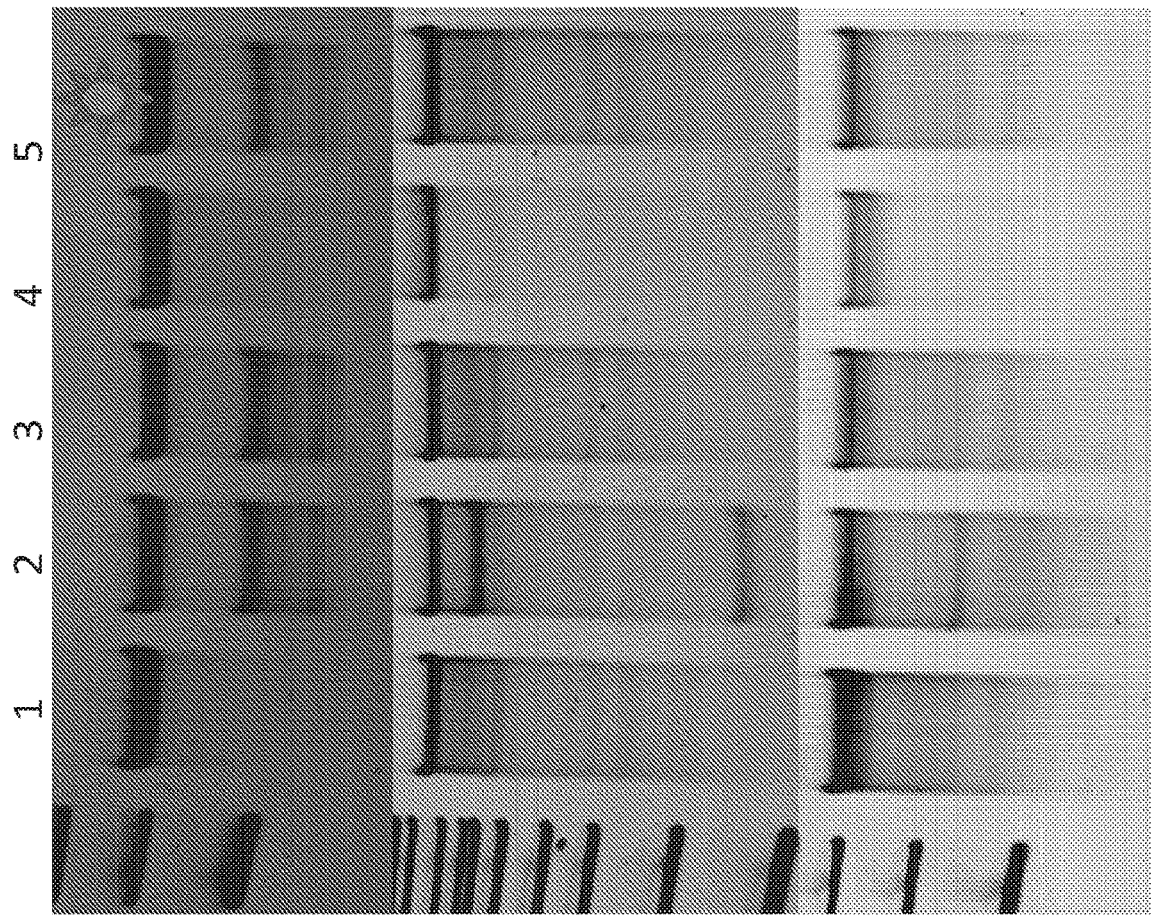
FIG. 24 shows protospacer2, EMX1; Lane 1 shows GFP Control; Lane 2 shows Full gRNA; Lane 3 shows Tru-gRNA; Lane 4 shows 10-bp hp-gRNA; and Lane 5 shows 6-bp hp-gRNA, hairpin1. Conversions—Surv_OT1=DS_OT2; Surv_OT53=DS_OT3.
Figure 25A:
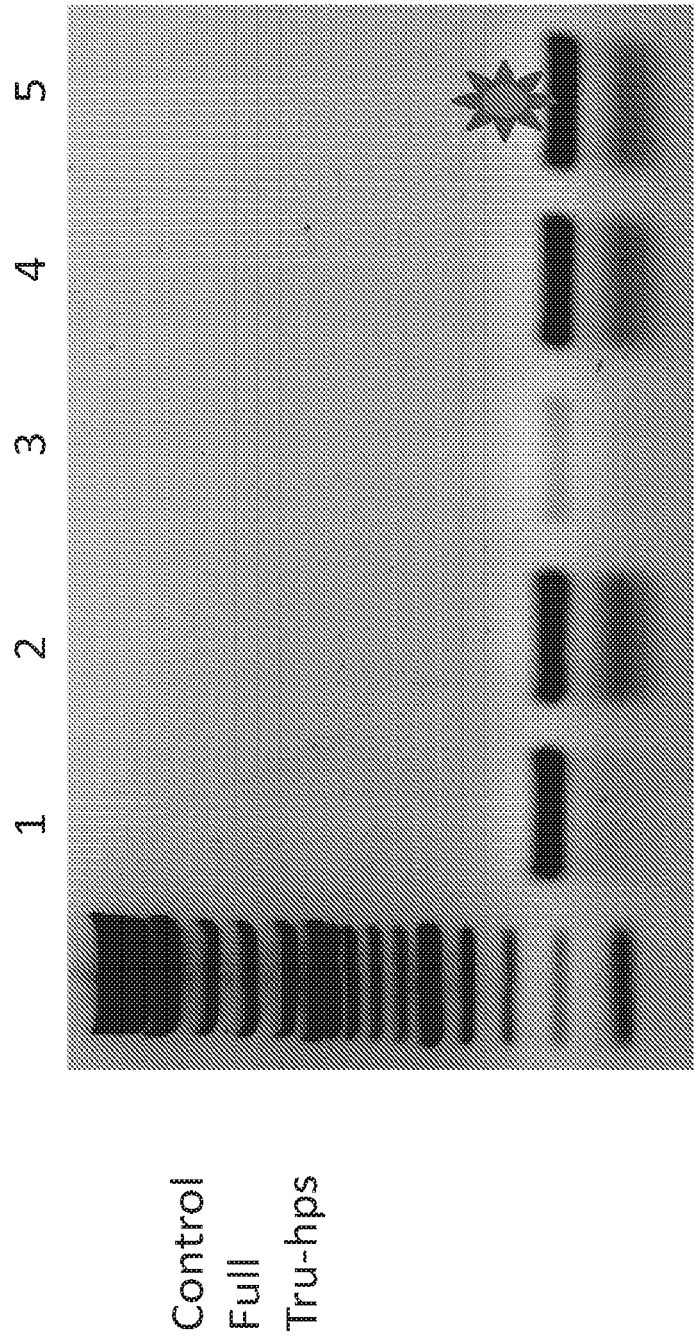
FIGS. 25A and 25B show protospacer2, EMX1, tru-hps, internal loops.
Figure 25B:
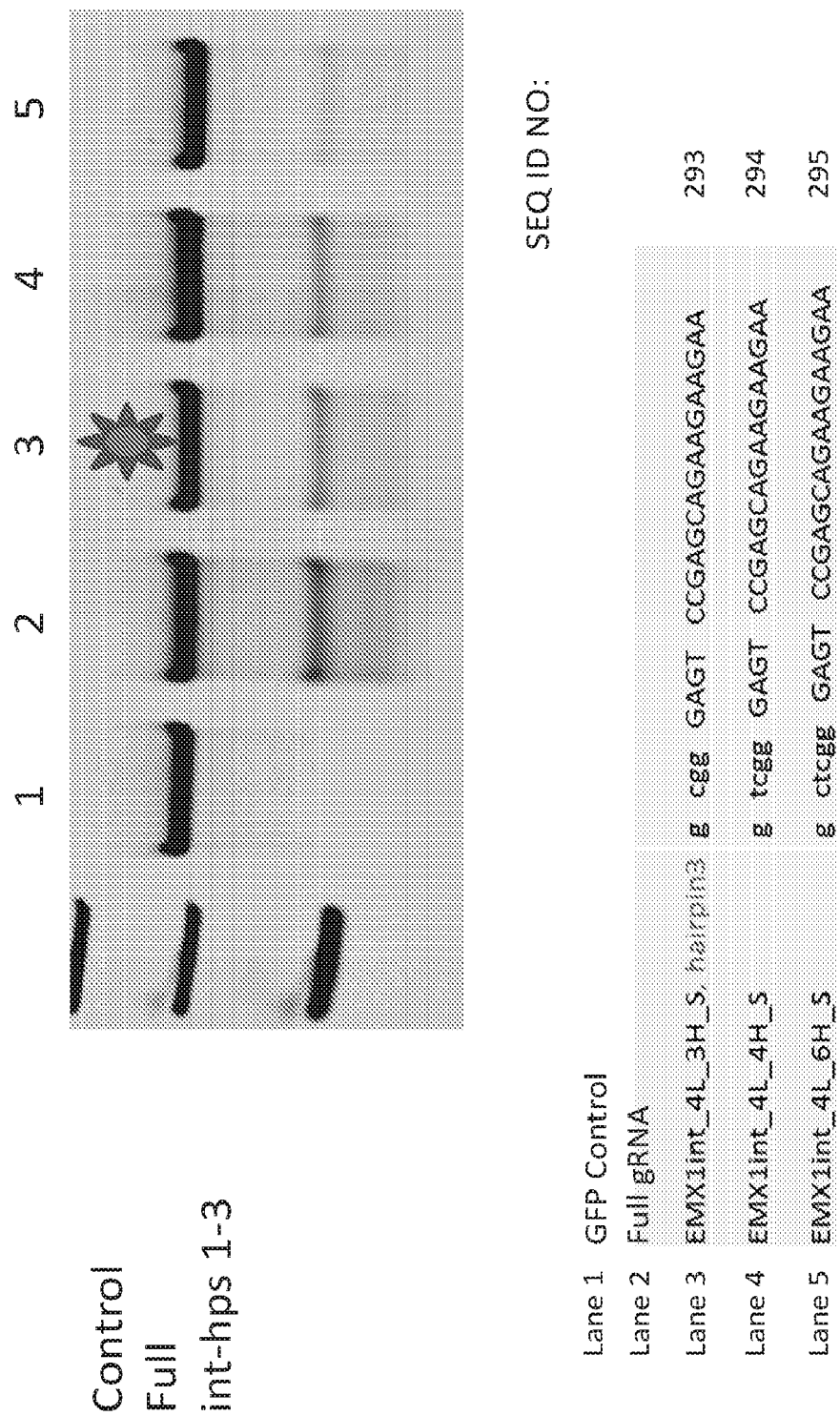
Figure 26B:
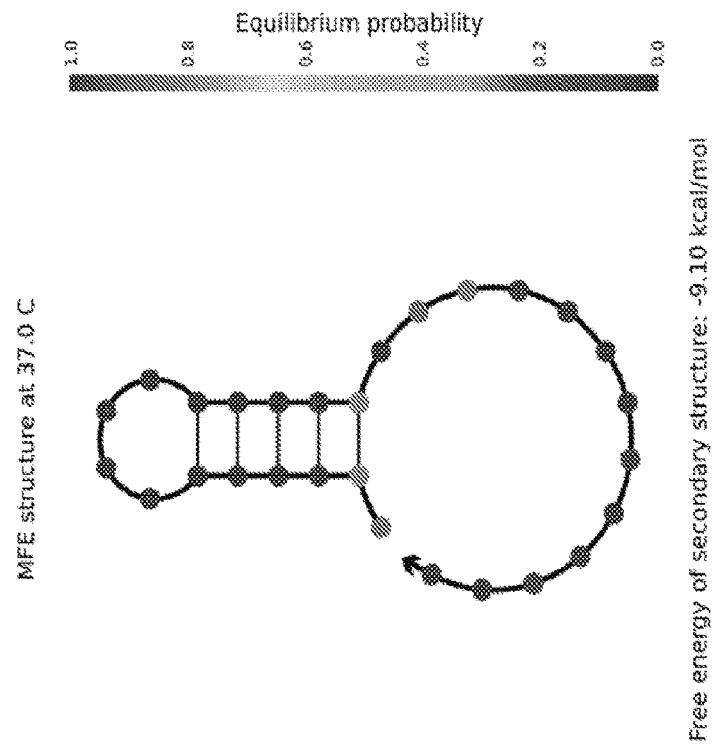
FIGS. 26A-26C show hairpin structures.
Figure 26A:
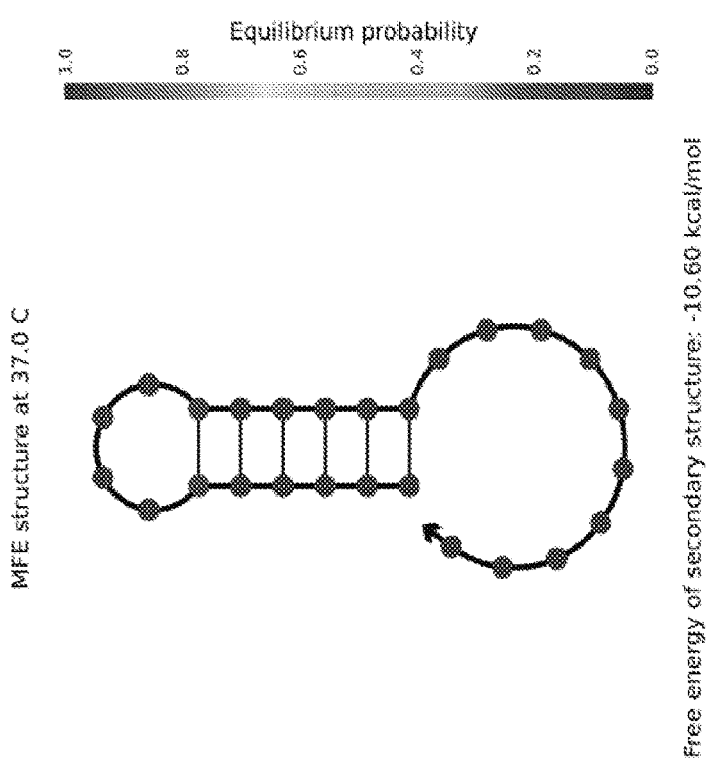
Figure 26C:
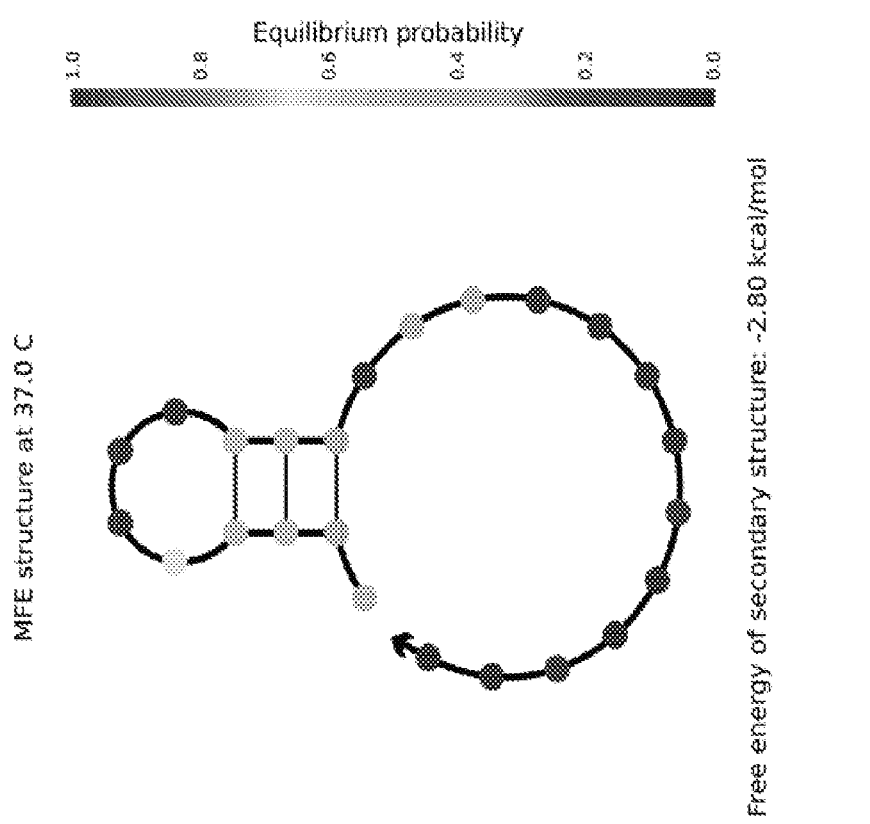
Figure 27:
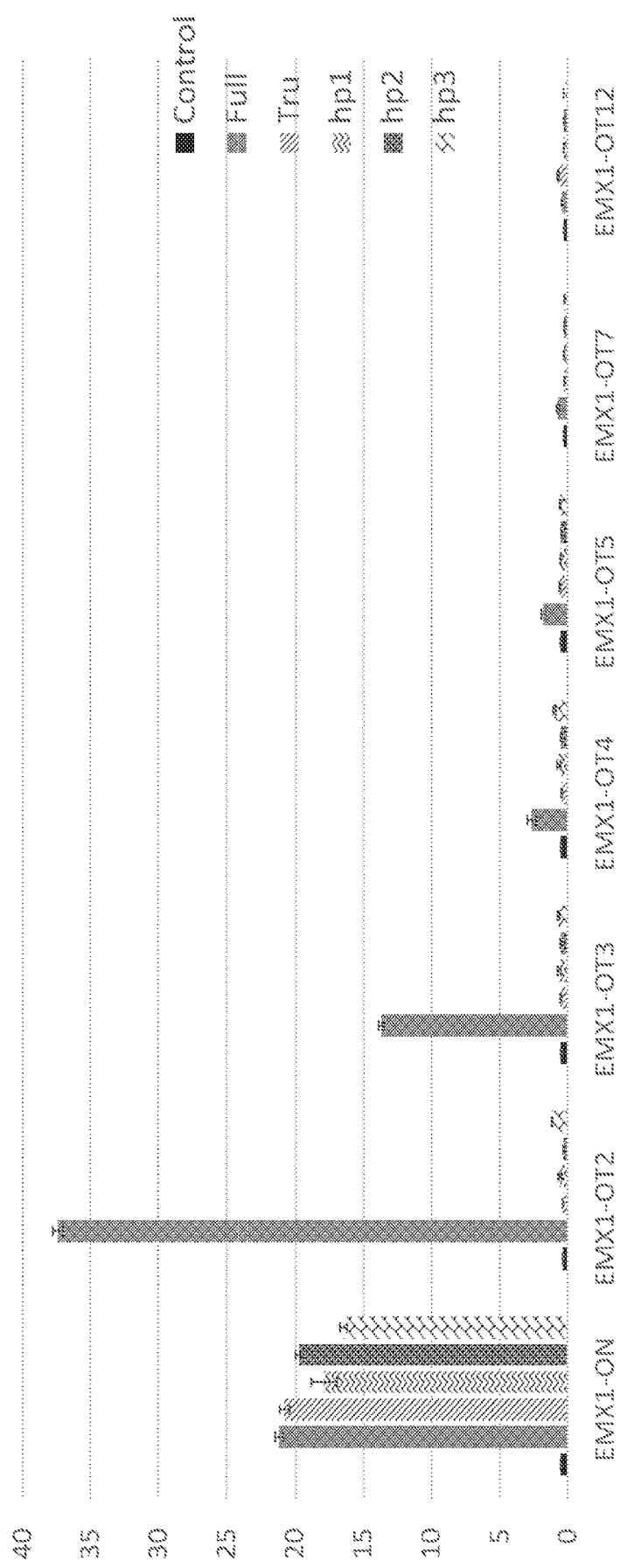
FIG. 27 shows EMX1, Indel rates, all sites.
Figure 28:
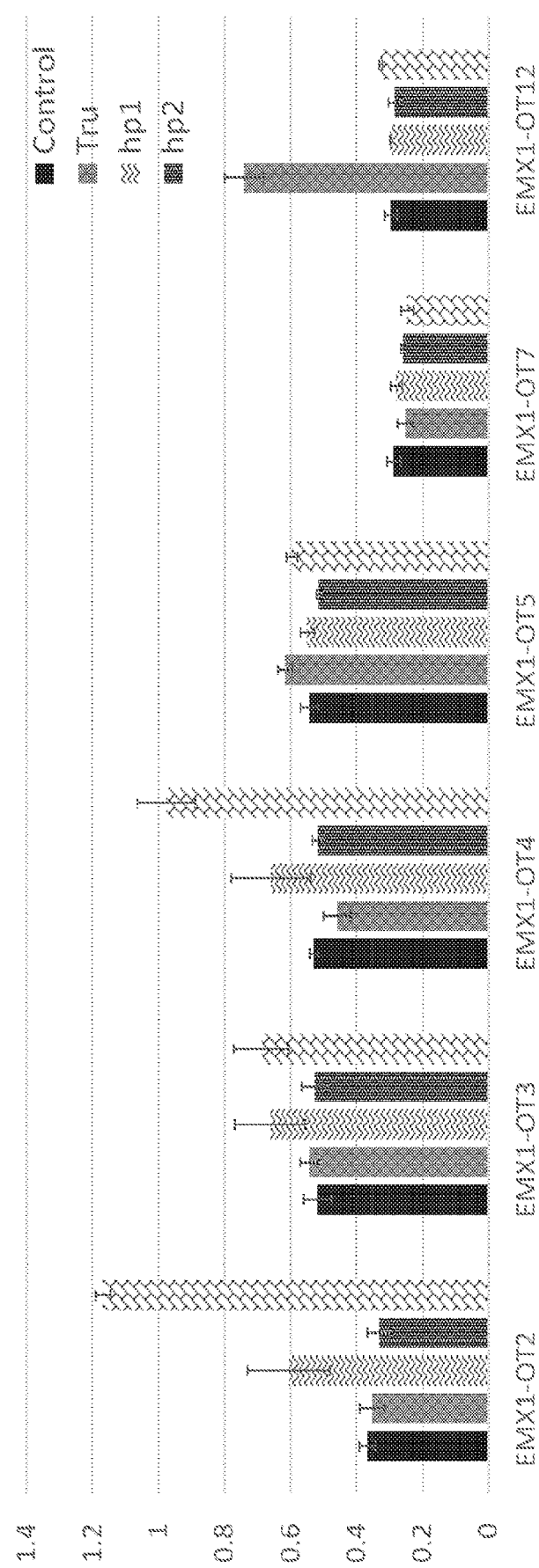
FIG. 28 shows EMX1, indel rates, low-rate offtargets.
Figure 29:
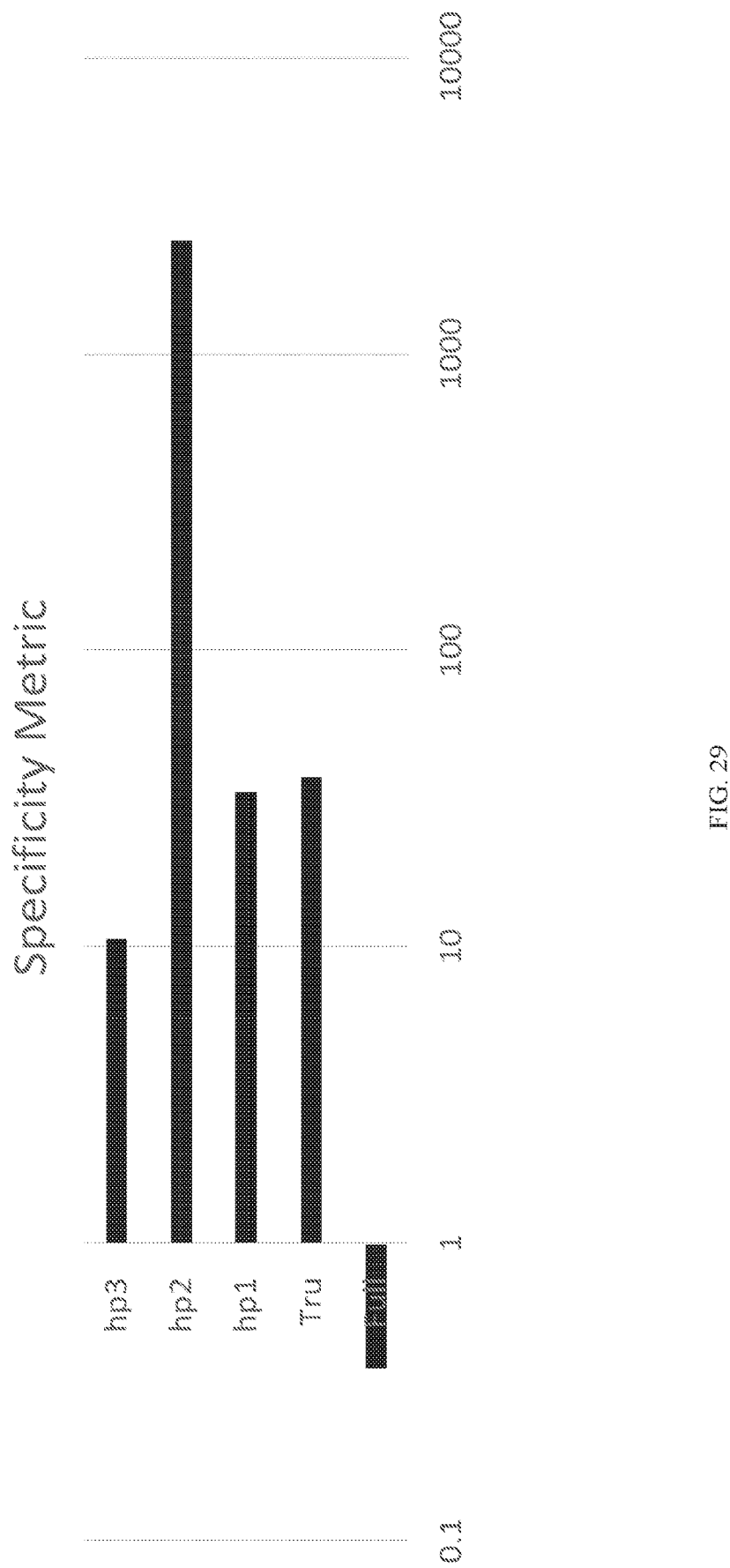
FIG. 29 shows EMX1, ontarget/sum(offtargets).
Figure 30:
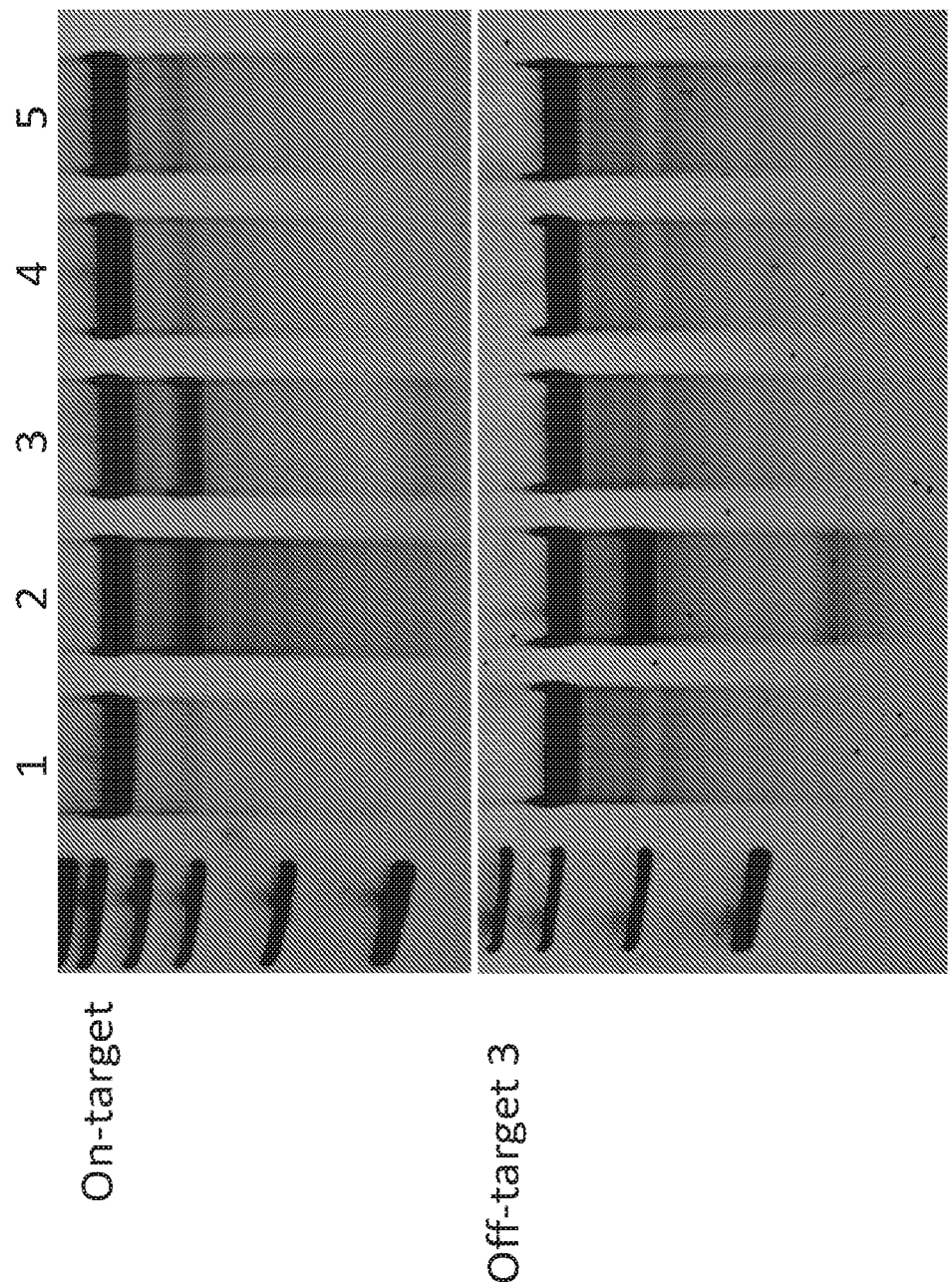
FIG. 30 shows protospacer3, VEGFA1. Lane 1 shows GFP Control; Lane 2 shows Full gRNA; Lane 3 shows Tru-gRNA; Lane 4 shows 10-bp hp-gRNA; and Lane 5 shows 6-bp hp-gRNA.
Figure 31A:
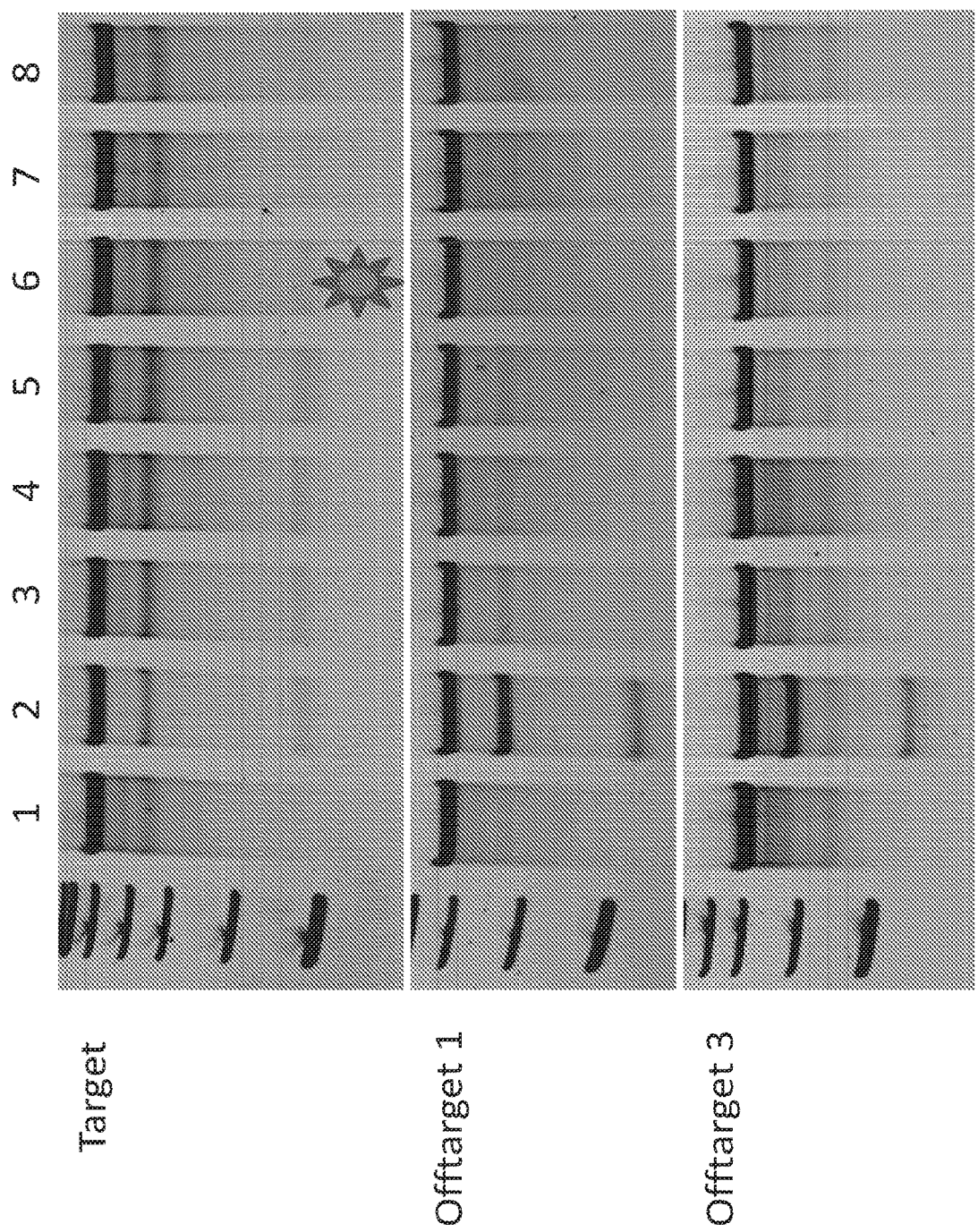
FIG. 31 shows protospacer3, VEGFA1: pam proximal hairpins. Lane 1 shows GFP control; Lane 2 shows Full gRNA; Lane 3 shows hp-gRNA1; Lane 4 shows hp-gRNA2; Lane 5 shows hp-gRNA3; Lane 6 shows hp-gRNA4; Lane 7 shows hp-gRNA5; and Lane 8 shows hp-gRNA6.
Figure 32:
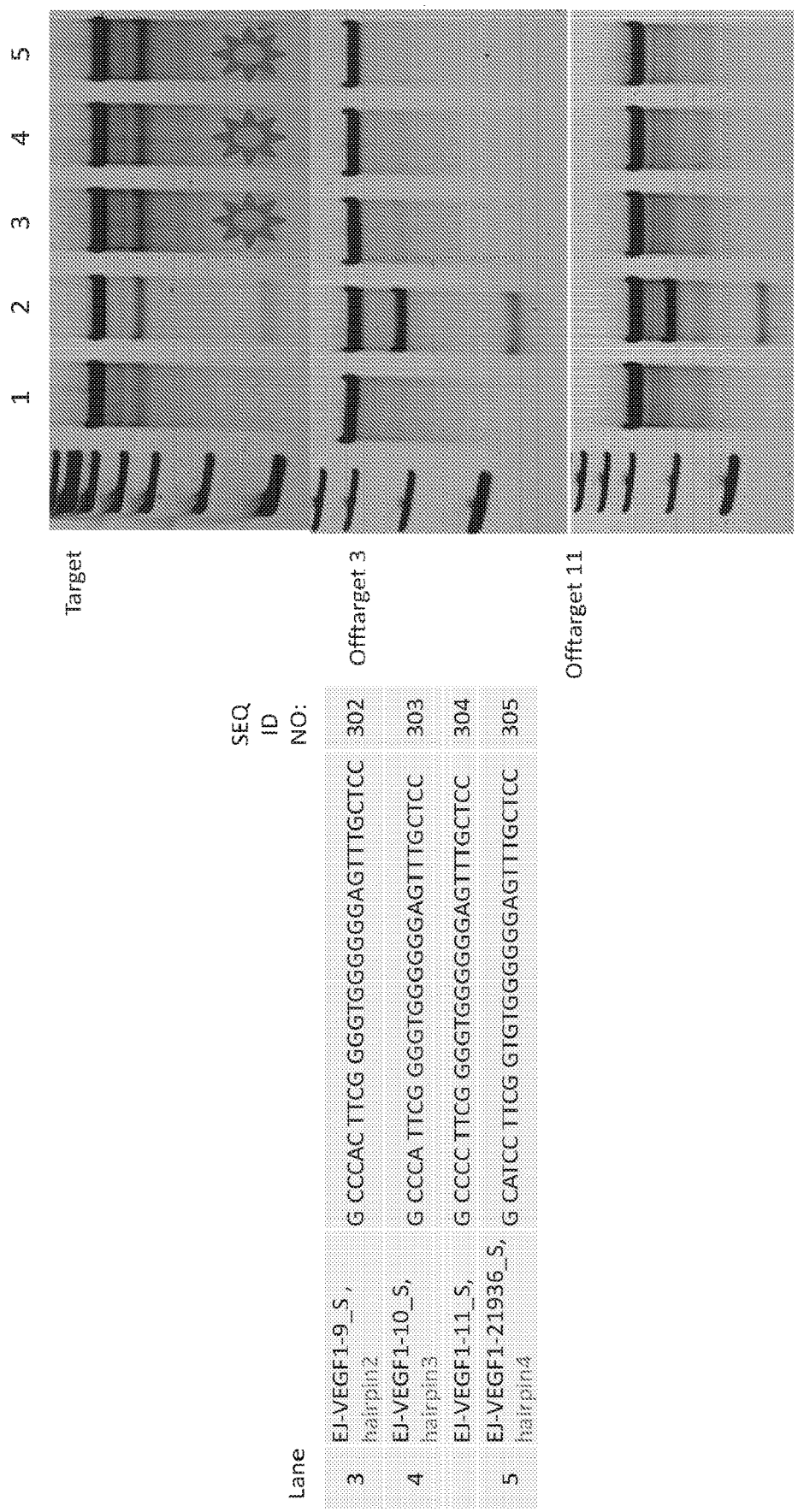
FIG. 32 shows protospacer3, VEGFA1: pam proximal hairpins.
Figure 33:
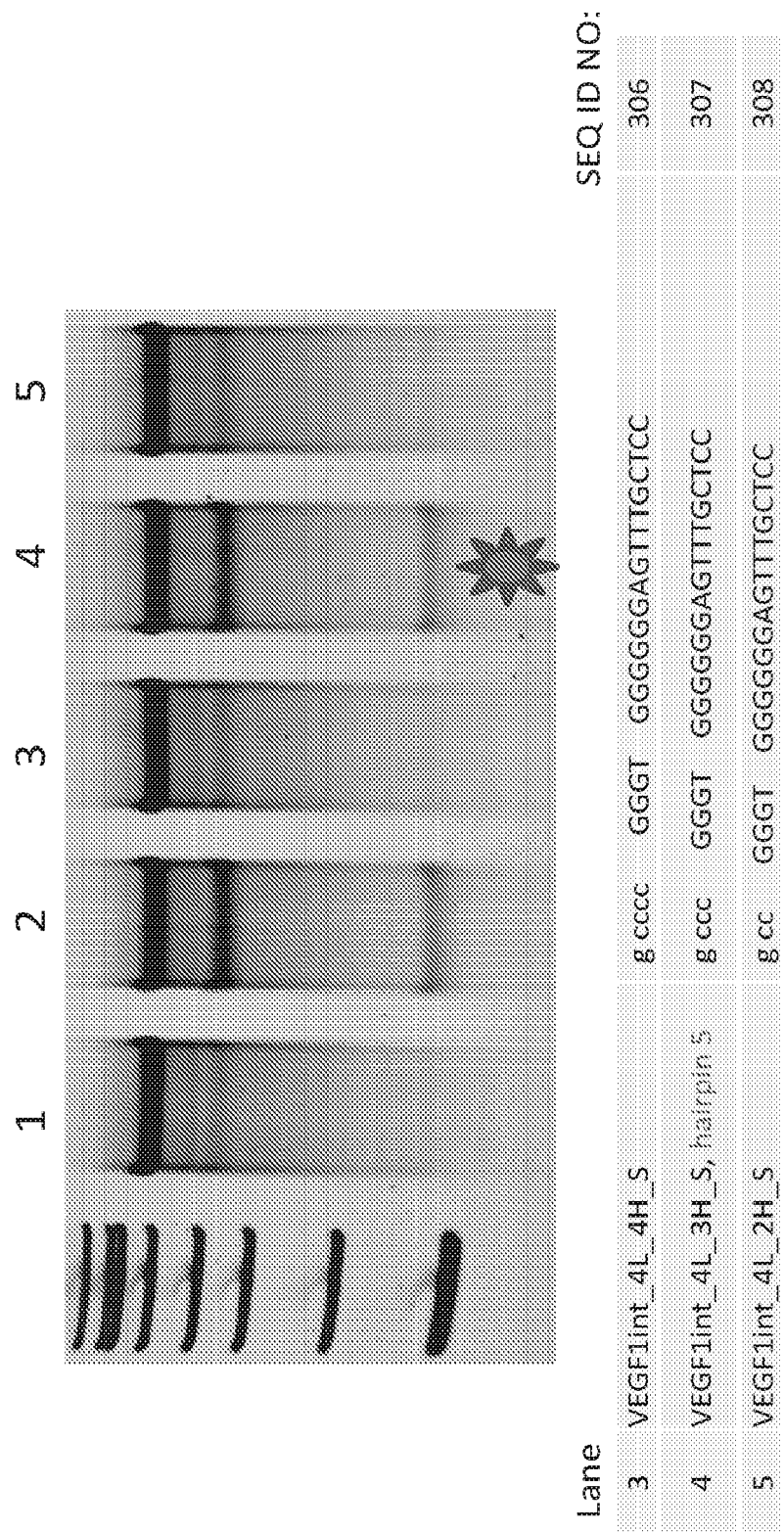
FIG. 33 shows protospacer3, VEGF1, internal loops. Lane 1 shows Control; lane 2 shows Full; lane 3 shows 2 nt hp; lane 4 shows 3 nt hp, hairpin 5; and lane 5 shows 4 nt hp.
Figure 34B:
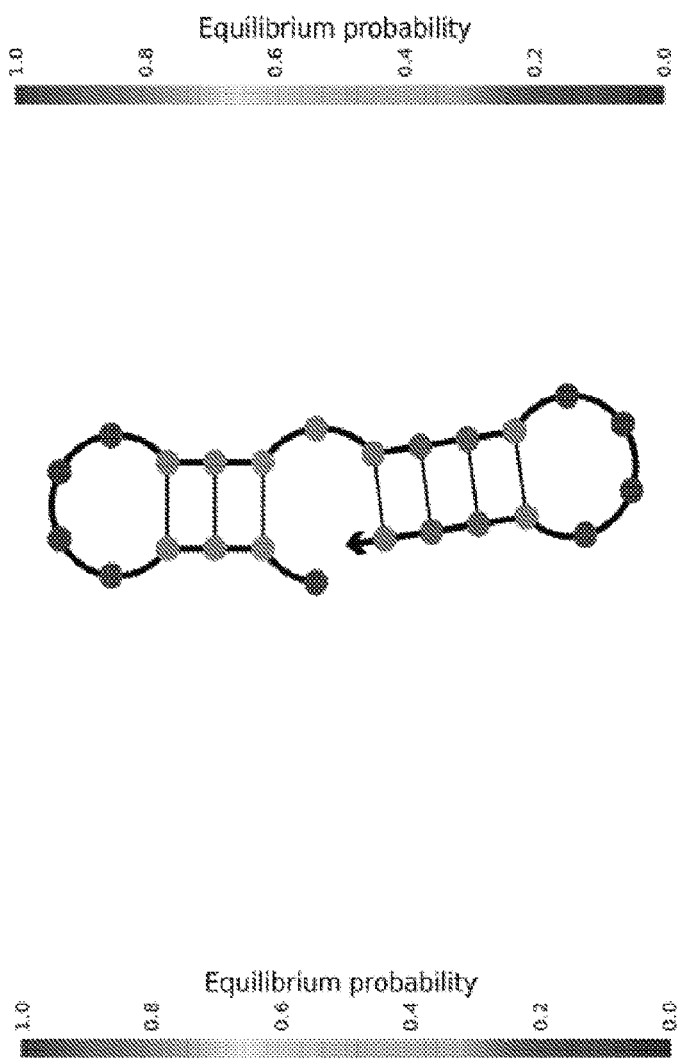
FIGS. 34A and 34B show Deep-seq Experiments for hairpins 1, 2, and 3 failed.
Figure 34A:
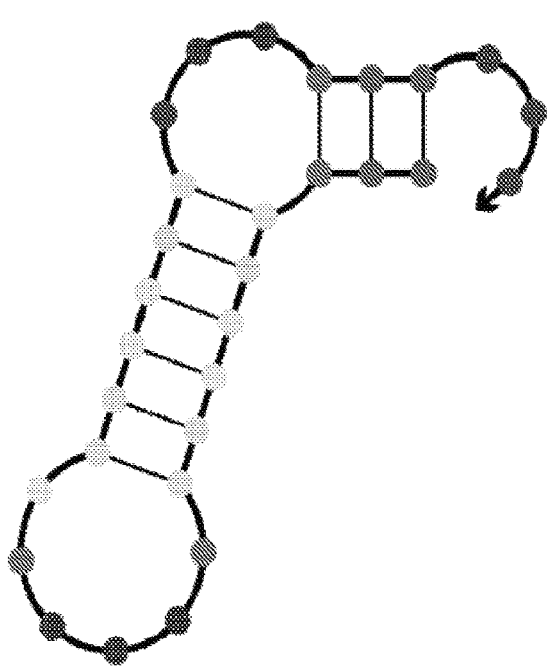
Figure 35:
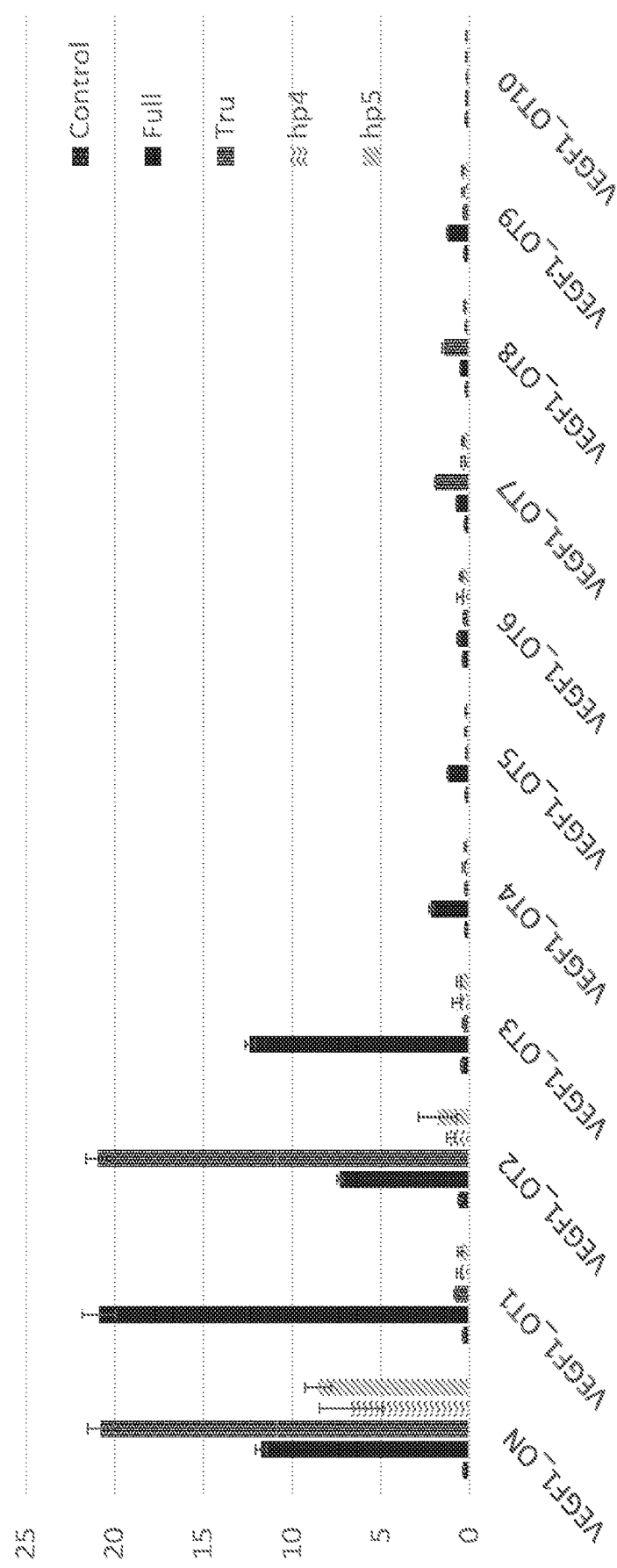
FIG. 35 shows VEGF1, indel rates, all sites.
Figure 36:
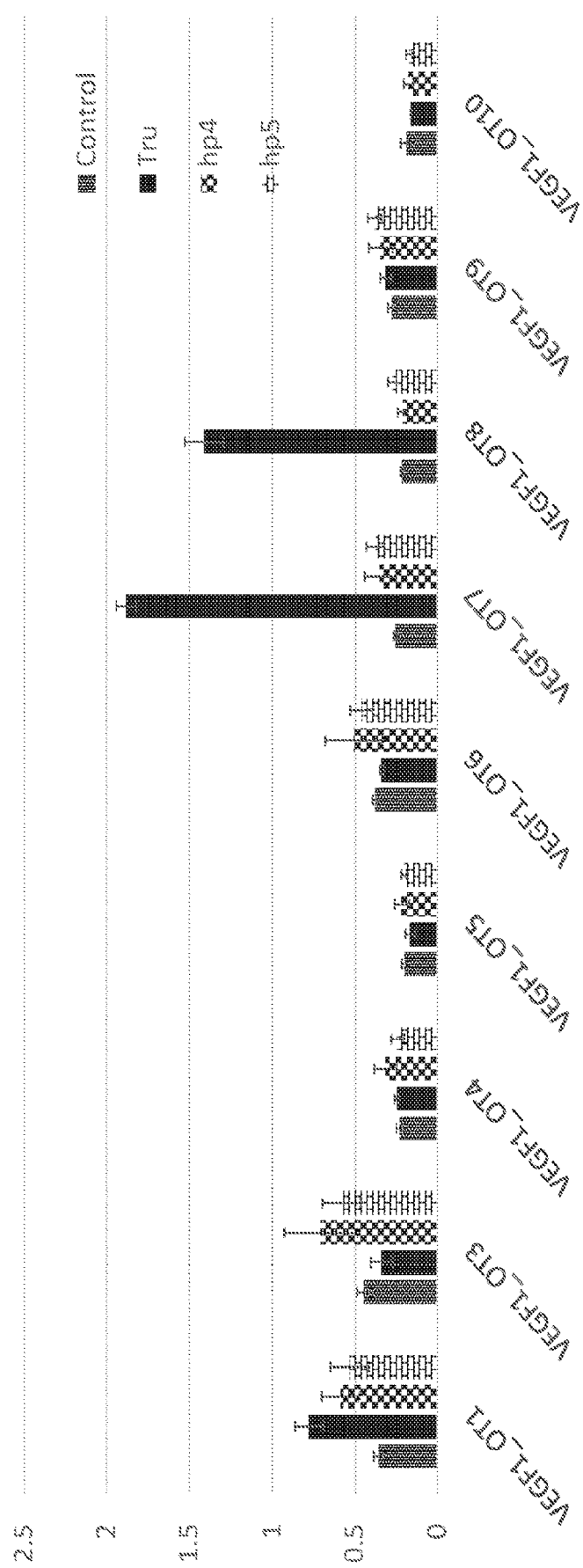
FIG. 36 shows VEGF1, indel rates, low-rate offtargets.
Figure 37:
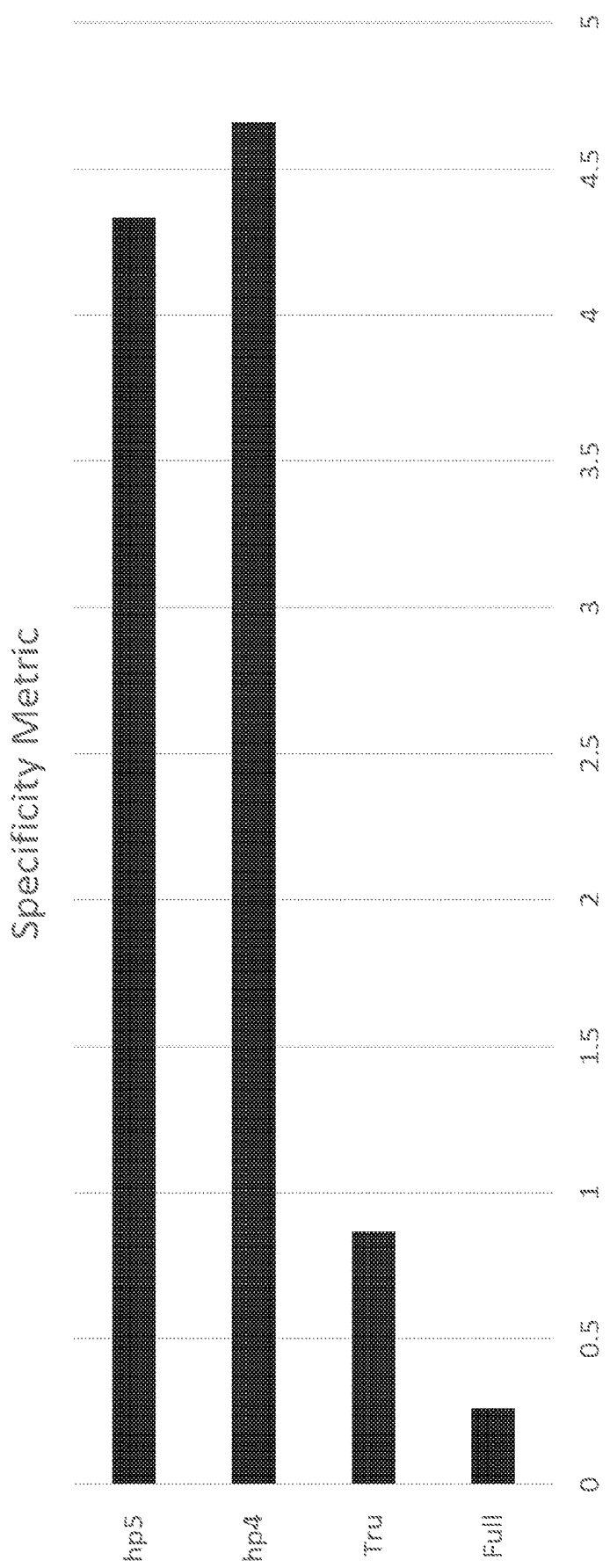
FIG. 37 shows VEGF1, ontarget/sum(offtargets).
Figure 38:
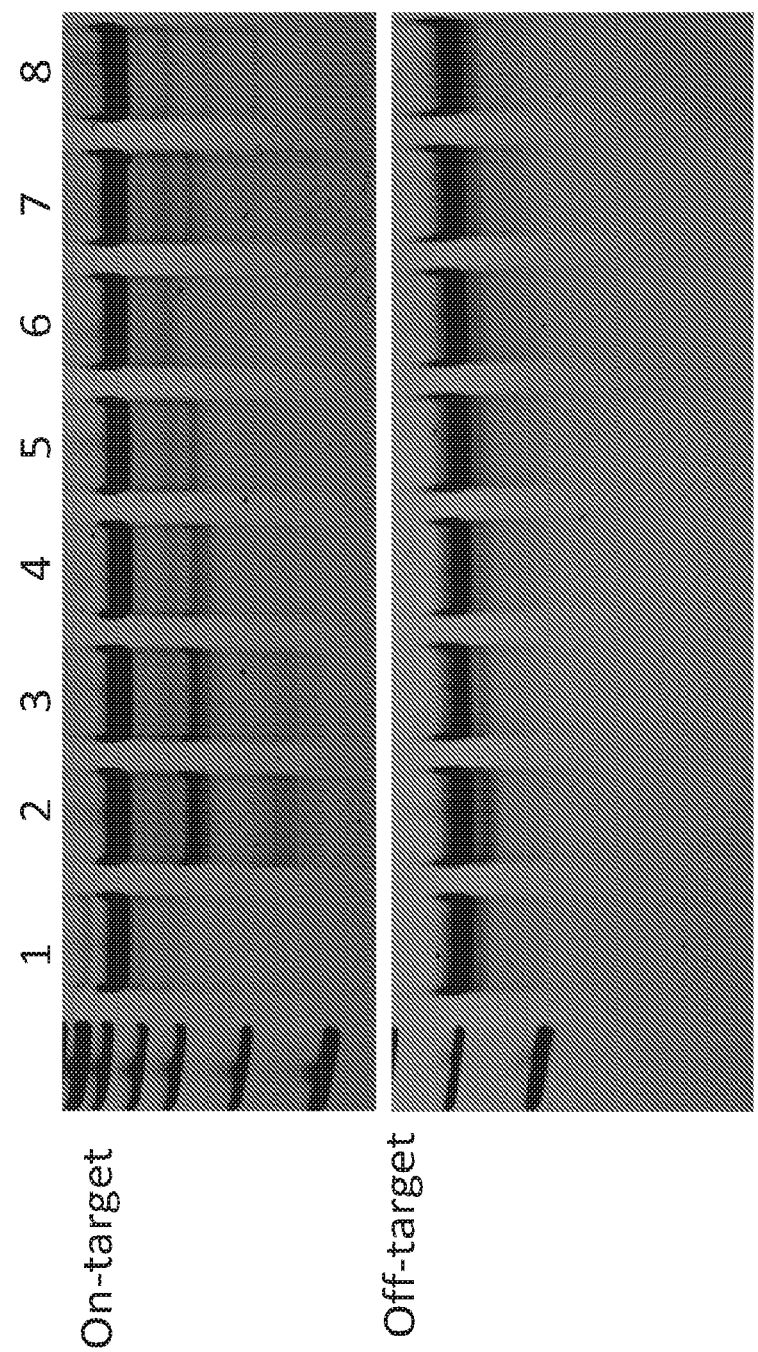
FIG. 38 shows protospacer 4, VEGFA3. Lane 1 shows GFP Control; Lane 2 shows Full gRNA, Lane 3 shows Tru-gRNA; Lane 4 shows 3-bp hp-gRNA; Lane 5 shows 4-bp hp-gRNA; Lane 6 shows 5-bp hp-gRNA; Lane 7 shows 6-bp hp-gRNA; and Lane 8 shows 10-bp hp-gRNA.
Figure 39A:
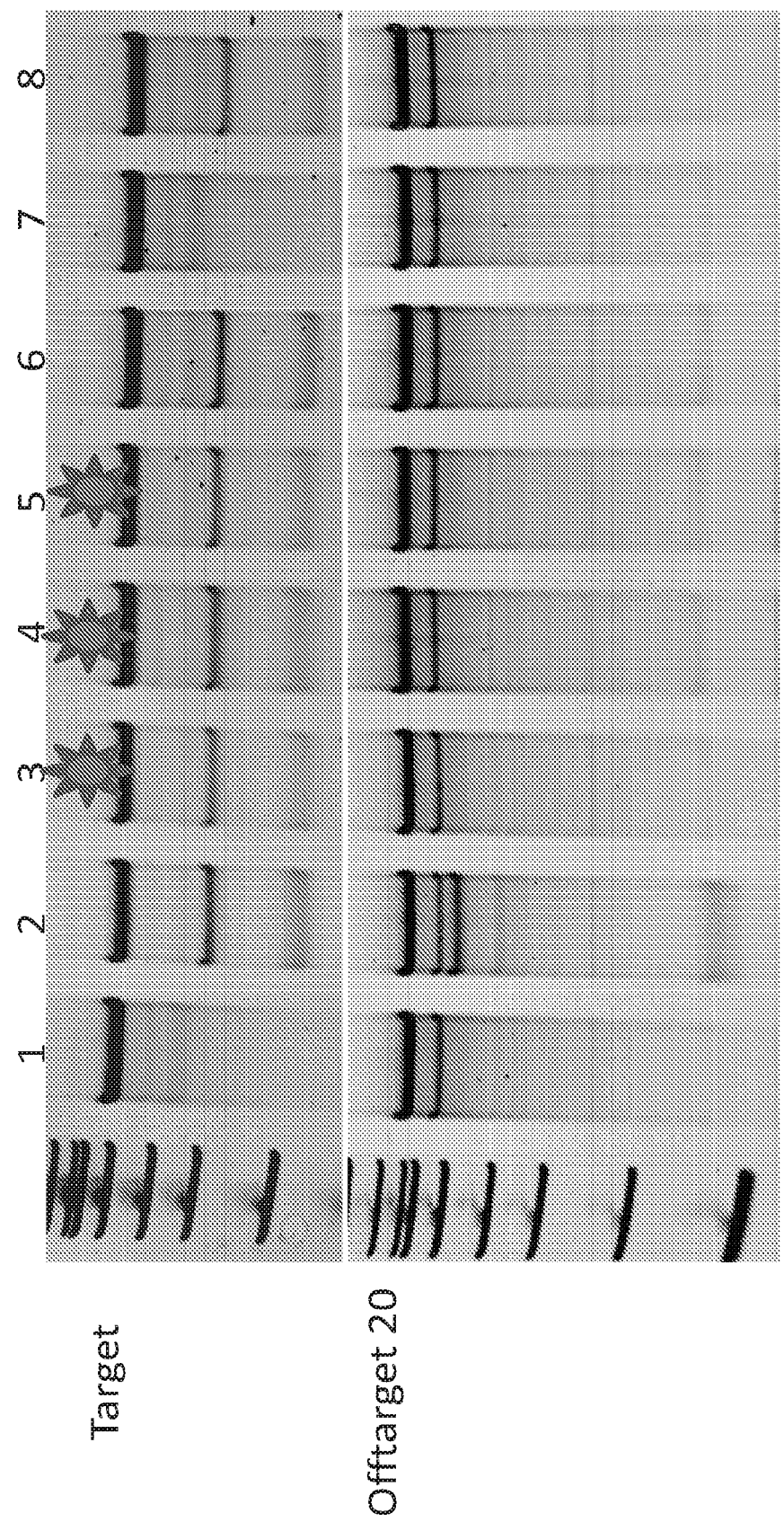
FIG. 39 shows gRNA4, VEGFA3: pam proximal hairpins. Lane 1 shows GFP control; Lane 2 shows Full gRNA; Lane 3 shows hp-gRNA1; Lane 4 shows hp-gRNA2; Lane 5 shows hp-gRNA3; Lane 6 shows hp-gRNA4; Lane 7 shows hp-gRNA5; and Lane 8 shows hp-gRNA6.
Figure 40B:
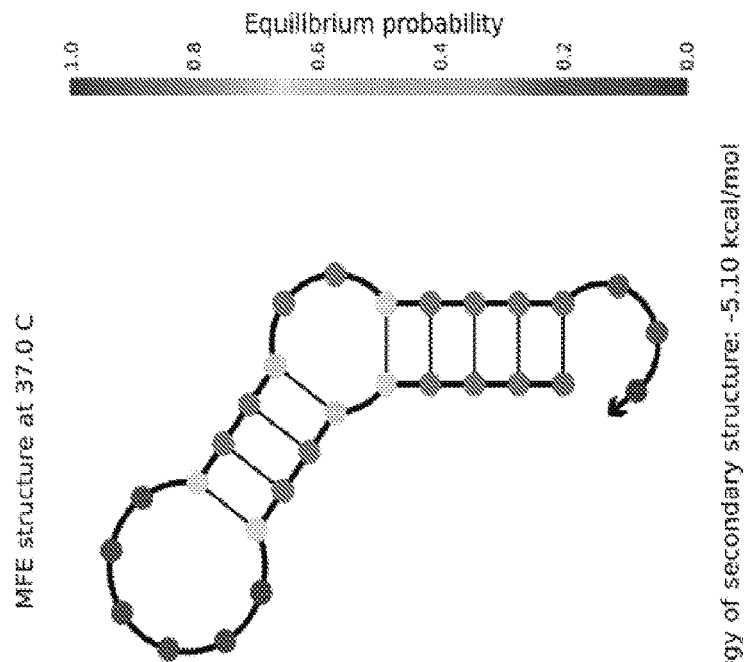
FIG. 40B shows Hairpin 2-4 bp hairpin targeting 3'-region with G-U wobble pairs.
Figure 40A:
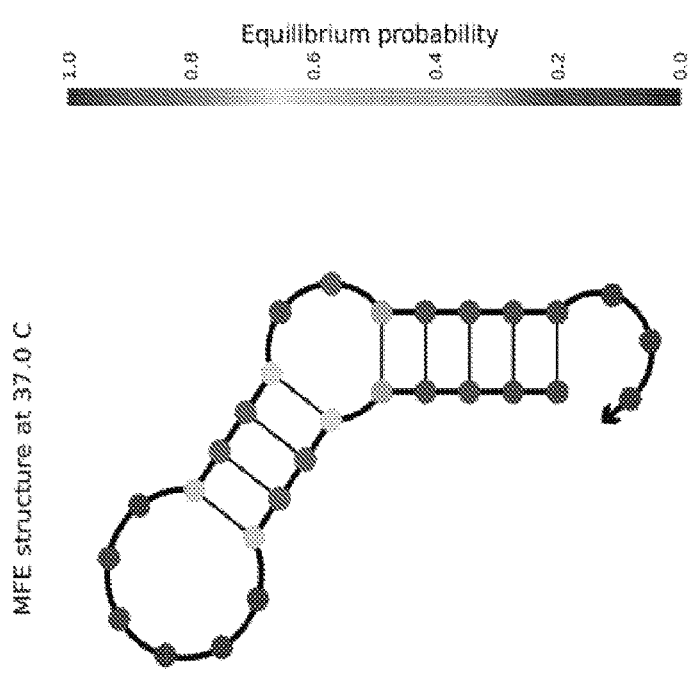
FIG. 40A shows Hairpin 1-4 bp hairpin targeting 3'-region.
Figure 40C:
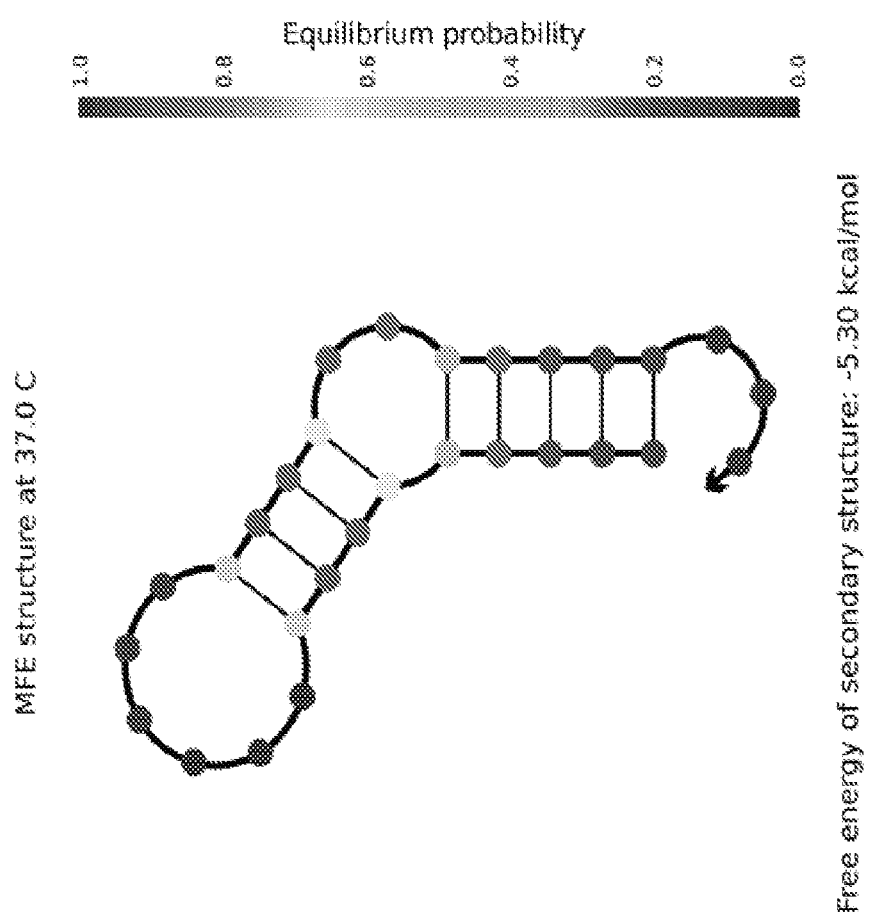
FIG. 40 shows Hairpin 3-4 bp hairpin targeting 3'-region with G-U wobble pair (variant design).
Figure 41:
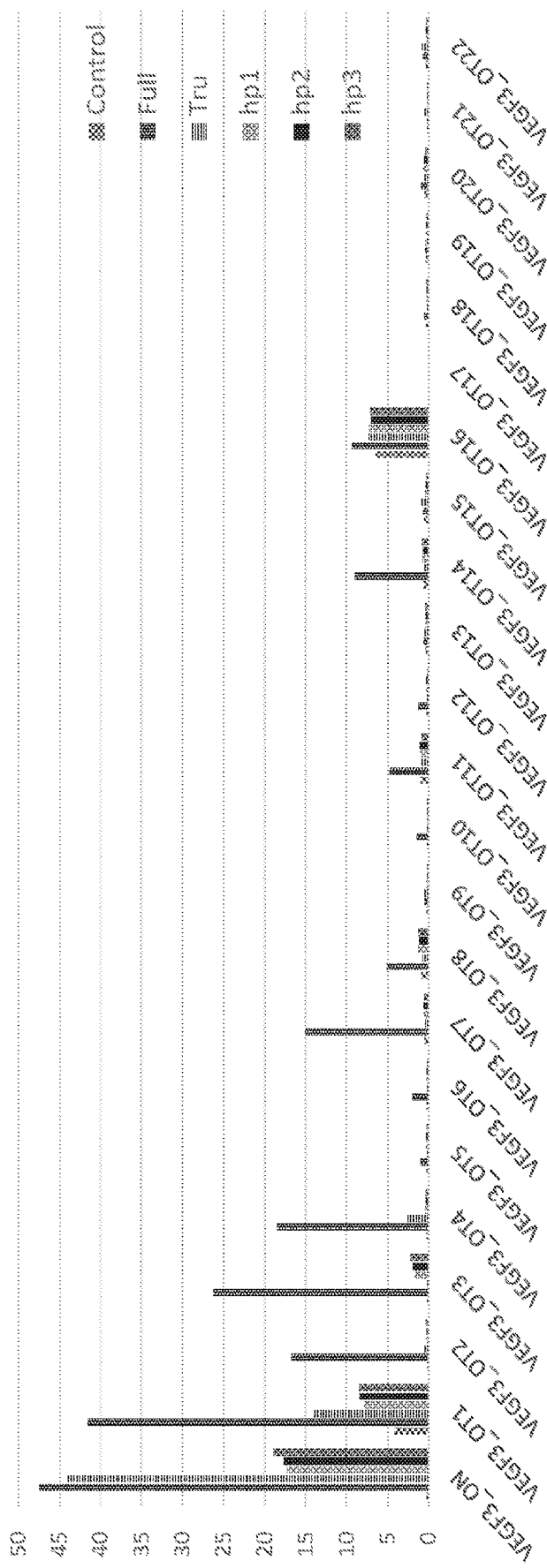
FIG. 41 shows VEGF3, indel rates, all sites.
Figure 42:
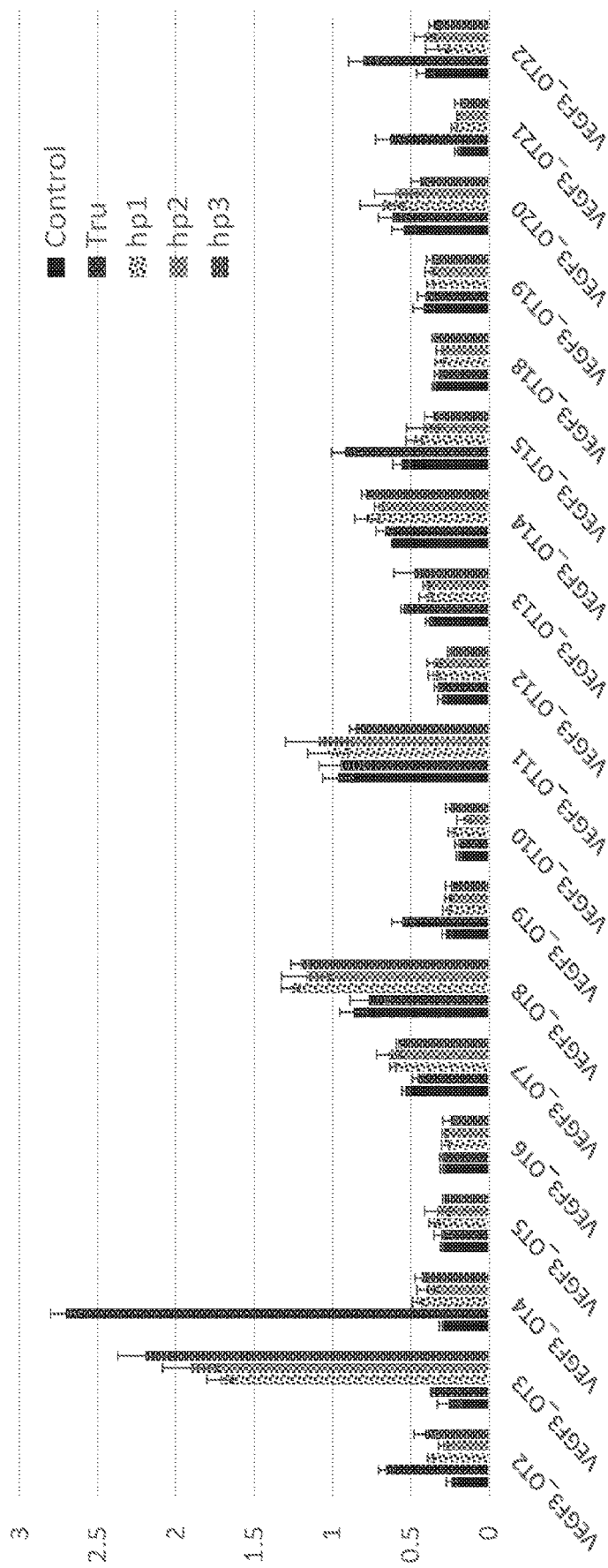
FIG. 42 shows VEGF3, indel rates, low-rate offtargets.
Figure 43:
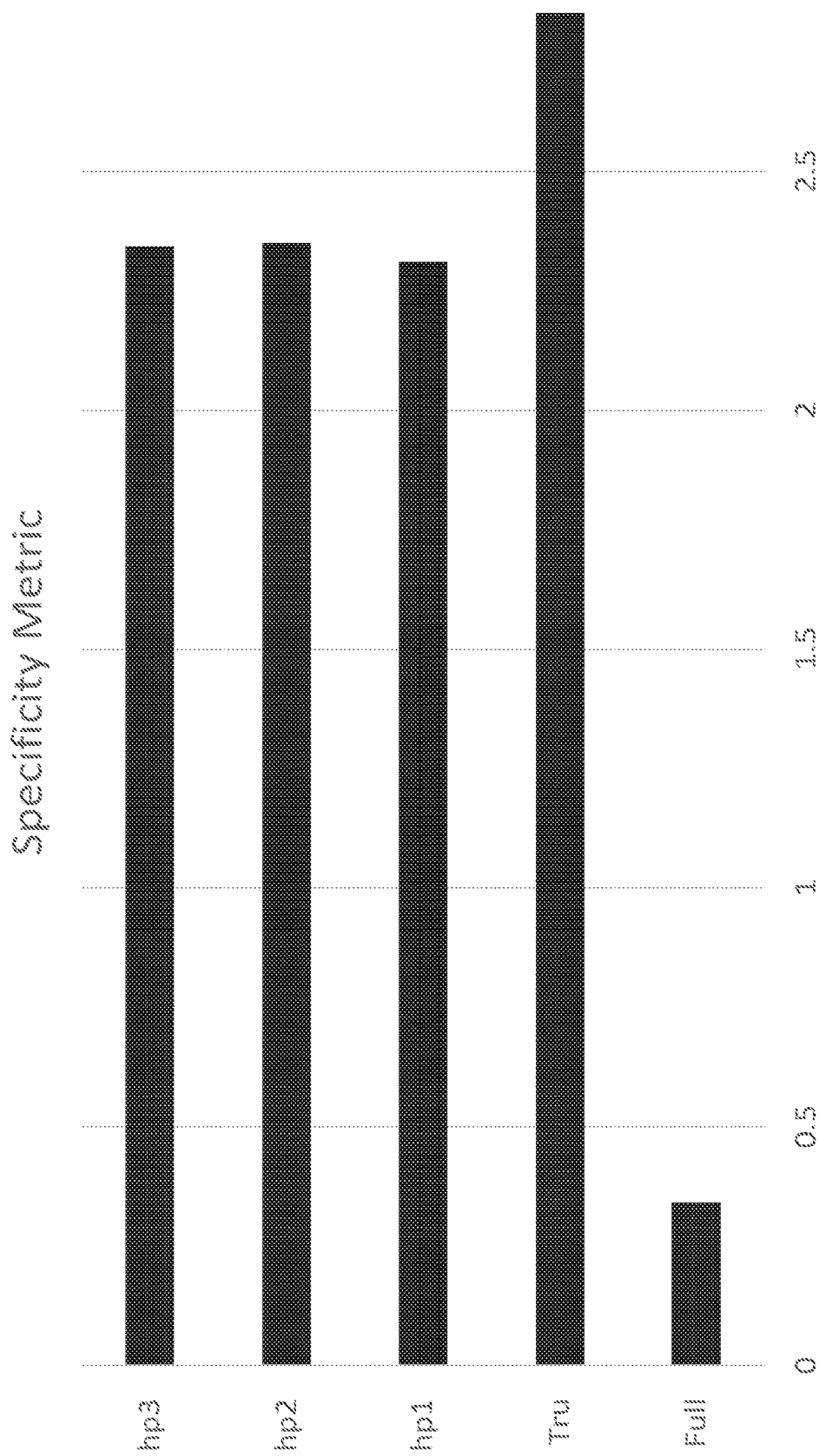
FIG. 43 shows VEGF3, ontarget/sum(offtargets).

Optimized gRNA activity was tested in living cells to investigate dCas9 binding specificity. Several hairpin gRNAs (hp-gRNAs) were designed for each of four target locations (protospacers) in the human genome (FIGS. 17 and 18). One was in the Dystrophin gene (FIGS. 19-23), another was in EMX1 gene (FIGS. 24-29 and 44), and two targets were in the VEGFA gene, labeled VEGFA1 (FIGS. 30-37) and VEGFA3 (FIGS. 38-43). All experiments were done in HEK293T cells.

Additional nucleotides (nt) were added to the 5'-end of full guide RNA (gRNAs, full length 20 nt) and designed to form Hairpins and secondary structures by hybridizing with the 5'-protospacer-targeting nucleotides, or nucleotides in the middle or the 3'-end of the protospacer-targeting region, in order to modulate binding and cleavage activity of Cas9 to protospacers.

Figure 44C:
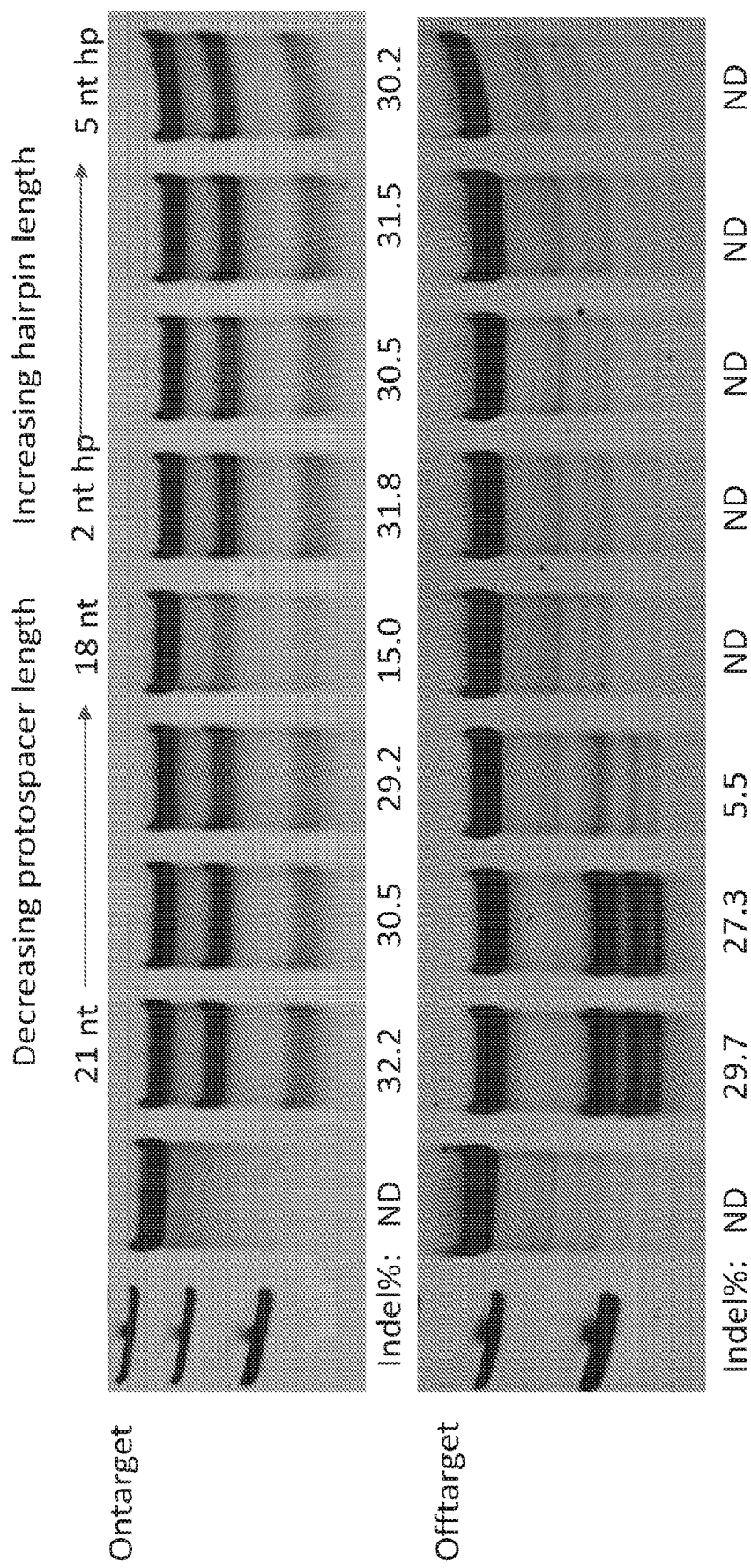
FIG. 44C shows the effect of decreasing protospacer length and increasing hairpin length on specificity.

One secondary structure of a VEGFA1-targeting hp-gRNA was computationally designed using the methods described herein to prevent binding at a known off-target site while allowing binding to the full protospacer (FIG. 44A-44C). The hp-gRNA was selected to have a binding lifetime greater than or equal to that of the full gRNA at the on-target site, and a binding lifetime less than or equal to that of the full-length gRNA at the top 3 off-target sites. Other 5'-structures were designed to include dG-rU wobble pairs to modulate the energetics of the secondary structures of the hp-gRNAs, or added to the end of truncated gRNAs (tru-gRNAs, <20 nt) which themselves have been shown to promote higher specificity of Cas9 activity.

Cell Work.

For the deep sequencing analysis, 293T cells were transfected with plasmids that expressed Cas9 and a gRNA of interest. The cells were incubated for 4 days, allowing for Cas9 and the gRNA to exert their maximum activity. The cells were then harvested and their genomic DNA was purified. gRNAs that were very well-characterized in the literature (i.e., their ontarget and off-target sites were known) were used.

Surveyor Assay.

Compared to Deep-Sequencing, the surveyor assay is lower in throughput and less sensitive. However the surveyor assay is faster and less technical in data analysis, providing gel images. Thus surveyors were done as a first pass, and the best conditions were analyzed in triplicated with Deep-sequencing. Both DeepSequencing and Surveyor are methods to quantify mutational events caused by Cas9+ gRNA.

The cell work for Surveyor was the same as described above. After genomic DNA was purified, primers were designed to amplify the targeted site. A pool of 200 k cells was used in this experiment and each one of them had a different mutation since DNA repair is stochastic. The site across 200 k cells was amplified to generate a heterogenous PCR product: some amplicons had deletions, some had insertions, and some were wild-type and unmodified, due to each cell stochastically (i.e. randomly, error prone) repairing Cas9 cut sites.

Figure 46:
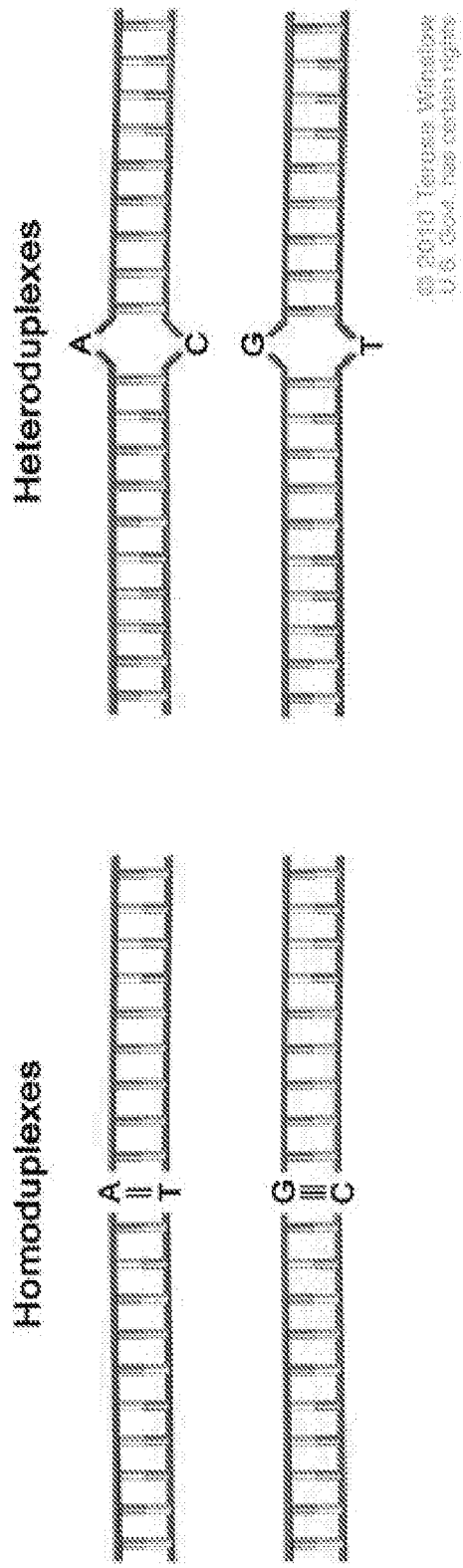
FIG. 46 shows a figure that describes the Surveyor assays.

The heterogenous-PCR pool was heated and repaired, and in some cases different strands annealed to each other: a wild-type DNA strand might bind to DNA with an insertion, or an insertion might bind to a deletion. When this happens a little "bubble" formed and this structure is called a DNA heteroduplex (see FIG. 46).

The surveyor nuclease was used to detect these heteroduplexes by digesting and cleaving them. DNA cleavage was then a proxy for Cas9's mutational activity. The PCR pool was separated on a gel and the intensity of these digested bands was used to quantify the rate of Cas9 activity.

Deep Sequencing.

Primers were designed to amplify these known targets/offtargets. A high-fidelity polymerase was used in this PCR. Illumina adapters were also present on these primers such that they could be barcoded and loaded onto the Illumina Mi-Seq platform. The # of hairpins, # of targets, # of offtargets, sequencing coverage, etc. are described in the figures and brief description of drawings. Good coverage was obtained across samples used in the analysis. The average number of reads/sample was 20,000. The sample with fewest # of reads was 1,700. A very small number of targets did not generate enough aligned reads and were not included in the analysis The resulting sequencing data was analyzed using the CRISPResso software (Pinello et al. *Nat Biotechnol.* (2016) 34(7):695-697)), which aligns deep-sequencing reads with specific sites of known off-target or on-target locations. This software's results was compared with in-house scripts, in which global alignment of the Deep-sequencing reads with the human genome was performed, and correlated very well.

Mutational rates were quantified using CRISPResso and the resulting data was displayed in the displayed histograms for each target gene.

Designs were first tested using Surveyor assays to test for indels after Cas9 and hp-gRNA expression in HEK cells at the target site and off-target sites known to be targeted using the standard gRNAs (see Table 6). Activity at these sites compared to the standard gRNA and truncated gRNAs (tru-gRNAs). These are shown below as gels showing cleavage by Surveyor nuclease of PCR'ed genomic DNA, where cleavage indicates mutagenesis by Cas9.

TABLE 6

| Protospacers | Genomic Targets |
| --- | --- |
| Dystrophin | 1 on-target, 1 off- on-target |
| EMX1 | 1 on-target, 7 off-target |
| VEGFA1 | 1 on-target, 10 off-target |
| VEGFA3 | 1 on-target, 22 off-target |

The most promising hp-gRNA designs were chosen for additional quantitative analysis using next-gen sequencing to evaluate Cas9 activity at on- and off-target sites in HEK cells. Specificity was defined as on-target hits/sum(off-target hits).

While Cas9 activity was generally equal to or slightly decreased when using hp-gRNAs, each hp-gRNAs selected for Deep-Seq experiments showed enhanced specificity over full gRNAs, and in most cases were equal to or greater than tru-gRNAs in terms of specificity.

In one case, a hp-gRNA hairpin targeting EMX1 exhibited >6000-fold improvement in specificity over full gRNA (vs. tru-gRNA with 100-fold improvement over gRNA). The VEGFA1-targeting hp-gRNA with a computationally-designed secondary structure using an in-house algorithm greatly outperformed the tru-gRNA activity in terms of specificity (18-fold vs. 3-fold improvement over gRNA). These hp-gRNAs were tested in conjunction with *S. pyogenes* Cas9. FIG. 44A-44C shows Surveyor assays of EMX1-targeting hp-gRNAs with Cas9 from S. aureus exhibiting on-target activity and no detectable off-target activity, in contrast to tru-gRNAs which show significant off-target activity.

Example 10

Hp-gRNA for CRISPR/Cpf1 System

Figure 47:
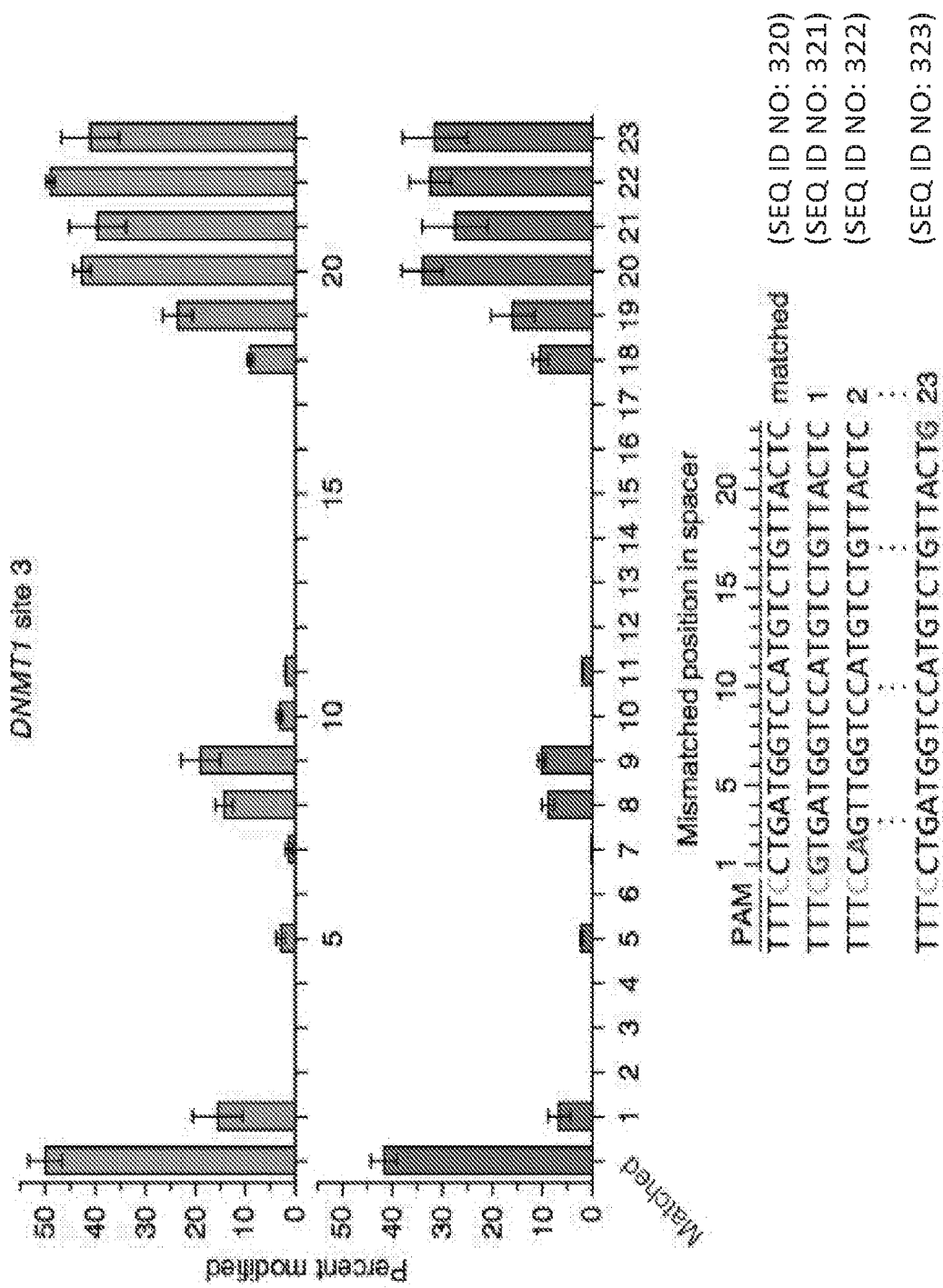
FIG. 47 shows tolerance of AsCpf1 and LbCpf1 to mismatched or truncated crRNAs and endogenous gene modification by AsCpf1 and LbCpf1 using crRNAs that contain singly mismatched bases. Activity determined by T7E1 assay; error bars, s.e.m.; n=3 (taken from Kleinstiver et al., Nat. Biotech. 34:869-875).

Experiments were designed to reproduce the results of Kleinstiver et al., *Nat. Biotech.* (2016) 34:869-874. Kleinstiver et al. used full-length gRNAs to show that Lachnospiraceae Cpf1 is susceptible to cut at off-target sites with mismatches at the 8-9 nucleotides in addition to PAM-distal sites, by using gRNAs which had mismatches with the target site at different locations (FIG. 47). In this example, hairpin guide RNAs used with the Type V CRISPR-Cas system CRISPR-Cpf1 were designed and tested as described above using the methods of the present invention.

To test off-target activity of Cpf1 with and without the additional secondary structure elements, the DNMT1 gene (TTTC CTGATGGGTCCATGTCTGTTACTC (SEQ ID NO: 330)) was targeted for cleavage by Cpf1. "Off-target activity" was tested by using guide RNAs which had a mismatched nucleotide at position 9, e.g. CTGATGGTgCATGTCTGTTA (SEQ ID NO: 331), using full-length guide RNAs 20 nucleotides long or truncated gRNAs 17 nucleotides long CTGATGGTgCATGTCTG (SEQ ID NO: 332). 9 nucleotide long secondary structure elments were added to the 3'-end of the Cpf1 guide RNAs to hybridize with the segment of the guide RNA surrounding the mismatched nucleotide, where in this case the 'linker' element were comprised of the 4 3'-nt of the protospacer-targeting segment, i.e., CTGATGGTgCATGTCT GTTA AGACATGcACCA (SEQ ID NO: 333) and CTGATGGTgCATG TCTG CATGcACCA (SEQ ID NO: 334). A Surveyor assay shows that that inclusion of these additional 3'-elements decreased or abolished the off-target activity at the DNMT1 site exhibited by the full or truncated gRNAs.

hp-gRNAs were designed with an "internal" hairpin design in which the PAM-distal 4 nucleotide served as the loop. The hairpin was added to the 3'-end of the gRNA. Table 7 shows the sequences of the hp-gRNA with a space in the sequences that separates this region. The mismatch is shown in lower case.

Figure 48:
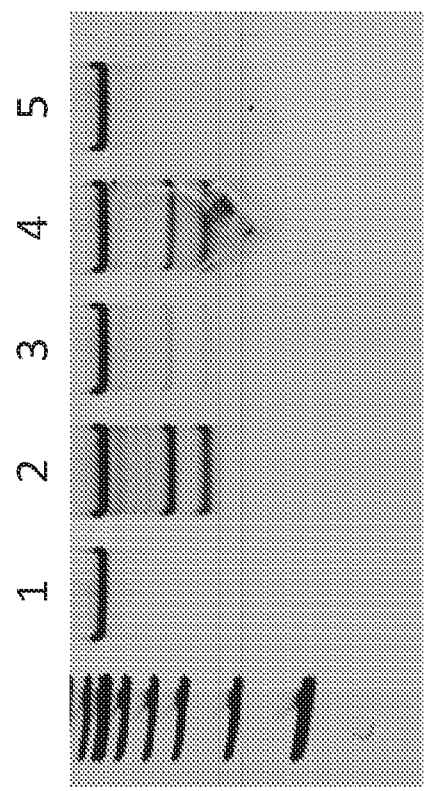
FIG. 48 shows surveyor assay results for hp-gRNAs used with a Type V CRISPR system in which a hairpin is added to the 3' end of a full-length gRNA to abolish off-target activity.

Surveyor results of these hp-gRNAs are shown in FIG. 48 and show that the addition of the hairpin to the 3'-end abolished off-target activity. Lane 1 shows the control; lane 2 shows a full-length gRNA containing a mismatched nucleotide at position 9; lane 3 shows the full-length gRNA containing a mismatched nucleotide at position 9 and an additional 3'-hairpin structure; lane 4 shows a truncated gRNA containing a mismatched nucleotide at position 9; and lane 5 shows the truncated gRNA containing a mismatched nucleotide at position 9 and an additional 3'-hairpin structure. The Surveyor primers used are also shown in Table 7.

Cpf1 tolerates mismatches at nucleotides 8-10 when using normal guide RNAs and cleaves DNA at those off-target sites (FIG. 47). As shown in FIG. 48, the Cpf1 hp-gRNA were able to abolish the off-target activity shown in the Kleinstiver, while the truncated gRNAs could not.

TABLE 7

Surveyor primers

| Label | Sequence | Expected product size |
| --- | --- | --- |
| CN391 DNMT1 (forward) | CTGGGACTCAGGCGGGTCAC (SEQ ID NO: 324) | 606 bp |
| CN406 DNMT1 reverse fixed | CCTCACACAACAGCTTCATGTCAGC (SEQ ID NO: 325) | |

Protospacer Sequences

| Label | Sequence |
| --- | --- |
| LbCpf1_9 mm_ 20 nt_S | CTGATGGTgCATGTCTGTTA (SEQ ID NO: 326) |
| LbCpf1_9 mm_ 17 nt_S | CTGATGGTgCATG TCTG (SEQ ID NO: 327) |
| LbCpf1_9 mm_ 20 nt_hp_S | CTGATGGTgCATGTCT GTTA AGACATGcACCA (SEQ ID NO: 328) |
| LbCpf1_9 mm_ 17 nt_hp_S | CTGATGGTgCATG TCTG CATGcACCA (SEQ ID NO: 329) |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method of generating an optimized guide RNA (gRNA), the method comprising: a) identifying a target region of interest, the target region of interest comprising a protospacer sequence; b) determining a polynucleotide sequence of a full-length gRNA that targets the target region of interest, the full-length gRNA comprising a protospacer-targeting sequence or segment; c) determining at least one or more off-target sites for the full-length gRNA; d) generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment is at the 5' end of the polynucleotide sequence of the full-length gRNA, the first gRNA optionally comprising a linker between the 5' end of the polynucleotide sequence of the full-length gRNA and the RNA segment, the linker comprising a polynucleotide sequence having a length of N nucleotides, the first gRNA capable of invading the protospacer sequence and binding to a DNA sequence that is complementary to the protospacer sequence and forming a protospacer-duplex, and the first gRNA capable of invading an off-target site and binding to a DNA sequence that is complementary to the off-target site and forming an off-target duplex; e) calculating an estimate or computationally simulating the invasion kinetics and lifetime that the first gRNA remains invaded in the protospacer and off-target site duplexes, wherein the dynamics of invasion are estimated nucleotide-by-nucleotide by determining the energetic differences between further invasion of a different gRNA and re-annealing of the first gRNA to the DNA sequence that is complementary to the protospacer sequence; f) comparing the estimated lifetimes at the protospacer and/or off-target sites of the first gRNA with the estimated lifetimes of the full-length gRNA or a truncated gRNA (tru-gRNA) at the protospacer and/or off-target sites; g) randomizing 0 to N nucleotides in the linker and 0 to M nucleotides in the first gRNA and generating a second gRNA and repeating step (e) with the second gRNA; h) identifying an optimized gRNA based on a gRNA sequence that satisfy a design criteria; and i) testing the optimized gRNA in vivo to determine the specificity of binding.

Clause 2. A method of generating an optimized guide RNA (gRNA), the method comprising: a) identifying a target region of interest, the target region of interest comprising a protospacer sequence; b) determining a polynucleotide sequence of a full-length gRNA that targets the target region of interest, the full-length gRNA comprising a protospacer-targeting sequence or segment; c) determining at least one or more off-target sites for the full-length gRNA; d) generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment is at the 3' end of the polynucleotide sequence of the full-length gRNA, the first gRNA optionally comprising a linker between the 3' end of the polynucleotide sequence of the full-length gRNA and the RNA segment, the linker comprising a polynucleotide sequence having a length of N nucleotides, the first gRNA capable of invading the protospacer sequence and binding to a DNA sequence that is complementary to the protospacer sequence and forming a protospacer-duplex, and the first gRNA capable of invading an off-target site and binding to a DNA sequence that is complementary to the off-target site and forming an off-target duplex; e) calculating an estimate or computationally simulating the invasion kinetics and lifetime that the first gRNA remains invaded in the protospacer and off-target site duplexes, wherein the dynamics of invasion are estimated nucleotide-by-nucleotide by determining the energetic differences between further invasion of a different gRNA and re-annealing of the first gRNA to the DNA sequence that is complementary to the protospacer sequence; f) comparing the estimated lifetimes at the protospacer and/or off-target sites of the first gRNA with the estimated lifetimes of the full-length gRNA or a truncated gRNA (tru-gRNA) at the protospacer and/or off-target sites; g) randomizing 0 to N nucleotides in the linker and 0 to M nucleotides in the first gRNA and generating a second gRNA and repeating step (e) with the second gRNA; h) identifying an optimized gRNA based on a gRNA sequence that satisfy a design criteria; and i) testing the optimized gRNA in vivo to determine the specificity of binding.

Clause 3. The method of clause 1 or 2, wherein the energetics of further invasion of a different gRNA is determined by determining the energetics of at least one of (I) breaking a DNA-DNA base-pairing, (II) forming an RNA-DNA base-pair, (III) energetic difference resulting from disrupting or forming different secondary structure within the uninvaded guide RNA, and (IV) forming or disrupting interactions between the displaced DNA strand that is complementary to the protospacer and any unpaired guide RNA nucleotides which are not involved in secondary structures.

Clause 4. The method of any one of clauses 1-3, wherein the energetics of re-annealing of the first gRNA to the DNA sequence that is complementary to the protospacer sequence is determined by determining the energetics of at least one of (I) forming a DNA-DNA base-pairing, (II) breaking an RNA-DNA base-pair, (III) energetic difference resulting from disrupting or forming different secondary structure within the newly uninvaded guide RNA, and (IV) forming or disrupting interactions between the displaced DNA strand that is complementary to the protospacer and any unpaired guide RNA nucleotides which are not involved in secondary structures.

Clause 5. The method of clause 3 or 4, further comprising determining the energetic considerations from at least one of (V) base-pairing across mismatches, (VI) interactions with the Cas9 protein, and/or (VII) additional heuristics, wherein the additional heuristics relate to binding lifetime, extent of invasion, stability of invading guide RNA, or other calculated/simulated properties of gRNA invasion to Cas9 cleavage activity.

Clause 6. The method of any one of clauses 1-5, wherein the full-length gRNA comprises between about 15 and 20 nucleotides.

Clause 7. The method of any one of clauses 1-5, wherein M is between 1 and 20.

Clause 8. The method of clause 7, wherein M is between 4 and 10.

Clause 9. The method of any one of clauses 1-8, wherein the RNA segment comprises between 2 and 15 nucleotides that complement the protospacer-targeting sequence.

Clause 10. The method of any one of clauses 1-9, wherein N is between 1 and 20.

Clause 11. The method of clause 10, wherein N is between 3 and 10.

Clause 12. The method of any one of clauses 1-11, wherein the RNA segment and/or protospacer-targeting sequence provide a secondary structure.

Clause 13. The method of clause 12, wherein the secondary structure is formed by partially hybridizing the protospacer-targeting sequence with the RNA segment.

Clause 14. The method of clause 13, wherein the secondary structure modulates DNA binding or cleavage by Cas9 by disrupting invasion of the protospacer duplex or off-target duplex by the optimized gRNA.

Clause 15. The method of any one of clauses 12-14, wherein the secondary structure is formed by hybridizing all or part of the RNA segment to nucleotides in the 5'-end of the protospacer-targeting sequence or segment, nucleotides in the middle of the protospacer-targeting sequence or segment, and/or nucleotides in the 3'-end of the protospacer-targeting sequence or segment.

Clause 16. The method of any one of clauses 12-15, wherein the secondary structure is a hairpin.

Clause 17. The method of any one of clauses 12-16, wherein the secondary structure is stable at room temperature or 37° C.

Clause 18. The method of any one of clauses 12-17, wherein the overall equilibrium free energy of the secondary structure is less than about 2 kcal/mol at room temperature or 37° C.

Clause 19. The method of any one of clauses 1-18, wherein the RNA segment hybridizes or forms non-canonical base pairs with at least two nucleotides of the protospacer-targeting sequence or segment.

Clause 20. The method of clause 19, wherein the non-canonical base pair is rU-rG.

Clause 21. The method of any one of clauses 1-20, wherein the optimized gRNA is used with a CRISPR/Cas9-based system or CRISPR/Cpf1-based system in a cell.

Clause 22. The method of any one of clauses 1-21, wherein the secondary structure protects the optimized gRNA within the CRISPR/Cas9-based system or CRISPR/Cpf1-based system to prevent degradation within the cell.

Clause 23. The method of any one of clauses 1-22, wherein 1-20 nucleotides are randomized in the linker.

Clause 24. The method of any one of clauses 1-23, wherein 1-20 nucleotides are randomized in the RNA segment.

Clause 25. The method of any one of clauses 1-24, wherein step (g) is repeated X number of times, thereby generating X number of gRNAs and repeating step (e) with each X number of gRNAs, wherein X is between 0 to 20.

Clause 26. The method of any one of clauses 1-25, wherein the invasion kinetics and lifetime are calculated using kinetic Monte Carlo method or Gillespie algorithm.

Clause 27. The method of any one of clauses 1-26, wherein the invasion kinetics is the rate at which the guide RNA invades the protospacer duplex to full invasion such that the protospacer is completely invaded and/or the rate at which the segment of protospacer DNA bound to the gRNA expands as it is displaced from its complementary strand and bound to the gRNA nucleotide-by-nucleotide from its PAM proximal region through to full invasion.

Clause 28. The method of any one of clauses 1-27, wherein the design criteria comprises specificity, modulation of binding lifetime, and/or estimated cleavage specificity.

Clause 29. The method of clause 28, wherein the design criteria comprises an optimized gRNA having a binding lifetime greater than or equal to the binding lifetime of a full-length gRNA to the on-target site and/or a binding lifetime less than or equal to the binding lifetime of a full-length gRNA to an off-target site.

Clause 30. The method of clause 29, wherein the design criteria comprises an optimized gRNA having a binding lifetime less than or equal to the binding lifetime of a full-length gRNA to at least three off-target sites, wherein the off-target sites are predicted to be the closest off-target sites or predicted to have the highest identity to the on-target sites.

Clause 31. The method of clause 28, wherein the design criteria comprises a lifetime or cleavage rate at an off-target site that is less than or equal to the lifetime or cleavage rate of a full-length gRNA or truncated gRNA at the off-target site and/or a predicted on-target activity rate that is greater than 10% of the predicted on-target activity rate of a full-length gRNA or truncated gRNA.

Clause 32. The method of any one of clauses 1-31, wherein the optimized gRNA is tested in step i) using surveyor assay, next-gen sequencing techniques, or GUIDE-Seq.

Clause 33. The method of any one of clauses 1-32, wherein the optimized gRNA is designed to minimize binding at an off-target site and allow binding to a protospacer sequence.

Clause 34. The method of any one of clauses 1-33, wherein the off-target site is a known or predicted off-target site.

Clause 35. The method of any one of clauses 1-34, wherein the full-length gRNA targets a mammalian gene.

Clause 36. The method of any one of clauses 1-35, wherein the target gene comprises an endogenous target gene or a transgene.

Clause 37. The method of any one of clauses 1-36, wherein the target gene comprises a disease-relevant gene.

Clause 38. The method of any one of clauses 1-37, wherein the target gene is a DMD, EMX1, or VEGFA gene.

Clause 39. The method of clause 38, wherein the VEGFA gene is VEGFA1 or VEGFA3.

Clause 40. An optimized gRNA generated by the method of any one of clauses 1-39.

Clause 41. The optimized gRNA of clause 40, wherein the gRNA can discriminate between on- and off-target sites with minimal thermodynamic energetic differences between the sites.

Clause 42. The optimized gRNA of clause 40 or 41, wherein the optimized gRNA modulates strand invasion into the protospacer.

Clause 43. The optimized gRNA of any one of clauses 40-42, wherein the optimized gRNA comprises a nucleotide sequence of at least one of SEQ ID NOs: 149-315, 321-323, and 326-329.

Clause 44. An isolated polynucleotide encoding the optimized gRNA of any one of clauses 40-43.

Clause 45. A vector comprising the isolated polynucleotide of clause 44.

Clause 46. A cell comprising the isolated polynucleotide of clause 44 or the vector of clause 45.

Clause 47. A kit comprising the isolated polynucleotide of clause 44, the vector of clause 45, or the cell of clause 46.

Clause 48. A method of epigenomic editing in a target cell or a subject, the method comprising contacting a cell or a subject with an effective amount of the optimized gRNA molecule of any one of clauses 40-43 or the isolated polynucleotide of clause 44 and a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

Clause 49. A method of site specific DNA cleavage in a target cell or a subject, the method comprising contacting a cell or a subject with an effective amount of the optimized gRNA molecule of any one of clauses 40-43 or the isolated polynucleotide of clause 44 and a fusion protein or Cas9 protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

Clause 50. A method of genome editing in a cell, the method comprising administering to the cell an effective amount of the optimized gRNA molecule of any one of clauses 40-43 or the isolated polynucleotide of clause 44 and a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

Clause 51. The method of clause 50, wherein the genome editing comprises correcting a mutant gene or inserting a transgene.

Clause 52. The method of clause 51, wherein correcting a mutant gene comprises deleting, rearranging, or replacing the mutant gene.

Clause 53. The method of any one of clauses 51 or 52, wherein correcting the mutant gene comprises nuclease-mediated non-homologous end joining or homology-directed repair.

Clause 54. A method of modulating gene expression in a cell, the method comprising contacting the cell with an effective amount of the optimized gRNA molecule of any one of clauses 40-43 or the isolated polynucleotide of clause 44 and a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

Clause 55. The method of clause 54, wherein the gene expression of the at least one target gene is modulated when gene expression levels of the at least one target gene are increased or decreased compared to normal gene expression levels for the at least one target gene.

Clause 56. The method of clause 54 or 55, wherein the fusion protein comprises a dCas9 domain and a transcriptional activator.

Clause 57. The method of clause 56, wherein the fusion protein comprises the amino acid sequence of SEQ ID NO: 2.

Clause 58. The method of clause 54 or 55, wherein the fusion protein comprises a dCas9 domain and a transcriptional repressor.

Clause 59. The method of clause 58, wherein the fusion protein comprises the amino acid sequence of SEQ ID NO:3.

Clause 60. The method of clause 54 or 55, wherein the fusion protein comprises a dCas9 domain and a site-specific nuclease.

Clause 61. The method of any one of clauses 48-60 wherein the optimized gRNA is encoded by a polynucleotide sequence and packaged into a lentiviral vector.

Clause 62. The method of clause 61, wherein the lentiviral vector comprises an expression cassette comprising a promoter operably linked to the polynucleotide sequence encoding the gRNA.

Clause 63. The method of clause 62, wherein the promoter operably linked to the polynucleotide encoding the optimized gRNA is inducible.

Clause 64. The method of any one of clauses 61-63, herein the lentiviral vector further comprises a polynucleotide sequence encoding the Cas9 protein or fusion protein.

Clause 65. The method of any one of clauses 48-64, wherein the at least one target gene is a disease-relevant gene.

Clause 66. The method of any one of clauses 48-65, wherein the target cell is a eukaryotic cell.

Clause 67. The method of any one of clauses 48-66, wherein the target cell is a mammalian cell.

The method of any one of clauses 48-67, wherein the target cell is a HEK293T cell.

APPENDIX

Sequences

*Streptococcus pyogenes* Cas 9 (with D10A, H840A)(SEQ ID NO: 1)
```
MDKKYSIGLAIGTNSVGWAVITDEYKVPSKKFKVLGNTDRHSIKKNLIGALLFDSGETA
EATRLKRTARRRYTRRKNRICYLQEIFSNEMAKVDDSFFHRLEESFLVEEDKKHERHPIF
GNIVDEVAYHEKYPTIYHLRKKLVDSTDKADLRLIYLALAHMIKFRGHFLIEGDLNPDNS
DVDKLFIQLVQTYNQLFEENPINASGVDAKAILSARLSKSRRLENLIAQLPGEKKNGLFG
NLIALSLGLTPNFKSNFDLAEDAKLQLSKDTYDDDLDNLLAQIGDQYADLFLAAKNLSD
AILLSDILRVNTEITKAPLSASMIKRYDEHHQDLTLLKALVRQQLPEKYKEIFFDQSKNGY
AGYIDGGASQEEFYKFIKPILEKMDGTEELLVKLNREDLLRKQRTFDNGSIPHQIHLGEL
HAILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPA
FLSGEQKKAIVDLLFKTNRKVTVKQLKEDYFKKIECFDSVEISGVEDRFNASLGTYHDLL
KIIKDKDFLDNEENEDILEDIVLTLTLFEDREMIEERLKTYAHLFDDKVMKQLKRRRYTG
WGRLSRKLINGIRDKQSGKTILDFLKSDGFANRNFMQLIHDDSLTFKEDIQKAQVSGQG
DSLHEHIANLAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQELDINRLSD
YDVDAIVPQSFLKDDSIDNKVLTRSDKNRGKSDNVPSEEVVKKMKNYWRQLLNAKLIT
QRKFDNLTKAERGGLSELDKAGFIKRQLVETRQITKHVAQILDSRMNTKYDENDKLIRE
VKVITLKSKLVSDERKDFQFYKVREINNYHHAHDAYLNAVVGTALIKKYPKLESEFVYG
```

APPENDIX-continued

Sequences

```
DYKVYDVRKMIAKSEQEIGKATAKYFFYSNIMNFEKTEITLANGEIRKRPLIETNGETGEI
VWDKGRDFATVRKVLSMPQVNIVKKTEVQTGGFSKESILPKRNSDKLIARKKDWDPKK
YGGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLKGS
PEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGD
``` dCas9$^{p300\ Core}$: (Addgene Plasmid 61357) amino acid sequence; 3X "Flag" Epitope, Nuclear Localization Sequence, *Streptococcus pyogenes* Cas9 (D10A, H840A), p300 Core Effector, "HA" Epitope (SEQ ID NO: 2)

```
MDYKDHDGDYKDHDIDYKDDDDKMAPKKKRKVGRGMDKKYSIGLAIGTNSVGWA
VITDEYKVPSKKFKVLGNTDRHSIKKNLIGALLFDSGETAEATRLKRTARRRYTRR
KNRICYLQEIFSNEMAKVDDSFFHRLEESFLVEEDKKHERHPIFGNIVDEVAYHEKY
PTIYHLRKKLVDSTDKADLRLIYLALAHMIKFRGHFLIEGDLNPDNSDVDKLFIQLV
QTYNQLFEENPINASGVDAKAILSARLSKSRRLENLIAQLPGEKKNGLFGNLIALSL
GLTPNFKSNFDLAEDAKLQLSKDTYDDDLDNLLAQIGDQYADLFLAAKNLSDAILL
SDILRVNTEITKAPLSASMIKRYDEHHQDLTLLKALVRQQLPEKYKEIFFDQSKNGY
AGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETI
TPWNFEEVVDKGASAQSFIERMTNFDKNLPNEKVLPKHSLLYEYFTVYNELTKVK
YVTEGMRKPAFLSGEQKKAIVDLLFKTNRKVTVKQLKEDYFKKIECFDSVEISGVE
DRFNASLGTYHDLLKIIKDKDFLDNEENEDILEDIVLTLTLFEDREMIEERLKTYAH
LFDDKVMKQLKRRRYTGWGRLSRKLINGIRDKQSGKTILDFLKSDGFANRNFMQL
IHDDSLTFKEDIQKAQVSGQGDSLHEHIANLAGSPAIKKGILQTVKVVDELVKVMG
RHKPENIVIEMARENQTTQKGQKNSRERMKRIEEGIKELGSQILKEHPVENTQLQN
EKLYLYYLQNGRDMYVDQELDINRLSDYDVDAIVPQSFLKDDSIDNKVLTRSDKNR
GKSDNVPSEEVVKKMKNYWRQLLNAKLITQRKFDNLTKAERGGLSELDKAGFIKR
QLVETRQITKHVAQILDSRMNTKYDENDKLIREVKVITLKSKLYSDFRKDFQFYKV
REINNYHHAHDAYLNAVVGTALIKKYPKLESEFVYGDYKYYDVRKMIAKSEQEIG
KATAKYFFYSNIMNFFKTEITLANGEIRKRPLIETNGETGEIVWDKGRDFATVRKVL
SMPQVNIVKKTEVQTGGFSKESILPKRNSDKLIARKKDWDPKKYGGFDSPTVAYSV
LVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQK
QLFVEQHKHYLDEHEQISEFSKRVILADANLDKVLSAYNKEIRDKPIREQAENIIHLF
TLTNLGAPAAFKYFDTTIDRKRYTSTKEVLDATLIHQSITGLYETRIDLSQLGGDPIA
GSKASPKKKRKVGRAIFKPEELRQALMPTLEALYRQDPESLPFRQPVDPQLLGIPD
YFDIVKSPMDLSTIKRKLDTGQYQEPWQYVDDIWLMFNNAWLYNRKTSRVYKYCS
KLSEVFEQEIDPVMQSLGYCCGRKLEFSPQTLCCYGKQLCTIPRDATYYSYQNRYH
FCEKCFNEIQGESVSLGDDPSQPQTTINKEQFSKRKNDTLDPELFVECTECGRKMH
QICVLHHEIIWPAGFVCDGCLKKSARTRKENKFSAKRLPSTRLGTFLENRYNDFLR
RQNHPESGEVTVRVVHASDKTVEVKPGMKARFVDSGEMAESFPYRTKALFAFEEI
DGVDLCFFGMHVQEYGSDCPPPNQRRVYISYLDSVHFFRPKCLRTAVYHEILIGYL
EYVKKLGYTTGHIWACPPSEGDDYIFHCHPPDQKIPKPKRLQEWYKKMLDKAVSE
RIVHDYKDIFKQATEDRLTSAKELPYFEGDFWPNVLEESIKELEQEEEERKREENTS
NESTDVTKGDSKNAKKKNNKKTSKNKSSLSRGNKKKPGMPNVSNDLSGKLYATM
EKHKEVFFVIRLIAGPAANSLPPIVDPDPLIPCDLMDGRDAFLTLARDKHLEFSSLRR
AQWSTMCMLVELHTQSQDYPYDVPDYAS
``` dCas9$^{KRAB}$ (SEQ ID NO: 3)

```
MDYKDHDGDYKDHDIDYKDDDDKMAPKKKRKVGRGMDKKYSIGLAIGTNSVGWAVI
TDEYKVPSKKFKVLGNTDRHSIKKNLIGALLFDSGETAEATRLKRTARRRYTRRKNRIC
YLQEIFSNEMAKVDDSFFHRLEESFLVEEDKKHERHPIFGNIVDEVAYHEKYPTIYHLRK
KLVDSTDKADLRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTEITKAPLSASM
IKRYDEHHQDLTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYPFLKDNREKIE
KILTFRIPYYVGPLARGNSRFAWMTRKSEETITPWNFEEVVDKGASAQSFIERMTNFDKN
LPNEKVLPKHSLLYEYFTVYNELTKVKYVTEGMRKPAFLSGEQKKAIVDLLFKTNRKVT
VKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTIL
DFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEH
PVENTQLQNEKLYLYYLQNGRDMYVDQELDINRLSDYDVDAIVPQSFLKDDSIDNKVL
TRSDKNRGKSDNVPSEEVVKKMKNYWRQLLNAKLITQRKFDNLTKAERGGLSELDKA
GFIKRQLVETRQITKHVAQILDSRMNTKYDENDKLIREVKVITLKSKLVSDFRKDFQFYK
VREINNYHHAHDAYLNAVVGTALIKKYPKLESEFVYGDYKVYDVRKMIAKSEQEIGKA
TAKYFFYSNIMNFFKTEITLANGEIRKRPLIETNGETGEIVWDKGRDFATVRKVLSMPQV
NIVKKTEVQTGGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKYSLFELENGRKR
MLASAGELQKGNELALPSKYVNFLYLASHYEKLKGSPEDNEQKQLFVEQHKHYLDEIIE
QISEFSKRVILADANLDKVLSAYNKHRDKPIREQAENIIHLFTLTNLGAPAAFKYFDTTID
RKRYTSTKEVLDATLIHQSITGLYETRIDLSQLGGDSRADPKKKRKVASDAKSLTAWSR
TLVTFKDVFVDFTREEWKLLDTAQQILYRNVMLENYKNLVSLGYQLTKPDVILRLEKGE
EPWLVEREIHQETHPDSETAFEIKSSVPKKKRKVAS
```

| APPENDIX-continued |
|---|
| Sequences |

Nm-dCas9$^{p300\ Core}$: (Addgene Plasmid 61365) amino acid sequence; *Neisseria meningitidis* Cas9 (D16A, D587A, H588A, N611A), Nuclear Localization Sequence, p300 Core Effector, "HA" Epitope (SEQ ID NO: 5)

```
MAAFKPNPINYILGLAIGIASVGWAMVEIDEDENPICLIDLGVRVFERAEVPKTGDS
LAMARRLARSVRRLTRRRAHRLLRARRLLKREGVLQAADFDENGLIKSLPNTPWQ
LRAAALDRKLTPLEWSAVLLHLIKHRGYLSQRKNEGETADKELGALLKGVADNA
HALQTGDFRTPAELALNKFEKESGHIRNQRGDYSHTFSRKDLQAELILLFEKQKEF
GNPHVSGGLKEGIETLLMTQRPALSGDAVQKMLGHCTFEPAEPKAAKNTYTAERF
IWLTKLNNLRILEQGSERPLTDTERATLMDEPYRKSLTYAQARKLLGLEDTAFFK
GLRYGKDNAEASTLMEMKAYHAISRALEKEGLKDKKSPLNLSPELQDEIGTAFSLF
KTDEDITGRLKDRIQPEILEALLKHISFDKFVQISLKALRRIVPLMEQGKRYDEACA
EIYGDHYGKKNTEEKIYLPPIPADEIRNPVVLRALSQARKVINGVVRRYGSPARIHIE
TAREVGKSFKDRKEIEKRQEENRKDREKAAAKFREYFPNFVGEPKSKDILKLRLYE
QQHGKCLYSGKEINLGRLNEKGYVEIAAALPFSRTWDDSFNNKVLVLGSEAQNKG
NQTPYEYFNGKDNSREWQEFKARVETSRFPRSKKQRILLQKFDEDGFKERNLNDT
RYVNRFLCQFVADRMRLTGKGKKRVFASNGQITNLLRGFWGLRKVRAENDRHHA
LDAVVVACSTVAMQQKITRFVRYKEMNAFDGKTIDKETGEVLHQKTHFPQPWEFF
AQEVMIRVFGKPDGKPEFEEADTPEKLRTLLAEKLSSRPEAVHEYVTPLFVSRAPN
RKMSGQGHMETVKSAKRLDEGVSVLRVPLTQLKLKDLEKMVREREPKLYEALK
ARLEAHKDDPAKAFAEPPFYKYDKAGNRTQQVKAVRVEQVQKTGVIVVRNHNGIA
DNATMVRVDVFEKGDKYYLVPIYSWQVAKGILPDRAVVQGKDEEDWQLIDDSFNF
KFSLHPNDLVEVITKKARMFGYFASCHRGTGNINIRIHDLDHKIGKNGILEGIGVKT
ALSFQKYQIDELGKEIRPCRLKKRPPVRSRADPKKKRKVEASGRAIFKPEELRQAL
MPTLEALYRQDPESLPFRQPVDPQLLGIPDYFDIVKSPMDLSTIKRKLDTGQYQEP
WQYVDDIWLMFNNAWLYNRKTSRVYKYCSKLSEVFEQEIDPVMQSLGYCCGRKL
EFSPQTLCCYGKQLCTIPRDATYYSYQNRYHFCEKCFNEIQGESVSLGDDPSQPQTT
INKEQFSKRKNDTLDPELFVECTECGRKMHQICVLHHEIIWPAGFVCDGCLKKSAR
TRKENKFSAKRLPSTRLGTFLENRVNDFLRRQNHPESGEVTVRVVHASDKTVEVKP
GMKARFVDSGEMAESFPYRTKALFAFEEIDGVDLCFFGMHVQEYGSDCPPPNQRR
VYISYLDSVHFFRPKCLRTAVYHEILIGYLEYVKKLGYTTGHIWACPPSEGDDYIFH
CHPPDQKIPKPKRLQEWYKKMLDKAVSERIVHDYKDIFKQATEDRLTSAKELPYF
EGDFWPNVLEESIKELEQEEEERKREENTSNESTDVTKGDSKNAKKKNNKKTSKN
KSSLSRGNKKKPGMPNVSNDLSQKLYATMEKHKEVFFVIRLIAGPAANSLPPIVDPD
PLIPCDLMDGRDAFLTLARDKHLEFSSLRRAQWSTMCMLVELHTSQDYPYDVPD
YAS
```

---

What is claimed:

1. A method of generating an optimized guide RNA (gRNA), the method comprising:
(a) identifying a target region of interest, the target region of interest comprising a protospacer sequence;
(b) determining a polynucleotide sequence of a full-length gRNA that targets the target region of interest, the full-length gRNA comprising a protospacer-targeting sequence or segment;
(c) determining one or more off-target sites for the full-length gRNA;
(d) generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment being at the 5' end or the 3' end of the polynucleotide sequence of the full-length gRNA, the first gRNA optionally comprising a linker between the 5' end or the 3' end of the polynucleotide sequence of the full-length gRNA and the RNA segment, the linker comprising a polynucleotide sequence having a length of N nucleotides, the first gRNA being capable of invading the protospacer sequence and binding to a DNA sequence that is complementary to the protospacer sequence and forming a protospacer-duplex, and the first gRNA being capable of invading an off-target site and binding to a DNA sequence that is complementary to the off-target site and forming an off-target duplex;
(e) calculating an estimate of or computationally simulating the invasion kinetics and lifetimes of the first gRNA remaining invaded in the protospacer and off-target site duplexes, wherein the invasion kinetics and lifetimes are estimated or computationally simulated nucleotide-by-nucleotide by determining the energetic differences between further invasion of a different gRNA and re-binding of the first gRNA to the DNA sequence that is complementary to the protospacer sequence;
(f) comparing the estimated or computationally simulated lifetimes at the protospacer and off-target sites of the first gRNA with the estimated or computationally simulated lifetimes of the full-length gRNA or a truncated gRNA (tru-gRNA) at the protospacer and off-target sites;
(g) randomizing 1 to N nucleotides in the linker and 1 to M nucleotides in the RNA segment of the first gRNA and generating a second gRNA and repeating step (e) with the second gRNA;
(h) identifying an optimized gRNA, wherein the optimized gRNA has a binding lifetime greater than or equal to that of the full-length gRNA at the protospacer, and/or a binding lifetime less than or equal to that of the full-length gRNA at the off-target site; and
(i) testing the optimized gRNA in vivo to determine the specificity of binding.

2. The method of claim 1, wherein the energetics of further invasion of a different gRNA are determined by determining the energetics of at least one of (I) breaking a DNA-DNA base-pairing, (II) forming an RNA-DNA base-pair, (III) an energetic difference resulting from disrupting or forming different secondary structure within the uninvaded guide RNA, and (IV) forming or disrupting interactions between the displaced DNA strand that is complementary to the protospacer and any unpaired guide RNA nucleotides which are not involved in forming secondary structures.

3. The method of claim 2, wherein the energetics of re-annealing of the first gRNA to the DNA sequence that is complementary to the protospacer sequence are determined by determining the energetics of at least one of (I) forming a DNA-DNA base-pairing, (II) breaking an RNA-DNA base-pair, (III) an energetic difference resulting from disrupting or forming different secondary structure within the newly uninvaded guide RNA, and (IV) forming or disrupting interactions between the displaced DNA strand that is complementary to the protospacer and any unpaired guide RNA nucleotides which are not involved in secondary structures.

4. The method of claim 3, further comprising determining the energetic considerations from at least one of (V) base-pairing mismatches, (VI) interactions with a Cas9 protein, and/or (VII) additional heuristics, wherein the additional heuristics relate to binding lifetime, extent of invasion, or stability of the invading guide RNA.

5. The method of claim 1, wherein the full-length gRNA comprises about 15 to 20 nucleotides, and/or
wherein M is from 1 to 20, and/or
wherein the RNA segment comprises 2 to 15 nucleotides that complement the protospacer-targeting sequence, and/or
wherein N is from 1 to 20, and/or
wherein the RNA segment and/or protospacer-targeting sequence provide a secondary structure.

6. The method of claim 1, wherein the optimized gRNA is used with a CRISPR/Cas9-based system or CRISPR/Cpf1-based system in a cell.

7. The method of claim 1, wherein 1-20 nucleotides are randomized in the linker, and/or
wherein 1-20 nucleotides are randomized in the RNA segment, and/or
wherein step (g) is repeated X number of times, thereby generating X number of gRNAs and step (e) is repeated with each gRNA of the X number of gRNAs, wherein X is from 1 to 20, and/or
wherein the invasion kinetics and lifetimes are calculated using a kinetic Monte Carlo method or a Gillespie algorithm, wherein the invasion kinetics comprise the rate at which the guide RNA invades the protospacer duplex to full invasion such that the protospacer is completely invaded and/or the rate at which the segment of protospacer DNA bound to the gRNA expands as it is displaced from its complementary strand and bound to the gRNA nucleotide-by-nucleotide from its PAM proximal region through to full invasion, and/or
wherein the optimized gRNA has increased binding specificity for the protospacer compared to the full-length gRNA.

8. The method of claim 1, wherein the RNA segment and protospacer-targeting sequence or segment provide a secondary structure,
wherein the secondary structure is formed by hybridizing all or part of the RNA segment to nucleotides in the 5'-end of the protospacer-targeting sequence or segment, nucleotides in the middle of the protospacer-targeting sequence or segment, and/or nucleotides in the 3'-end of the protospacer-targeting sequence or segment, and
wherein the secondary structure is a hairpin.

9. The method of claim 6, wherein the CRISPR/Cas9-based system is a Type II or Type V CRISPR/Cas9-based system.

10. The method of claim 1, wherein the invasion kinetics and lifetimes that the first gRNA remains invaded in the protospacer and off-target site duplexes are computationally simulated or have estimates calculated in step (e) by a processor.

11. A method of treating a subject, the method comprising:
(i) generating an optimized guide RNA (gRNA) by:
   (a) identifying a target region of interest, the target region of interest comprising a protospacer sequence;
   (b) determining a polynucleotide sequence of a full-length gRNA that targets the target region of interest, the full-length gRNA comprising a protospacer-targeting sequence or segment;
   (c) determining one or more off-target sites for the full-length RNA;
   (d) generating a polynucleotide sequence of a first gRNA, the first gRNA comprising the polynucleotide sequence of the full-length gRNA and a RNA segment, the RNA segment comprising a polynucleotide sequence having a length of M nucleotides that is complementary to a nucleotide segment of the protospacer-targeting sequence or segment, the RNA segment being at the 5' end or the 3' end of the polynucleotide sequence of the full-length gRNA, the first gRNA optionally comprising a linker between the 5' end or the 3' end of the polynucleotide sequence of the full-length gRNA and the RNA segment, the linker comprising a polynucleotide sequence having a length of N nucleotides, the first gRNA being capable of invading the protospacer sequence and binding to a DNA sequence that is complementary to the protospacer sequence and forming a protospacer-duplex, and the first gRNA being capable of invading an off-target site and binding to a DNA sequence that is complementary to the off-target site and forming an off-target duplex;
   (e) calculating an estimate of or computationally simulating the invasion kinetics and lifetimes of the first gRNA remaining invaded in the protospacer and off-target site duplexes, wherein the invasion kinetics and lifetimes are estimated or computationally simulated nucleotide-by-nucleotide by determining the energetic differences between further invasion of a different gRNA and re-binding of the first gRNA to the DNA sequence that is complementary to the protospacer sequence;
   (f) comparing the estimated or computationally simulated lifetimes at the protospacer and off-target sites of the first gRNA with the estimated or computationally simulated lifetimes of the full-length gRNA or a truncated gRNA (tru-gRNA) at the protospacer and off-target sites;
   (g) randomizing 1 to N nucleotides in the linker and 1 to M nucleotides in the RNA segment of the first gRNA and generating a second gRNA and repeating step (e) with the second gRNA;
   (h) identifying an optimized gRNA, wherein the optimized gRNA has a binding lifetime greater than or equal to that of the full-length gRNA at the protospacer, and/or a binding lifetime less than or equal to that of the full-length gRNA at the off-target site; and
   (i) testing the optimized gRNA in vivo to determine the specificity of binding; and
(ii) administering to the subject a DNA targeting system comprising the optimized gRNA and a fusion protein or Cas9 protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

\* \* \* \* \*

SEQUENCE LISTING

<160> NUMBER OF SEQ ID NOS: 348

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140
```

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
        180                 185                 190

Asn Gln Leu Phe Glu Glu Asn Pro Ile Asn Ala Ser Gly Val Asp Ala
    195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560
```

-continued

```
Val Lys Gln Leu Lys Glu Asp Tyr Phe Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
```

```
              980             985             990
Val Gly Thr Ala Leu Ile Lys Lys Tyr Pro Lys Leu Glu  Ser Glu Phe
                995            1000            1005
Val Tyr Gly Asp Tyr Lys Val Tyr Asp Val Arg Lys Met Ile Ala
   1010            1015            1020
Lys Ser Glu Gln Glu Ile Gly Lys Ala Thr Ala Lys Tyr Phe Phe
   1025            1030            1035
Tyr Ser Asn Ile Met Asn Phe Phe Lys Thr Glu Ile Thr Leu Ala
   1040            1045            1050
Asn Gly Glu Ile Arg Lys Arg Pro Leu Ile Glu Thr Asn Gly Glu
   1055            1060            1065
Thr Gly Glu Ile Val Trp Asp Lys Gly Arg Asp Phe Ala Thr Val
   1070            1075            1080
Arg Lys Val Leu Ser Met Pro Gln Val Asn Ile Val Lys Lys Thr
   1085            1090            1095
Glu Val Gln Thr Gly Gly Phe Ser Lys Glu Ser Ile Leu Pro Lys
   1100            1105            1110
Arg Asn Ser Asp Lys Leu Ile Ala Arg Lys Lys Asp Trp Asp Pro
   1115            1120            1125
Lys Lys Tyr Gly Gly Phe Asp Ser Pro Thr Val Ala Tyr Ser Val
   1130            1135            1140
Leu Val Val Ala Lys Val Glu Lys Gly Lys Ser Lys Lys Leu Lys
   1145            1150            1155
Ser Val Lys Glu Leu Leu Gly Ile Thr Ile Met Glu Arg Ser Ser
   1160            1165            1170
Phe Glu Lys Asn Pro Ile Asp Phe Leu Glu Ala Lys Gly Tyr Lys
   1175            1180            1185
Glu Val Lys Lys Asp Leu Ile Ile Lys Leu Pro Lys Tyr Ser Leu
   1190            1195            1200
Phe Glu Leu Glu Asn Gly Arg Lys Arg Met Leu Ala Ser Ala Gly
   1205            1210            1215
Glu Leu Gln Lys Gly Asn Glu Leu Ala Leu Pro Ser Lys Tyr Val
   1220            1225            1230
Asn Phe Leu Tyr Leu Ala Ser His Tyr Glu Lys Leu Lys Gly Ser
   1235            1240            1245
Pro Glu Asp Asn Glu Gln Lys Gln Leu Phe Val Glu Gln His Lys
   1250            1255            1260
His Tyr Leu Asp Glu Ile Ile Glu Gln Ile Ser Glu Phe Ser Lys
   1265            1270            1275
Arg Val Ile Leu Ala Asp Ala Asn Leu Asp Lys Val Leu Ser Ala
   1280            1285            1290
Tyr Asn Lys His Arg Asp Lys Pro Ile Arg Glu Gln Ala Glu Asn
   1295            1300            1305
Ile Ile His Leu Phe Thr Leu Thr Asn Leu Gly Ala Pro Ala Ala
   1310            1315            1320
Phe Lys Tyr Phe Asp Thr Thr Ile Asp Arg Lys Arg Tyr Thr Ser
   1325            1330            1335
Thr Lys Glu Val Leu Asp Ala Thr Leu Ile His Gln Ser Ile Thr
   1340            1345            1350
Gly Leu Tyr Glu Thr Arg Ile Asp Leu Ser Gln Leu Gly Gly Asp
   1355            1360            1365

<210> SEQ ID NO 2
```

```
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Met Asp Lys Lys Tyr Ser Ile Gly Leu Ala Ile Gly Thr
        35                  40                  45

Asn Ser Val Gly Trp Ala Val Ile Thr Asp Glu Tyr Lys Val Pro Ser
50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Tyr Thr Arg Arg Lys Asn
            100                 105                 110

Arg Ile Cys Tyr Leu Gln Glu Ile Phe Ser Asn Glu Met Ala Lys Val
            115                 120                 125

Asp Asp Ser Phe Phe His Arg Leu Glu Glu Ser Phe Leu Val Glu Glu
        130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
        355                 360                 365

Leu Leu Lys Ala Leu Val Arg Gln Gln Leu Pro Glu Lys Tyr Lys Glu

-continued

```
                370                 375                 380
Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
                420                 425                 430

Leu Leu Arg Lys Gln Arg Thr Phe Asp Asn Gly Ser Ile Pro His Gln
                435                 440                 445

Ile His Leu Gly Glu Leu His Ala Ile Leu Arg Arg Gln Glu Asp Phe
                450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
                500                 505                 510

Phe Glu Glu Val Val Asp Lys Gly Ala Ser Ala Gln Ser Phe Ile Glu
                515                 520                 525

Arg Met Thr Asn Phe Asp Lys Asn Leu Pro Asn Glu Lys Val Leu Pro
                530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
                595                 600                 605

Cys Phe Asp Ser Val Glu Ile Ser Gly Val Glu Asp Arg Phe Asn Ala
                610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
                675                 680                 685

Arg Arg Tyr Thr Gly Trp Gly Arg Leu Ser Arg Lys Leu Ile Asn Gly
                690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
                755                 760                 765

Lys Lys Gly Ile Leu Gln Thr Val Lys Val Val Asp Glu Leu Val Lys
                770                 775                 780

Val Met Gly Arg His Lys Pro Glu Asn Ile Val Ile Glu Met Ala Arg
785                 790                 795                 800
```

```
Glu Asn Gln Thr Thr Gln Lys Gly Gln Lys Asn Ser Arg Glu Arg Met
                805                 810                 815
Lys Arg Ile Glu Gly Ile Lys Glu Leu Gly Ser Gln Ile Leu Lys
            820                 825                 830
Glu His Pro Val Glu Asn Thr Gln Leu Gln Asn Glu Lys Leu Tyr Leu
                835                 840                 845
Tyr Tyr Leu Gln Asn Gly Arg Asp Met Tyr Val Asp Gln Glu Leu Asp
850                 855                 860
Ile Asn Arg Leu Ser Asp Tyr Asp Val Asp Ala Ile Val Pro Gln Ser
865                 870                 875                 880
Phe Leu Lys Asp Asp Ser Ile Asp Asn Lys Val Leu Thr Arg Ser Asp
                885                 890                 895
Lys Asn Arg Gly Lys Ser Asp Asn Val Pro Ser Glu Glu Val Val Lys
                900                 905                 910
Lys Met Lys Asn Tyr Trp Arg Gln Leu Leu Asn Ala Lys Leu Ile Thr
                915                 920                 925
Gln Arg Lys Phe Asp Asn Leu Thr Lys Ala Glu Arg Gly Gly Leu Ser
                930                 935                 940
Glu Leu Asp Lys Ala Gly Phe Ile Lys Arg Gln Leu Val Glu Thr Arg
945                 950                 955                 960
Gln Ile Thr Lys His Val Ala Gln Ile Leu Asp Ser Arg Met Asn Thr
                965                 970                 975
Lys Tyr Asp Glu Asn Asp Lys Leu Ile Arg Glu Val Lys Val Ile Thr
                980                 985                 990
Leu Lys Ser Lys Leu Val Ser Asp Phe Arg Lys Asp Phe Gln Phe Tyr
                995                 1000                1005
Lys Val Arg Glu Ile Asn Asn Tyr His His Ala His Asp Ala Tyr
    1010                1015                1020
Leu Asn Ala Val Val Gly Thr Ala Leu Ile Lys Lys Tyr Pro Lys
    1025                1030                1035
Leu Glu Ser Glu Phe Val Tyr Gly Asp Tyr Lys Val Tyr Asp Val
    1040                1045                1050
Arg Lys Met Ile Ala Lys Ser Glu Gln Glu Ile Gly Lys Ala Thr
    1055                1060                1065
Ala Lys Tyr Phe Phe Tyr Ser Asn Ile Met Asn Phe Phe Lys Thr
    1070                1075                1080
Glu Ile Thr Leu Ala Asn Gly Glu Ile Arg Lys Arg Pro Leu Ile
    1085                1090                1095
Glu Thr Asn Gly Glu Thr Gly Glu Ile Val Trp Asp Lys Gly Arg
    1100                1105                1110
Asp Phe Ala Thr Val Arg Lys Val Leu Ser Met Pro Gln Val Asn
    1115                1120                1125
Ile Val Lys Lys Thr Glu Val Gln Thr Gly Gly Phe Ser Lys Glu
    1130                1135                1140
Ser Ile Leu Pro Lys Arg Asn Ser Asp Lys Leu Ile Ala Arg Lys
    1145                1150                1155
Lys Asp Trp Asp Pro Lys Lys Tyr Gly Gly Phe Asp Ser Pro Thr
    1160                1165                1170
Val Ala Tyr Ser Val Leu Val Val Ala Lys Val Glu Lys Gly Lys
    1175                1180                1185
Ser Lys Lys Leu Lys Ser Val Lys Glu Leu Leu Gly Ile Thr Ile
    1190                1195                1200
```

-continued

```
Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
    1250                1255                1260

Pro Ser Lys Tyr Val Asn Phe Leu Tyr Leu Ala Ser His Tyr Glu
    1265                1270                1275

Lys Leu Lys Gly Ser Pro Glu Asp Asn Glu Gln Lys Gln Leu Phe
    1280                1285                1290

Val Glu Gln His Lys His Tyr Leu Asp Glu Ile Ile Glu Gln Ile
    1295                1300                1305

Ser Glu Phe Ser Lys Arg Val Ile Leu Ala Asp Ala Asn Leu Asp
    1310                1315                1320

Lys Val Leu Ser Ala Tyr Asn Lys His Arg Asp Lys Pro Ile Arg
    1325                1330                1335

Glu Gln Ala Glu Asn Ile Ile His Leu Phe Thr Leu Thr Asn Leu
    1340                1345                1350

Gly Ala Pro Ala Ala Phe Lys Tyr Phe Asp Thr Thr Ile Asp Arg
    1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
    1385                1390                1395

Gln Leu Gly Gly Asp Pro Ile Ala Gly Ser Lys Ala Ser Pro Lys
    1400                1405                1410

Lys Lys Arg Lys Val Gly Arg Ala Ile Phe Lys Pro Glu Glu Leu
    1415                1420                1425

Arg Gln Ala Leu Met Pro Thr Leu Glu Ala Leu Tyr Arg Gln Asp
    1430                1435                1440

Pro Glu Ser Leu Pro Phe Arg Gln Pro Val Asp Pro Gln Leu Leu
    1445                1450                1455

Gly Ile Pro Asp Tyr Phe Asp Ile Val Lys Ser Pro Met Asp Leu
    1460                1465                1470

Ser Thr Ile Lys Arg Lys Leu Asp Thr Gly Gln Tyr Gln Glu Pro
    1475                1480                1485

Trp Gln Tyr Val Asp Asp Ile Trp Leu Met Phe Asn Asn Ala Trp
    1490                1495                1500

Leu Tyr Asn Arg Lys Thr Ser Arg Val Tyr Lys Tyr Cys Ser Lys
    1505                1510                1515

Leu Ser Glu Val Phe Glu Gln Glu Ile Asp Pro Val Met Gln Ser
    1520                1525                1530

Leu Gly Tyr Cys Cys Gly Arg Lys Leu Glu Phe Ser Pro Gln Thr
    1535                1540                1545

Leu Cys Cys Tyr Gly Lys Gln Leu Cys Thr Ile Pro Arg Asp Ala
    1550                1555                1560

Thr Tyr Tyr Ser Tyr Gln Asn Arg Tyr His Phe Cys Glu Lys Cys
    1565                1570                1575

Phe Asn Glu Ile Gln Gly Glu Ser Val Ser Leu Gly Asp Asp Pro
    1580                1585                1590

Ser Gln Pro Gln Thr Thr Ile Asn Lys Glu Gln Phe Ser Lys Arg
```

```
            1595                1600                1605
Lys Asn Asp Thr Leu Asp Pro Glu Leu Phe Val Glu Cys Thr Glu
            1610                1615                1620

Cys Gly Arg Lys Met His Gln Ile Cys Val Leu His His Glu Ile
            1625                1630                1635

Ile Trp Pro Ala Gly Phe Val Cys Asp Gly Cys Leu Lys Lys Ser
            1640                1645                1650

Ala Arg Thr Arg Lys Glu Asn Lys Phe Ser Ala Lys Arg Leu Pro
            1655                1660                1665

Ser Thr Arg Leu Gly Thr Phe Leu Glu Asn Arg Val Asn Asp Phe
            1670                1675                1680

Leu Arg Arg Gln Asn His Pro Glu Ser Gly Glu Val Thr Val Arg
            1685                1690                1695

Val Val His Ala Ser Asp Lys Thr Val Glu Val Lys Pro Gly Met
            1700                1705                1710

Lys Ala Arg Phe Val Asp Ser Gly Glu Met Ala Glu Ser Phe Pro
            1715                1720                1725

Tyr Arg Thr Lys Ala Leu Phe Ala Phe Glu Glu Ile Asp Gly Val
            1730                1735                1740

Asp Leu Cys Phe Phe Gly Met His Val Gln Glu Tyr Gly Ser Asp
            1745                1750                1755

Cys Pro Pro Pro Asn Gln Arg Arg Val Tyr Ile Ser Tyr Leu Asp
            1760                1765                1770

Ser Val His Phe Phe Arg Pro Lys Cys Leu Arg Thr Ala Val Tyr
            1775                1780                1785

His Glu Ile Leu Ile Gly Tyr Leu Glu Tyr Val Lys Lys Leu Gly
            1790                1795                1800

Tyr Thr Thr Gly His Ile Trp Ala Cys Pro Pro Ser Glu Gly Asp
            1805                1810                1815

Asp Tyr Ile Phe His Cys His Pro Pro Asp Gln Lys Ile Pro Lys
            1820                1825                1830

Pro Lys Arg Leu Gln Glu Trp Tyr Lys Lys Met Leu Asp Lys Ala
            1835                1840                1845

Val Ser Glu Arg Ile Val His Asp Tyr Lys Asp Ile Phe Lys Gln
            1850                1855                1860

Ala Thr Glu Asp Arg Leu Thr Ser Ala Lys Glu Leu Pro Tyr Phe
            1865                1870                1875

Glu Gly Asp Phe Trp Pro Asn Val Leu Glu Glu Ser Ile Lys Glu
            1880                1885                1890

Leu Glu Gln Glu Glu Glu Glu Arg Lys Arg Glu Glu Asn Thr Ser
            1895                1900                1905

Asn Glu Ser Thr Asp Val Thr Lys Gly Asp Ser Lys Asn Ala Lys
            1910                1915                1920

Lys Lys Asn Asn Lys Lys Thr Ser Lys Asn Lys Ser Ser Leu Ser
            1925                1930                1935

Arg Gly Asn Lys Lys Lys Pro Gly Met Pro Asn Val Ser Asn Asp
            1940                1945                1950

Leu Ser Gln Lys Leu Tyr Ala Thr Met Glu Lys His Lys Glu Val
            1955                1960                1965

Phe Phe Val Ile Arg Leu Ile Ala Gly Pro Ala Ala Asn Ser Leu
            1970                1975                1980

Pro Pro Ile Val Asp Pro Asp Pro Leu Ile Pro Cys Asp Leu Met
            1985                1990                1995
```

Asp Gly Arg Asp Ala Phe Leu Thr Leu Ala Arg Asp Lys His Leu
2000            2005                2010

Glu Phe Ser Ser Leu Arg Arg Ala Gln Trp Ser Thr Met Cys Met
2015            2020                2025

Leu Val Glu Leu His Thr Gln Ser Gln Asp Tyr Pro Tyr Asp Val
2030            2035                2040

Pro Asp Tyr Ala Ser
2045

<210> SEQ ID NO 3
<211> LENGTH: 1521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Met Asp Lys Lys Tyr Ser Ile Gly Leu Ala Ile Gly Thr
        35                  40                  45

Asn Ser Val Gly Trp Ala Val Ile Thr Asp Glu Tyr Lys Val Pro Ser
50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp

-continued

```
                  290                 295                 300
Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
                340                 345                 350

Ser Ala Ser Met Ile Lys Arg Tyr Asp Glu His His Gln Asp Leu Thr
            355                 360                 365

Leu Leu Lys Ala Leu Val Arg Gln Gln Leu Pro Glu Lys Tyr Lys Glu
        370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
                420                 425                 430

Leu Leu Arg Lys Gln Arg Thr Phe Asp Asn Gly Ser Ile Pro His Gln
            435                 440                 445

Ile His Leu Gly Glu Leu His Ala Ile Leu Arg Arg Gln Glu Asp Phe
        450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
                500                 505                 510

Phe Glu Glu Val Val Asp Lys Gly Ala Ser Ala Gln Ser Phe Ile Glu
            515                 520                 525

Arg Met Thr Asn Phe Asp Lys Asn Leu Pro Asn Glu Lys Val Leu Pro
        530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
            595                 600                 605

Cys Phe Asp Ser Val Glu Ile Ser Gly Val Glu Asp Arg Phe Asn Ala
        610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
        690                 695                 700

Ile Arg Asp Lys Gln Ser Gly Lys Thr Ile Leu Asp Phe Leu Lys Ser
705                 710                 715                 720
```

Asp Gly Phe Ala Asn Arg Asn Phe Met Gln Leu Ile His Asp Asp Ser
            725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Asp Glu Leu Val Lys
        770                 775                 780

Val Met Gly Arg His Lys Pro Glu Asn Ile Val Ile Glu Met Ala Arg
785             790                 795                 800

Glu Asn Gln Thr Thr Gln Lys Gly Gln Lys Asn Ser Arg Glu Arg Met
            805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
            850                 855                 860

Ile Asn Arg Leu Ser Asp Tyr Asp Val Asp Ala Ile Val Pro Gln Ser
865             870                 875                 880

Phe Leu Lys Asp Asp Ser Ile Asp Asn Lys Val Leu Thr Arg Ser Asp
            885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
            915                 920                 925

Gln Arg Lys Phe Asp Asn Leu Thr Lys Ala Glu Arg Gly Gly Leu Ser
            930                 935                 940

Glu Leu Asp Lys Ala Gly Phe Ile Lys Arg Gln Leu Val Glu Thr Arg
945             950                 955                 960

Gln Ile Thr Lys His Val Ala Gln Ile Leu Asp Ser Arg Met Asn Thr
            965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
            995                 1000                1005

Lys Val Arg Glu Ile Asn Asn Tyr His His Ala His Asp Ala Tyr
        1010                1015                1020

Leu Asn Ala Val Val Gly Thr Ala Leu Ile Lys Lys Tyr Pro Lys
        1025                1030                1035

Leu Glu Ser Glu Phe Val Tyr Gly Asp Tyr Lys Val Tyr Asp Val
        1040                1045                1050

Arg Lys Met Ile Ala Lys Ser Glu Gln Glu Ile Gly Lys Ala Thr
        1055                1060                1065

Ala Lys Tyr Phe Phe Tyr Ser Asn Ile Met Asn Phe Phe Lys Thr
        1070                1075                1080

Glu Ile Thr Leu Ala Asn Gly Glu Ile Arg Lys Arg Pro Leu Ile
        1085                1090                1095

Glu Thr Asn Gly Glu Thr Gly Glu Ile Val Trp Asp Lys Gly Arg
        1100                1105                1110

Asp Phe Ala Thr Val Arg Lys Val Leu Ser Met Pro Gln Val Asn
        1115                1120                1125

```
Ile Val Lys Lys Thr Glu Val Gln Thr Gly Gly Phe Ser Lys Glu
1130               1135              1140

Ser Ile Leu Pro Lys Arg Asn Ser Asp Lys Leu Ile Ala Arg Lys
1145               1150              1155

Lys Asp Trp Asp Pro Lys Lys Tyr Gly Gly Phe Asp Ser Pro Thr
1160               1165              1170

Val Ala Tyr Ser Val Leu Val Ala Lys Val Glu Lys Gly Lys
1175               1180              1185

Ser Lys Lys Leu Lys Ser Val Lys Glu Leu Leu Gly Ile Thr Ile
1190               1195              1200

Met Glu Arg Ser Ser Phe Glu Lys Asn Pro Ile Asp Phe Leu Glu
1205               1210              1215

Ala Lys Gly Tyr Lys Glu Val Lys Lys Asp Leu Ile Ile Lys Leu
1220               1225              1230

Pro Lys Tyr Ser Leu Phe Glu Leu Glu Asn Gly Arg Lys Arg Met
1235               1240              1245

Leu Ala Ser Ala Gly Glu Leu Gln Lys Gly Asn Glu Leu Ala Leu
1250               1255              1260

Pro Ser Lys Tyr Val Asn Phe Leu Tyr Leu Ala Ser His Tyr Glu
1265               1270              1275

Lys Leu Lys Gly Ser Pro Glu Asp Asn Glu Gln Lys Gln Leu Phe
1280               1285              1290

Val Glu Gln His Lys His Tyr Leu Asp Glu Ile Ile Glu Gln Ile
1295               1300              1305

Ser Glu Phe Ser Lys Arg Val Ile Leu Ala Asp Ala Asn Leu Asp
1310               1315              1320

Lys Val Leu Ser Ala Tyr Asn Lys His Arg Asp Lys Pro Ile Arg
1325               1330              1335

Glu Gln Ala Glu Asn Ile Ile His Leu Phe Thr Leu Thr Asn Leu
1340               1345              1350

Gly Ala Pro Ala Ala Phe Lys Tyr Phe Asp Thr Thr Ile Asp Arg
1355               1360              1365

Lys Arg Tyr Thr Ser Thr Lys Glu Val Leu Asp Ala Thr Leu Ile
1370               1375              1380

His Gln Ser Ile Thr Gly Leu Tyr Glu Thr Arg Ile Asp Leu Ser
1385               1390              1395

Gln Leu Gly Gly Asp Ser Arg Ala Asp Pro Lys Lys Lys Arg Lys
1400               1405              1410

Val Ala Ser Asp Ala Lys Ser Leu Thr Ala Trp Ser Arg Thr Leu
1415               1420              1425

Val Thr Phe Lys Asp Val Phe Val Asp Phe Thr Arg Glu Glu Trp
1430               1435              1440

Lys Leu Leu Asp Thr Ala Gln Gln Ile Leu Tyr Arg Asn Val Met
1445               1450              1455

Leu Glu Asn Tyr Lys Asn Leu Val Ser Leu Gly Tyr Gln Leu Thr
1460               1465              1470

Lys Pro Asp Val Ile Leu Arg Leu Glu Lys Gly Glu Glu Pro Trp
1475               1480              1485

Leu Val Glu Arg Glu Ile His Gln Glu Thr His Pro Asp Ser Glu
1490               1495              1500

Thr Ala Phe Glu Ile Lys Ser Ser Val Pro Lys Lys Lys Arg Lys
1505               1510              1515

Val Ala Ser
```

1520

<210> SEQ ID NO 4
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Tyr Lys Val Tyr Asp Val Arg Lys Met Ile Ala Lys Ser Glu Gln Glu
1               5                   10                  15

Ile Gly Lys Ala Thr Ala Lys Tyr Phe Phe Tyr Ser Asn Ile Met Asn
                20                  25                  30

Phe Phe Lys Thr Glu Ile Thr Leu Ala Asn Gly Glu Ile Arg Lys Arg
            35                  40                  45

Pro Leu Ile Glu Thr Asn Gly Glu Thr Gly Glu Ile Val Trp Asp Lys
50                  55                  60

Gly Arg Asp Phe Ala Thr Val Arg Lys Val Leu Ser Met Pro Gln Val
65                  70                  75                  80

Asn Ile Val Lys Lys Thr Glu Val Gln Thr Gly Gly Phe Ser Lys Glu
                85                  90                  95

Ser Ile Leu Pro Lys Arg Asn Ser Asp Lys Leu Ile Ala Arg Lys Lys
            100                 105                 110

Asp Trp Asp Pro Lys Lys Tyr Gly Gly Phe Asp Ser Pro Thr Val Ala
            115                 120                 125

Tyr Ser Val Leu Val Val Ala Lys Val Glu Lys Gly Lys Ser Lys Lys
130                 135                 140

Leu Lys Ser Val Lys Glu Leu Leu Gly Ile Thr Ile Met Glu Arg Ser
145                 150                 155                 160

Ser Phe Glu Lys Asn Pro Ile Asp Phe Leu Glu Ala Lys Gly Tyr Lys
                165                 170                 175

Glu Val Lys Lys Asp Leu Ile Ile Lys Leu Pro Lys Tyr Ser Leu Phe
            180                 185                 190

Glu Leu Glu Asn Gly Arg Lys Arg Met Leu Ala Ser Ala Gly Glu Leu
            195                 200                 205

Gln Lys Gly Asn Glu Leu Ala Leu Pro Ser Lys Tyr Val Asn Phe Leu
210                 215                 220

Tyr Leu Ala Ser His Tyr Glu Lys Leu Lys Gly Ser Pro Glu Asp Asn
225                 230                 235                 240

Glu Gln Lys Gln Leu Phe Val Glu Gln His Lys His Tyr Leu Asp Glu
                245                 250                 255

Ile Ile Glu Gln Ile Ser Glu Phe Ser Lys Arg Val Ile Leu Ala Asp
            260                 265                 270

Ala Asn Leu Asp Lys Val Leu Ser Ala Tyr Asn Lys His Arg Asp Lys
            275                 280                 285

Pro Ile Arg Glu Gln Ala Glu Asn Ile Ile His Leu Phe Thr Leu Thr
290                 295                 300

Asn Leu Gly Ala Pro Ala Ala Phe Lys Tyr Phe Asp Thr Thr Ile Asp
305                 310                 315                 320

Arg Lys Arg Tyr Thr Ser Thr Lys Glu Val Leu Asp Ala Thr Leu Ile
                325                 330                 335

His Gln Ser Ile Thr Gly Leu Tyr Glu Thr Arg Ile Asp Leu Ser Gln
            340                 345                 350

```
Leu Gly Gly Asp Pro Ile Ala Gly Ser Lys Ala Ser Pro Lys Lys Lys
            355                 360                 365

Arg Lys Val Gly Arg Ala Ile Phe Lys Pro Glu Glu Leu Arg Gln Ala
    370                 375                 380

Leu Met Pro Thr Leu Glu Ala Leu Tyr Arg Gln Asp Pro Glu Ser Leu
385                 390                 395                 400

Pro Phe Arg Gln Pro Val Asp Pro Gln Leu Leu Gly Ile Pro Asp Tyr
                405                 410                 415

Phe Asp Ile Val Lys Ser Pro Met Asp Leu Ser Thr Ile Lys Arg Lys
                420                 425                 430

Leu Asp Thr Gly Gln Tyr Gln Glu Pro Trp Gln Tyr Val Asp Asp Ile
            435                 440                 445

Trp Leu Met Phe Asn Asn Ala Trp Leu Tyr Asn Arg Lys Thr Ser Arg
    450                 455                 460

Val Tyr Lys Tyr Cys Ser Lys Leu Ser Glu Val Phe Glu Gln Glu Ile
465                 470                 475                 480

Asp Pro Val Met Gln Ser Leu Gly Tyr Cys Cys Gly Arg Lys Leu Glu
                485                 490                 495

Phe Ser Pro Gln Thr Leu Cys Cys Tyr Gly Lys Gln Leu Cys Thr Ile
                500                 505                 510

Pro Arg Asp Ala Thr Tyr Tyr Ser Tyr Gln Asn Arg Tyr His Phe Cys
            515                 520                 525

Glu Lys Cys Phe Asn Glu Ile Gln Gly Glu Ser Val Ser Leu Gly Asp
    530                 535                 540

Asp Pro Ser Gln Pro Gln Thr Thr Ile Asn Lys Glu Gln Phe Ser Lys
545                 550                 555                 560

Arg Lys Asn Asp Thr Leu Asp Pro Glu Leu Phe Val Glu Cys Thr Glu
                565                 570                 575

Cys Gly Arg Lys Met His Gln Ile Cys Val Leu His His Glu Ile Ile
                580                 585                 590

Trp Pro Ala Gly Phe Val Cys Asp Gly Cys Leu Lys Lys Ser Ala Arg
            595                 600                 605

Thr Arg Lys Glu Asn Lys Phe Ser Ala
    610                 615

<210> SEQ ID NO 5
<211> LENGTH: 1726
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ala Phe Lys Pro Asn Pro Ile Asn Tyr Ile Leu Gly Leu Ala
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Ala His Arg Leu Leu
65                  70                  75                  80

Arg Ala Arg Arg Leu Leu Lys Arg Glu Gly Val Leu Gln Ala Ala Asp
                85                  90                  95
```

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
            115                 120                 125

Ala Val Leu Leu His Leu Ile Lys His Arg Gly Tyr Leu Ser Gln Arg
        130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
            195                 200                 205

Gln Ala Glu Leu Ile Leu Leu Phe Glu Lys Gln Lys Glu Phe Gly Asn
        210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
            275                 280                 285

Leu Glu Gln Gly Ser Glu Arg Pro Leu Thr Asp Thr Glu Arg Ala Thr
        290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
        450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

```
Phe Lys Asp Arg Lys Glu Ile Glu Lys Arg Gln Glu Asn Arg Lys
            515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Ala Ala Ala Leu Pro Phe
            580                 585                 590

Ser Arg Thr Trp Asp Asp Ser Phe Asn Asn Lys Val Leu Val Leu Gly
            595                 600                 605

Ser Glu Ala Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
    675                 680                 685

Gly Lys Gly Lys Lys Arg Val Phe Ala Ser Asn Gly Gln Ile Thr Asn
690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
            755                 760                 765

Lys Thr His Phe Pro Gln Pro Trp Glu Phe Phe Ala Gln Glu Val Met
770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
            835                 840                 845

Ser Ala Lys Arg Leu Asp Glu Gly Val Ser Val Leu Arg Val Pro Leu
850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
            915                 920                 925

Gln Lys Thr Gly Val Trp Val Arg Asn His Asn Gly Ile Ala Asp Asn
```

```
                    930             935             940
Ala Thr Met Val Arg Val Asp Val Phe Glu Lys Gly Asp Lys Tyr Tyr
945                 950             955             960

Leu Val Pro Ile Tyr Ser Trp Gln Val Ala Lys Gly Ile Leu Pro Asp
                    965             970             975

Arg Ala Val Val Gln Gly Lys Asp Glu Glu Asp Trp Gln Leu Ile Asp
                980             985             990

Asp Ser Phe Asn Phe Lys Phe Ser  Leu His Pro Asn Asp  Leu Val Glu
            995             1000            1005

Val Ile  Thr Lys Lys Ala Arg  Met Phe Gly Tyr Phe  Ala Ser Cys
    1010            1015            1020

His Arg  Gly Thr Gly Asn Ile  Asn Ile Arg Ile His  Asp Leu Asp
    1025            1030            1035

His Lys  Ile Gly Lys Asn Gly  Ile Leu Glu Gly Ile  Gly Val Lys
    1040            1045            1050

Thr Ala  Leu Ser Phe Gln Lys  Tyr Gln Ile Asp Glu  Leu Gly Lys
    1055            1060            1065

Glu Ile  Arg Pro Cys Arg Leu  Lys Lys Arg Pro  Val Arg Ser
    1070            1075            1080

Arg Ala  Asp Pro Lys Lys Lys  Arg Lys Val Glu Ala  Ser Gly Arg
    1085            1090            1095

Ala Ile  Phe Lys Pro Glu Glu  Leu Arg Gln Ala Leu  Met Pro Thr
    1100            1105            1110

Leu Glu  Ala Leu Tyr Arg Gln  Asp Pro Glu Ser Leu  Pro Phe Arg
    1115            1120            1125

Gln Pro  Val Asp Pro Gln Leu  Leu Gly Ile Pro Asp  Tyr Phe Asp
    1130            1135            1140

Ile Val  Lys Ser Pro Met Asp  Leu Ser Thr Ile Lys  Arg Lys Leu
    1145            1150            1155

Asp Thr  Gly Gln Tyr Gln Glu  Pro Trp Gln Tyr Val  Asp Asp Ile
    1160            1165            1170

Trp Leu  Met Phe Asn Asn Ala  Trp Leu Tyr Asn Arg  Lys Thr Ser
    1175            1180            1185

Arg Val  Tyr Lys Tyr Cys Ser  Lys Leu Ser Glu Val  Phe Glu Gln
    1190            1195            1200

Glu Ile  Asp Pro Val Met Gln  Ser Leu Gly Tyr Cys  Cys Gly Arg
    1205            1210            1215

Lys Leu  Glu Phe Ser Pro Gln  Thr Leu Cys Cys Tyr  Gly Lys Gln
    1220            1225            1230

Leu Cys  Thr Ile Pro Arg Asp  Ala Thr Tyr Tyr Ser  Tyr Gln Asn
    1235            1240            1245

Arg Tyr  His Phe Cys Glu Lys  Cys Phe Asn Glu Ile  Gln Gly Glu
    1250            1255            1260

Ser Val  Ser Leu Gly Asp Asp  Pro Ser Gln Pro Gln  Thr Thr Ile
    1265            1270            1275

Asn Lys  Glu Gln Phe Ser Lys  Arg Lys Asn Asp Thr  Leu Asp Pro
    1280            1285            1290

Glu Leu  Phe Val Glu Cys Thr  Glu Cys Gly Arg Lys  Met His Gln
    1295            1300            1305

Ile Cys  Val Leu His His Glu  Ile Ile Trp Pro Ala  Gly Phe Val
    1310            1315            1320

Cys Asp  Gly Cys Leu Lys Lys  Ser Ala Arg Thr Arg  Lys Glu Asn
    1325            1330            1335
```

-continued

```
Lys Phe Ser Ala Lys Arg Leu Pro Ser Thr Arg Leu Gly Thr Phe
    1340                1345                1350

Leu Glu Asn Arg Val Asn Asp Phe Leu Arg Arg Gln Asn His Pro
    1355                1360                1365

Glu Ser Gly Glu Val Thr Val Arg Val Val His Ala Ser Asp Lys
    1370                1375                1380

Thr Val Glu Val Lys Pro Gly Met Lys Ala Arg Phe Val Asp Ser
    1385                1390                1395

Gly Glu Met Ala Glu Ser Phe Pro Tyr Arg Thr Lys Ala Leu Phe
    1400                1405                1410

Ala Phe Glu Glu Ile Asp Gly Val Asp Leu Cys Phe Phe Gly Met
    1415                1420                1425

His Val Gln Glu Tyr Gly Ser Asp Cys Pro Pro Asn Gln Arg
    1430                1435                1440

Arg Val Tyr Ile Ser Tyr Leu Asp Ser Val His Phe Phe Arg Pro
    1445                1450                1455

Lys Cys Leu Arg Thr Ala Val Tyr His Glu Ile Leu Ile Gly Tyr
    1460                1465                1470

Leu Glu Tyr Val Lys Lys Leu Gly Tyr Thr Thr Gly His Ile Trp
    1475                1480                1485

Ala Cys Pro Pro Ser Glu Gly Asp Asp Tyr Ile Phe His Cys His
    1490                1495                1500

Pro Pro Asp Gln Lys Ile Pro Lys Pro Lys Arg Leu Gln Glu Trp
    1505                1510                1515

Tyr Lys Lys Met Leu Asp Lys Ala Val Ser Glu Arg Ile Val His
    1520                1525                1530

Asp Tyr Lys Asp Ile Phe Lys Gln Ala Thr Glu Asp Arg Leu Thr
    1535                1540                1545

Ser Ala Lys Glu Leu Pro Tyr Phe Glu Gly Asp Phe Trp Pro Asn
    1550                1555                1560

Val Leu Glu Glu Ser Ile Lys Glu Leu Glu Gln Glu Glu Glu
    1565                1570                1575

Arg Lys Arg Glu Glu Asn Thr Ser Asn Glu Ser Thr Asp Val Thr
    1580                1585                1590

Lys Gly Asp Ser Lys Asn Ala Lys Lys Lys Asn Lys Lys Thr
    1595                1600                1605

Ser Lys Asn Lys Ser Ser Leu Ser Arg Gly Asn Lys Lys Pro
    1610                1615                1620

Gly Met Pro Asn Val Ser Asn Asp Leu Ser Gln Lys Leu Tyr Ala
    1625                1630                1635

Thr Met Glu Lys His Lys Glu Val Phe Phe Val Ile Arg Leu Ile
    1640                1645                1650

Ala Gly Pro Ala Ala Asn Ser Leu Pro Pro Ile Val Asp Pro Asp
    1655                1660                1665

Pro Leu Ile Pro Cys Asp Leu Met Asp Gly Arg Asp Ala Phe Leu
    1670                1675                1680

Thr Leu Ala Arg Asp Lys His Leu Glu Phe Ser Ser Leu Arg Arg
    1685                1690                1695

Ala Gln Trp Ser Thr Met Cys Met Leu Val Glu Leu His Thr Gln
    1700                1705                1710

Ser Gln Asp Tyr Pro Tyr Asp Val Pro Asp Tyr Ala Ser
    1715                1720                1725
```

<210> SEQ ID NO 6
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
ggggccacua gggacaggau guuuuagagc uagaaauagc aaguuaaaau aaggcuaguc      60
cguuaucaac uugaaaaagu ggcaccgagu cggugcuuuu                            100

<210> SEQ ID NO 7
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggccacuagg acaggaugu uuuagagcua gaaauagcaa guuaaaauaa ggcuaguccg       60
uuaucaacuu gaaaaagugg caccgagucg gugcuuuu                              98

<210> SEQ ID NO 8
<211> LENGTH: 112
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
ggggccccuu cggggccac uagggacagg auguuuuaga gcuagaaaua gcaaguuaaa       60
auaaggcuag uccguuauca acuugaaaaa guggcaccga gucggugcuu uu              112

<210> SEQ ID NO 9
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9
gguaguggcc ccuucggggg ccacuaggga caggauguuu uagagcuaga aauagcaagu      60
uaaaauaagg cuaguccguu aucaacuuga aaaaguggca ccgagucggu gcuuuu          116

<210> SEQ ID NO 10
<211> LENGTH: 1198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
ccaggatcag tgaaacgcac cagacagccg cgtcagagca gctcaggttc tgggagaggg      60
tagcgcaggg tggccactga gaaccgggca ggtcacgcat ccccccttc cctcccaccc       120 cctgccaagc tctccctccc aggatcctct ctggctccat cgtaagcaaa ccttagaggt      180
tctggcaagg agagagatgg ctccaggaaa tgggggtgtg tcaccagata aggaatctgc      240

| | | |
|---|---|---|
| ctaacaggag gtgggggtta gacccaatat caggagacta ggaaggagga ggcctaagga | 300 | |
| tggggctttt ctgtcaccaa tcctgtccct agtggcccca ctgtggggtg gagggacag | 360 | |
| ataaaagtac ccagaaccag agccacatta accggccctg ggaatataag gtggtcccag | 420 | |
| ctcggggaca caggatccct ggaggcagca aacatgctgt cctgaagtgg acataggggc | 480 | |
| ccggggttgga ggaagaagac tagctgagct ctcggacccc tggaagatgc catgacaggg | 540 | |
| ggctggaaga gctagcacag actagagagg taaggggggt aggggagctg cccaaatgaa | 600 | |
| aggagtgaga ggtgacccgg aatccacagg agaacggggt gtccaggcaa agaaagcaag | 660 | |
| aggatggaga ggtggctaaa gccagggaga cggggtactt tggggttgtc cagaaaaacg | 720 | |
| gtgatgatgc aggcctacaa gaaggggagg cgggacgcaa gggagacatc cgtcggagaa | 780 | |
| ggccatccta agaaacgaga gatggcacag gccccagaag gagaaggaaa agggaaccca | 840 | |
| gcgagtgaag acggcatggg gttgggtgag ggaggagaga tgcccggaga ggacccagac | 900 | |
| acggggagga tccgctcaga ggacatcacg tggtgcagcg ccgagaagga agtgctccgg | 960 | |
| aaagagcatc cttgggcagc aacacagcag agagcaaggg gaagagggag tggaggaaga | 1020 | |
| cggaacctga aggaggcggc agggaaggat ctgggccagc cgtagaggtg acccaggcca | 1080 | |
| caagctgcag acagaaagcg gcacaggccc aggggagaga atgcaggtca gagaaagcag | 1140 | |
| gacctgcctg ggaagggggaa acagtgggcc agaggcggcg cagaagccag tagagctc | 1198 | |

<210> SEQ ID NO 11
<211> LENGTH: 986
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | | |
|---|---|---|
| catgacgtgc agcaagcgcg ctgacgcagc taatttttatc tatgtgcttc gtcatacgtg | 60 | |
| atgcatatac tctctgctag ctgactcatt cagctgtact cactcgctgt tgagtctcat | 120 | |
| acagcgcgag atcaaatgag tcatccaatc ctgtccctag tggcccctat cgtgacactg | 180 | |
| cactgcagcg tacgcgacag agctagactt cgtttcaata cagactagct actgcgtctg | 240 | |
| cagagcgctc tcttgtcact tacatcgaag tcaacgcgct cgcgttcaga gatcttctcc | 300 | |
| aatcctactt tcgacaattt tcgctctcag cgtttgtgtc tgtgcgcgca cacagtctgt | 360 | |
| gcttcgcttg caactaacgt agcgcttcag cgcatcgtca aagagcgaaa gagtcacagt | 420 | |
| gtctgtgttc acgtctctat cttctagtt ctccaatcct gtcccaaaat tgtcgaagac | 480 | |
| agagtttcgc gaattcgcag cagcgcgatc tctgctcact gcaatctctg actgctgctt | 540 | |
| ttaagcaatt ctcgcagctc agcatgagta cttgcgatta cagcagtgct cgccaatcct | 600 | |
| gtccctagtg attttgcagc gtcagcagag ctgatgagat gcagttcagc atcgcagacg | 660 | |
| agcagcacga agcgagcatc tgtagaaaat cgatcgacgc gcacttgcag agacaccaaa | 720 | |
| aattgtcgaa agtgaagcct tgtctctcgt tcgcatcaag acacgctatt tctgtctctt | 780 | |
| aaatgtttca aaaacacatc atgtcttctt cgtgcgagtt cgatgcgcgt gtgcgagacc | 840 | |
| acgcctgtcc ctagtggccc ctgactctct gtgcattttg agctgcgaaa gtaaagatat | 900 | |
| cgttcattgc agagacagag ctagtactag tctcagttct tgcactatgc tctcgatgtc | 960 | |
| tctcttagtg attcagcgca tcgtcg | 986 | |

<210> SEQ ID NO 12

<211> LENGTH: 1078
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

| | | | | | |
|---|---|---|---|---|---|
| gacctgcagg | catgcaagct | tgggctagcg | gagagtcagt | tcgcggtact | ggaggaggcg | 60 |
| gcgcaacgtc | gccagctgtc | tgcacaggag | aaatccctgc | tggcgcataa | agatgagacg | 120 |
| ctggagtaca | aacgccagct | ggctgcactt | ggcgacaagg | ttacgtatca | ggagcgcctg | 180 |
| aacgcgctgg | cgcagcaggc | ggataaattc | gcacagcagc | aacgggcaaa | acgggccgcc | 240 |
| attgatgcga | aaagccgggg | gctgactgac | cggcaggcag | aacgggaagc | cacggaacag | 300 |
| cgcctgaagg | aacagtatgg | cgataatccg | ctggcgctga | ataacgtcat | gtcagagcag | 360 |
| aaaaagacct | gggcggctga | agaccagctt | cgcgggaact | ggatggcagg | cctgaagtcc | 420 |
| ggctggccat | gggctgaggc | cagctgaggt | accgctgagg | attgctgagg | tgtacagacg | 480 |
| ctcaagtcag | aggtggcgag | agctcccgga | gtggctcaca | gtcggtggtc | cggcagtaca | 540 |
| atggattacc | gtaagacgga | aatcactccc | gggtatatga | agagacgac | cactgccagg | 600 |
| gacgaaagtg | caatgcggca | tacctcagtg | gcgtggagtg | caggtataca | gattaatccg | 660 |
| gcagcgtccg | tcgttgttga | tattgcttat | gaaggctccg | gcagtggcga | ctggcgtact | 720 |
| gacggattca | tcgttggggt | cggttataaa | ttctgattag | ccaggtaaca | cagtgttatg | 780 |
| acagcccgcc | ggaaccggtg | ggctttttg | tggggtgaat | atggcagtaa | agatttcagg | 840 |
| agtcctgaaa | gacggcacag | gaaaaccggt | acagaactgc | accattcagc | tgaaagccag | 900 |
| acgtaacagc | accacggtgg | tggtgaacac | ggtgggctca | gagaatccgg | atgaagccgg | 960 |
| gcgttacagc | atggatgtgg | agtacggtca | gtacagtgtc | atcctgcagg | ttgacggttt | 1020 |
| tccaccatcg | cacgccggga | ccatcaccgt | gtatgaagat | tcacaaccgg | ggacgctg | 1078 |

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttcttcttct gctcggactc          20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttcttcttct gctcggactc          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttcttcttct gctcggactc					20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttcttcttct gctcggactc					20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttcttcttct gctcggactc					20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttcttcttct gctcggactc					20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttcttcttct gctcggactc					20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttcttcttct gctcggactc					20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 21
ttcttcttct gctcggactc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttcttcttct gctcggactc                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttcttcttct gctcggactc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttcttcttct gctcggactc                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttcttcttct gctcggactc                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttcttcttct gctcggactc                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
```
ttcttcttct gctcggactc					20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttcttcttct gctcggactc					20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttcttcttct gctcggactc					20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttcttcttct gctcggactc					20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttcttcttct gctcggactc					20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttcttcttct gctcggactc					20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccctagtcat tggaggtgac                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccctagtcat tggaggtgac                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccctagtcat tggaggtgac                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccctagtcat tggaggtgac                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ccctagtcat tggaggtgac                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccctagtcat tggaggtgac                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccctagtcat tggaggtgac                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccctagtcat tggaggtgac                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccctagtcat tggaggtgac                                                   20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccctagtcat tggaggtgac                                                   20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
atggggagga catcgatgtc                                                   20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
atggggagga catcgatgtc                                                   20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
atggggagga catcgatgtc                                                   20

```
<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
atggggagga catcgatgtc                                                   20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atggggagga catcgatgtc                                                   20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atggggagga catcgatgtc                                                   20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atggggagga catcgatgtc                                                   20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atggggagga catcgatgtc                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atggggagga catcgatgtc                                                   20
```

```
<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atggggagga catcgatgtc                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atcacatcaa ccggtggcgc                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atcacatcaa ccggtggcgc                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atcacatcaa ccggtggcgc                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atcacatcaa ccggtggcgc                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atcacatcaa ccggtggcgc                                              20

<210> SEQ ID NO 58
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atcacatcaa ccggtggcgc                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
atcacatcaa ccggtggcgc                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atcacatcaa ccggtggcgc                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atcacatcaa ccggtggcgc                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atcacatcaa ccggtggcgc                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gagtttctca tctgtgcccc                                              20

<210> SEQ ID NO 64
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccagcttctg ccgtttgtac                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccagcttctg ccgtttgtac                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccagcttctg ccgtttgtac                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttcctcctcc agcttctgcc                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttcctcctcc agcttctgcc                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttcctcctcc agcttctgcc                                              20

<210> SEQ ID NO 70
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 70
ttcctcctcc agcttctgcc                                                   20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ttcctcctcc agcttctgcc                                                   20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ccggttgatg tgatgggagc                                                   20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ccggttgatg tgatgggagc                                                   20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ccggttgatg tgatgggagc                                                   20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ccggttgatg tgatgggagc                                                   20

<210> SEQ ID NO 76
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 76
gcagcaagca gcactctgcc                                                    20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcagcaagca gcactctgcc                                                    20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcttgggccc acgcaggggc                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcttgggccc acgcaggggc                                                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcttcgtggc aatgcgccac                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcttgggccc acgcaggggc                                                    20

<210> SEQ ID NO 82
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 82
aagctggact ctggccactc                                                   20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ttcttcttct gctcggactc                                                   20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ttcttcttct gctcggactc                                                   20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttcttcttct gctcggactc                                                   20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gagtttctca tctgtgcccc                                                   20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttcctcctcc agcttctgcc                                                   20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 88
ttcctcctcc agcttctgcc                                              20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
agcagaagaa gaagggctcc                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aagctggact ctggccactc                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ccctagtcat tggaggtgac                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ccctagtcat tggaggtgac                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccctagtcat tggaggtgac                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ccctagtcat tggaggtgac                                           20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccctagtcat tggaggtgac                                           20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ccctagtcat tggaggtgac                                           20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ccctagtcat tggaggtgac                                           20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ccctagtcat tggaggtgac                                           20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccctagtcat tggaggtgac                                           20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 100
ccctagtcat tggaggtgac                                                   20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atggggagga catcgatgtc                                                   20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atggggagga catcgatgtc                                                   20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
atggggagga catcgatgtc                                                   20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atggggagga catcgatgtc                                                   20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atggggagga catcgatgtc                                                   20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
```

```
atggggagga catcgatgtc                                            20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
atggggagga catcgatgtc                                            20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atggggagga catcgatgtc                                            20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
atggggagga catcgatgtc                                            20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
atggggagga catcgatgtc                                            20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atcacatcaa ccggtggcgc                                            20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
```
atcacatcaa ccggtggcgc  20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
atcacatcaa ccggtggcgc  20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
atcacatcaa ccggtggcgc  20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atcacatcaa ccggtggcgc  20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
atcacatcaa ccggtggcgc  20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
atcacatcaa ccggtggcgc  20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atcacatcaa ccggtggcgc  20

```
<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
atcacatcaa ccggtggcgc                                                 20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
atcacatcaa ccggtggcgc                                                 20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gagtttctca tctgtgcccc                                                 20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccagcttctg ccgtttgtac                                                 20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ccagcttctg ccgtttgtac                                                 20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ccagcttctg ccgtttgtac                                                 20
```

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ttcctcctcc agcttctgcc                                                20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ttcctcctcc agcttctgcc                                                20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ttcctcctcc agcttctgcc                                                20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ttcctcctcc agcttctgcc                                                20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ttcctcctcc agcttctgcc                                                20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccggttgatg tgatgggagc                                                20

```
<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ccggttgatg tgatgggagc                                               20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccggttgatg tgatgggagc                                               20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ccggttgatg tgatgggagc                                               20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcagcaagca gcactctgcc                                               20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcagcaagca gcactctgcc                                               20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gcttgggccc acgcaggggc                                               20

<210> SEQ ID NO 137
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gcttgggccc acgcaggggc                                                   20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gcttcgtggc aatgcgccac                                                   20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gcttgggccc acgcaggggc                                                   20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aagctggact ctggccactc                                                   20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ttcttcttct gctcggactc                                                   20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ttcttcttct gctcggactc                                                   20

<210> SEQ ID NO 143
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ttcttcttct gctcggactc                                               20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gagtttctca tctgtgcccc                                               20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ttcctcctcc agcttctgcc                                               20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ttcctcctcc agcttctgcc                                               20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
agcagaagaa gaagggctcc                                               20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
aagctggact ctggccactc                                               20

<210> SEQ ID NO 149
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 149
guguccgagc agaagaagaa                                                   20

<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gacuccgagc agaagaagaa                                                   20

<210> SEQ ID NO 151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gagaccgagc agaagaagaa                                                   20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gagugcgagc agaagaagaa                                                   20

<210> SEQ ID NO 153
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gagucggagc agaagaagaa                                                   20

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gagucccagc agaagaagaa                                                   20

<210> SEQ ID NO 155
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 155
gaguccgugc agaagaagaa                                                    20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gaguccgacc agaagaagaa                                                    20

<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
gaguccgagg agaagaagaa                                                    20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gaguccgagc ugaagaagaa                                                    20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
guguccgagc agaagaagaa                                                    20

<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gacuccgagc agaagaagaa                                                    20

<210> SEQ ID NO 161
<211> LENGTH: 20
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 161
gagaccgagc agaagaagaa          20

<210> SEQ ID NO 162
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 162
gagugcgagc agaagaagaa          20

<210> SEQ ID NO 163
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 163
gagucggagc agaagaagaa          20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 164
gagucccagc agaagaagaa          20

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 165
gaguccgugc agaagaagaa          20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 166
gaguccgacc agaagaagaa          20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 167
gaguccgagg agaagaagaa 20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
gaguccgagc ugaagaagaa 20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gacaccucca augacuaggg 20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gugaccucca augacuaggg 20

<210> SEQ ID NO 171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
gucuccucca augacuaggg 20

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gucagcucca augacuaggg 20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 173
gucacgucca augacuaggg                                                    20

<210> SEQ ID NO 174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
gucaccacca augacuaggg                                                    20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
gucaccugca augacuaggg                                                    20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
gucaccucga augacuaggg                                                    20

<210> SEQ ID NO 177
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
gucaccuccu augacuaggg                                                    20

<210> SEQ ID NO 178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gucaccucca uugacuaggg                                                    20

<210> SEQ ID NO 179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 179
gucaucgaug uccuccccau                                              20

<210> SEQ ID NO 180
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
gagaucgaug uccuccccau                                              20

<210> SEQ ID NO 181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gacuucgaug uccuccccau                                              20

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
gacaacgaug uccuccccau                                              20

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gacauggaug uccuccccau                                              20

<210> SEQ ID NO 184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gacauccaug uccuccccau                                              20

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
```
gacaucguug uccuccccau                                              20

<210> SEQ ID NO 186
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
gacaucgaag uccuccccau                                              20

<210> SEQ ID NO 187
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gacaucgauc uccuccccau                                              20

<210> SEQ ID NO 188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gacaucgaug accuccccau                                              20

<210> SEQ ID NO 189
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gggccaccgg uugaugugau                                              20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gccccaccgg uugaugugau                                              20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gcggcaccgg uugaugugau 20

<210> SEQ ID NO 192
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 192
gcgcgaccgg uugaugugau 20

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 193
gcgccuccgg uugaugugau 20

<210> SEQ ID NO 194
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 194
gcgccagcgg uugaugugau 20

<210> SEQ ID NO 195
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 195
gcgccacggg uugaugugau 20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 196
gcgccacccg uugaugugau 20

<210> SEQ ID NO 197
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 197
gcgccaccgc uugaugugau 20

<210> SEQ ID NO 198
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gcgccaccgg augaugugau                                                20

<210> SEQ ID NO 199
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gggccacaga ugagaaacuc                                                20

<210> SEQ ID NO 200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
guucaaacgg cagaagcugg                                                20

<210> SEQ ID NO 201
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
guacuaacgg cagaagcugg                                                20

<210> SEQ ID NO 202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
guacaaacgg gagaagcugg                                                20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
gccagaagcu ggaggaggaa                                                20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ggcacaagcu ggaggaggaa                                                      20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
ggcagaaccu ggaggaggaa                                                      20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ggcagaagca ggaggaggaa                                                      20

<210> SEQ ID NO 207
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
ggcagaagcu cgaggaggaa                                                      20

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gcacccauca caucaaccgg                                                      20

<210> SEQ ID NO 209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
gcucccuuca caucaaccgg                                                      20

```
<210> SEQ ID NO 210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
gcucccaaca caucaaccgg                                                    20

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gcucccauca gaucaaccgg                                                    20

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
ggcagugugc ugcuugcugc                                                    20

<210> SEQ ID NO 213
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ggcagagugc agcuugcugc                                                    20

<210> SEQ ID NO 214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
gccccagcgu gggcccaagc                                                    20

<210> SEQ ID NO 215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
gccccugccu gggcccaagc                                                    20

<210> SEQ ID NO 216
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
guggcccauu gccacgaagc                                                     20

<210> SEQ ID NO 217
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gccccugcgu cggcccaagc                                                     20

<210> SEQ ID NO 218
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
gaguggccug aguccagcuu                                                     20

<210> SEQ ID NO 219
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gagaccgagc agaagaagaa                                                     20

<210> SEQ ID NO 220
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gaguccgagg agaagaagaa                                                     20

<210> SEQ ID NO 221
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
gaguccgagc ugaagaagaa                                                     20

<210> SEQ ID NO 222
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ggggcacagu ugagaaacuc                                              20

<210> SEQ ID NO 223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ggcagaaggu ggaggaggaa                                              20

<210> SEQ ID NO 224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ggcagaagca ggaggaggaa                                              20

<210> SEQ ID NO 225
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ggagcccuug uucuucugcu                                              20

<210> SEQ ID NO 226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
gaguggccug aguccagcuu                                              20

<210> SEQ ID NO 227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gacaccucca augacuaggg                                              20

<210> SEQ ID NO 228
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 228
gugaccucca augacuaggg                                                    20

<210> SEQ ID NO 229
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
gucuccucca augacuaggg                                                    20

<210> SEQ ID NO 230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
gucagcucca augacuaggg                                                    20

<210> SEQ ID NO 231
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
gucacgucca augacuaggg                                                    20

<210> SEQ ID NO 232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gucaccacca augacuaggg                                                    20

<210> SEQ ID NO 233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
gucaccugca augacuaggg                                                    20

<210> SEQ ID NO 234
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 234
gucaccucga augacuaggg                                               20

<210> SEQ ID NO 235
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
gucaccuccu augacuaggg                                               20

<210> SEQ ID NO 236
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
gucaccucca uugacuaggg                                               20

<210> SEQ ID NO 237
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
gucaucgaug uccuccccau                                               20

<210> SEQ ID NO 238
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
gagaucgaug uccuccccau                                               20

<210> SEQ ID NO 239
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
gacuucgaug uccuccccau                                               20

<210> SEQ ID NO 240
<211> LENGTH: 20
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 240
gacaacgaug uccuccccau                                                    20

<210> SEQ ID NO 241
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
gacauggaug uccuccccau                                                    20

<210> SEQ ID NO 242
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gacauccaug uccuccccau                                                    20

<210> SEQ ID NO 243
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
gacaucguug uccuccccau                                                    20

<210> SEQ ID NO 244
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gacaucgaag uccuccccau                                                    20

<210> SEQ ID NO 245
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gacaucgauc uccuccccau                                                    20

<210> SEQ ID NO 246
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 246
gacaucgaug accuccccau                                          20

<210> SEQ ID NO 247
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
gggccaccgg uugaugugau                                          20

<210> SEQ ID NO 248
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gccccaccgg uugaugugau                                          20

<210> SEQ ID NO 249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
gcggcaccgg uugaugugau                                          20

<210> SEQ ID NO 250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gcgcgaccgg uugaugugau                                          20

<210> SEQ ID NO 251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
gcgccuccgg uugaugugau                                          20

<210> SEQ ID NO 252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gcgccagcgg uugaugugau                                                         20

<210> SEQ ID NO 253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
gcgccacggg uugaugugau                                                         20

<210> SEQ ID NO 254
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gcgccacccg uugaugugau                                                         20

<210> SEQ ID NO 255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gcgccaccgc uugaugugau                                                         20

<210> SEQ ID NO 256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gcgccaccgg augaugugau                                                         20

<210> SEQ ID NO 257
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gggccacaga ugagaaacuc                                                         20

<210> SEQ ID NO 258
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 258
guucaaacgg cagaagcugg                                         20

<210> SEQ ID NO 259
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
guacuaacgg cagaagcugg                                         20

<210> SEQ ID NO 260
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
guacaaacgg gagaagcugg                                         20

<210> SEQ ID NO 261
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gccagaagcu ggaggaggaa                                         20

<210> SEQ ID NO 262
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
ggcacaagcu ggaggaggaa                                         20

<210> SEQ ID NO 263
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ggcagaaccu ggaggaggaa                                         20

<210> SEQ ID NO 264
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
```
ggcagaagca ggaggaggaa                                              20

<210> SEQ ID NO 265
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ggcagaagcu cgaggaggaa                                              20

<210> SEQ ID NO 266
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
gcacccauca caucaaccgg                                              20

<210> SEQ ID NO 267
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
gcucccuuca caucaaccgg                                              20

<210> SEQ ID NO 268
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
gcucccaaca caucaaccgg                                              20

<210> SEQ ID NO 269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
gcucccauca gaucaaccgg                                              20

<210> SEQ ID NO 270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270

```
ggcagugugc ugcuugcugc                                          20

<210> SEQ ID NO 271
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
ggcagagugc agcuugcugc                                          20

<210> SEQ ID NO 272
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
gccccagcgu gggcccaagc                                          20

<210> SEQ ID NO 273
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
gccccugccu gggcccaagc                                          20

<210> SEQ ID NO 274
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
guggcccauu gccacgaagc                                          20

<210> SEQ ID NO 275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
gccccugcgu cggcccaagc                                          20

<210> SEQ ID NO 276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
gaguggccug aguccagcuu                                          20
```

<210> SEQ ID NO 277
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
gagaccgagc agaagaagaa                                              20

<210> SEQ ID NO 278
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
gaguccgagg agaagaagaa                                              20

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gaguccgagc ugaagaagaa                                              20

<210> SEQ ID NO 280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
ggggcacagu ugagaaacuc                                              20

<210> SEQ ID NO 281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ggcagaaggu ggaggaggaa                                              20

<210> SEQ ID NO 282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
ggcagaagca ggaggaggaa                                              20

-continued

<210> SEQ ID NO 283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ggagcccuug uucuucugcu                                                      20

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
gaguggccug aguccagcuu                                                      20

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gagttcctac tcagactgtt actc                                                 24

<210> SEQ ID NO 286
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gtgagttcct actcagactg ttactc                                               26

<210> SEQ ID NO 287
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
gtctgagttc ctactcagac tgttactc                                             28

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gtattcgtac tcagactgtt actc                                                 24

```
<210> SEQ ID NO 289
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gagtattcgt actcagactg ttactc                                          26

<210> SEQ ID NO 290
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gacttcggtc cgagcagaag aagaa                                           25

<210> SEQ ID NO 291
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ggacttcggt ccgagcagaa gaagaa                                          26

<210> SEQ ID NO 292
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gcggacttcg gtccgagcag aagaagaa                                        28

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gcgggagtcc gagcagaaga agaa                                            24

<210> SEQ ID NO 294
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
gtcgggagtc cgagcagaag aagaa                                           25

<210> SEQ ID NO 295
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gctcgggagt ccgagcagaa gaagaa                                          26

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
gttcacttcg gggtgggggg agtttgctcc                                      30

<210> SEQ ID NO 297
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
gttcattcgg ggtgggggga gtttgctcc                                       29

<210> SEQ ID NO 298
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gtccttcggg gtgggggag tttgctcc                                         28

<210> SEQ ID NO 299
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
gcttccttcg gggtgggggg agtttgctcc                                      30

<210> SEQ ID NO 300
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gtttccttcg gggtgggggg agtttgctcc                                      30

<210> SEQ ID NO 301
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gctccttcgg ggtgggggga gtttgctcc                                     29

<210> SEQ ID NO 302
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
gcccacttcg gggtggggggg agtttgctcc                                   30

<210> SEQ ID NO 303
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gcccattcgg ggtgggggga gtttgctcc                                     29

<210> SEQ ID NO 304
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304 gcccctttcgg ggtgggggga gtttgctcc                                    29

<210> SEQ ID NO 305
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gcatccttcg gtgtgggggg agtttgctcc                                    30

<210> SEQ ID NO 306
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gccccgggtg ggggagttt gctcc                                          25

<210> SEQ ID NO 307
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 307
gcccgggtgg ggggagtttg ctcc                                          24

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
gccgggtggg gggagtttgc tcc                                           23

<210> SEQ ID NO 309
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gcacgttcgg gtgagtgagt gtgtgcgtg                                     29

<210> SEQ ID NO 310
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
gtacgttcgg gtgagtgagt gtgtgcgtg                                     29

<210> SEQ ID NO 311
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gcatgttcgg gtgagtgagt gtgtgcgtg                                     29

<210> SEQ ID NO 312
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gtatgttcgg gtgagtgagt gtgtgcgtg                                     29

<210> SEQ ID NO 313
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 313
gcgcgttcgg gtgagtgagt gtgtgcgtg                                29

<210> SEQ ID NO 314
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gcgtgttcgg gtgagtgagt gtgtgcgtg                                29

<210> SEQ ID NO 315
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gtaggttcgc ctactcagac tgttactc                                 28

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ggcctcccca aagcctggcc a                                        21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gacctcccca tagcctggcc a                                        21

<210> SEQ ID NO 318
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318 gggagt                                                         6

<210> SEQ ID NO 319
<211> LENGTH: 6
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 319 gggagg 6

<210> SEQ ID NO 320
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 320
tttcctgatg gtccatgtct gttactc 27

<210> SEQ ID NO 321
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
tttcgtgatg gtccatgtct gttactc 27

<210> SEQ ID NO 322
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 322
tttccagttg gtccatgtct gttactc 27

<210> SEQ ID NO 323
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 323
tttcctgatg gtccatgtct gttactg 27

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 324
ctgggactca ggcgggtcac 20

<210> SEQ ID NO 325
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 325
cctcacacaa cagcttcatg tcagc                                            25

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ctgatggtgc atgtctgtta                                                  20

<210> SEQ ID NO 327
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ctgatggtgc atgtctg                                                     17

<210> SEQ ID NO 328
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ctgatggtgc atgtctgtta agacatgcac ca                                    32

<210> SEQ ID NO 329
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ctgatggtgc atgtctgcat gcacca                                           26

<210> SEQ ID NO 330
<211> LENGTH: 28
<212> TYPE: DNA
<213> ORGANISM: Unknown
<220> FEATURE:
<223> OTHER INFORMATION: Description of Unknown:
      DNMT1 oligonucleotide

<400> SEQUENCE: 330
tttcctgatg ggtccatgtc tgttactc                                         28

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ctgatggtgc atgtctgtta                                              20

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
ctgatggtgc atgtctg                                                 17

<210> SEQ ID NO 333
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
ctgatggtgc atgtctgtta agacatgcac ca                                32

<210> SEQ ID NO 334
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ctgatggtgc atgtctgcat gcacca                                       26

<210> SEQ ID NO 335
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gtgagtaggt tcgcctactc agactgttac tc                                32

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
atcctgtccc tagtggcccc                                              20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 337 gggggccacta gggacaggat                                              20

<210> SEQ ID NO 338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338 gggggccacua gggacaggau                                              20

<210> SEQ ID NO 339
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
ggccacuagg gacaggau                                                 18

<210> SEQ ID NO 340
<211> LENGTH: 20
<212> TYPE: DNA
<213> ORGANISM: Unknown
<220> FEATURE:
<223> OTHER INFORMATION: Description of Unknown:
      VEGFA1 target site oligonucleotide

<400> SEQUENCE: 340
gggtgggggg agtttgctcc                                               20

<210> SEQ ID NO 341
<211> LENGTH: 20
<212> TYPE: DNA
<213> ORGANISM: Unknown
<220> FEATURE:
<223> OTHER INFORMATION: Description of Unknown:
      VEGFA1 off-target site oligonucleotide

<400> SEQUENCE: 341
ggatggaggg agtttgctcc                                               20

<210> SEQ ID NO 342
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 342

His His His His His His
1               5

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<223> OTHER INFORMATION: 5'-Biotinylation

<400> SEQUENCE: 343
ccaggatcag tgaaacgcac                                              20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
gagctctact ggcttctgcg                                              20

<210> SEQ ID NO 345
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-Biotinylation

<400> SEQUENCE: 345
catgacgtgc agcaagc                                                 17

<210> SEQ ID NO 346
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
cgacgatgcg ctgaatc                                                 17

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-Biotinylation

<400> SEQUENCE: 347
gacctgcagg catgcaagct tgg                                          23

<210> SEQ ID NO 348
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
cagcgtcccc ggttgtgaat ct                                           22
```